US012599656B2

(12) United States Patent　　　(10) Patent No.:　US 12,599,656 B2
Loughhead et al.　　　　　　　　(45) **Date of Patent:　\*Apr. 14, 2026**

(54) METHODS FOR TREATING HPV-ASSOCIATED DISEASES

(71) Applicant: STEMCELL TECHNOLOGIES CANADA INC., Vancouver (CA)

(72) Inventors: Scott Loughhead, Durham, NC (US); LeeAnn Talarico, Milton, MA (US); Alfonso Vicente-Suarez, Brookline, MA (US); Matt Booty, Watertown, MA (US); Howard Bernstein, Cambridge, MA (US); Katarina Blagovic, Cambridge, MA (US); Armon R. Sharei, Somerville, MA (US); Kelan Hlavaty, Belmont, MA (US); Melissa Myint, Watertown, MA (US)

( \* ) Notice: Subject to any disclaimer, the term of this patent is extended or adjusted under 35 U.S.C. 154(b) by 1255 days.

This patent is subject to a terminal disclaimer.

(21) Appl. No.: 16/980,341

(22) PCT Filed: Mar. 11, 2019

(86) PCT No.: PCT/US2019/021703
§ 371 (c)(1),
(2) Date: Sep. 11, 2020

(87) PCT Pub. No.: WO2019/178005
PCT Pub. Date: Sep. 19, 2019

(65) Prior Publication Data
US 2021/0038709 A1　　Feb. 11, 2021

Related U.S. Application Data

(60) Provisional application No. 62/812,225, filed on Feb. 28, 2019, provisional application No. 62/794,517,
(Continued)

(51) Int. Cl.
A01N 61/00　　(2006.01)
A61K 33/243　　(2019.01)
(Continued)

(52) U.S. Cl.
CPC ............ A61K 39/12 (2013.01); A61K 33/243 (2019.01); A61K 40/11 (2025.01); A61K 40/13 (2025.01);
(Continued)

(58) Field of Classification Search
None
See application file for complete search history.

(56) References Cited

U.S. PATENT DOCUMENTS 4,055,799 A　　10/1977　Coster
4,376,634 A　　3/1983　Prior et al.
(Continued)

FOREIGN PATENT DOCUMENTS

CN　　101031641 A　　9/2007
CN　　101795705 A　　8/2010
(Continued)

OTHER PUBLICATIONS

Adamo, A. et al. (Aug. 7, 2012, e-pub. Jul. 10, 2012). "Microfluidics-Based Assessment of Cell Deformability," Anal Chem 84(15):6438-6443, 13 pages.
(Continued)

*Primary Examiner* — M Franco G Salvoza
(74) *Attorney, Agent, or Firm* — SMART & BIGGAR LP; Micheline Gravelle

(57) ABSTRACT
The present application provides immune cells comprising an HPV antigen and an adjuvant, methods of manufacturing such modified immune cells, and methods of using such modified immune cells for treating an HPV-associated disease, preventing an HPV-associated disease and/or for
(Continued)

modulating an immune response in an individual with an HPV-associated disease.

9 Claims, 43 Drawing Sheets

Specification includes a Sequence Listing.

Related U.S. Application Data filed on Jan. 18, 2019, provisional application No. 62/641,988, filed on Mar. 12, 2018.

(51) Int. Cl.

| | |
|---|---|
| *A61K 39/12* | (2006.01) |
| *A61K 40/11* | (2025.01) |
| *A61K 40/13* | (2025.01) |
| *A61K 40/19* | (2025.01) |
| *A61K 40/24* | (2025.01) |
| *A61K 40/42* | (2025.01) |
| *A61K 40/46* | (2025.01) |
| *A61K 45/06* | (2006.01) |
| *A61P 35/00* | (2006.01) |
| *A61K 39/00* | (2006.01) |

(52) U.S. Cl.

CPC .............. *A61K 40/19* (2025.01); *A61K 40/24* (2025.01); *A61K 40/428* (2025.01); *A61K 40/46* (2025.01); *A61K 45/06* (2013.01); *A61P 35/00* (2018.01); *A61K 2039/55516* (2013.01); *A61K 2039/55561* (2013.01); *A61K 2039/585* (2013.01); *A61K 2239/31* (2023.05); *A61K 2239/39* (2023.05); *C12N 2710/20034* (2013.01)

(56) References Cited

U.S. PATENT DOCUMENTS

| | | | |
|---|---|---|---|
| 4,835,457 | A | 5/1989 | Hanss |
| 5,023,054 | A | 6/1991 | Sato |
| 8,147,867 | B2 | 4/2012 | Tong |
| 9,364,504 | B2 | 6/2016 | Godfrin |
| 9,950,049 | B2 | 4/2018 | Godfrin |
| 10,124,336 | B2 | 11/2018 | Sharei |
| 10,526,573 | B2 | 1/2020 | Ding |
| 10,696,944 | B2 | 6/2020 | Sharei |
| 10,780,151 | B2 | 9/2020 | Godfrin |
| 10,870,112 | B2 | 12/2020 | Sharei |
| 11,692,168 | B2 * | 7/2023 | Sharei ................ A61K 39/4622 424/204.1 |
| 2004/0197898 | A1 | 10/2004 | Nakatani |
| 2006/0134067 | A1 | 6/2006 | Liu |
| 2006/0134772 | A1 | 6/2006 | Miles |
| 2007/0243523 | A1 | 10/2007 | Ionescu-zanetti |
| 2007/0249038 | A1 | 10/2007 | Adamo |
| 2008/0026465 | A1 | 1/2008 | Nakata |
| 2008/0241844 | A1 | 10/2008 | Kellogg |
| 2008/0311140 | A1 | 12/2008 | Lee |
| 2009/0280518 | A1 | 11/2009 | Adamo |
| 2010/0203068 | A1 | 8/2010 | Betz |
| 2010/0249621 | A1 | 9/2010 | Ichitani |
| 2011/0030808 | A1 | 2/2011 | Chiou |
| 2011/0300205 | A1 | 12/2011 | Geall |
| 2012/0009140 | A1 | 1/2012 | Godfrin |
| 2012/0207745 | A1 | 8/2012 | Godfrin |
| 2014/0287509 | A1 | 9/2014 | Sharei |
| 2016/0193605 | A1 | 7/2016 | Sharei |
| 2016/0324946 | A1 | 11/2016 | Godfrin |
| 2018/0003696 | A1 | 1/2018 | Sharei |
| 2018/0016539 | A1 | 1/2018 | Ding |
| 2018/0142198 | A1 | 5/2018 | Sharei |
| 2018/0201889 | A1 | 7/2018 | Sharei |
| 2018/0245089 | A1 | 8/2018 | Sharei |
| 2018/0344822 | A1 | 12/2018 | Godfrin |
| 2019/0017072 | A1 | 1/2019 | Ditommaso |
| 2019/0030536 | A1 | 1/2019 | Sharei |
| 2019/0093073 | A1 | 3/2019 | Sharei |
| 2019/0111082 | A1 | 4/2019 | Gilbert |
| 2019/0382796 | A1 | 12/2019 | Gilbert |
| 2020/0277566 | A1 | 9/2020 | Sharei |
| 2020/0316604 | A1 | 10/2020 | Dadgar |
| 2020/0318066 | A1 | 10/2020 | Sharei |
| 2021/0038709 | A1 | 2/2021 | Loughhead |

FOREIGN PATENT DOCUMENTS

| | | | |
|---|---|---|---|
| CN | 103987836 | A | 8/2014 |
| CN | 105452288 | A | 3/2016 |
| CN | 107109362 | A | 8/2017 |
| JP | H01196566 | A | 8/1989 |
| JP | H03257366 | A | 11/1991 |
| JP | 2010025852 | A | 2/2010 |
| JP | 2010530362 | A | 9/2010 |
| JP | 2012526853 | A | 11/2012 |
| JP | 2017533702 | A | 11/2017 |
| NO | 2007067032 | A1 | 6/2007 |
| RU | 2424792 | C2 | 7/2011 |
| RU | 2539989 | C1 | 1/2015 |
| WO | 2002067863 | A2 | 9/2002 |
| WO | 2003020039 | A1 | 3/2003 |
| WO | 2005060993 | A1 | 7/2005 |
| WO | 2006105251 | A2 | 10/2006 |
| WO | 2007001677 | A2 | 1/2007 |
| WO | 2007001677 | A3 | 7/2007 |
| WO | 2008021465 | A2 | 2/2008 |
| WO | 2009002159 | A2 | 12/2008 |
| WO | 2009002159 | A3 | 2/2009 |
| WO | 2009019317 | A1 | 2/2009 |
| WO | 2010016800 | A1 | 2/2010 |
| WO | 2010132867 | A1 | 11/2010 |
| WO | 2011051346 | A1 | 5/2011 |
| WO | 2011079217 | A1 | 6/2011 |
| WO | 2011119492 | A2 | 9/2011 |
| WO | 2012069568 | A2 | 5/2012 |
| WO | 2013059343 | A1 | 4/2013 |
| WO | 2013185032 | A1 | 12/2013 |
| WO | 2014165707 | A2 | 10/2014 |
| WO | 2015023982 | A1 | 2/2015 |
| WO | 2016070136 | A1 | 5/2016 |
| WO | 2016077761 | A1 | 5/2016 |
| WO | 2016115179 | A1 | 7/2016 |
| WO | 2017008063 | A1 | 1/2017 |
| WO | 2017041050 | A1 | 3/2017 |
| WO | 2017041051 | A1 | 3/2017 |
| WO | 2017117418 | A1 | 7/2017 |
| WO | 2017123663 | A1 | 7/2017 |
| WO | 2017192785 | A1 | 11/2017 |
| WO | 2017192786 | A1 | 11/2017 |
| WO | 2018106849 | A1 | 6/2018 |
| WO | 2019113125 | A1 | 6/2019 |
| WO | 2019126212 | A1 | 6/2019 |
| WO | 2019178005 | A2 | 9/2019 |
| WO | 2019178006 | A2 | 9/2019 |
| WO | 2019178005 | A3 | 10/2019 |
| WO | 2020072833 | A1 | 4/2020 |
| WO | 2020154696 | A1 | 7/2020 |
| WO | 2020176789 | A1 | 9/2020 |
| WO | 2020210162 | A1 | 10/2020 |

OTHER PUBLICATIONS

Bolhassani, A. et al. (Feb. 1, 2014, e-pub. Oct. 15, 2013). "Polymeric Nanoparticles, Potent Vectors for Vaccine Delivery Targeting Cancer and Infectious Diseases," Hum Vaccin & Immunother 10(2):321-332.

Chen, C. et al. (2009, e-pub. May 14, 2009). "Patch Clamping on Plane Glass-Fabrication of Hourglass Aperture and High Yield Ion Channel Recording," Lab Chip 9:2370-2380.

(56) References Cited

OTHER PUBLICATIONS

Chen, Xian-Zhen et al. (2010, e-pub. Jul. 4, 2009). "Toll Like Receptor Agonists Augment HPV 11 E7-Specific T Cell Responses By Modulating Monocyte-Derived Dendritic Cells", Arch Dermatol Res. 302(1):57-65.

Ding, X. et al. (Mar. 9, 2017). "High-throughput nuclear delivery and rapid expression of DNA via mechanical and electrical cellmembrane disruption," Nature Biomedical Engineering 1(3):39, 15 pages.

Hallow D.M. et al. (Mar. 1, 2008, e-pub. Sep. 18, 2007). "Shear-Induced Intracellular Loading of Cells With Molecules by Controlled Microfluidics", Biotechnology and Bioengineering 99(4):846-854.

Hillerdal, V. et al. (Jan. 18, 2014). "Systemic Treatment With CAR-engineered T Cells Against PSCA Delays Subcutaneous Tumor Growth And Prolongs Survival Of Mice," BMC Cancer 14(30):1-9.

Hosokawa, M. et al. (Aug. 1, 2010). "Size-Selective Microcavity Array for Rapid and Efficient Detection of Circulating Tumor Cells", Analytical Chemistry 82(15):6629-6635.

Howarth, M. et al. (May 2008). "Monovalent, Reduced-Size Quantum Dots For Imaging Receptors On Living Cells," Nature Methods 5(5):397-399, 7 pages.

Indrova, M. et al. (Jan. 1, 2004). "Immunogenicity of Dendritic Cell-Based HPV16 E6/E7 Peptide Vaccines: CTL Activation and Protective Effects", Folia Biologica 50:184-193.

International Preliminary Report on Patentability mailed Nov. 15, 2018, for Patent Application No. PCT/US2017/030933, filed May 3, 2017, 13 pages.

International Preliminary Report on Patentability mailed on Jun. 18, 2020, for International Patent Application No. PCT/US2018/063931, filed Dec. 4, 2018, 9 pages.

International Preliminary Report on Patentability, issued Sep. 15, 2020, for Patent Application No. PCT/US2019/021703, filed Mar. 11, 2019, 10 pages.

International Search Report and Written Opinion of the International Searching Authority mailed Apr. 16, 2020, for International Patent Application No. PCT/US2020/020194, 16 pages.

International Search Report and Written Opinion of the International Searching Authority mailed Feb. 25, 2013, for International Patent Application No. PCT/US12/060646, filed Oct. 17, 2012, 10 pages.

International Search Report and Written Opinion of the International Searching Authority mailed Mar. 19, 2019, for International Patent Application No. PCT/US2018/063931, filed Dec. 14, 2018, 14 pages.

International Search Report and Written Opinion of the International Searching Authority mailed Oct. 16, 2019 for International Patent Application No. PCT/US2019/021705, filed Mar. 11, 2019, 25 pages.

International Search Report and Written Opinion of the International Searching Authority mailed on Mar. 11, 2016, for International Patent Application No. PCT/US2015/058489, filed Oct. 30, 2015, 18 pages.

International Search Report and Written Opinion of the International Searching Authority mailed Sep. 18, 2019, for International Patent Application No. PCT/US2019/021703, filed Mar. 11, 2019, 19 pages.

International Search Report and Written Opinion of the Searching Authority mailed on Feb. 12, 2020, for International Patent Application No. PCT/US2019/054586, filed Oct. 3, 2019, 27 pages.

International Search Report mailed Jul. 21, 2017, for International Patent Application No. PCT/2017030933 filed May 3, 2017, 4 pages.

Invitation to Pay Additional Fees mailed Dec. 19, 2019, for International Patent Application No. PCT/US2019/054586, filed Oct. 3, 2019, 8 pages.

Invitation to Pay Additional Fees mailed Jul. 24, 2019, for International Patent Application No. PCT/US2019/021703, filed Mar. 11, 2019, 14 pages.

Kada, G. et al. (Mar. 14, 1999). "Rapid Estimation of Avidin and Streptavidin by Fluorescence Quenching or Fluorescence Polarization," Biochim. Biophys. Acta. 1427(1):44-48.

Kaka, A. S. et al. (Sep. 1, 2009). Genetic Modification of T Cells With IL-21 Enhances Antigen Presentation and Generation of Central Memory Tumor-specific Cytotoxic T-lymphocytes, Journal of Immunology 32(7):726-736.

Kenter, G. G. et al. (Nov. 5, 2009). "Vaccination against HPV-16 Oncoproteins for Vulvar Intraepithelial Neoplasia", The New England Journal Of Medicine 361(19):1838-1847, 14 pages. (Including Supplemental Material).

Kim, D. et al. (2009, e-pub Apr. 13, 2009). "Microengineered Platforms for Cell Mechanobiology," Annual Review of Biomedical Engineering 11:203-233.

Lee, L. et al. (Nov. 16, 2012, e-pub. Dec. 2012). "Non-Endocytic Delivery of Functional Engineered Nanoparticles into the Cytoplasm of Live Cells Using a Novel, High-Throughput Microfluidic Device," Nano Letters 12 (12):6322-6327, 34 pages. (Including Supplemental Material).

Li, J. et al. (Jun. 30, 2016, May 19, 2016). "The Combination Of Pleurotus Ferulaewater Extract And CpG-ODN Enhances The Immune Responses And Antitumor Efficacy Of HPV Peptides Pulsed Dendritic Cell-Based Vaccine", Vaccine 34(31):3568-3575.

Li, J. et al. (Oct. 31, 2017). "Microfluidic-Enabled Intracellular Delivery of Membrane Impermeable Inhibitors to Study Target Engagement in Human Primary Cells," ACS Chemical Biology 12(12):2970-2974.

Liang, X. et al. (Aug. 20, 2015, e-pub. May 21, 2015). "Rapid and Highly Efficient Mammalian Cell Engineering via Cas9 Protein Transfection", J. Biotech 208:44-53.

Lin, B.K. et al. (Jun. 26, 2013). "Highly selective biomechanical separation of cancer cells from leukocytes using 1-19 microfluidic ratchets and hydrodynamic concentrator," Biomicrofluidics 7(3):1-11.

Liu, W. et al. (Jan. 20, 2010). "Compact Biocompatible Quantum Dots Via RAFT-Mediated Synthesis of Imidazole-Based Random Copolymer Ligand," JACS 132(2):472-483, 27 pages.

Liu, Y/ et al. (Sep. 19, 2012, e-pub. Jul. 13, 2012). "Spatially Selective Reagent Delivery Into Cancer Cells Using A Two-Layer Microfluidic Culture System," Anal Chim Acta 743(1):125-130, 20 pages. (including Supplemental Material).

Liu, Z.et al. (Jul. 28, 2014). "Molecular Imaging in Tracking Tumor Specific Cytotoxic T Lymphocytes (CTLs)," Theranostics 4(10):990-1001.

Loughhead, S.M. et al. (Dec. 1, 2018). "SQZing Cells To Rapidly Generate Antigen Presenting Cells (APC) For Solid Tumor Immune Therapies With Efficient, Scalable Manufacturing," Abstract, Annals Of Oncology 29(Suppl No. 10):1page, (Abstract No. 38P).

Maratou, E. et al. (Apr. 2007). "Glucose Transporter Expression On The Plasma Membrane Of Resting And Activated White Blood Cells," Eur J Clin Invest 37(4):282-290.

Matthews, B.D. et al. (2006). "Cellular Adaptation to Mechanical Stress: Role of Integrins, Rho, Cytoskeletal Tension And Mechanosensitive Ion Channels," Journal of Cell Science 119:508-518.

Moser, B. et al. (Jul. 2011, e-pub. May 15, 2011). "gamma delta T-APCs: A Novel Tool For Immunotherapy?," Cellular And Molecular Life Sciences 68(14):2443-2452.

Murphy, J.S. et al. (Sep. 1, 1956, e-pub May 2004). "Measurement of Wall Shearing Stress in the Boundary Layer by Means of an Evaporating Liquid Film," Journal of Applied Physics 27(9):1097-1103, 9 pages.

Papaioannou, N.E. et al. (2016). "Harnessing the Immune System to Improve Cancer Therapy," Annals of Translational Medicine 4(14):261, 15 pages.

Patel, K. et al. (Dec. 1, 2016). "Combination Immunotherapy with NY-ESO-1-Specific CAR+ T Cells with T-Cell Vaccine Improves Anti-Myeloma Effect," Blood Journal 128(22):3366, 1 page (Poster).

Plummer, E. et al. (Mar.-Apr. 2011, e-pub. Sep. 24, 2010). "Viral Nanoparticles and Virus-Like Particles: Platforms for Contemporary Vaccine Design," Wiley Interdiscip Rev Nanomed Nanobiotechnol. 3(2):174-196.

Rughetti, A. et al. (Sep. 2000). "Transfected Human Dendritic Cells to Induce Antitumor Immunity", Gene Therapy 7(17):1458-1466.

(56) References Cited

OTHER PUBLICATIONS

Rutella, S. et al. (Sep. 1, 2006). "Tolerogenic Dendritic Cells: Cytokine Modulation Comes of Age", Blood 180(5):1435-1440.

Sercombe, L. et al. (2015, e-pub. Dec. 1, 2015). "Advances and Challenges of Liposome Assisted Drug Delivery," Front Pharmacol. 6:286, 13 pages.

Sharei, A. (Jun. 26, 2013). "Cell Squeezing: A Vector-Free Microfluidic Platform for Intracellular Delivery of Macromolecules," MIT Thesis (Public, located here: https://dspace.mit.edu/bitstream/handle/1721.1/81688/860804208-MIT.pdf?sequence=2) 165 pages.

Sharei, A. et al. (2015, e-pub. Apr. 13, 2015). "Ex Vivo Cytosolic Delivery of Functional Macromolecules to Immune Cells", PLoS One 10(4):e011803, 12 pages.

Sharei, A. et al. (Feb. 5, 2013, e-pub. Jan. 22, 2013). "A Vector-Free Mircrofuidic platform for Intracellular Delivery", Proc Natl Acad Sci U.S.A. 110(6):2082-2087.

Sharei, A. et al. (Nov. 7, 2013). "Cell Squeezing as a Robust, Microfluidic Intracellular Delivery Platform," Journal of Visualized Experiments (81):e50980, 9 pages.

Sharei, A. et al. (Oct. 31, 2012). "(483d) Microfluidic Cell Deformation As a Robust, Vector-Free Method for Cytosolic Delivery of Macromolecules," 12AIChE Proceedings Annual Meeting (https://www.aiche.org/conferences/aiche-annual-meeting/2012/proceeding/paper/483d-microfluidic-cell-deformation-robust-vector-free-method-cytosolic-delivery-macromolecules) last visited on Feb. 4, 2021, 8 pages.

Shelby, J.P. et al. (Dec. 9, 2003). "A Microfluidic Model for Single-Cell Capillary Obstruction by Plasmodium Falciparum-Infected Erythrocytes," PNAS 100(25):14618-14622.

Song, A.Y. et al. (2006). "Scientific Basis for the Use of Hypotonic Solutions with Ultrasonic Liposuction," Aesth. Plast. Surg. 30:233-238, 3 pages.

Steinman, R.M. et al. (Apr. 1, 2003). "Tolerogenic Dendritic Cells", Annu. Rev. Immunol. 21:685-711.

Stewart, M.P. et al. (Oct. 12, 2016). "In Vitro and Ex Vitro Strategies for Intracellular Delivery", Nature 538 (7624):183-192, 23 pages.

Suresh, T. et al. (2017). "The Emerging Role of Immunotherapy in Head and Neck Squamous Cell Cancer," in The American Journal of Hematology/Oncology 13(6):20-27, 8 pages.

Szeto, G.L. et al. (May 22, 2015). "Microfluidic Squeezing for Intracellular Antigen Loading in Polyclonal B-Cells as Cellular Vaccines," Scientific Reports 5:10276, 13 pages.

Talarico, L. et al. (Nov. 2017). "Engineered Antigen Presenting T Cells for the Treatment of Solid Tumor Cancers," EMBASE, 32nd Annual Meeting and Pre-Conference Programs of the Society for Immunotherapy of Cancer, SITC 2017, Journal for Immuno Therapy of Cancer 5(Suppl. 2):EMB-619371158, 1 page. (Abstract).

Tsaoir, C. et al. (Jun. 2016). "Scalable Antibody Production from CHO Cell Line of Choice Using Flow Electroporation," Poster, Cell Line Development Jun. 2016, © 2016 MaxCyte, Inc., located at: https://www.maxcyte.com/wp-content/uploads/2017/10/scalable-ab-production-from-cho-cells.pdf, last retrieved on Apr. 2, 2019, 1 page. (Poster).

U.S. Appl. No. 16/098,405, filed May 3, 2017, by Loughhead et al. (A copy not submitted herewith bursuant to the waiver of 37 C.F.R. § 1.98(a)(2)(iii) issued by the Office on Sep. 21, 2004.).

U.S. Appl. No. 16/769,993, filed Dec. 4, 2018, by Sharei et al. (Copy not submitted herewith pursuant to the waiver of 37 C.F.R. § 1.98(a)(2)(iii) issued by the Office on Sep. 21, 2004.).

U.S. Appl. No. 16/954,113, filed Dec. 18, 2018, by Loughhead et al. (Copy not submitted herewith pursuant to the waiver of 37 C.F.R. § 1.98(a)(2)(iii) issued by the Office on Sep. 21, 2004.).

U.S. Appl. No. 16/980,339, filed Mar. 11, 2019, by Loughhead et al. (Copy not submitted herewith pursuant to the waiver of 37 C.F.R. § 1.98(a)(2)(iii) issued by the Office on Sep. 21, 2004.).

U.S. Appl. No. 17/000,007, filed Aug. 21, 2020, by Godfrin et al. (Copy not submitted herewith pursuant to the waiver of 37 C.F.R. § 1.98(a)(2)(iii) issued by the Office on Sep. 21, 2004.).

U.S. Appl. No. 17/075,116, filed Oct. 20, 2020, by Sharei et al. (Copy not submitted herewith pursuant to the waiver of 37 C.F.R. § 1.98(a)(2)(iii) issued by the Office on Sep. 21, 2004.).

U.S. Appl. No. 17/169,357, filed Feb. 5, 2021, by Godfrini et al. (Copy not submitted herewith pursuant to the waiver of 37 C.F.R. § 1.98(a)(2)(iii) issued by the Office on Sep. 21, 2004.).

U.S. Appl. No. 62/812,225, filed Feb. 28, 2019, by Sharei et al. (Copy not submitted herewith pursuant to the waiver of 37 C.F.R. § 1.98(a)(2)(iii) issued by the Office on Sep. 21, 2004.).

Verma, R. R. et al. (Nov. 2013, e-pub. Sep. 6, 2013). "E6 protein of human papillomavirus 16 (HPV16) expressed in *Escherichia coli* sans a stretch of hydrophobic amino acids, enables purification of GST-[Delta]E6 in the soluble form and retains the binding ability to p53," Protein Expression And Purification 92(1):41-47.

Wang, H.L. et al. (Jan. 2014, e-pub. Aug. 3, 2013). "In Vitro And In Vivo Evaluations Of Human Papillomavirus Type 16 (HPV16)-Derived Peptide-Loaded Dendritic Cells (DCs) With A CpG oligodeoxynucleotide (CpG-ODN) Adjuvant As Tumor Vaccines For Immunotherapy Of Cervical Cancer," Gynecologic Oncology 289(1):155-162.

Williams, A.R. et al. (Nov. 5, 1999). "Filtroporation: A Simple, Reliable Technique For Transfection and Macromolecular Loading of Cells in Suspension," Biotechnology and Bioengineering 65(3):341-346.

Written Opinion of the International Searching Authority mailed Jul. 21, 2017, for Patent Application No. PCT/US2017/030933, filed May 3, 2017, 11 pages.

Zarnitsyn, V.G. et al. (2008, e-pub. Nov. 10, 2007). "Electrosonic Ejector Microarray For Drug And Gene Delivery," Biomed Microdevices 10:299-308.

Ditommaso Tia et al "Cell engineering with microfluidic squeezing preserves functionality of primary immune cells in vivo", Proceedings of the National Academy of Sciences, vol. 115, No. 46, Oct. 31, 2018 (Oct. 31, 2018), XP055978186, ISSN: 0027-8424, DOI: 10.1073/pnas.1809671115.

\* cited by examiner

FIG. 1A

| | -4 | -2 | 0 | +4 | +7 |
|---|---|---|---|---|---|
| | START GROWING TC-1 CELLS | SPLIT TC-1 CELLS | TUMOR INJECTION | PRIME GROUPS B-E | BOOST GROUPS B-E |

| Groups | Tumor Dose | Treatment | | | | | | |
|---|---|---|---|---|---|---|---|---|
| | | Vaccination Regime | SQZ'd T Cells | Dose/ mouse | Frequency | Co-Injection | Dose/ mouse | Mice |
| A | | N/A | Untreated | | N/A | | | |
| B | 50k TC-1 | Therapeutic | E7+CpG SQZ'd | 5M Prime; 5M Boost | Day +4, +7 | None | | 10 |
| C | | | | 2.5M Prime; 2.5M Boost | | | | |
| D | | | | 5M Prime; 1M Boost | | | | |
| E | | | | 2.5M Prime; 1M Boost | | | | |

FIG. 2A

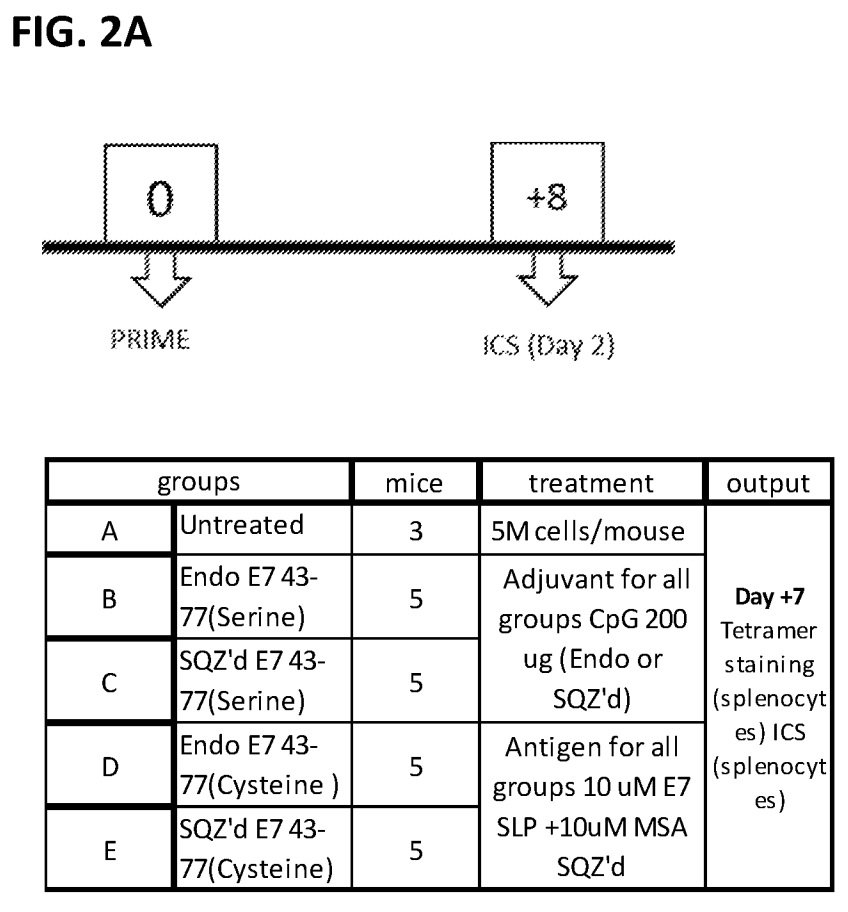

| groups | | mice | treatment | output |
|---|---|---|---|---|
| A | Untreated | 3 | 5M cells/mouse | |
| B | Endo E7 43-77(Serine) | 5 | Adjuvant for all groups CpG 200 ug (Endo or SQZ'd) | Day +7 Tetramer staining (splenocytes) ICS (splenocytes) |
| C | SQZ'd E7 43-77(Serine) | 5 | | |
| D | Endo E7 43-77(Cysteine ) | 5 | Antigen for all groups 10 uM E7 SLP +10uM MSA SQZ'd | |
| E | SQZ'd E7 43-77(Cysteine) | 5 | | |

| GROUPS | | #MICE | DOSE |
|---|---|---|---|
| A | Untreated | 3 | |
| B | LMW poly I:C+OVA SQZ'd | 5 | Prime 5M cells/mouse |
| C | LMW poly I:C+OVA Endo | 5 | |
| D | HMW poly I:C+OVA SQZ'd | 5 | |
| E | HMW poly I:C+OVA Endo | 5 | |
| F | CpG + OVA SQZ'd | 5 | |

0 → PRIME

+7 → Tet staining (Splenocytes)/ ICS (Day 1)

+8 → ICS (Day 2)

| | groups | mice | treatment |
|---|---|---|---|
| A | Untreated | 3 | |
| B | Endo OVA+CpG (200ug/mL) | 5 | |
| C | SQZ'd OVA+CpG (200ug/mL) | 5 | Prime 5M cells/mouse |
| D | Endo OVA+CpG (100ug/mL) | 5 | |
| E | SQZ'd OVA+CpG (100ug/mL) | 5 | |
| F | Endo OVA+CpG (50ug/mL) | 5 | |
| G | SQZ'd OVA+CpG (50ug/mL) | 5 | |

FIG. 9A

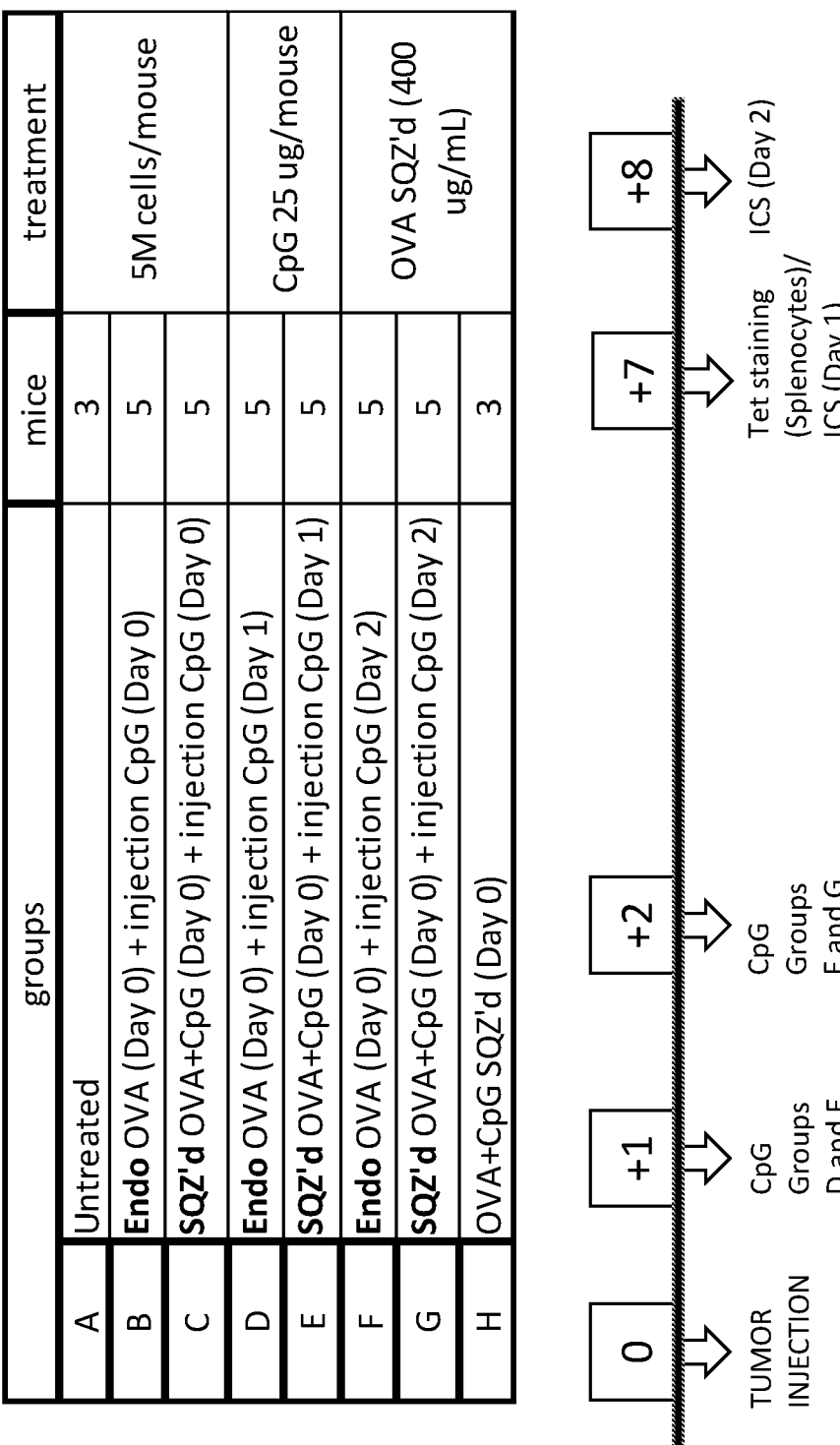

| | groups | mice | treatment |
|---|---|---|---|
| A | Untreated | 3 | 5M cells/mouse |
| B | Endo OVA (Day 0) + injection CpG (Day 0) | 5 | |
| C | SQZ'd OVA+CpG (Day 0) + injection CpG (Day 0) | 5 | CpG 25 ug/mouse |
| D | Endo OVA (Day 0) + injection CpG (Day 1) | 5 | |
| E | SQZ'd OVA+CpG (Day 0) + injection CpG (Day 1) | 5 | OVA SQZ'd (400 ug/mL) |
| F | Endo OVA (Day 0) + injection CpG (Day 2) | 5 | |
| G | SQZ'd OVA+CpG (Day 0) + injection CpG (Day 2) | 5 | |
| H | OVA+CpG SQZ'd (Day 0) | 3 | |

| 0 | +1 | +2 | +7 | +8 |
|---|---|---|---|---|
| TUMOR INJECTION | CpG Groups D and E | CpG Groups F and G | Tet staining (Splenocytes)/ ICS (Day 1) | ICS (Day 2) |

| Groups | | Treatment | | | | Mice |
|---|---|---|---|---|---|---|
| | SQZ'd T cells | Dose/mouse | Co-injection | Dose/mouse | |
| A | Untreated | 5M | N/A | N/A | 10 |
| B | E7 SQZ'd | | CpG | 25 ug | |
| C | | | IFNα | 10K IU | |
| D | E7+CpG SQZ'd | | None | | |
| E | | | CpG | 25 ug | |
| F | | | IFNα | 10K IU | |

DAY -14          DAY -7          DAY 0

PRIME          BOOST          TUMOR INJECTION

| Groups | Treatment | # cells X10⁶ (T) | TC-1 cells X10⁵ | # Mice | Treatment |
|---|---|---|---|---|---|
| A | Untreated | 0 | 0.5 | 10 | Day -7 and -14 |
| B | E7+CpG SQZ'd T cells | 5 | | 10 | |
| C | E7+CpG Endo T cells | 5 | | 5 | |
| D | E7 SQZ'd T cells | 5 | | 5 | |
| E | CpG SQZ'd T cells | 5 | | 5 | |
| F | E7+E6+CpG SQZ'd T cells | 5 | | 10 | |
| G | E6+CpG SQZ'd T | 5 | | 9 | |

-14 ⇨ PRIME

-8 ⇨ BOOST

-3 ⇨ TETRAMER

0 ⇨ TUMOR INJECTION

Groups:
- A) CpG Injection
- B) IFNα Injection
- C) SQZ (No Adjuvant)
- D) SQZ + CpG
- E) SQZ + IFNα

TUMOR IMPLANT — 0

PRIME — 10

TIL ANALYSIS — 17

Gated on CD45⁺ CD8⁺

CpG Only — E7+ 1.28

IFNα Only — E7+ 0.98

SQZ Only — E7+ 39.7

SQZ + CpG — E7+ 69.8

SQZ + IFNα — E7+ 80.8

E7 Tetramer

Timeline:

| 0 | +4 | +7 | +11 | +14 | +21 |
|---|----|----|-----|-----|-----|
| TUMOR INJECTION | PRIME GROUP B | BOOST-1 GROUP B / PRIME GROUP C / PRIME GROUP D | BOOST-2 GROUP B | BOOST-1 GROUP C / BOOST-1 GROUP D | BOOST-2 GROUP C |

| Groups | Tumor Dose | Treatment | | | | | | Mice |
|--------|-----------|-----------|---|---|---|---|---|------|
| | | Vaccination Regime | SQZ'd T Cells | Dose/ mouse | Frequency | Co- Injection | Dose/ mouse | |
| A | 50k TC-1 | N/A | Untreated | | | N/A | | None |
| B | | Therapeutic | E7+CpG SQZ'd | 5M | Day +4, +7, +11 | | | 10 |
| C | | | | | Day +7, +14, +21 | | | |
| D | | | | | Day +7, +14 | | | |

FIG. 15

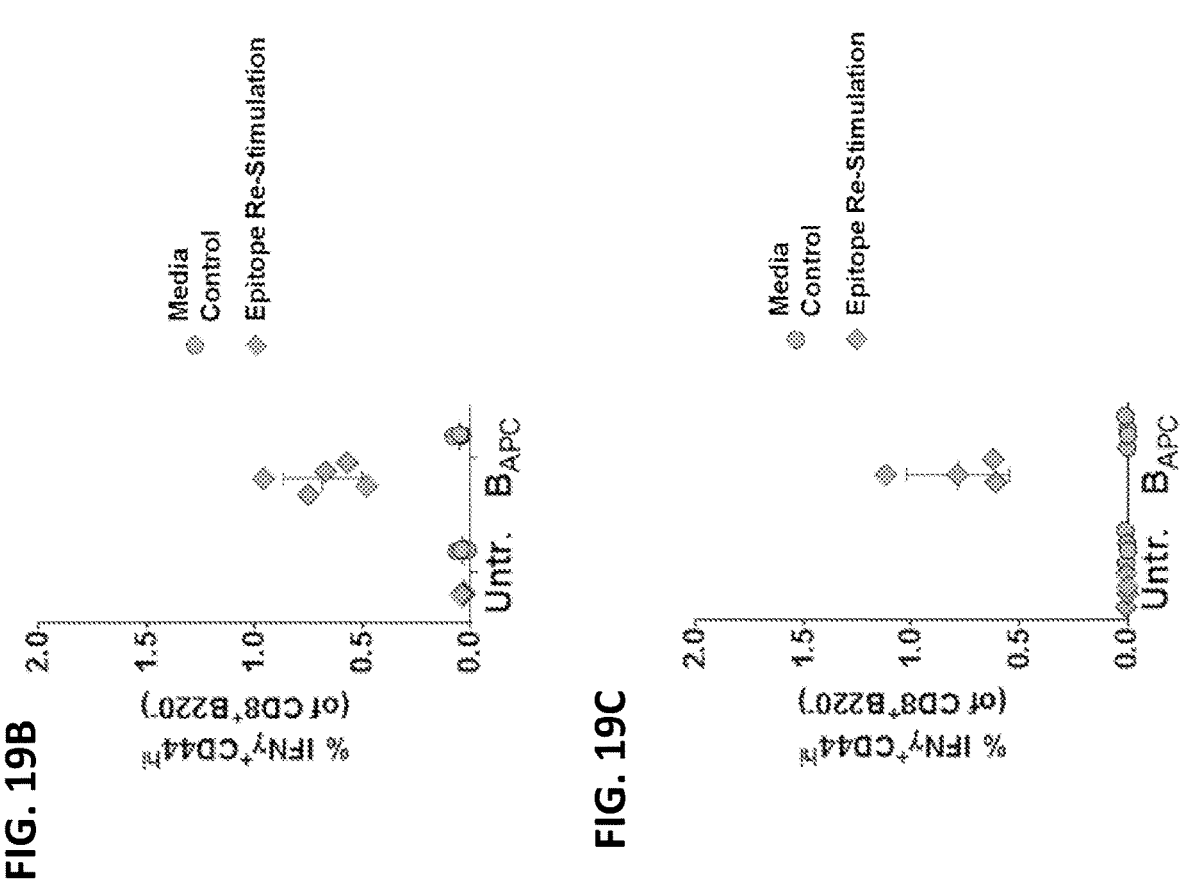
FIG. 19B
FIG. 19C
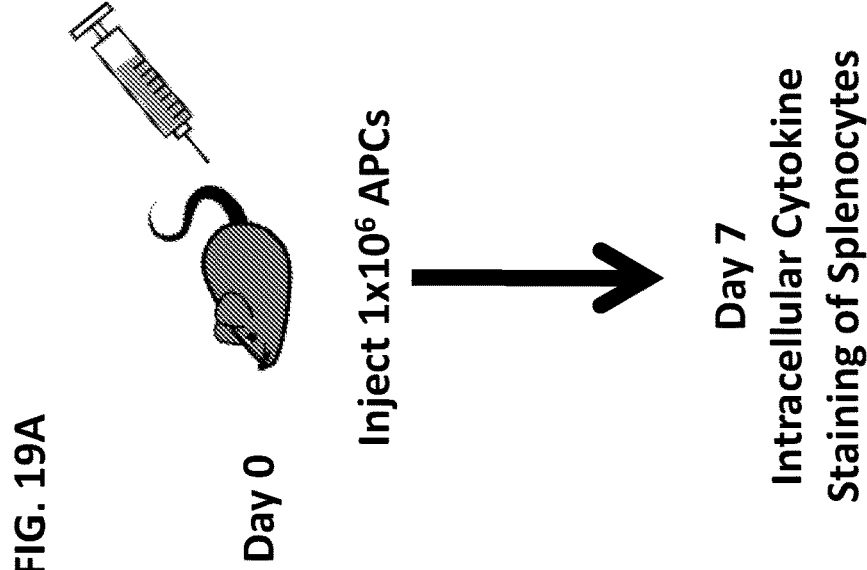
FIG. 19A

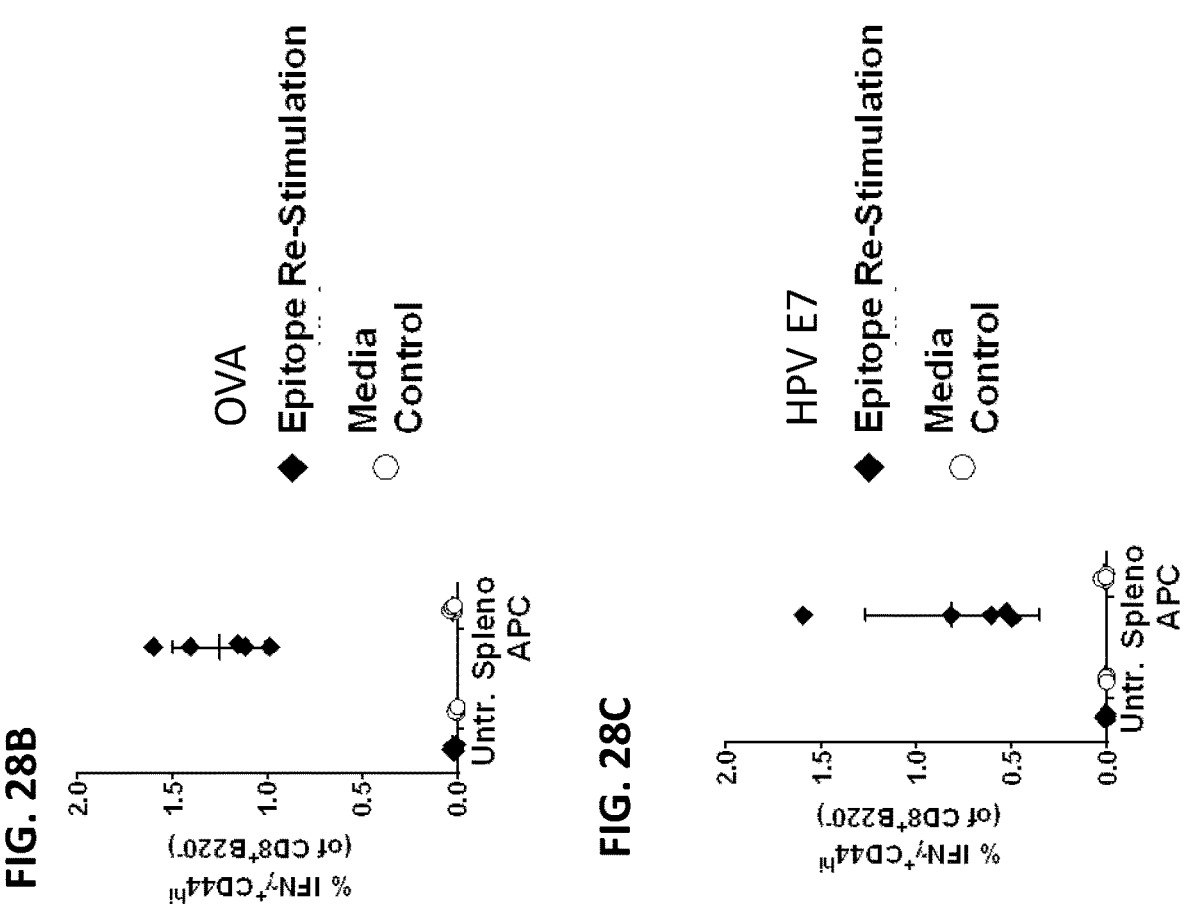
FIG. 28B
FIG. 28C
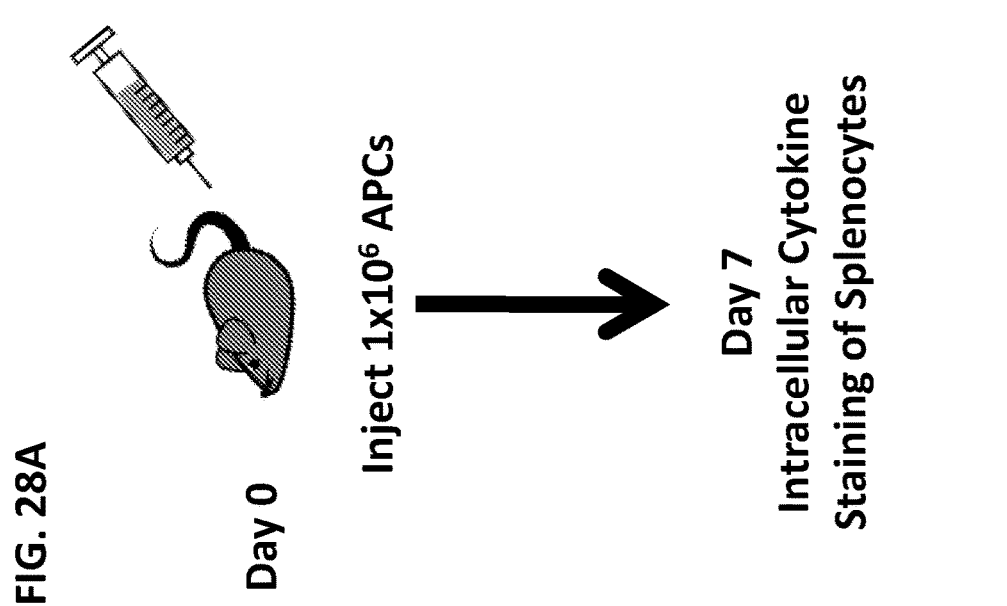
FIG. 28A

SEQUENCE LISTING

<160> NUMBER OF SEQ ID NOS: 51

<210> SEQ ID NO 1
<211> LENGTH: 10
<212> TYPE: PRT
<213> ORGANISM: Unknown
<220> FEATURE:
<223> OTHER INFORMATION: Human papilloma virus

<400> SEQUENCE: 1

Thr Ile His Asp Ile Ile Leu Glu Cys Val
1               5                   10

<210> SEQ ID NO 2
<211> LENGTH: 10
<212> TYPE: PRT
<213> ORGANISM: Unknown
<220> FEATURE:
<223> OTHER INFORMATION: Human papilloma virus

<400> SEQUENCE: 2

Glu Val Tyr Asp Phe Ala Phe Arg Asp Leu
1               5                   10

<210> SEQ ID NO 3
<211> LENGTH: 10
<212> TYPE: PRT
<213> ORGANISM: Unknown
<220> FEATURE:
<223> OTHER INFORMATION: Human papilloma virus

<400> SEQUENCE: 3

Tyr Met Leu Asp Leu Gln Pro Glu Thr Thr
1               5                   10

<210> SEQ ID NO 4
<211> LENGTH: 9
<212> TYPE: PRT
<213> ORGANISM: Unknown
<220> FEATURE:
<223> OTHER INFORMATION: Human papilloma virus

<400> SEQUENCE: 4

Arg Ala His Tyr Asn Ile Val Thr Phe
1               5

<210> SEQ ID NO 5
<211> LENGTH: 10
<212> TYPE: PRT

```
<213> ORGANISM: Artificial Sequence
<220> FEATURE:
<223> OTHER INFORMATION: Synthetic Construct

<400> SEQUENCE: 5

Leu Pro Gln Leu Ser Thr Glu Leu Gln Thr
1               5                   10

<210> SEQ ID NO 6
<211> LENGTH: 8
<212> TYPE: PRT
<213> ORGANISM: Unknown
<220> FEATURE:
<223> OTHER INFORMATION: Human papilloma virus

<400> SEQUENCE: 6

Gln Leu Cys Thr Glu Leu Gln Thr
1               5

<210> SEQ ID NO 7
<211> LENGTH: 7
<212> TYPE: PRT
<213> ORGANISM: Unknown
<220> FEATURE:
<223> OTHER INFORMATION: Human papilloma virus

<400> SEQUENCE: 7

Lys Gln Gln Leu Leu Arg Arg
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Val Tyr Ser Lys Gln Gln Leu Leu Arg Arg
1               5                   10

<210> SEQ ID NO 9
<211> LENGTH: 10
<212> TYPE: PRT
<213> ORGANISM: Unknown
<220> FEATURE:
<223> OTHER INFORMATION: Human papilloma virus

<400> SEQUENCE: 9

Met His Gly Asp Thr Pro Thr Leu His Glu
1               5                   10

<210> SEQ ID NO 10
<211> LENGTH: 6
<212> TYPE: PRT
<213> ORGANISM: Unknown
<220> FEATURE:
<223> OTHER INFORMATION: Human papilloma virus

<400> SEQUENCE: 10

Gly Gln Ala Glu Pro Asp
1               5

<210> SEQ ID NO 11
<211> LENGTH: 16
<212> TYPE: PRT
<213> ORGANISM: Artificial Sequence
```

<220> FEATURE:
<223> OTHER INFORMATION: Synthetic Construct

<400> SEQUENCE: 11

Tyr Ser Lys Gln Gln Leu Leu Arg Arg Glu Val Tyr Asp Phe Ala Phe
1               5                   10                  15

<210> SEQ ID NO 12
<211> LENGTH: 7
<212> TYPE: PRT
<213> ORGANISM: Unknown
<220> FEATURE:
<223> OTHER INFORMATION: Human papilloma virus

<400> SEQUENCE: 12

Tyr Cys Lys Gln Gln Leu Leu
1               5

<210> SEQ ID NO 13
<211> LENGTH: 8
<212> TYPE: PRT
<213> ORGANISM: Unknown
<220> FEATURE:
<223> OTHER INFORMATION: Human papilloma virus

<400> SEQUENCE: 13

Cys Ile Val Tyr Arg Asp Gly Asn
1               5

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

Ser Ile Val Tyr Arg Asp Gly Asn Pro Tyr Ala Val Ser Asp Lys
1               5                   10                  15

<210> SEQ ID NO 15
<211> LENGTH: 15
<212> TYPE: PRT
<213> ORGANISM: Unknown
<220> FEATURE:
<223> OTHER INFORMATION: Human papilloma virus

<400> SEQUENCE: 15

Asp Leu Tyr Cys Tyr Glu Gln Leu Asn Asp Ser Ser Glu Glu Glu
1               5                   10                  15

<210> SEQ ID NO 16
<211> LENGTH: 20
<212> TYPE: PRT
<213> ORGANISM: Unknown
<220> FEATURE:
<223> OTHER INFORMATION: Human papilloma virus

<400> SEQUENCE: 16

Cys Cys Lys Cys Asp Ser Thr Leu Arg Leu Cys Val Gln Ser Thr His
1               5                   10                  15

Val Asp Ile Arg
            20

<210> SEQ ID NO 17
<211> LENGTH: 20

```
<212> TYPE: PRT
<213> ORGANISM: Artificial Sequence
<220> FEATURE:
<223> OTHER INFORMATION: Synthetic Construct

<400> SEQUENCE: 17

Ser Ser Lys Ser Asp Ser Thr Leu Arg Leu Ser Val Gln Ser Thr His
1               5                   10                  15

Val Asp Ile Arg
            20

<210> SEQ ID NO 18
<211> LENGTH: 36
<212> TYPE: PRT
<213> ORGANISM: Artificial Sequence
<220> FEATURE:
<223> OTHER INFORMATION: Synthetic Construct

<400> SEQUENCE: 18

Leu Pro Gln Leu Ser Thr Glu Leu Gln Thr Thr Ile His Asp Ile Ile
1               5                   10                  15

Leu Glu Cys Val Tyr Ser Lys Gln Gln Leu Leu Arg Arg Glu Val Tyr
            20                  25                  30

Asp Phe Ala Phe
            35

<210> SEQ ID NO 19
<211> LENGTH: 25
<212> TYPE: PRT
<213> ORGANISM: Artificial Sequence
<220> FEATURE:
<223> OTHER INFORMATION: Synthetic Construct

<400> SEQUENCE: 19

Gln Leu Cys Thr Glu Leu Gln Thr Thr Ile His Asp Ile Ile Leu Glu
1               5                   10                  15

Cys Val Tyr Cys Lys Gln Gln Leu Leu
            20                  25

<210> SEQ ID NO 20
<211> LENGTH: 25
<212> TYPE: PRT
<213> ORGANISM: Artificial Sequence
<220> FEATURE:
<223> OTHER INFORMATION: Synthetic Construct

<400> SEQUENCE: 20

Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25

<210> SEQ ID NO 21
<211> LENGTH: 35
<212> TYPE: PRT
<213> ORGANISM: Artificial Sequence
<220> FEATURE:
<223> OTHER INFORMATION: Synthetic Construct

<400> SEQUENCE: 21

Val Tyr Ser Lys Gln Gln Leu Leu Arg Arg Glu Val Tyr Asp Phe Ala
1               5                   10                  15

Phe Arg Asp Leu Ser Ile Val Tyr Arg Asp Gly Asn Pro Tyr Ala Val
            20                  25                  30
```

```
Ser Asp Lys
        35

<210> SEQ ID NO 22
<211> LENGTH: 35
<212> TYPE: PRT
<213> ORGANISM: Artificial Sequence
<220> FEATURE:
<223> OTHER INFORMATION: Synthetic Construct

<400> SEQUENCE: 22

Met His Gly Asp Thr Pro Thr Leu His Glu Tyr Met Leu Asp Leu Gln
1               5                  10                  15

Pro Glu Thr Thr Asp Leu Tyr Cys Tyr Glu Gln Leu Asn Asp Ser Ser
            20                  25                  30

Glu Glu Glu
        35

<210> SEQ ID NO 23
<211> LENGTH: 25
<212> TYPE: PRT
<213> ORGANISM: Artificial Sequence
<220> FEATURE:
<223> OTHER INFORMATION: Synthetic Construct

<400> SEQUENCE: 23

Gln Leu Cys Thr Glu Leu Gln Thr Tyr Met Leu Asp Leu Gln Pro Glu
1               5                  10                  15

Thr Thr Tyr Cys Lys Gln Gln Leu Leu
            20                  25

<210> SEQ ID NO 24
<211> LENGTH: 35
<212> TYPE: PRT
<213> ORGANISM: Artificial Sequence
<220> FEATURE:
<223> OTHER INFORMATION: Synthetic Construct

<400> SEQUENCE: 24

Gly Gln Ala Glu Pro Asp Arg Ala His Tyr Asn Ile Val Thr Phe Cys
1               5                  10                  15

Cys Lys Cys Asp Ser Thr Leu Arg Leu Cys Val Gln Ser Thr His Val
            20                  25                  30

Asp Ile Arg
        35

<210> SEQ ID NO 25
<211> LENGTH: 35
<212> TYPE: PRT
<213> ORGANISM: Artificial Sequence
<220> FEATURE:
<223> OTHER INFORMATION: Synthetic Construct

<400> SEQUENCE: 25

Gly Gln Ala Glu Pro Asp Arg Ala His Tyr Asn Ile Val Thr Phe Ser
1               5                  10                  15

Ser Lys Ser Asp Ser Thr Leu Arg Leu Ser Val Gln Ser Thr His Val
            20                  25                  30

Asp Ile Arg
        35

<210> SEQ ID NO 26
```

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
ggggtcaacg ttgaggggggg                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct

<400> SEQUENCE: 27
gggggacgat cgtcggggggg                                              20

<210> SEQ ID NO 28
<211> LENGTH: 21
<212> TYPE: DNA
<213> ORGANISM: Artificial Sequence
<220> FEATURE:
<223> OTHER INFORMATION: Synthetic Construct

<400> SEQUENCE: 28
ggggacgacg tcgtgggggg g                                             21

<210> SEQ ID NO 29
<211> LENGTH: 20
<212> TYPE: DNA
<213> ORGANISM: Artificial Sequence
<220> FEATURE:
<223> OTHER INFORMATION: Synthetic Construct

<400> SEQUENCE: 29
tccatgacgt tcctgatgct                                               20

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
tccatgacgt tcctgacgtt                                               20

<210> SEQ ID NO 31
<211> LENGTH: 24
<212> TYPE: DNA
<213> ORGANISM: Artificial Sequence
<220> FEATURE:
<223> OTHER INFORMATION: Synthetic Construct

<400> SEQUENCE: 31
tcgtcgtttt gtcgttttgt cgtt                                          24

<210> SEQ ID NO 32
<211> LENGTH: 22
<212> TYPE: DNA
<213> ORGANISM: Artificial Sequence
<220> FEATURE:
<223> OTHER INFORMATION: Synthetic Construct

<400> SEQUENCE: 32
```

-continued

```
tcgtcgttgt cgttttgtcg tt                                          22

<210> SEQ ID NO 33
<211> LENGTH: 23
<212> TYPE: DNA
<213> ORGANISM: Artificial Sequence
<220> FEATURE:
<223> OTHER INFORMATION: Synthetic Construct

<400> SEQUENCE: 33
tcgacgttcg tcgttcgtcg ttc                                         23

<210> SEQ ID NO 34
<211> LENGTH: 26
<212> TYPE: DNA
<213> ORGANISM: Artificial Sequence
<220> FEATURE:
<223> OTHER INFORMATION: Synthetic Construct

<400> SEQUENCE: 34
tcgcgacgtt cgcccgacgt tcggta                                      26

<210> SEQ ID NO 35
<211> LENGTH: 22
<212> TYPE: DNA
<213> ORGANISM: Artificial Sequence
<220> FEATURE:
<223> OTHER INFORMATION: Synthetic Construct

<400> SEQUENCE: 35
tcgtcgtttt cggcgcgcgc cg                                          22

<210> SEQ ID NO 36
<211> LENGTH: 25
<212> TYPE: DNA
<213> ORGANISM: Artificial Sequence
<220> FEATURE:
<223> OTHER INFORMATION: Synthetic Construct

<400> SEQUENCE: 36
tcgtcgtcgt tcgaacgacg ttgat                                       25

<210> SEQ ID NO 37
<211> LENGTH: 29
<212> TYPE: DNA
<213> ORGANISM: Artificial Sequence
<220> FEATURE:
<223> OTHER INFORMATION: Synthetic Construct

<400> SEQUENCE: 37
tcgcgaacgt tcgccgcgtt cgaacgcgg                                   29

<210> SEQ ID NO 38
<211> LENGTH: 35
<212> TYPE: PRT
<213> ORGANISM: Artificial Sequence
<220> FEATURE:
<223> OTHER INFORMATION: Synthetic Construct

<400> SEQUENCE: 38

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30
```

```
Glu Glu Glu
        35

<210> SEQ ID NO 39
<211> LENGTH: 35
<212> TYPE: PRT
<213> ORGANISM: Artificial Sequence
<220> FEATURE:
<223> OTHER INFORMATION: Synthetic Construct

<400> SEQUENCE: 39

Leu Tyr Cys Tyr Glu Gln Leu Asn Asp Ser Ser Glu Glu Glu Asp Glu
1               5                   10                  15

Ile Asp Gly Pro Ala Gly Gln Ala Glu Pro Asp Arg Ala His Tyr Asn
            20                  25                  30

Ile Val Thr
        35

<210> SEQ ID NO 40
<211> LENGTH: 35
<212> TYPE: PRT
<213> ORGANISM: Artificial Sequence
<220> FEATURE:
<223> OTHER INFORMATION: Synthetic Construct

<400> SEQUENCE: 40

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 41
<211> LENGTH: 35
<212> TYPE: PRT
<213> ORGANISM: Artificial Sequence
<220> FEATURE:
<223> OTHER INFORMATION: Synthetic Construct

<400> SEQUENCE: 41

Thr Leu Arg Leu Cys Val Gln Ser Thr His Val Asp Ile Arg Thr Leu
1               5                   10                  15

Glu Asp Leu Leu Met Gly Thr Leu Gly Ile Val Cys Pro Ile Cys Ser
            20                  25                  30

Gln Lys Pro
        35

<210> SEQ ID NO 42
<211> LENGTH: 32
<212> TYPE: PRT
<213> ORGANISM: Artificial Sequence
<220> FEATURE:
<223> OTHER INFORMATION: Synthetic Construct

<400> SEQUENCE: 42

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

<210> SEQ ID NO 43
<211> LENGTH: 32
```

```
<212> TYPE: PRT
<213> ORGANISM: Artificial Sequence
<220> FEATURE:
<223> OTHER INFORMATION: Synthetic Construct

<400> SEQUENCE: 43

Leu Pro Gln Leu Cys Thr Glu Leu Gln Thr Thr Ile His Asp Ile Ile
1               5                   10                  15

Leu Glu Cys Val Tyr Cys Lys Gln Gln Leu Leu Arg Arg Glu Val Tyr
            20                  25                  30

<210> SEQ ID NO 44
<211> LENGTH: 25
<212> TYPE: PRT
<213> ORGANISM: Artificial Sequence
<220> FEATURE:
<223> OTHER INFORMATION: Synthetic Construct

<400> SEQUENCE: 44

Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25

<210> SEQ ID NO 45
<211> LENGTH: 26
<212> TYPE: PRT
<213> ORGANISM: Artificial Sequence
<220> FEATURE:
<223> OTHER INFORMATION: Synthetic Construct

<400> SEQUENCE: 45

Arg Asp Leu Cys Ile Val Tyr Arg Asp Gly Asn Pro Tyr Ala Val Cys
1               5                   10                  15

Asp Lys Cys Leu Lys Phe Tyr Ser Lys Ile
            20                  25

<210> SEQ ID NO 46
<211> LENGTH: 25
<212> TYPE: PRT
<213> ORGANISM: Artificial Sequence
<220> FEATURE:
<223> OTHER INFORMATION: Synthetic Construct

<400> SEQUENCE: 46

Asp Lys Cys Leu Lys Phe Tyr Ser Lys Ile Ser Glu Tyr Arg His Tyr
1               5                   10                  15

Cys Tyr Ser Leu Tyr Gly Thr Thr Leu
            20                  25

<210> SEQ ID NO 47
<211> LENGTH: 25
<212> TYPE: PRT
<213> ORGANISM: Artificial Sequence
<220> FEATURE:
<223> OTHER INFORMATION: Synthetic Construct

<400> SEQUENCE: 47

His Tyr Cys Tyr Ser Leu Tyr Gly Thr Thr Leu Glu Gln Gln Tyr Asn
1               5                   10                  15

Lys Pro Leu Cys Asp Leu Leu Ile Arg
            20                  25

<210> SEQ ID NO 48
```

```
<211> LENGTH: 32
<212> TYPE: PRT
<213> ORGANISM: Artificial Sequence
<220> FEATURE:
<223> OTHER INFORMATION: Synthetic Construct

<400> SEQUENCE: 48

Tyr Gly Thr Thr Leu Glu Gln Gln Tyr Asn Lys Pro Leu Cys Asp Leu
1               5                   10                  15

Leu Ile Arg Cys Ile Asn Cys Gln Lys Pro Leu Cys Pro Glu Glu Lys
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Synthetic Construct

<400> SEQUENCE: 49

Arg Cys Ile Asn Cys Gln Lys Pro Leu Cys Pro Glu Glu Lys Gln Arg
1               5                   10                  15

His Leu Asp Lys Lys Gln Arg Phe His Asn Ile Arg Gly Arg Trp Thr
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Synthetic Construct

<400> SEQUENCE: 50

Asp Lys Lys Gln Arg Phe His Asn Ile Arg Gly Arg Trp Thr Gly Arg
1               5                   10                  15

Cys Met Ser Cys Cys Arg Ser Ser Arg Thr Arg Arg Glu Thr Gln Leu
            20                  25                  30

<210> SEQ ID NO 51
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9, 10, 11, 12, 13, 14, 15, 16, 17
<223> OTHER INFORMATION: Xaa = Any Amino Acid

<400> SEQUENCE: 51

Gln Leu Cys Thr Glu Leu Gln Thr Xaa Xaa Xaa Xaa Xaa Xaa Xaa Xaa
1               5                   10                  15

Xaa Tyr Cys Lys Gln Gln Leu Leu
            20
```

METHODS FOR TREATING HPV-ASSOCIATED DISEASES

CROSS REFERENCE TO RELATED APPLICATIONS

This application is a national stage application under 35 U.S.C. § 371 of International Application No. PCT/US2019/021703, filed internationally on Mar. 11, 2019, which claims priority to U.S. Provisional Application No. 62/641,988, filed Mar. 12, 2018, U.S. Provisional Application No. 62/794,517, filed Jan. 18, 2019, U.S. Provisional Application No. 62/812,225, filed Feb. 28, 2019, which are hereby incorporated by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750322001600SEQLIST.TXT, date recorded: Sep. 10, 2020, size: 14 KB).

FIELD OF THE INVENTION

The present disclosure relates generally to immune cells comprising an antigen and an adjuvant, methods of manufacturing such modified immune cells, and methods of using such modified immune cells for treating an HPV-associated disease, preventing an HPV-associated disease and for modulating an immune response in an individual with an HPV-associated disease.

BACKGROUND OF THE INVENTION

Papillomaviruses are small nonenveloped DNA viruses with a virion size of ~55 nm in diameter. More than 100 HPV genotypes are completely characterized, and a higher number is presumed to exist. HPV is a known cause of cervical cancers, as well as some vulvar, vaginal, penile, oropharyngeal, anal, and rectal cancers. Although most HPV infections are asymptomatic and clear spontaneously, persistent infections with one of the oncogenic HPV types can progress to precancer or cancer. Other HPV-associated diseases can include common warts, plantar warts, flat warts, anogenital warts, anal lesions, epidermodysplasia, focal epithelial hyperplasia, mouth papillomas, verrucous cysts, laryngeal papillomatosis, squamous intraepithelial lesions (SILs), cervical intraepithelial neoplasia (CIN), vulvar intraepithelial neoplasia (VIN) and vaginal intraepithelial neoplasia (VAIN).

Many of the known human papillomavirus (HPV) types cause benign lesions with a subset being oncogenic. Based on epidemiologic and phylogenetic relationships, HPV types are classified into fifteen "high risk types" (HPV 16, 18, 31, 33, 35, 39, 45, 51, 52, 56, 58, 59, 68, 73, and 82) and three "probable high risk types" (HPV 26, 53, and 66), which together are known to manifest as low and high grade cervical changes and cancers, as well as other anogenital cancers such as vulval, vaginal, penile, anal, and perianal cancer, as well as head and neck cancers. Recently, the association of high risk types HPV 16 and 18 with breast cancer was also described. Eleven HPV types classified as "low risk types" (HPV 6, 11, 40, 42, 43, 44, 54, 61, 70, 72, and 81) are known to manifest as benign low-grade cervical changes, genital warts and recurrent respiratory papillomatosis. Cutaneous HPV types 5, 8, and 92 are associated with skin cancer. In some HPV-associated cancers, the immune system is depressed and correspondingly, the antitumor response is significantly impaired. See Suresh and Burtness *Am J Hematol Oncol* 13(6):20-27 (2017).

Immunotherapy can be divided into two main types of interventions, either passive or active. Passive protocols include administration of pre-activated and/or engineered cells (e.g., CAR T cells), disease-specific therapeutic antibodies, and/or cytokines. Active immunotherapy strategies are directed at stimulating immune system effector functions in vivo. Several current active protocols include vaccination strategies with disease-associated peptides, lysates, or allogeneic whole cells, infusion of autologous DCs as vehicles for tumor antigen delivery, and infusion of immune checkpoint modulators. See Papaioannou, Nikos E., et al. *Annals of translational medicine* 4.14 (2016). Adoptive immunotherapy can be employed to modulate the immune response, enhance antitumor activity, and achieve the goal of treating or preventing HPV-associated cancers.

$CD8^+$ cytotoxic T lymphocytes (CTL) and $CD4^+$ helper T (Th) cells stimulated by disease-associated antigens have the potential to target and destroy diseased cells. The methods described herein are used to generate modified immune cells de novo in high throughput and efficiently, thus inducing a robust T cell response to HPV antigens.

All references cited herein, including patent applications and publications, are incorporated by reference in their entirety. The patent publications WO2017041050, WO2016070136 are hereby expressly incorporated by reference in their entirety.

BRIEF SUMMARY OF THE INVENTION

In some aspects, the invention provides a method for treating a human papilloma virus (HPV)-associated disease in an individual, the method comprising administering to the individual an effective amount of a composition comprising modified immune cells, wherein the modified immune cells comprise an HPV antigen and an adjuvant, wherein the adjuvant is presented intracellularly. In some aspects, the invention provides a method for preventing an HPV-associated disease in an individual, the method comprising administering to the individual an effective amount of a composition comprising modified immune cells, wherein the modified immune cells comprise an HPV antigen and an adjuvant, wherein the adjuvant is presented intracellularly. In some aspects, the invention provides a method for modulating an immune response in an individual with an HPV-associated disease, the method comprising administering to the individual an effective amount of a composition comprising modified immune cells, wherein the modified immune cells comprise an HPV antigen and an adjuvant, wherein the adjuvant is presented intracellularly.

In some embodiments, the invention provides a method for treating an HPV-associated disease in an individual, the method comprising administering to the individual an effective amount of a composition comprising modified immune cells, wherein the modified immune cells comprise an HPV antigen and an adjuvant, wherein the adjuvant is presented intracellularly; wherein the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the antigen and the adjuvant to pass through to form a perturbed input cell; and b) incubating the perturbed input cell with the HPV antigen and the adjuvant for a sufficient time to allow the HPV antigen and the adjuvant to enter the perturbed input cell; thereby generating the modified immune cells. In some embodiments, the invention provides a method for preventing an HPV-associated disease in an individual, the method comprising administering to the individual an effective amount of a composition comprising modified immune cells, wherein the modified immune cells comprise an HPV antigen and an adjuvant, wherein the adjuvant is presented intracellularly; wherein the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the HPV antigen and the adjuvant to pass through to form a perturbed input cell; and b) incubating the perturbed input cell with the HPV antigen and the adjuvant for a sufficient time to allow the HPV antigen and the adjuvant to enter the perturbed input cell; thereby generating the modified immune cells. In some embodiments, the invention provides a method for modulating an immune response in an individual with an HPV-associated disease, the method comprising administering to the individual an effective amount of a composition comprising modified immune cells, wherein the modified immune cells comprise an HPV antigen and an adjuvant, wherein the adjuvant is presented intracellularly; wherein the modified immune cells are prepared by a) passing a cell suspension comprising an input cell comprising an HPV antigen through a cell-deforming constriction, wherein a diameter of the constriction is a function of a diameter of the input cell in the suspension, thereby causing perturbations of the input cell large enough for the HPV antigen and the adjuvant to pass through to form a perturbed input cell; and b) incubating the perturbed input cell with the antigen and the adjuvant for a sufficient time to allow the HPV antigen and the adjuvant to enter the perturbed input cell; thereby generating the modified immune cells. In some embodiments, the diameter of the constriction is less than the diameter of the cell. In some embodiments the diameter of the constriction is about 20% to 99% of the diameter of the cell. In some embodiments, the diameter of the constriction is about 20% to less than about 60% of the diameter of the cell. In some embodiments, the constriction is in a channel. In some embodiments, a deforming force is applied to the input cell as it passes through the constriction.

In some embodiments, the HPV antigen and/or the adjuvant are present in the cytosol and/or endosomes. In some embodiments, the antigen and/or adjuvant are present in multiple compartments of the cell. In some embodiments, the modified immune cell further comprises an HPV antigen and/or an adjuvant on the outside of the cell. In some embodiments, the concentration of adjuvant incubated with the perturbed input cell is between about 0.1 μM and about 1 mM. In some embodiments, the concentration of HPV antigen incubated with the perturbed input cell is between about 0.1 μM and about 1 mM. In some embodiments, the ratio of HPV antigen to adjuvant incubated with the perturbed input cell is between about 10000:1 and about 1:10000.

In some embodiments, the immune response is enhanced. In some embodiments, the immune response to the HPV antigen is enhanced.

In some embodiments, the adjuvant is CpG ODN, IFN-α, STING agonists, RIG-I agonists or poly I:C. In some embodiments, the adjuvant is CpG ODN. In some embodiments, the CpG ODN is CpG ODN 1018, CpG ODN 1826 or CpG ODN 2006. In some embodiments, the modified immune cell comprises more than one adjuvant.

In some embodiments, the HPV antigen is a pool of multiple polypeptides that elicit a response against the same and or different HPV antigens. In some embodiments, an antigen in the pool of multiple antigens does not decrease the immune response directed toward other antigens in the pool of multiple antigens. In some embodiments, the HPV antigen is a polypeptide comprising an antigenic HPV epitope and one or more heterologous peptide sequences. In some embodiments, the HPV antigen complexes with itself, with other antigens, or with the adjuvant. In some embodiments, the HPV antigen is an HPV-16 or an HPV-18 antigen. In some embodiments, the HPV antigen is comprised of an HLA-A2-specific epitope. In some embodiments, the HPV antigen is an HPV E6 antigen or an HPV E7 antigen. In some embodiments, the modified immune cell comprises an HPV E6 antigen and an HPV E7 antigen. In some embodiments, the HPV antigen is a polypeptide comprising an antigenic epitope that is flanked on the N-terminus and/or the C-terminus by one or more heterologous peptide sequences. In some embodiments, the HLA-A2-restricted peptide comprises the amino acid sequence of any one of SEQ ID NOs: 1-4. In some embodiments, the N-terminal flanking polypeptide comprises the amino acid sequence of any one of SEQ ID NOs: 5-10 and/or the C-terminal flanking polypeptide comprises the amino acid sequence of any one of SEQ ID NOs: 11-17. In some embodiments, the HPV antigen comprises an amino acid sequence with at least 90% similarity to any one of SEQ ID NOs:18-26. In some embodiments, the HPV antigen comprises an amino acid sequence with at least 90% similarity to SEQ ID NO:23. In some embodiments, the HPV antigen is capable of being processed into an MHC class I-restricted peptide. In some embodiments, the HPV antigen is capable of being processed into an MHC class II-restricted peptide.

In some embodiments, the modified immune cell comprises the adjuvant at a concentration between about 0.1 μM and about 1 mM. In some embodiments, the modified immune cell comprises the HPV antigen at a concentration between about 0.1 μM and about 1 mM. In some embodiments, the ratio of the HPV antigen to the adjuvant is between about 10000:1 to about 1:10000.

In some embodiments, the modified immune cell further comprises an agent that enhances the viability and/or function of the modified immune cell as compared to a corresponding modified immune cell that does not comprise the agent. In some embodiments, the agent is a compound that enhances endocytosis, a stabilizing agent or a co-factor. In some embodiments, the agent is albumin. In some embodiments, the albumin is mouse, bovine, or human albumin. In some embodiments, the agent is a divalent metal cation, glucose, ATP, potassium, glycerol, trehalose, D-sucrose, PEG1500, L-arginine, L-glutamine, or EDTA. In some embodiments, the agent comprises mouse serum albumin (MSA). In some embodiments, the modified immune cells are further modified to increase expression of one or more of co-stimulatory molecules. In some embodiments, the co-stimulatory molecule is B7-H2, B7-1, B7-2, CD70, LIGHT, HVEM, CD40, 4-1BBL, OX40L, TL1A, GITRL, CD30L, TIM4, SLAM, CD48, CD58, CD155, or CD112. In some embodiments, the cell comprises a nucleic acid that results in increased expression of the one or more co-stimulatory molecules.

In some embodiments, the immune cell is a T cell, a dendritic cell, a monocyte, a macrophage, a myeloid cell, a granulocyte, a neutrophil, a mast cell, a natural killer cell, an innate lymphoid cell, a basophil, or a hematopoetic precursor cell. In some embodiments, the immune cell is not a B cell.

In some embodiments, the immune cell is a T cell. In some embodiments, the T cell comprises a further modification to modulate MHC class I expression. In some embodiments, the T cell comprises a further modification to modulate MHC class II expression. In some embodiments, the T cell comprises a further modification to reduce MHC class I and/or MHC class II expression. In some embodiments, the further modification comprises reducing MHC class I and/or MHC class II expression using siRNA, shRNA, CRISPR/Cas9, ZFN, TALEN, Cre recombinase or a mega nuclease. In some embodiments, the T cell comprises a further modification to increase MHC class I and/or MHC class II expression. In some embodiments, the further modification comprises increasing MHC class I and/or MHC class II expression using RNA or plasmid DNA. In some embodiments, an innate immune response mounted in an individual in response to administration, in an allogeneic context, of the further modified T cells is reduced compared to an innate immune response mounted in an individual in response to administration, in an allogeneic context, of corresponding modified T cells that do not comprise the further modification. In some embodiments, the circulating half-life of the further modified T cells in an individual to which they were administered is modulated compared to the circulating half-life of corresponding modified T cells that do not comprise the further modification in an individual to which they were administered. In some embodiments, the T cell includes one or more of helper T cells, cytotoxic T cells, memory T cells, CIK cells and natural killer T cells. In some embodiments, the T cell includes one or more of CD3+ T cells, CD4+ T cells, CD8+ T cells, CD45RA+ T cells, CD45RO+ T cells, and γδ-T cells. In some embodiments, the modified cell is allogeneic to the individual. In some embodiments, the modified cell is autologous to the individual. In some embodiments, the individual is pre-conditioned to have modulated inflammation and/or a modulated immune response.

In some embodiments, the methods further comprise administering to the individual an adjuvant. In some embodiments, the adjuvant is IFNα or CpG ODN. In some embodiments, the composition comprising the modified immune cells and the adjuvant are administered simultaneously. In some embodiments, the composition comprising the modified immune cells and the adjuvant are administered sequentially. In some embodiments, the composition comprising the modified immune cells is administered prior to administering the adjuvant. In some embodiments, the composition comprising the modified immune cells is administered following administration of the adjuvant.

In some embodiments, the composition comprising the modified immune cells is administered in combination with administration of an immune checkpoint inhibitor. In some embodiments, the composition comprising the modified immune cells and the immune checkpoint inhibitor are administered simultaneously. In some embodiments, the composition comprising the modified immune cells and the immune checkpoint inhibitor are administered sequentially. In some embodiments, the composition comprising the modified immune cells is administered prior to administering the immune checkpoint inhibitor. In some embodiments, the composition comprising the modified immune cells is administered following administration of the immune checkpoint inhibitor. In some embodiments, the immune checkpoint inhibitor is targeted to one or more of PD-1, PD-L1, CTLA-4, LAG3 or TIM-3. In some embodiments, the immune checkpoint inhibitor is targeted to one or more of PD-1, PD-L1, CTLA-4, LAG3, TIM-3, TIGIT, VISTA, TIM1, B7-H4 (VTCN1) or BTLA.

In some embodiments, administration of the composition comprising the modified immune cells to the individual results in activation and/or expansion of cytotoxic T lymphocytes (CTLs) specific for the HPV antigen. In some embodiments, administration of the composition comprising the modified immune cells to the individual results in activation and/or expansion of helper T ($T_h$) cells specific for the antigen.

In some embodiments, the effective amount of the composition comprises between about $1 \times 10^6$ and about $1 \times 10^{12}$ modified immune cells. In some embodiments, the method comprises multiple administrations of the composition comprising the modified immune cells. In some embodiments, the method comprises a first administration of the composition comprising the modified immune cells followed by a second administration of the composition comprising the modified immune cells. In some embodiments, the second administration is about one month following the first administration.

In some embodiments, the HPV-associated disease is an HPV-associated cancer. In some embodiments, the HPV-associated cancer is cervical cancer, anal cancer, oropharyngeal cancer, vaginal cancer, vulvar cancer, penile cancer, skin cancer or head and neck cancer. In some embodiments, the HPV-associated disease is an HPV-associated infectious disease.

In some aspects, the invention provides a method for treating a human papilloma virus (HPV)-related disease in an individual, the method comprising administering to the individual an effective amount of a composition comprising modified immune cells, wherein the modified immune cells comprise an HPV antigen comprising an amino acid with at least 90% similarity to any one of SEQ ID NOs:18-25. In some aspects, the invention provides a method for preventing an HPV-associated disease in an individual, the method comprising administering to the individual an effective amount of a composition comprising modified immune cells, wherein the modified immune cells comprise an HPV antigen comprising an amino acid sequence with at least 90% similarity to any one of SEQ ID NOs:18-25. In some aspects, the invention provides a method for modulating an immune response in an individual with an HPV-associated disease, the method comprising administering to the individual an effective amount of a composition comprising modified immune cells, wherein the modified immune cells comprise an HPV antigen comprising an amino acid sequence with at least 90% similarity to any one of SEQ ID NOs:18-25. In some embodiments, the modified immune cells comprise an HPV antigen comprising an amino acid sequence of any one of SEQ ID NOs:18-25. In some embodiments, the modified immune cells comprise an HPV antigen comprising the amino acid sequence of SEQ ID NO:23.

In some aspects, the invention provides a method for treating an HPV-associated disease in an individual, the method comprising administering to the individual an effective amount of a composition comprising modified immune cells, wherein the modified immune cells comprise an HPV antigen comprising an amino acid sequence with at least 90% similarity to any one of SEQ ID NOs:18-25; wherein the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the antigen to pass through to form a perturbed input cell; and b) incubating the perturbed input cell with the HPV antigen for a sufficient time to allow the HPV antigen to enter the perturbed input cell; thereby generating the modified immune cells. In some aspects, the invention provides a method for preventing an HPV-associated disease in an individual, the method comprising administering to the individual an effective amount of a composition comprising modified immune cells, wherein the modified immune cells comprise an HPV antigen, wherein the modified immune cells comprise an HPV antigen comprising an amino acid sequence with at least 90% similarity to any one of SEQ ID NOs:18-25; wherein the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the HPV antigen to pass through to form a perturbed input cell; and b) incubating the perturbed input cell with the HPV antigen for a sufficient time to allow the HPV antigen to enter the perturbed input cell; thereby generating the modified immune cells. In some aspects the invention provides a method for modulating an immune response in an individual with an HPV-associated disease, the method comprising administering to the individual an effective amount of a composition comprising modified immune cells, wherein the modified immune cells comprise an HPV antigen comprising an amino acid sequence with at least 90% similarity to any one of SEQ ID NOs:18-25; wherein the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the HPV antigen to pass through to form a perturbed input cell; and b) incubating the perturbed input cell with the HPV antigen for a sufficient time to allow the HPV antigen to enter the perturbed input cell; thereby generating the modified immune cells. In some embodiments, the modified immune cells comprise an HPV antigen comprising an amino acid sequence of any one of SEQ ID NOs:18-25. In some embodiments, the modified immune cells comprise an HPV antigen comprising the amino acid sequence of SEQ ID NO:23. In some embodiments, the diameter of the constriction is less than the diameter of the cell. In some embodiments, the diameter of the constriction is about 20% to 99% of the diameter of the cell. In some embodiments, the diameter of the constriction is about 20% to less than about 60% of the diameter of the cell. In some embodiments, the constriction is in a channel. In some embodiments, a deforming force is applied to the input cell as it passes through the constriction, In some embodiments, the method further comprises administering to the individual an adjuvant. In some embodiments, the adjuvant is IFNα or CpG ODN. In some embodiments, the composition comprising the modified immune cells and the adjuvant are administered simultaneously. In some embodiments, the composition comprising the modified immune cells and the adjuvant are administered sequentially. In some embodiments, the composition comprising the modified immune cells is administered prior to administering the adjuvant. In some embodiments, the composition comprising the modified immune cells is administered following administration of the adjuvant. In some embodiments, the modified immune cell further comprises an adjuvant. In some embodiments, the perturbed immune cell of step b is incubated with the HPV antigen and an adjuvant. In some embodiments, the HPV antigen and/or the adjuvant are present in the cytosol and/or endosomes. In some embodiments, the antigen and/or adjuvant are present in multiple compartments of the cell. In some embodiments, the modified immune cell further comprises an HPV antigen and/or an adjuvant on the outside of the cell.

In some embodiments, the concentration of adjuvant incubated with the perturbed input cell is between about 0.1 μM and about 1 mM. In some embodiments, the concentration of HPV antigen incubated with the perturbed input cell is between about 0.1 μM and about 1 mM. In some embodiments, the ratio of HPV antigen to adjuvant incubated with the perturbed input cell is between about 10000:1 to about 1:10000.

In some embodiments, the immune response is enhanced. In some embodiments, the immune response to the HPV antigen is enhanced.

In some embodiments, the adjuvant is CpG ODN, IFN-α, STING agonists, RIG-I agonists or poly I:C. In some embodiments, the adjuvant is CpG ODN. In some embodiments, the CpG ODN is CpG ODN 1018, CpG ODN 1826 or CpG ODN 2006. In some embodiments, the modified immune cell comprises more than one adjuvant.

In some embodiments, the HPV antigen is a pool of multiple polypeptides that elicit a response against the same and or different HPV antigens. In some embodiments, an antigen in the pool of multiple antigens does not decrease the immune response directed toward other antigens in the pool of multiple antigens. In some embodiments, the HPV antigen is a polypeptide comprising an antigenic HPV epitope and one or more heterologous peptide sequences. In some embodiments, the HPV antigen complexes with itself, with other antigens, or with the adjuvant. In some embodiments, the HPV antigen is an HPV-16 or an HPV-18 antigen. In some embodiments, the HPV antigen is comprised of an HLA-A2-specific epitope. In some embodiments, the HPV antigen is an HPV E6 antigen or an HPV E7 antigen. In some embodiments, the modified immune cell comprises an HPV E6 antigen and an HPV E7 antigen. In some embodiments, the HPV antigen is a polypeptide comprising an antigenic epitope that is flanked on the N-terminus and/or the C-terminus by one or more heterologous peptide sequences. In some embodiments, the HPV antigen is capable of being processed into an MHC class I-restricted peptide. In some embodiments, the HPV antigen is capable of being processed into an MHC class II-restricted peptide.

In some embodiments, the modified immune cell comprises the adjuvant at a concentration between about 0.1 μM and about 1 mM. In some embodiments, the modified immune cell comprises the HPV antigen at a concentration between about 0.1 μM and about 1 mM. In some embodiments, the ratio of the HPV antigen to the adjuvant is between about 10000:1 to about 1:10000.

In some embodiments, the modified immune cell further comprises an agent that enhances the viability and/or function of the modified immune cell as compared to a corresponding modified immune cell that does not comprise the agent. In some embodiments, the agent is a compound that enhances endocytosis, a stabilizing agent or a co-factor. In some embodiments, the agent is albumin. In some embodiments, the albumin is mouse, bovine, or human albumin. In some embodiments, the agent is a divalent metal cation, glucose, ATP, potassium, glycerol, trehalose, D-sucrose, PEG1500, L-arginine, L-glutamine, or EDTA. In some embodiments, the agent comprises mouse serum albumin (MSA). In some embodiments, the modified immune cells are further modified to increase expression of one or more of co-stimulatory molecules. In some embodiments, the co-stimulatory molecule is B7-H2, B7-1, B7-2, CD70, LIGHT, HVEM, CD40, 4-1BBL, OX40L, TL1A, GITRL, CD30L, TIM4, SLAM, CD48, CD58, CD155, or CD112. In some embodiments, the cell comprises a nucleic acid that results in increased expression of the one or more co-stimulatory molecules.

In some embodiments, the immune cell is a T cell, a dendritic cell, a monocyte, a macrophage, a myeloid cell, a granulocyte, a neutrophil, a mast cell, a natural killer cell, an innate lymphoid cell, a basophil, or a hematopoetic precursor cell. In some embodiments, the immune cell is not a B cell.

In some embodiments, the immune cell is a T cell. In some embodiments, the T cell comprises a further modification to modulate MHC class I expression. In some embodiments, the T cell comprises a further modification to modulate MHC class II expression. In some embodiments, the T cell comprises a further modification to reduce MHC class I and/or MHC class II expression. In some embodiments, the further modification comprises reducing MHC class I and/or MHC class II expression using siRNA, shRNA, CRISPR/Cas9, ZFN, TALEN, Cre recombinase or a mega nuclease. In some embodiments, the T cell comprises a further modification to increase MHC class I and/or MHC class II expression. In some embodiments, the further modification comprises increasing MHC class I and/or MHC class II expression using RNA or plasmid DNA. In some embodiments, an innate immune response mounted in an individual in response to administration, in an allogeneic context, of the further modified T cells is reduced compared to an innate immune response mounted in an individual in response to administration, in an allogeneic context, of corresponding modified T cells that do not comprise the further modification. In some embodiments, the circulating half-life of the further modified T cells in an individual to which they were administered is modulated compared to the circulating half-life of corresponding modified T cells that do not comprise the further modification in an individual to which they were administered. In some embodiments, the T cell includes one or more of helper T cells, cytotoxic T cells, memory T cells, CIK cells and natural killer T cells. In some embodiments, the T cell includes one or more of CD3+ T cells, CD4+ T cells, CD8+ T cells, CD45RA+ T cells, CD45RO+ T cells, and γδ-T cells. In some embodiments, the modified cell is allogeneic to the individual. In some embodiments, the modified cell is autologous to the individual. In some embodiments, the individual is pre-conditioned to have modulated inflammation and/or a modulated immune response.

In some embodiments, the methods further comprise administering to the individual an adjuvant. In some embodiments, the adjuvant is IFNα or CpG ODN. In some embodiments, the composition comprising the modified immune cells and the adjuvant are administered simultaneously. In some embodiments, the composition comprising the modified immune cells and the adjuvant are administered sequentially. In some embodiments, the composition comprising the modified immune cells is administered prior to administering the adjuvant. In some embodiments, the composition comprising the modified immune cells is administered following administration of the adjuvant.

In some embodiments, the composition comprising the modified immune cells is administered in combination with administration of an immune checkpoint inhibitor. In some embodiments, the composition comprising the modified immune cells and the immune checkpoint inhibitor are administered simultaneously. In some embodiments, the composition comprising the modified immune cells and the immune checkpoint inhibitor are administered sequentially. In some embodiments, the composition comprising the modified immune cells is administered prior to administering the immune checkpoint inhibitor. In some embodiments, the composition comprising the modified immune cells is administered following administration of the immune checkpoint inhibitor. In some embodiments, the immune checkpoint inhibitor is targeted to one or more of PD-1, PD-L1, CTLA-4, LAG3 or TIM-3. In some embodiments, the immune checkpoint inhibitor is targeted to one or more of PD-1, PD-L1, CTLA-4, LAG3, TIM-3, TIGIT, VISTA, TIM1, B7-H4 (VTCN1) or BTLA.

In some embodiments, administration of the composition comprising the modified immune cells to the individual results in activation and/or expansion of cytotoxic T lymphocytes (CTLs) specific for the HPV antigen. In some embodiments, administration of the composition comprising the modified immune cells to the individual results in activation and/or expansion of helper T ($T_h$) cells specific for the antigen.

In some embodiments, the effective amount of the composition comprises between about $1\times10^6$ and about $1\times10^{12}$ modified immune cells. In some embodiments, the method comprises multiple administrations of the composition comprising the modified immune cells. In some embodiments, the method comprises a first administration of the composition comprising the modified immune cells followed by a second administration of the composition comprising the modified immune cells. In some embodiments, the second administration is about one month following the first administration.

In some embodiments, the HPV-associated disease is an HPV-associated cancer. In some embodiments, the HPV-associated cancer is cervical cancer, anal cancer, oropharyngeal cancer, vaginal cancer, vulvar cancer, penile cancer, skin cancer or head and neck cancer. In some embodiments, the HPV-associated disease is an HPV-associated infectious disease.

In some aspects, the invention provides a composition comprising modified immune cells, wherein the modified immune cells comprise intracellularly a CpG ODN and an HPV antigen with at least 90% similarity to any one of SEQ ID NOs:18-25. In some embodiments, the HPV antigen comprises the amino acid sequence with at least 90% similarity to SEQ ID NO:23. In some embodiments, the modified immune cells comprise intracellularly a CpG ODN and an HPV antigen wherein the HPV antigen comprises the amino acid sequence of any one of SEQ ID NOs:18-25. In some embodiments, the HPV antigen comprises the amino acid sequence of SEQ ID NO:23.

In some embodiments, the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the HPV antigen and the CpG ODN to pass through to form a perturbed input cell; and b)

incubating the perturbed input cell with the HPV antigen and the CpG ODN for a sufficient time to allow the HPV antigen and the CpG ODN to enter the perturbed input cell; thereby generating the modified immune cells. In some embodiments, the diameter of the constriction is less than the diameter of the cell. In some embodiments, the diameter of the constriction is about 20% to about 99% of the diameter of the cell. In some embodiments, the diameter of the constriction is about 20% to less than about 60% of the diameter of the cell. In some embodiments, the constriction is in a channel. In some embodiments, a deforming force is applied to the input cell as it passes through the constriction.

In some embodiments, the composition further comprises an adjuvant. In some embodiments, the HPV antigen and/or the CpG ODN are present in the cytosol and/or endosomes. In some embodiments, the antigen and/or the CpG ODN are present in multiple compartments of the cell. In some embodiments, the modified immune cell further comprises an HPV antigen and/or a CpG ODN on the surface of the cell. In some embodiments, the concentration of CpG ODN incubated with the perturbed input cell is between about 0.1 μM and about 1 mM. In some embodiments, the concentration of HPV antigen incubated with the perturbed input cell is between about 0.1 μM and about 1 mM. In some embodiments, the ratio of HPV antigen to CpG ODN incubated with the perturbed input cell is between about 10000:1 to about 1:10000. In some embodiments, the CpG ODN is CpG ODN 1018, CpG ODN 1826 or CpG ODN 2006. In some embodiments, the modified immune cell comprises more than one adjuvant. In some embodiments, the adjuvant comprises CpG ODN, IFN-α, STING agonists, RIG-I agonists, or poly I:C.

In some embodiments, the HPV antigen is a pool of multiple polypeptides that elicit a response against the same and or different HPV antigens. In some embodiments, an antigen in the pool of multiple antigens does not decrease the immune response directed toward other antigens in the pool of multiple antigens. In some embodiments, the HPV antigen is a polypeptide comprising an antigenic HPV epitope and one or more heterologous peptide sequences. In some embodiments, the HPV antigen complexes with itself, with other antigens, with an adjuvant or with the CpG ODN. In some embodiments, the HPV antigen is comprised of an HLA-A2-specific epitope. In some embodiments, the HPV antigen is a polypeptide comprising an antigenic epitope that is flanked on the N-terminus and/or the C-terminus by one or more heterologous peptide sequences.

In some embodiments, the modified immune cell comprises the CpG ODN at a concentration between about 0.1 μM and about 1 mM. In some embodiments, the modified immune cell comprises the HPV antigen at a concentration between about 0.1 μM and about 1 mM. In some embodiments, the ratio of the HPV antigen to the CpG ODN is between about 10000:1 to about 1:10000.

In some aspects, the invention comprises a composition comprising modified immune cells, wherein the modified immune cells comprise an HPV antigen, wherein the HPV antigen comprises an amino acid sequence with at least 90% similarity to any one of SEQ ID NOs:18-25. In some embodiments, the HPV antigen comprises the amino acid sequence with at least 90% similarity to SEQ ID NO:23. In some embodiments, the HPV antigen comprises the amino acid sequence of any one of SEQ ID NOs:18-25. In some embodiments, the HPV antigen comprises the amino acid sequence of SEQ ID NO:23.

In some embodiments, the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the HPV antigen to pass through to form a perturbed input cell; and b) incubating the perturbed input cell with the HPV antigen for a sufficient time to allow the HPV antigen to enter the perturbed input cell; thereby generating the modified immune cells. In some embodiments, the diameter of the constriction is less than the diameter of the cell. In some embodiments, the diameter of the constriction is about 20% to about 99% of the diameter of the cell. In some embodiments, the diameter of the constriction is about 20% to less than about 60% of the diameter of the cell. In some embodiments, the constriction is in a channel. In some embodiments, a deforming force is applied to the input cell as it passes through the constriction.

In some embodiments, the composition further comprises an adjuvant. In some embodiments, the HPV antigen and/or the adjuvant are present in the cytosol and/or endosomes. In some embodiments, the antigen and/or adjuvant are present in multiple compartments of the cell. In some embodiments, the modified immune cell further comprises an HPV antigen and/or an adjuvant on the surface of the cell. In some embodiments, the concentration of adjuvant incubated with the perturbed input cell is between about 0.1 μM and about 1 mM. In some embodiments, the concentration of HPV antigen incubated with the perturbed input cell is between about 0.1 μM and about 1 mM. In some embodiments, the ratio of HPV antigen to adjuvant incubated with the perturbed input cell is between about 10000:1 to about 1:10000. In some embodiments, the adjuvant is CpG ODN, IFN-α, STING agonists, RIG-I agonists, or poly I:C. In some embodiments, the adjuvant is CpG ODN. In some embodiments, the CpG ODN is CpG ODN 1018, CpG ODN 1826 or CpG ODN 2006. In some embodiments, the modified immune cell comprises more than one adjuvant.

In some embodiments, the HPV antigen is a pool of multiple polypeptides that elicit a response against the same and or different HPV antigens. In some embodiments, an antigen in the pool of multiple antigens does not decrease the immune response directed toward other antigens in the pool of multiple antigens. In some embodiments, the HPV antigen is a polypeptide comprising an antigenic HPV epitope and one or more heterologous peptide sequences. In some embodiments, the HPV antigen complexes with itself, with other antigens, or with the adjuvant. In some embodiments, the HPV antigen is comprised of an HLA-A2-specific epitope. In some embodiments, the modified immune cell comprises the adjuvant at a concentration between about 0.1 μM and about 1 mM. In some embodiments, the modified immune cell comprises the HPV antigen at a concentration between about 0.1 μM and about 1 mM. In some embodiments, the ratio of the HPV antigen to the adjuvant is between about 10000:1 to about 1:10000. In some embodiments, the HPV antigen is capable of being processed into an MHC class I-restricted peptide. In some embodiments, the HPV antigen is capable of being processed into an MHC class II-restricted peptide.

In some embodiments, the modified immune cell further comprises an agent that enhances the viability and/or function of the modified immune cell as compared to a corresponding modified immune cell that does not comprise the agent. In some embodiments, the agent is a compound that enhances endocytosis, a stabilizing agent or a co-factor. In some embodiments, the agent is albumin. In some embodiments, the albumin is mouse, bovine, or human albumin. In some embodiments, the agent is a divalent metal cation, glucose, ATP, potassium, glycerol, trehalose, D-sucrose, PEG1500, L-arginine, L-glutamine, or EDTA. In some embodiments, the agent comprises MSA. In some embodiments, the cells are further modified to increase expression of one or more of co-stimulatory molecules. In some embodiments, the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the cell comprises a nucleic acid that results in increased expression of the one or more co-stimulatory molecules.

In some embodiments, the immune cell is a T cell, a dendritic cell, a monocyte, a macrophage, a myeloid cell, a granulocyte, a neutrophil, a mast cell, a natural killer cell, an innate lymphoid cell, a basophil, or a hematopoetic precursor cell. In some embodiments, the immune cell is not a B cell. In some embodiments, the immune cell is a T cell. In some embodiments, the T cell comprises a further modification to modulate MHC class I expression. In some embodiments, the T cell comprises a further modification to modulate MHC class II expression. In some embodiments, the T cell comprises a further modification to reduce MHC class I and/or MHC class II expression. In some embodiments, the further modification comprises reducing MHC class I and/or MHC class II expression using siRNA, shRNA, CRISPR/Cas9, ZFN, TALEN, Cre recombinase or a mega nuclease. In some embodiments, the T cell comprises a further modification to increase MHC class I and/or MHC class II expression. In some embodiments, the further modification comprises increasing MHC class I and/or MHC class II expression using RNA or plasmid DNA. In some embodiments, an innate immune response mounted in an individual in response to administration, in an allogeneic context, of the further modified T cells is reduced compared to an innate immune response mounted in an individual in response to administration, in an allogeneic context, of corresponding modified T cells that do not comprise the further modification. In some embodiments, the circulating half-life of the further modified T cells in an individual to which they were administered is modulated compared to the circulating half-life of corresponding modified T cells that do not comprise the further modification in an individual to which they were administered.

In some embodiments, the T cell includes one or more of helper T cells, cytotoxic T cells, memory T cells, CIK cells and natural killer T cells. In some embodiments, the T cell includes one or more of CD3+ T cells, CD4+ T cells, CD8+ T cells, CD45RA+ T cells, CD45RO+ T cells, and γδ-T cells. In some embodiments, the modified cell is allogeneic to an individual. In some embodiments, the modified cell is autologous to an individual. In some embodiments, an individual is pre-conditioned to have modulated inflammation and/or a modulated immune response.

In some embodiments, the composition further comprises an immune checkpoint inhibitor. In some embodiments, the immune checkpoint inhibitor is targeted to one or more of PD-1, PD-L1, CTLA-4, LAG3, TIM-3, LAG3, TIGIT, VISTA, TIM1, B7-H4 (VTCN1) or BTLA. In some embodiments, administration of the composition comprising the modified immune cells to an individual results in activation and/or expansion of cytotoxic T lymphocytes (CTLs) specific for the HPV antigen. In some embodiments, administration of the composition comprising the modified immune cells to an individual results in activation and/or expansion of helper T ($T_h$) cells specific for the antigen.

In some embodiments, the effective amount of the composition comprises between about $1 \times 10^6$ and about $1 \times 10^{12}$ modified immune cells. In some embodiments, the antigen comprises an amino acid sequence with at least 90% similarity to SEQ ID NO:23. In some embodiments, the antigen comprises the amino acid sequence of SEQ ID NO: 23.

In some embodiments, the immune cell is a T cell, a dendritic cell, a monocyte, a macrophage, a myeloid cell, a granulocyte, a neutrophil, a mast cell, a natural killer cell, an innate lymphoid cell, a basophil, or a hematopoetic precursor cell. In some embodiments, the immune cell is not a B cell. In some embodiments, the immune cell is a T cell. In some embodiments, the T cell comprises a further modification to modulate MHC class I expression. In some embodiments, the T cell comprises a further modification to modulate MHC class II expression. In some embodiments, the T cell comprises a further modification to reduce MHC class I and/or MHC class II expression. In some embodiments, the further modification comprises reducing MHC class I and/or MHC class II expression using siRNA, shRNA, CRISPR/Cas9, ZFN, TALEN, Cre recombinase or a mega nuclease. In some embodiments, the T cell comprises a further modification to increase MHC class I and/or MHC class II expression. In some embodiments, the further modification comprises increasing MHC class I and/or MHC class II expression using RNA or plasmid DNA. In some embodiments, an innate immune response mounted in an individual in response to administration, in an allogeneic context, of the further modified T cells is reduced compared to an innate immune response mounted in an individual in response to administration, in an allogeneic context, of corresponding modified T cells that do not comprise the further modification. In some embodiments, the circulating half-life of the further modified T cells in an individual to which they were administered is modulated compared to the circulating half-life of corresponding modified T cells that do not comprise the further modification in an individual to which they were administered.

In some embodiments, the T cell includes one or more of helper T cells, cytotoxic T cells, memory T cells, CIK cells and natural killer T cells. In some embodiments, the T cell includes one or more of CD3+ T cells, CD4+ T cells, CD8+ T cells, CD45RA+ T cells, CD45RO+ T cells, and γδ-T cells. In some embodiments, the modified cell is allogeneic to an individual. In some embodiments, the modified cell is autologous to an individual. In some embodiments, an individual is pre-conditioned to have modulated inflammation and/or a modulated immune response.

In some embodiments, the composition further comprises an immune checkpoint inhibitor. In some embodiments, the immune checkpoint inhibitor is targeted to one or more of PD-1, PD-L1, CTLA-4, LAG3, or TIM-3. In some embodiments, administration of the composition comprising the modified immune cells to an individual results in activation and/or expansion of cytotoxic T lymphocytes (CTLs) specific for the HPV antigen. In some embodiments, administration of the composition comprising the modified immune cells to an individual results in activation and/or expansion of helper T ($T_h$) cells specific for the antigen.

In some embodiments, the effective amount of the composition comprises between about $1 \times 10^6$ and about $1 \times 10^{12}$ modified immune cells. In some embodiments, the antigen comprises an amino acid sequence with at least 90% similarity to SEQ ID NO:23. In some embodiments, the antigen comprises the amino acid sequence of SEQ ID NO: 23.

In some aspects, the invention provides a method for treating or preventing an HPV-associated disease in an individual, the method comprising administering to the individual an effective amount of a composition comprising modified immune cells, wherein the modified immune cells comprise an HPV antigen and an adjuvant, wherein the adjuvant is presented intracellularly; wherein the modified immune cells are prepared by a) passing a cell suspension comprising an input cell comprising an HPV antigen through a cell-deforming constriction, wherein a diameter of the constriction is a function of a diameter of the input cell in the suspension, thereby causing perturbations of the input cell large enough for the antigen and the adjuvant to pass through to form a perturbed input cell; and b) incubating the perturbed input cell with the adjuvant for a sufficient time to allow the adjuvant to enter the perturbed input cell; thereby generating the modified immune cells. In some aspects, the invention provides a method for treating or preventing an HPV-associated disease in an individual, the method comprising administering to the individual an effective amount of a composition comprising modified immune cells, wherein the modified immune cells comprise an HPV antigen and an adjuvant, wherein the adjuvant is presented intracellularly; wherein the modified immune cells are prepared by a) passing a cell suspension comprising an input cell comprising the adjuvant through a cell-deforming constriction, wherein a diameter of the constriction is a function of a diameter of the input cell in the suspension, thereby causing perturbations of the input cell large enough for the HPV antigen to pass through to form a perturbed input cell; and b) incubating the perturbed input cell with the HPV antigen for a sufficient time to allow the HPV antigen to enter the perturbed input cell; thereby generating the modified immune cells.

In some embodiments, the diameter of the constriction is less than the diameter of the cell. In some embodiments, the diameter of the constriction is about 20% to about 99% of the diameter of the cell. In some embodiments, the diameter of the constriction is about 20% to less than about 60% of the diameter of the cell. In some embodiments, the constriction is in a channel. In some embodiments, a deforming force is applied to the input cell as it passes through the constriction.

In some embodiments, the HPV antigen and/or the adjuvant are present in the cytosol and/or endosomes. In some embodiments, the antigen and/or adjuvant are present in multiple compartments of the cell. In some embodiments, the concentration of adjuvant incubated with the perturbed input cell is between about 0.1 µM and about 1 mM. In some embodiments, the concentration of HPV antigen incubated with the perturbed input cell is between about 0.1 µM and about 1 mM.

In some embodiments, the adjuvant is CpG ODN, IFN-α, STING agonists, RIG-I agonists or poly I:C. In some embodiments, the adjuvant is CpG ODN. In some embodiments, the CpG ODN is CpG ODN 1018, CpG ODN 1826 or CpG ODN 2006.

In some embodiments, the HPV antigen is an HPV-16 or an HPV-18 antigen. In some embodiments, the HPV antigen is an HPV E6 antigen or an HPV E7 antigen. In some embodiments, the HPV antigen comprises an amino acid sequence with at least 90% similarity to any one of SEQ ID NOs:18-25. In some embodiments, the HPV antigen comprises an amino acid sequence of any one of SEQ ID NOs:18-25. In some embodiments, the HPV antigen comprises an amino acid sequence with at least 90% similarity to SEQ ID NO:23. In some embodiments, the HPV antigen comprises an amino acid sequence of SEQ ID NO:23.

In some aspects, the invention provides a method for treating or preventing an HPV-associated disease in an individual comprising administering to the individual a modified immune cell associated with an HPV antigen, wherein the modified immune cell is prepared by a process comprising the steps of: a) incubating an input cell with the HPV antigen and/or an adjuvant for a sufficient time to allow the HPV antigen to associate with the input cell; thereby generating the modified immune cell associated with the antigen. In some embodiments, the HPV antigen comprises an amino acid sequence with at least 90% similarity to any one of SEQ ID NOs:18-25. In some embodiments, the HPV antigen comprises the amino acid sequence of SEQ ID NO:23. In some embodiments, the adjuvant is CpG ODN. In some embodiments, the CpG ODN is CpG ODN 1018, CpG ODN 1826 or CpG ODN 2006.

BRIEF DESCRIPTION OF THE DRAWINGS

FIG. 1A shows a representative schematic of the treatment groups and schedule.

FIG. 2A shows a representative schematic for evaluating E7 antigens.

FIG. 9A is a schematic of an experiment evaluating the dosing schedule of CpG ODN on immune responses.

FIG. 14A is a schematic of an experiment to determine a vaccination schedule for both prime and boost of $T_{APC}$ s loaded with an E7 synthetic long peptide (SLP)+CpG.

FIG. 15 shows the results of an experiment to show that SQZ'd $T_{APC}$s can present antigen directly.

FIG. 19A shows a representative schematic of an experiment to evaluate the ability of B cell as APCs to induce an endogenous response. FIG. 19B shows the levels of IFN-γ positive CD8+ T cells induced by B9-23 challenge, generated in response to OVA-loaded $B_{APC}$ vaccination. FIG. 19C shows the levels of IFN-γ positive CD8+ T cells induced by E7 challenge, generated in response to E7-loaded $B_{APC}$ vaccination.

FIG. 28A shows a representative schematic of an experiment to evaluate the ability of splenocytes as APCs to induce an endogenous response. FIG. 28B shows the levels of IFN-α positive CD8+ T cells induced by B9-23 challenge, generated in response to OVA-loaded splenocyte$_{APC}$ vaccination. FIG. 28C shows the levels of IFN-γ positive CD8+ T cells induced by E7 challenge, generated in response to E7-loaded splenocyte$_{APC}$ vaccination.

DETAILED DESCRIPTION OF THE INVENTION

Figure 1B:
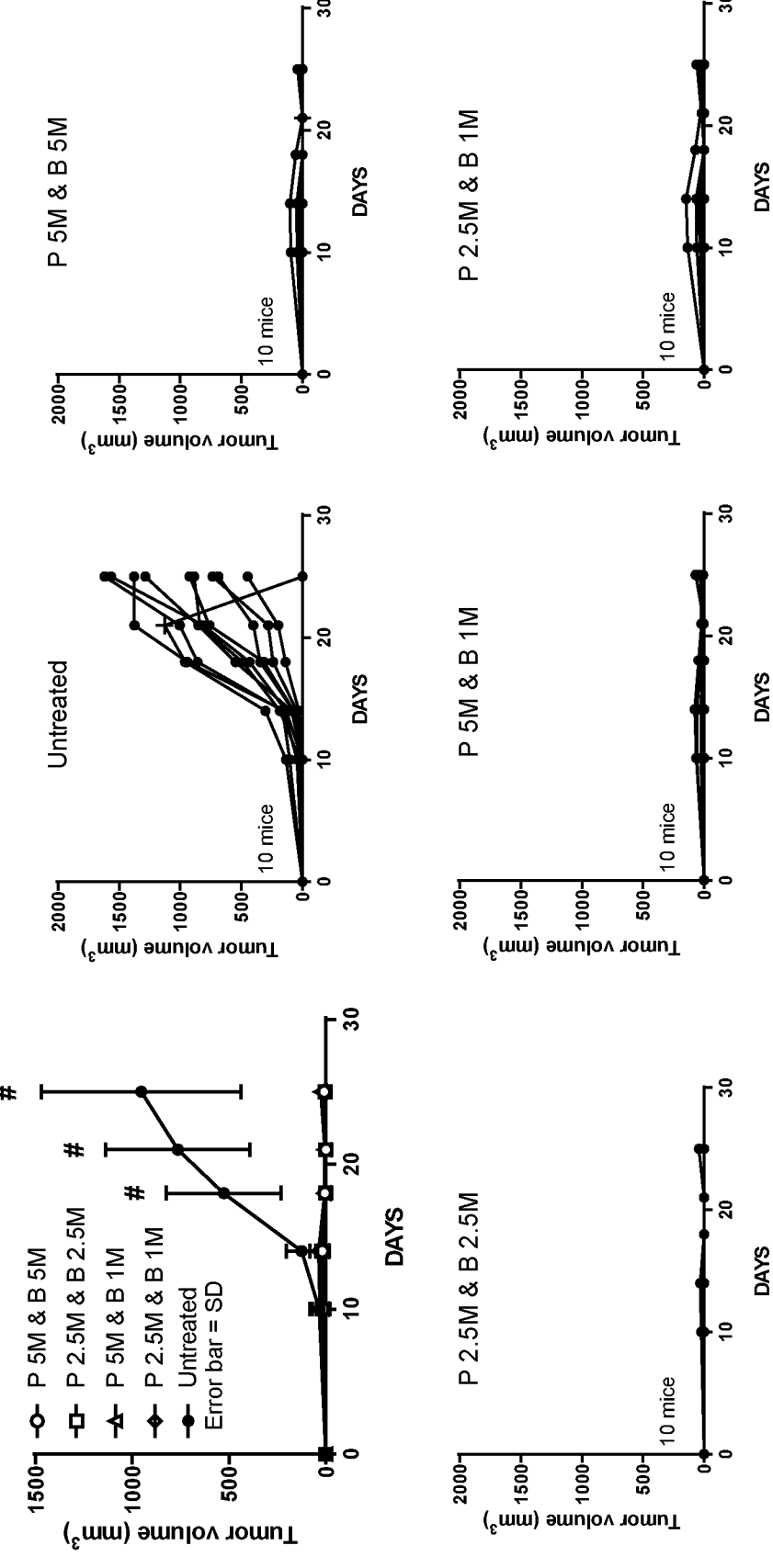
FIG. 1B shows tumor growth, as measured by the formula $((\text{length} \times \text{width}^2)/2)$ compared between mice from the untreated group (no adoptive transfer of T cells) and the treatment groups B-E outlined in FIG. 1A.

In some aspects, the present invention provides methods for treating and preventing an HPV-associated disease, and/or modulating the immune response in an individual with an HPV-associated disease comprising administering to the individual a composition comprising modified immune cells, wherein the modified immune cells comprise intracellularly an HPV antigen and intracellularly an adjuvant. In some aspects, the present invention provides methods for treating and preventing an HPV-associated disease, and/or modulating the immune response in an individual with an HPV-associated disease, the method comprising administering to the individual an effective amount of a composition comprising modified immune cells, wherein the modified immune cells comprise intracellularly an HPV antigen and intracellularly an adjuvant; wherein the modified immune cells are prepared by first passing a cell suspension comprising an input cell through a cell-deforming constriction, wherein a diameter of the constriction is a function of a diameter of the input cell in the suspension, thereby causing perturbations of the input cell large enough for the antigen and the adjuvant to pass through to form a perturbed input cell; and then incubating the perturbed input cell with the HPV antigen and the adjuvant for a sufficient time to allow the HPV antigen and the adjuvant to enter the perturbed input cell; thereby generating the modified immune cells. Certain aspects of the present disclosure relate to methods for generating a composition comprising modified immune cells, wherein an immune cell is passed through a constriction, wherein the constriction deforms the cell thereby causing a perturbation of the cell such that an HPV antigen and/or an adjuvant enters the immune cell to be modified.

In some aspects, the present invention provides methods for treating and preventing an HPV-associated disease, and/or modulating the immune response in an individual with an HPV-associated disease comprising administering to the individual a composition comprising modified immune cells, wherein the modified immune cells comprise intracellularly an HPV antigen. In some aspects, the present invention provides methods for treating and preventing an HPV-associated disease, and/or modulating the immune response in an individual with an HPV-associated disease, the method comprising administering to the individual an effective amount of a composition comprising modified immune cells, wherein the modified immune cells comprise intracellularly an HPV antigen, wherein the modified immune cells are prepared by first passing a cell suspension comprising an input cell through a cell-deforming constriction, wherein a diameter of the constriction is a function of a diameter of the input cell in the suspension, thereby causing perturbations of the input cell large enough for the antigen to pass through to form a perturbed input cell; and then incubating the perturbed input cell with the HPV antigen for a sufficient time to allow the HPV antigen to enter the perturbed input cell; thereby generating the modified immune cells. Certain aspects of the present disclosure relate to methods for generating a composition comprising modified immune cells, wherein an immune cell is passed through a constriction, wherein the constriction deforms the cell thereby causing a perturbation of the cell such that an HPV antigen enters the immune cell to be modified. In some further embodiments, the method for treating and preventing an HPV-associated disease, and/or modulating the immune response in an individual with an HPV-associated disease further comprises administering an adjuvant to the individual. In some embodiments, the composition of modified immune cells further comprises an adjuvant (e.g., a CpG oligonucleotide (CpG ODN) or IFNα. In some embodiments, the modified immune cells further comprises intracellularly an adjuvant, such as a CpG ODN.

General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4*th* ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6*th* ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999);

*The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 2011)

Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

It is understood that aspects and embodiments of the invention described herein include "comprising," "consisting," and "consisting essentially of" aspects and embodiments.

The term "about" as used herein refers to the usual error range for the respective value readily known to the skilled person in this technical field. Reference to "about" a value or parameter herein includes (and describes) embodiments that are directed to that value or parameter per se.

As used herein, "treatment" is an approach for obtaining beneficial or desired clinical results. "Treatment" as used herein, covers any administration or application of a therapeutic for disease in a mammal, including a human. For purposes of this invention, beneficial or desired clinical results include, but are not limited to, any one or more of: alleviation of one or more symptoms, diminishment of extent of disease, preventing or delaying spread (e.g., metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods of the invention contemplate any one or more of these aspects of treatment.

In the context of cancer, the term "treating" includes any or all of: inhibiting growth of cancer cells, inhibiting replication of cancer cells, lessening of overall tumor burden and ameliorating one or more symptoms associated with the disease.

The term "pore" as used herein refers to an opening, including without limitation, a hole, tear, cavity, aperture, break, gap, or perforation within a material. In some examples, (where indicated) the term refers to a pore within a surface of the present disclosure. In other examples, (where indicated) a pore can refer to a pore in a cell membrane.

The term "membrane" as used herein refers to a selective barrier or sheet containing pores. The term includes a pliable sheetlike structure that acts as a boundary or lining. In some examples, the term refers to a surface or filter containing pores. This term is distinct from the term "cell membrane".

The term "filter" as used herein refers to a porous article that allows selective passage through the pores. In some examples the term refers to a surface or membrane containing pores.

The term "heterogeneous" as used herein refers to something which is mixed or not uniform in structure or composition. In some examples the term refers to pores having varied sizes, shapes or distributions within a given surface.

The term "homogeneous" as used herein refers to something which is consistent or uniform in structure or composition throughout. In some examples, the term refers to pores having consistent sizes, shapes, or distribution within a given surface.

The term "homologous" as used herein refers to a molecule which is derived from the same organism. In some examples, the term refers to a nucleic acid or protein which is normally found or expressed within the given organism.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

The term "heterologous" as it relates to amino acid sequences such as peptide sequences and polypeptide sequences, denotes sequences that are not normally joined together, and/or are not normally associated with a particular cell. Thus, a "heterologous" region of a peptide sequence is a segment of amino acids within or attached to another amino acid molecule that is not found in association with the other molecule in nature. For example, a heterologous region of a peptide construct could include the amino acid sequence of the peptide flanked by sequences not found in association with the amino acid sequence of the peptide in nature. Another example of a heterologous peptide sequence is a construct where the peptide sequence itself is not found in nature (e.g., synthetic sequences having amino acids different as coded from the native gene). Similarly, a cell transformed with a vector that expresses an amino acid construct which is not normally present in the cell would be considered heterologous for purposes of this invention. Allelic variation or naturally occurring mutational events do not give rise to heterologous peptides, as used herein.

As used herein, the term "inhibit" may refer to the act of blocking, reducing, eliminating, or otherwise antagonizing the presence, or an activity of, a particular target. Inhibition may refer to partial inhibition or complete inhibition. For example, inhibiting an immune response may refer to any act leading to a blockade, reduction, elimination, or any other antagonism of an immune response. In other examples, inhibition of the expression of a nucleic acid may include, but not limited to reduction in the transcription of a nucleic acid, reduction of mRNA abundance (e.g., silencing mRNA transcription), degradation of mRNA, inhibition of mRNA translation, and so forth.

As used herein, the term "suppress" may refer to the act of decreasing, reducing, prohibiting, limiting, lessening, or otherwise diminishing the presence, or an activity of, a particular target. Suppression may refer to partial suppression or complete suppression. For example, suppressing an immune response may refer to any act leading to decreasing, reducing, prohibiting, limiting, lessening, or otherwise diminishing an immune response. In other examples, suppression of the expression of a nucleic acid may include, but not limited to reduction in the transcription of a nucleic acid, reduction of mRNA abundance (e.g., silencing mRNA transcription), degradation of mRNA, inhibition of mRNA translation, and so forth.

As used herein, the term "enhance" may refer to the act of improving, boosting, heightening, or otherwise increasing the presence, or an activity of, a particular target. For example, enhancing an immune response may refer to any act leading to improving, boosting, heightening, or otherwise increasing an immune response. In one exemplary example, enhancing an immune response may refer to employing an antigen and/or adjuvant to improve, boost, heighten, or otherwise increase an immune response. In other examples, enhancing the expression of a nucleic acid may include, but not limited to increase in the transcription of a nucleic acid, increase in mRNA abundance (e.g., increasing mRNA transcription), decrease in degradation of mRNA, increase in mRNA translation, and so forth.

As used herein, the term "modulate" may refer to the act of changing, altering, varying, or otherwise modifying the presence, or an activity of, a particular target. For example, modulating an immune response may refer to any act leading to changing, altering, varying, or otherwise modifying an immune response. In some examples, "modulate" refers to enchancing the presence or activity of a particular target. In some examples, "modulate" refers to suppressing the presence or activity of a particular target. In other examples, modulating the expression of a nucleic acid may include, but not limited to a change in the transcription of a nucleic acid, a change in mRNA abundance (e.g., increasing mRNA transcription), a corresponding change in degradation of mRNA, a change in mRNA translation, and so forth.

As used herein, the term "induce" may refer to the act of initiating, prompting, stimulating, establishing, or otherwise producing a result. For example, inducing an immune response may refer to any act leading to initiating, prompting, stimulating, establishing, or otherwise producing a desired immune response. In other examples, inducing the expression of a nucleic acid may include, but not limited to initiation of the transcription of a nucleic acid, initiation of mRNA translation, and so forth.

As used herein, a "peripheral blood mononuclear cells" or "PBMCs" refers to a heterogeneous population of blood cells having a round nucleus. Examples of cells that may be found in a population of PBMCs include lymphocytes such as T cells, B cells, NK cells (including NKT cells and CIK cells) and monocytes such as macrophages and dendritic cells. A "plurality of PBMCs" as used herein refers to a preparation of PBMCs comprising cells of at least two types of blood cells. In some embodiments, a plurality of PBMCs comprises two or more of T cells, B cells, NK cells, macrophages or dendritic cells. In some embodiments, a plurality of PBMCs comprises three or more of T cells, B cells, NK cells, macrophages or dendritic cells. In some embodiments, a plurality of PBMCs comprises four or more of T cells, B cells, NK cells, macrophages or dendritic cells. In some embodiments, a plurality of PBMCs comprises T cells, B cells, NK cells, macrophages and dendritic cells.

PBMCs can be isolated by means known in the art. For example, PBMCs can be derived from peripheral blood of an individual based on density of PBMCs compared to other blood cells. In some embodiments, PBMCs are derived from peripheral blood of an individual using Ficoll (e.g., a ficoll gradient). In some embodiments, PBMCs are derived from peripheral blood of an individual using ELUTRA® cell separation system.

In some embodiments, a population of PBMCs is isolated from an individual. In some embodiments, a plurality of PBMCs is an autologous population of PBMCs where the population is derived from a particular individual, manipulated by any of the methods described herein, and returned to the particular individual. In some embodiments, a plurality of PBMCs is an allogeneic population of PBMCs where the population is derived from one individual, manipulated by any of the methods described herein, and administered to a second individual.

In some embodiments, a plurality of PBMCs is a reconstituted preparation of PBMCs. In some embodiments, the plurality of PBMCs may be generated by mixing cells typically found in a population of PBMCs; for example, by mixing populations of two or more of T cells, B cells, NK cells, or monocytes.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and phosphorothioates, and thus can be an oligodeoxynucleoside phosphoramidate (P-NH2), a mixed phosphorothioate-phosphodiester oligomer, or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

As used herein, the term "adjuvant" refers to a substance which modulates and/or engenders an immune response. Generally, the adjuvant is administered in conjunction with an antigen to effect enhancement of an immune response to the antigen as compared to antigen alone. Various adjuvants are described herein.

The terms "CpG oligodeoxynucleotide" and "CpG ODN" herein refer to DNA molecules of 10 to 30 nucleotides in length containing a dinucleotide of cytosine and guanine separated by a phosphate (also referred to herein as a "CpG" dinucleotide, or "CpG"). The CpG ODNs of the present disclosure contain at least one unmethylated CpG dinucleotide. That is, the cytosine in the CpG dinucleotide is not methylated (i.e., is not 5-methylcytosine). CpG ODNs may have a partial or complete phosphorothioate (PS) backbone.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

For any of the structural and functional characteristics described herein, methods of determining these characteristics are known in the art.

Microfluidic Systems and Components Thereof

Microfluidic Channels to Provide Cell-Deforming Constrictions

In some aspects, the present invention provides methods for treating and preventing an HPV-associated disease, and/or modulating the immune response in an individual with an HPV-associated disease, the method comprising administering to the individual an effective amount of a composition comprising modified immune cells, wherein the modified immune cells comprise intracellularly an HPV antigen and intracellularly an adjuvant; wherein the modified immune cells are prepared by first passing a cell suspension comprising an input cell through a cell-deforming constriction, wherein a diameter of the constriction is a function of a diameter of the input cell in the suspension, thereby causing perturbations of the input cell large enough for the antigen and the adjuvant to pass through to form a perturbed input cell; and then incubating the perturbed input cell with the HPV antigen and the adjuvant for a sufficient time to allow the HPV antigen and the adjuvant to enter the perturbed input cell; thereby generating the modified immune cells. In some embodiments, the constriction is contained within a microfluidic channel. In some embodiments, multiple constrictions can be placed in parallel and/or in series within the microfluidic channel. In some embodiments, a deforming force is applied to the input cell as it passes through the constriction. Exemplary microfluidic channels containing cell-deforming constrictions for use in the methods disclosed herein are described in WO2013059343. Exemplary surfaces having pores for use in the methods disclosed herein are described in WO2017041050.

In some embodiments, the microfluidic channel includes a lumen and is configured such that an immune cell suspended in a buffer can pass through, wherein the microfluidic channel includes a constriction. The microfluidic channel can be made of any one of a number of materials, including silicon, metal (e.g., stainless steel), plastic (e.g., polystyrene), ceramics, glass, crystalline substrates, amorphous substrates, or polymers (e.g., Poly-methyl methacrylate (PMMA), PDMS, Cyclic Olefin Copolymer (COC), etc.). Fabrication of the microfluidic channel can be performed by any method known in the art, including dry etching, wet etching, photolithography, injection molding, laser ablation, or SU-8 masks.

In some embodiments, the constriction within the microfluidic channel includes an entrance portion, a centerpoint, and an exit portion. In some embodiments, the length, depth, and width of the constriction within the microfluidic channel can vary. In some embodiments, the diameter of the constriction within the microfluidic channel is a function of the diameter of the immune cell. In some embodiments, the diameter of the constriction within the microfluidic channel is about 20%, to about 99% of the diameter of the immune cell. In some embodiments, the constriction size is about 20%, about 30%, about 40%, about 50%, about 60%, about 70%, about 80%, about 90%, or about 99% of the immune cell diameter. In some embodiments, the constriction size is about 20%, about 30%, about 40%, about 50%, about 60%, about 70%, about 80%, about 90%, or about 99% of the minimum cross-sectional distance of the immune cell. In some embodiments, the channel comprises a constriction width of between about 2 μm and about 10 μm or any width or range of widths therebetween. For example, the constriction width can be any one of about 2 μm, about 3 μm, about 4 μm, about 5 μm, about 6 μm, or about 7 μm. In some embodiments, the channel comprises a constriction length of about 10 μm and a constriction width of about 4 μm. The cross-section of the channel, the entrance portion, the centerpoint, and the exit portion can also vary. For example, the cross-sections can be circular, elliptical, an elongated slit, square, hexagonal, or triangular in shape. The entrance portion defines a constriction angle, wherein the constriction angle is optimized to reduce clogging of the channel and optimized for enhanced delivery of a compound into the immune cell. The angle of the exit portion can vary as well. For example, the angle of the exit portion is configured to reduce the likelihood of turbulence that can result in non-laminar flow. In some embodiments, the walls of the entrance portion and/or the exit portion are linear. In other embodiments, the walls of the entrance portion and/or the exit portion are curved. The flow rate through the channel can also be adjusted. In some embodiments, the flow rate through the channel is between about 0.001 mL/cm$^2$/sec to about 100 L/cm$^2$/sec or any rate or range of rates therebetween.

In some embodiments according to any one of the methods or compositions described herein, wherein the immune cell is a plurality of PBMCs, the diameter of the constriction is a function of a diameter of the PBMCs, such as the mean diameter of a plurality of PBMCs, or a mean diameter of a subpopulation within plurality of the PBMCs. In some embodiments, the diameter of a cell is measured by the minimum cross-sectional distance of the cell (e.g. a cell within the plurality of PBMCs).

In some embodiments according to any one of the methods or compositions described herein, wherein the immune cell is a plurality of PBMCs, the diameter of the constriction is about 10% to about 99% of the mean diameter of the plurality of input PBMCs. In some embodiments, the diameter of the constriction is any one of about 10% to about 90%, about 10% to about 80%, about 10% to about 70%, about 20% to about 60%, about 40% to about 60%, or about 30% to about 45% of the mean diameter of the plurality of input PBMCs. In some embodiments, the diameter of the constriction is any one of about 10% to about 20%, about 20% to about 30%, about 30% to about 40%, about 40% to about 50%, about 50% to about 60%, about 60% to about 70%, about 70% to about 80%, about 80% to about 90%, or about 90% to about 99% of the mean diameter of the plurality of input PBMCs. In some embodiments, the diameter of the constriction is any one of about 10%, 15%, 20%, 25%, 30%, 35%, 40%, 45%, 50%, 55%, 60%, 65%, 70%, 75%, 80%, 85%, 90%, 95%, or 99% of the mean diameter of the plurality of input PBMCs.

In some embodiments according to any one of the methods or compositions described herein, wherein the immune cell is a plurality of PBMCs, the diameter of the constriction is about 10% to about 99% of the mean diameter of a subpopulation of cells having the smallest diameter within the plurality of input PBMCs. In some embodiments, the diameter of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of a subpopulation of cells having the smallest diameter within the plurality of input PBMCs. In some embodiments, the diameter of the constriction is any one of about 10% to about 20%, about 20% to about 30%, about 30% to about 40%, about 40% to about 50%, about 50% to about 60%, about 60% to about 70%, about 70% to about 80%, about 80% to about 90%, or about 90% to about 99% of the mean diameter of a subpopulation of cells having the smallest diameter within the plurality of input PBMCs. In some embodiments, the diameter of the constriction is any one of about 10%, 15%, 20%, 25%, 30%, 35%, 40%, 45%, 50%, 55%, 60%, 65%, 70%, 75%, 80%, 85%, 90%, 95%, or 99% of the mean diameter of a subpopulation of cells having the smallest diameter within the plurality of input PBMCs. In some embodiments, the subpopulation of cells having the smallest mean diameter within the plurality of input PBMCs is a population of lymphocytes, wherein the diameter of the population of lymphocytes is about 6 μm to about 10 μm. In some embodiments, the mean diameter of the population of lymphocytes is about 7 μm. In some embodiments, the population of lymphocytes is a population of T cells. In some embodiments, the lymphocytes are T cells. In some embodiments, the subpopulation of cells having the smallest mean diameter within the plurality of input PBMCs are T cells.

In some embodiments according to any one of the methods or compositions described herein, wherein the immune cell is a plurality of PBMCs, the diameter of the constriction is about 10% to about 99% of the mean diameter of a subpopulation of cells having the largest diameter within the plurality of input PBMCs. In some embodiments, the diameter of the constriction is any one of about 10% to about 90%, about 10% to about 80%, about 10% to about 70%, about 20% to about 60%, about 40% to about 60%, about 30% to about 45%, about 15% to about 30%, about 15% to about 20%, about 20% to about 25%, about 25% to about 30%, about 20% to about 30%, about 30% to about 70%, or about 30% to about 60% of the mean diameter of a subpopulation of cells having the largest diameter within the plurality of input PBMCs. In some embodiments, the diameter of the constriction is any one of about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 99% of the mean diameter of a subpopulation of cells having the largest diameter within the plurality of input PBMCs. In some embodiments, the diameter of the constriction is any one of about 5%, 10%, 15%, 20%, 25%, 30%, 35%, 40%, 45%, 50%, 55%, 60%, 65%, 70%, 75%, 80%, 85%, 90%, 95%, or 99% of the mean diameter of a subpopulation of cells having the largest diameter within the plurality of input PBMCs. In some embodiments, the subpopulation of cells having the largest mean diameter within the plurality of input PBMCs is a population of monocytes, wherein the diameter of the population of monocytes is about 15 μm to about 25 μm. In some embodiments, the mean diameter of the population of monocytes is about 20 μm. In some embodiments, the subpopulation of cells having the largest mean diameter within the plurality of input PBMCs are monocytes.

In some embodiments according to any one of the methods or compositions described herein, the diameter of the constriction is about 3 μm to about 15 μm. In some embodiments, the diameter of the constriction is about 3 μm to about 10 μm. In some embodiments, the diameter of the constriction is about 4 μm to about 10 μm. In some embodiments, the diameter of the constriction is about 4.2 μm to about 6 μm. In some embodiments, the diameter of the constriction is about 4.2 μm to about 4.8 μm. In some embodiments, the diameter of the constriction is any one of about 2 μm to about 14 μm, about 4 μm to about 12 μm, about 6 μm to about 9 μm, about 4 μm to about 6 μm, about 4 μm to about 5 μm, about 3.5 μm to about 7 μm, about 3.5 μm to about 6.3 μm, about 3.5 μm to about 5.6 μm, about 3.5 μm to about 4.9 μm, about 4.2 μm to about 6.3 μm, about 4.2 μm to about 5.6 μm, or about 4.2 μm to about 4.9 μm. In some embodiments, the diameter of the constriction is any one of about 2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 10.5 μm, 11 μm, 11.5 μm, 12 μm, 12.5 μm, 13 μm, 13.5 μm, 14 μm, 14.5 μm or 15 μm. In some embodiments, the diameter of the constriction is any one of about 4.0 μm, 4.1 μm, 4.2 μm, 4.3 μm, 4.4 μm, 4.5 μm, 4.6 μm, 4.7 μm, 4.8 μm, 4.9 μm, or 5.0 μm In some embodiments, the diameter of the constriction is about 4.5 μm.

In some embodiments according to any one of the methods or compositions described herein, the input immune cell is passed through the constriction at a flow rate between about 0.001 mL/min to about 200 mL/min or any rate or range of rates therebetween. In some embodiments, the flow rate is between about 0.001 mL/min to about 175 mL/min, about 0.001 mL/min to about 150 mL/min, about 0.001 mL/min to about 125 mL/min, about 0.001 mL/min to about 100 mL/min, about 0.001 mL/min to about 50 mL/min, about 0.001 mL/min to about 25 mL/min, about 0.001 mL/min to about 10 mL/min, about 0.001 mL/min to about 7.5 mL/min, about 0.001 mL/min to about 5.0 mL/min, about 0.001 mL/min to about 2.5 mL/min, about 0.001 mL/min to about 1 mL/min, about 0.001 mL/min to about 0.1 mL/min or about 0.001 mL/min to about 0.01 mL/min. In some embodiments, the flow rate is between about 0.001 mL/min to about 200 mL/min, about 0.01 mL/min to about 200 mL/min, about 0.1 mL/min to about 200 mL/min, about 1 mL/min to about 200 mL/min, about 10 mL/min to about 200 mL/min, about 50 mL/min to about 200 mL/min, about 75 mL/min to about 200 mL/min, about 100 mL/min to about 200 mL/min, about 150 mL/min to about 200 mL/min, about 0.5 mL/min to about 200 mL/min, about 1 mL/min to about 200 mL/min, about 2.5 mL/min to about 200 mL/min, about 5 mL/min to about 200 mL/min, about 7.5 mL/min to about 200 mL/min, about 10 mL/min to about 200 mL/min, about 25 mL/min to about 200 mL/min, or about 175 mL/min to about 200 mL/min. In some embodiments, the input immune cell is passed through the constriction at a flow rate between about 10 mL/min to about 200 mL/min.

In some embodiments, the input immune cell is passed through the constriction at a flow rate of about 100 mL/min.

In some embodiments according to any one of the methods or compositions described herein, the constriction can have any shape known in the art; e.g. a 3-dimensional shape or a 2-dimensional shape. The 2-dimensional shape, such as the cross-sectional shape, of the constriction can be, without limitation, circular, elliptical, round, square, star-shaped, triangular, polygonal, pentagonal, hexagonal, heptagonal, or octagonal. The 3-dimensional shape of the constriction can be, without limitation, cylindrical, conical, or cuboidal. In some embodiments, the cross-sectional shape of the constriction is a rectangle. In some embodiments, the cross-sectional shape of the constriction is a slit. In some embodiments, the cross-sectional shape of the constriction is a slit comprising a width of about 4 μm to about 10 μm and/or a depth of about 1 μm to about 200 μm. In some embodiments, the cross-sectional shape of the constriction is a slit comprising a width of about 3 μm to about 6 μm and/or a depth of about 20 μm to about 120 μm. In some embodiments, the cross-sectional shape of the constriction is a slit comprising a width of about 4.2 μm to about 6 μm and/or a depth of about 20 μm to about 120 μm. In some embodiments, the cross-sectional shape of the constriction is a slit comprising a width of about 4.2 μm to about 6 μm and/or a depth of about 40 μm to about 120 μm. In some embodiments, the cross-sectional shape of the constriction is a slit comprising a width of about 4.2 μm to about 6 μm and/or a depth of about 20 μm to about 80 μm. In some embodiments, the cross-sectional shape of the constriction is a slit comprising a width of about 4.5 μm and/or a depth of about 80 μm. In some embodiments, the slit comprises a length of about 5 μm to about 50 μm. In some embodiments, the slit comprises a length of about 10 μm to about 30 μm. In some embodiments, the slit comprises a length of about 2 μm to about 50 μm. In some embodiments, the slit comprises a length of any one of about 2 μm to about 5 μm, about 5 μm to about 10 μm, about 10 μm to about 15 μm, about 15 μm to about 20 μm, about 20 μm to about 25 μm, about 25 μm to about 30 μm, about 30 μm to about 35 μm, about 35 μm to about 40 μm, about 40 μm to about 45 μm, or about 45 μm to about 50 μm. In some embodiments, the slit comprises a length of about 10 μm.

Surface Having Pores to Provide Cell Deforming Constrictions

In some aspects, the present invention provides methods for treating and preventing an HPV-associated disease, and/or enhancing the immune response in an individual with an HPV-associated disease, the method comprising administering to the individual an effective amount of a composition comprising modified immune cells, wherein the modified immune cells comprise intracellularly an HPV antigen and an adjuvant; wherein the modified immune cells are prepared by first passing a cell suspension comprising an input cell through a cell-deforming constriction, wherein a diameter of the constriction is a function of a diameter of the input cell in the suspension thereby causing perturbations of the input cell large enough for the antigen and the adjuvant to pass through to form a perturbed input cell; and then incubating the perturbed input cell with the HPV antigen and the adjuvant for a sufficient time to allow the HPV antigen and the adjuvant to enter the perturbed input cell; thereby generating the modified immune cells. In some embodiments, a deforming force is applied to the input cell as it passes through the constriction. In some embodiments, the constriction is a pore or contained within a pore. In some embodiments, the pore is contained in a surface. Exemplary surfaces having pores for use in the methods disclosed herein are described in WO2017041050.

The surfaces as disclosed herein can be made of any one of a number of materials and take any one of a number of forms. In some embodiments, the surface is a filter. In some embodiments, the surface is a membrane. In some embodiments, the filter is a tangential flow filter. In some embodiments, the surface is a sponge or sponge-like matrix. In some embodiments, the surface is a matrix.

In some embodiments the surface is a tortuous path surface. In some embodiments, the tortuous path surface comprises cellulose acetate. In some embodiments, the surface comprises a material selected from, without limitation, synthetic or natural polymers, polycarbonate, silicon, glass, metal, alloy, cellulose nitrate, silver, cellulose acetate, nylon, polyester, polyethersulfone, polyacrylonitrile (PAN), polypropylene, PVDF, polytetrafluorethylene, mixed cellulose ester, porcelain, and ceramic.

The surface disclosed herein can have any shape known in the art; e.g. a 3-dimensional shape. The 2-dimensional shape of the surface can be, without limitation, circular, elliptical, round, square, star-shaped, triangular, polygonal, pentagonal, hexagonal, heptagonal, or octagonal. In some embodiments, the surface is round in shape. In some embodiments, the surface 3-dimensional shape is cylindrical, conical, or cuboidal.

The surface can have various cross-sectional widths and thicknesses. In some embodiments, the surface cross-sectional width is between about 1 mm and about 1 m or any cross-sectional width or range of cross-sectional widths therebetween. In some embodiments, the surface has a defined thickness. In some embodiments, the surface thickness is uniform. In some embodiments, the surface thickness is variable. For example, in some embodiments, portions of the surface are thicker or thinner than other portions of the surface. In some embodiments, the surface thickness varies by about 1% to about 90% or any percentage or range of percentages therebetween. In some embodiments, the surface is between about 0.01 $\mu$m to about 5 mm thick or any thickness or range of thicknesses therebetween.

In some embodiments, the constriction is a pore or contained within a pore. The cross-sectional width of the pores is related to the type of immune cell to be treated. In some embodiments, the pore size is a function of the diameter of the immune cell or cluster of immune cells to be treated. In some embodiments, the pore size is such that an immune cell is perturbed upon passing through the pore. In some embodiments, the pore size is less than the diameter of the immune cell. In some embodiments, the pore size is about 10% to about 99% of the diameter of the immune cell. In some embodiments, the pore size is about 10%, about 15%, about 20%, about 30%, about 40%, about 50%, about 60%, about 70%, about 80%, about 90%, or about 99% of the immune cell diameter. Optimal pore size or pore cross-sectional width can vary based upon the application and/or immune cell type. In some embodiments, the pore size is about 2 $\mu$m to about 14 $\mu$m. In some embodiments, the pore size is about 2 $\mu$m, about 3 $\mu$m, about 4 $\mu$m, about 5 $\mu$m, about 8 $\mu$m, about 10 $\mu$m, about 12 $\mu$m, or about 14 $\mu$m. In some embodiments, the cross-sectional width is about 2 $\mu$m to about 14 $\mu$m. In some embodiments, the pore cross-sectional is about 2 $\mu$m, about 3 $\mu$m, about 4 $\mu$m, about 5 $\mu$m, about 8 $\mu$m, about 10 $\mu$m, about 12 $\mu$m, or about 14 $\mu$m.

The entrances and exits of the pore passage may have a variety of angles. The pore angle can be selected to minimize clogging of the pore while immune cells are passing through. For example, the angle of the entrance or exit portion can be between about 0 and about 90 degrees. In some embodiments, the entrance or exit portion can be greater than 90 degrees. In some embodiments, the pores have identical entrance and exit angles. In some embodiments, the pores have different entrance and exit angles. In some embodiments, the pore edge is smooth, e.g. rounded or curved. A smooth pore edge has a continuous, flat, and even surface without bumps, ridges, or uneven parts. In some embodiments, the pore edge is sharp. A sharp pore edge has a thin edge that is pointed or at an acute angle. In some embodiments, the pore passage is straight. A straight pore passage does not contain curves, bends, angles, or other irregularities. In some embodiments, the pore passage is curved. A curved pore passage is bent or deviates from a straight line. In some embodiments, the pore passage has multiple curves, e.g. about 2, 3, 4, 5, 6, 7, 8, 9, 10 or more curves. The flow rate through the pore can also be adjusted. In some embodiments, the flow rate through the pore is between about 0.001 mL/cm$^2$/sec to about 100 L/cm$^2$/sec or any rate or range of rates therebetween.

The pores can have any shape known in the art, including a 2-dimensional or 3-dimensional shape. The pore shape (e.g., the cross-sectional shape) can be, without limitation, circular, elliptical, round, square, star-shaped, triangular, polygonal, pentagonal, hexagonal, heptagonal, and octagonal. In some embodiments, the cross-section of the pore is round in shape. In some embodiments, the 3-dimensional shape of the pore is cylindrical or conical. In some embodiments, the pore has a fluted entrance and exit shape. In some embodiments, the pore shape is homogenous (i.e. consistent or regular) among pores within a given surface. In some embodiments, the pore shape is heterogeneous (i.e. mixed or varied) among pores within a given surface.

The surfaces described herein can have a range of total pore numbers. In some embodiments, the pores encompass about 10% to about 80% of the total surface area. In some embodiments, the surface contains about 1.0×10$^5$ to about 1.0×10$^{30}$ total pores or any number or range of numbers therebetween. In some embodiments, the surface comprises between about 10 and about 1.0×10$^{15}$ pores/mm$^2$ surface area.

The pores can be distributed in numerous ways within a given surface. In some embodiments, the pores are distributed in parallel within a given surface. In one such example, the pores are distributed side-by-side in the same direction and are the same distance apart within a given surface. In some embodiments, the pore distribution is ordered or homogeneous. In one such example, the pores are distributed in a regular, systematic pattern or are the same distance apart within a given surface. In some embodiments, the pore distribution is random or heterogeneous. In one such example, the pores are distributed in an irregular, disordered pattern or are different distances apart within a given surface. In some embodiments, multiple surfaces are distributed in series. The multiple surfaces can be homogeneous or heterogeneous in surface size, shape, and/or roughness. The multiple surfaces can further contain pores with homogeneous or heterogeneous pore size, shape, and/or number, thereby enabling the simultaneous delivery of a range of compounds into different immune cell types.

In some embodiments, an individual pore has a uniform width dimension (i.e. constant width along the length of the pore passage). In some embodiments, an individual pore has a variable width (i.e. increasing or decreasing width along the length of the pore passage). In some embodiments, pores within a given surface have the same individual pore depths. In some embodiments, pores within a given surface have different individual pore depths. In some embodiments, the pores are immediately adjacent to each other. In some embodiments, the pores are separated from each other by a distance. In some embodiments, the pores are separated from each other by a distance of about 0.001 μm to about 30 mm or any distance or range of distances therebetween.

In some embodiments, the surface is coated with a material. The material can be selected from any material known in the art, including, without limitation, Teflon, an adhesive coating, surfactants, proteins, adhesion molecules, antibodies, anticoagulants, factors that modulate cellular function, nucleic acids, lipids, carbohydrates, or transmembrane proteins. In some embodiments, the surface is coated with polyvinylpyrrolidone (PVP). In some embodiments, the material is covalently attached to the surface. In some embodiments, the material is non-covalently attached or adsorbed to the surface. In some embodiments, the surface molecules are released as the immune cells pass through the pores.

In some embodiments, the surface has modified chemical properties. In some embodiments, the surface is polar. In some embodiments, the surface is hydrophilic. In some embodiments, the surface is non-polar. In some embodiments, the surface is hydrophobic. In some embodiments, the surface is charged. In some embodiments, the surface is positively and/or negatively charged. In some embodiments, the surface can be positively charged in some regions and negatively charged in other regions. In some embodiments, the surface has an overall positive or overall negative charge. In some embodiments, the surface can be any one of smooth, electropolished, rough, or plasma treated. In some embodiments, the surface comprises a zwitterion or dipolar compound. In some embodiments, the surface is plasma treated.

In some embodiments, the surface is contained within a larger module. In some embodiments, the surface is contained within a syringe, such as a plastic or glass syringe. In some embodiments, the surface is contained within a plastic filter holder. In some embodiments, the surface is contained within a pipette tip.

Cell Perturbations

In some embodiments, the invention provides methods for modulating an immune response by passing a cell suspension comprising an immune cell through a constriction, thereby causing a perturbation of the immune cell such that an antigen and/or adjuvant enters the immune cell, wherein the perturbation in the immune cell is a breach in the immune cell that allows material from outside the immune cell to move into the immune cell (e.g., a hole, tear, cavity, aperture, pore, break, gap, perforation). In some embodiments, a deforming force is applied to the input cell as it passes through the constriction. The deformation can be caused by, for example, mechanical strain and/or shear forces. In some embodiments, the perturbation is a perturbation within the immune cell membrane. In some embodiments, the perturbation is transient. In some embodiments, the immune cell perturbation lasts from about $1.0 \times 10^{-9}$ seconds to about 2 hours, or any time or range of times therebetween. In some embodiments, the immune cell perturbation lasts for about $1.0 \times 10^{-9}$ second to about 1 second, about 1 second to about 1 minute, or about 1 minute to about 1 hour. In some embodiments, the immune cell perturbation lasts for between any one of about $1.0 \times 10^{-9}$ to about $1.0 \times 10^{-1}$, about $1.0 \times 10^{-9}$ to about $1.0 \times 10^{-2}$, about $1.0 \times 10^{-9}$ to about $1.0 \times 10^{-3}$, about $1.0 \times 10^{-9}$ to about $1.0 \times 10^{-4}$, about $1.0 \times 10^{-9}$ to about $1.0 \times 10^{-5}$, about $1.0 \times 10^{-9}$ to about $1.0 \times 10^{-6}$, about $1.0 \times 10^{-9}$ to about $1.0 \times 10^{-7}$, or about $1.0 \times 10^{-9}$ to about $1.0 \times 10^{-8}$ seconds. In some embodiment, the immune cell perturbation lasts for any one of about $1.0 \times 10^{-8}$ to about $1.0 \times 10^{-1}$, about $1.0 \times 10^{-7}$ to about $1.0 \times 10^{-1}$, about $1.0 \times 10^{-6}$ to about $1.0 \times 10^{-1}$, about $1.0 \times 10^{-5}$ to about $1.0 \times 10^{-1}$, about $1.0 \times 10^{-4}$ to about $1.0 \times 10^{-1}$, about $1.0 \times 10^{-3}$ to about $1.0 \times 10^{-1}$, or about $1.0 \times 10^{-2}$ to about $1.0 \times 10^{-1}$ seconds. The immune cell perturbations (e.g., pores or holes) created by the methods described herein are not formed as a result of assembly of protein subunits to form a multimeric pore structure such as that created by complement or bacterial hemolysins.

As the immune cell passes through the constriction, the constriction temporarily imparts injury to the immune cell membrane that allows for passive diffusion of material through the perturbation. In some embodiments, the immune cell is only deformed for a brief period of time, on the order of 100 μs to minimize the chance of activating apoptotic pathways through cell signaling mechanisms, although other durations are possible (e.g., ranging from nanoseconds to hours). In some embodiments, the immune cell is deformed for about $1.0 \times 10^{-9}$ seconds to about 2 hours, or any time or range of times therebetween. In some embodiments, the immune cell is deformed for about $1.0 \times 10^{-9}$ second to about 1 second, about 1 second to about 1 minute, or about 1 minute to about 1 hour. In some embodiments, the immune cell is deformed for between any one of about $1.0 \times 10^{-9}$ to about $1.0 \times 10^{-1}$, about $1.0 \times 10^{-9}$ to about $1.0 \times 10^{-2}$, about $1.0 \times 10^{-9}$ to about $1.0 \times 10^{-3}$, about $1.0 \times 10^{-9}$ to about $1.0 \times 10^{-4}$, about $1.0 \times 10^{-9}$ to about $1.0 \times 10^{-5}$, about $1.0 \times 10^{-9}$ to about $1.0 \times 10^{-6}$, about $1.0 \times 10^{-9}$ to about $1.0 \times 10^{-7}$, or about $1.0 \times 10^{-9}$ to about $1.0 \times 10^{-8}$ seconds. In some embodiment, the immune cell is deformed for any one of about $1.0 \times 10^{-8}$ to about $1.0 \times 10^{-1}$, about $1.0 \times 10^{-7}$ to about $1.0 \times 10^{-1}$, about $1.0 \times 10^{-6}$ to about $1.0 \times 10^{-1}$, about $1.0 \times 10^{-5}$ to about $1.0 \times 10^{-1}$, about $1.0 \times 10^{-4}$ to about $1.0 \times 10^{-1}$, about $1.0 \times 10^{-3}$ to about $1.0 \times 10^{-1}$, or about $1.0 \times 10^{-2}$ to about $1.0 \times 10^{-1}$ seconds. In some embodiments, deforming the immune cell includes deforming the immune cell for a time ranging from, without limitation, about 1 μs to at least about 750 μs, e.g., at least about 1 μs, 10 μs, 50 μs, 100 μs, 500 μs, or 750 μs.

In some embodiments, the passage of the antigen and/or adjuvant into the immune cell occurs simultaneously with the immune cell passing through the constriction and/or the perturbation of the immune cell. In some embodiments, passage of the compound into the immune cell occurs after the immune cell passes through the constriction. In some embodiments, passage of the compound into the immune cell occurs on the order of minutes after the immune cell passes through the constriction. In some embodiments, the passage of the compound into the immune cell occurs from about $1.0 \times 10^{-2}$ seconds to at least about 30 minutes after the immune cell passes through the constriction. For example, the passage of the compound into the immune cell occurs from about $1.0 \times 10^{-2}$ seconds to about 1 second, about 1 second to about 1 minute, or about 1 minute to about 30 minutes after the immune cell passes through the constriction. In some embodiments, the passage of the compound into the immune cell occurs about $1.0 \times 10^{-2}$ seconds to about 10 minutes, about $1.0 \times 10^{-2}$ seconds to about 5 minutes, about $1.0 \times 10^{-2}$ seconds to about 1 minute, about $1.0 \times 10^{-2}$ seconds to about 50 seconds, about $1.0 \times 10^{-2}$ seconds to about 30 seconds, about $1.0 \times 10^{-2}$ seconds to about 10 seconds, about $1.0 \times 10^{-2}$ seconds to about 1 second, or about $1.0 \times 10^{-2}$ seconds to about 0.1 second after the immune cell passes through the constriction. In some embodiments, the passage of the compound into the immune cell occurs about $1.0 \times 10^{-1}$ seconds to about 10 minutes, about 1 second to about 10 minutes, about 10 seconds to about 10 minutes, about 50 seconds to about 10 minutes, about 1 minute to about 10 minutes, or about 5 minutes to about 10 minutes after the immune cell passes through the constriction. In some embodiments, a perturbation in the immune cell after it passes through the constriction is corrected within the order of about five minutes after the immune cell passes through the constriction.

In some embodiments, the cell viability after passing through a constriction is about 5% to about 100%. In some embodiments, the cell viability after passing through the constriction is at least about 5%, 10%, 20%, 30%, 40%, 50%, 60%, 70%, 75%, 80%, 85%, 90%, 95%, or 99%. In some embodiments, the cell viability is measured from about $1.0 \times 10^{-2}$ seconds to at least about 10 days after the immune cell passes through the constriction. For example, the cell viability is measured from about $1.0 \times 10^{-2}$ seconds to about 1 second, about 1 second to about 1 minute, about 1 minute to about 30 minutes, or about 30 minutes to about 2 hours after the immune cell passes through the constriction. In some embodiments, the cell viability is measured about $1.0 \times 10^{-2}$ seconds to about 2 hours, about $1.0 \times 10^{-2}$ seconds to about 1 hour, about $1.0 \times 10^{-2}$ seconds to about 30 minutes, about $1.0 \times 10^{-2}$ seconds to about 1 minute, about $1.0 \times 10^{-2}$ seconds to about 30 seconds, about $1.0 \times 10^{-2}$ seconds to about 1 second, or about $1.0 \times 10^{-2}$ seconds to about 0.1 second after the immune cell passes through the constriction. In some embodiments, the cell viability is measured about 1.5 hours to about 2 hours, about 1 hour to about 2 hours, about 30 minutes to about 2 hours, about 15 minutes to about 2 hours, about 1 minute to about 2 hours, about 30 seconds to about 2 hours, or about 1 second to about 2 hours after the immune cell passes through the constriction. In some embodiments, the cell viability is measured about 2 hours to about 5 hours, about 5 hours to about 12 hours, about 12 hours to about 24 hours, or about 24 hours to about 10 days after the immune cell passes through the constriction.

Delivery Parameters

A number of parameters may influence the delivery of a compound to an immune cell for modulating an immune response by the methods described herein. In some embodiments, the cell suspension is contacted with the compound before, concurrently, or after passing through the constriction. The immune cell may pass through the constriction suspended in a solution that includes the compound to deliver, although the compound can be added to the cell suspension after the immune cells pass through the constriction. In some embodiments, the compound to be delivered is coated on the constriction.

Examples of parameters that may influence the delivery of the compound into the immune cell include, but are not limited to, the dimensions of the constriction, the entrance angle of the constriction, the surface properties of the constrictions (e.g., roughness, chemical modification, hydrophilic, hydrophobic, etc.), the operating flow speeds (e.g., cell transit time through the constriction), the immune cell concentration, the concentration of the compound in the cell suspension, and the amount of time that the immune cell recovers or incubates after passing through the constrictions can affect the passage of the delivered compound into the immune cell. Additional parameters influencing the delivery of the compound into the immune cell can include the velocity of the immune cell in the constriction, the shear rate in the constriction, the viscosity of the cell suspension, the velocity component that is perpendicular to flow velocity, and time in the constriction. Such parameters can be designed to control delivery of the compound. In some embodiments, the immune cell concentration ranges from about 10 to at least about $10^{12}$ cells/mL or any concentration or range of concentrations therebetween. In some embodiments, delivery compound concentrations can range from about 10 ng/mL to about 1 g/mL or any concentration or range of concentrations therebetween. In some embodiments, delivery compound concentrations can range from about 1 pM to at least about 2 M or any concentration or range of concentrations therebetween.

The temperature used in the methods of the present disclosure can be adjusted to affect compound delivery and cell viability. In some embodiments, the method is performed between about –5° C. and about 45° C. For example, the methods can be carried out at room temperature (e.g., about 20° C.), physiological temperature (e.g., about 37° C.), higher than physiological temperature (e.g., greater than about 37° C. to 45° C. or more), or reduced temperature (e.g., about –5° C. to about 4° C.), or temperatures between these exemplary temperatures.

Various methods can be utilized to drive the immune cells through the constrictions. For example, pressure can be applied by a pump on the entrance side (e.g. compressor), a vacuum can be applied by a vacuum pump on the exit side, capillary action can be applied through a tube, and/or the system can be gravity fed. Displacement based flow systems can also be used (e.g., syringe pump, peristaltic pump, manual syringe or pipette, pistons, etc.). In some embodiments, the immune cells are passed through the constrictions by positive pressure or negative pressure. In some embodiments, the immune cells are passed through the constrictions by constant pressure or variable pressure. In some embodiments, pressure is applied using a syringe. In some embodiments, the pressure is applied using a gas cylinder. In some embodiments, the pressure is applied using the gas cylinder positive pressure method. In some embodiments, pressure is applied using a pump. In some embodiments, the pump is a peristaltic pump or a diaphragm pump. In some embodiments, pressure is applied using a vacuum. In some embodiments, the immune cells are passed through the constrictions by g-force. In some embodiments, the immune cells are passed through the constrictions by centrifugal force. In some embodiments, the immune cells are passed through the constrictions by capillary pressure.

In some embodiments, fluid flow directs the immune cells through the constrictions. In some embodiments, the fluid flow is turbulent flow prior to the immune cells passing through the constriction. Turbulent flow is a fluid flow in which the velocity at a given point varies erratically in magnitude and direction. In some embodiments, the fluid flow through the constriction is laminar flow. Laminar flow involves uninterrupted flow in a fluid near a solid boundary in which the direction of flow at every point remains constant. In some embodiments, the fluid flow is turbulent flow after the immune cells pass through the constriction. The velocity at which the immune cells pass through the constrictions can be varied. In some embodiments, the immune cells pass through the constrictions at a uniform cell speed. In some embodiments, the immune cells pass through the constrictions at a fluctuating cell speed.

In other embodiments, a combination treatment is used to modulate an immune response by passing a cell suspension comprising an immune cell through a constriction, wherein the constriction deforms the immune cell thereby causing a perturbation of the immune cell such that an antigen and/or adjuvant enters the immune cell, e.g., the methods described herein, followed by exposure to an electric field downstream of the constriction. In some embodiments, the immune cell is passed through an electric field generated by at least one electrode after passing through the constriction. In some embodiments, the electric field assists in delivery of compounds to a second location inside the immune cell such as the immune cell nucleus. For example, the combination of a cell-deforming constriction and an electric field delivers a plasmid encoding an antibody into the immune cell (e.g., the cell nucleus), resulting in the de novo production of antibody. In some embodiments, one or more electrodes are in proximity to the cell-deforming constriction to generate an electric field. In some embodiments, the electric field is between about 0.1 kV/m to about 100 MV/m, or any number or range of numbers therebetween. In some embodiments, an integrated circuit is used to provide an electrical signal to drive the electrodes. In some embodiments, the immune cells are exposed to the electric field for a pulse width of between about 1 ns to about 1 s and a period of between about 100 ns to about 10 s or any time or range of times therebetween.

Cell Suspensions for Delivery to Immune Cells

The cell suspension may be a mixed or purified population of immune cells. In some embodiments, the cell suspension is a mixed cell population, such as whole blood or PBMCs. In further embodiments, the mixed cell population is a mixture of defined or purified populations. In some embodiments, the cell suspension is a purified cell population, such as a purified population of immune cells.

The composition of the cell suspension (e.g., osmolarity, salt concentration, serum content, cell concentration, pH, etc.) can impact delivery of the compound for modulating an immune response. In some embodiments, the suspension comprises whole blood. Alternatively, the cell suspension is a mixture of cells in a physiological saline solution or physiological medium other than blood. In some embodiments, the cell suspension comprises an aqueous solution. In some embodiments, the aqueous solution comprises cell culture medium, (phosphate buffered saline) PBS, salts, metal ions, sugars, growth factors, animal derived products, bulking materials, surfactants, lubricants, lipids, vitamins, amino acids, proteins, cell cycle inhibitors, and/or an agent that impacts actin polymerization. In some embodiments, the cell culture medium is X-VIVO™ 10, X-VIVO™ 15, DMEM, Opti-MEM®, IMDM, or RPMI. Additionally, solution buffer can include one or more lubricants (pluronics or other surfactants) that can be designed, for example, to reduce or eliminate clogging of the constriction and improve cell viability. Exemplary surfactants include, without limitation, poloxamer, polysorbates, sugars or sugar alcohols such as mannitol, sorbitol, animal derived serum, and albumin protein.

In some configurations with certain types of immune cells, the immune cells can be incubated in one or more solutions that aid in the delivery of the compound to the interior of the immune cell. In some embodiments, the aqueous solution comprises an agent that impacts actin polymerization. In some embodiments, the agent that impacts actin polymerization is Latrunculin A, Cytochalasin, and/or Colchicine. For example, the immune cells can be incubated in a depolymerization solution such as Lantrunculin A (0.1 µg/mL) for 1 hour prior to delivery to depolymerize the actin cytoskeleton. As an additional example, the immune cells can be incubated in 10 µM Colchicine (Sigma) for 2 hours prior to delivery to depolymerize the microtubule network.

In some embodiments, the cell population is enriched prior to use in the disclosed methods. For example, cells are obtained from a bodily fluid, e.g., peripheral blood, and optionally enriched or purified to concentrate immune cells. Cells may be enriched by any methods known in the art, including without limitation, magnetic cell separation, fluorescent activated cell sorting (FACS), or density gradient centrifugation.

The viscosity of the cell suspension can also impact the methods disclosed herein. In some embodiments, the viscosity of the cell suspension ranges from about 8.9×10-4 Pa·s to about 4.0×10-3 Pa·s or any value or range of values therebetween. In some embodiments, the viscosity ranges between any one of about $8.9\times10^{-4}$ Pa·s to about $4.0\times10^{-3}$ Pa·s or any value or range of values therebetween. In some embodiments, the viscosity ranges between any one of about $8.9\times10^{-4}$ Pa·s to about $4.0\times10^{-3}$ Pa·s, about $8.9\times10^{-4}$ Pa·s to about $3.0\times10^{-3}$ Pa·s, about $8.9\times10^{-4}$ Pa·s to about $2.0\times10^{-3}$ Pa·s, or about $8.9\times10^{-3}$ Pa·s to about $1.0\times10^{-3}$ Pa·s. In some embodiments, the viscosity ranges between any one of about 0.89 cP to about 4.0 cP, about 0.89 cP to about 3.0 cP, about 0.89 cP to about 2.0 cP, or about 0.89 cP to about 1.0 cP. In some embodiments, a shear thinning effect is observed, in which the viscosity of the cell suspension decreases under conditions of shear strain. Viscosity can be measured by any method known in the art, including without limitation, viscometers, such as a glass capillary viscometer, or rheometers. A viscometer measures viscosity under one flow condition, while a rheometer is used to measure viscosities which vary with flow conditions. In some embodiments, the viscosity is measured for a shear thinning solution such as blood. In some embodiments, the viscosity is measured between about −5° C. and about 45° C. For example, the viscosity is measured at room temperature (e.g., about 20° C.), physiological temperature (e.g., about 37° C.), higher than physiological temperature (e.g., greater than about 37° C. to 45° C. or more), reduced temperature (e.g., about −5° C. to about 4° C.), or temperatures between these exemplary temperatures.

Antigens and Adjuvants to Enhance an Immune Response

Certain aspects of the present disclosure relate to a method of treating a patient by introducing the immune cells modified according to the methods described herein to a patient. In some embodiments, the immune cells are for use in immunotherapy. In some aspects, the disclosure relates to a method for treating a human papilloma virus (HPV)-related disease in an individual, the method comprising administering to the individual an effective amount of a composition comprising modified immune cells, wherein the modified immune cells comprise intracellularly an HPV antigen and intracellularly an adjuvant. In some aspects, the disclosure relates to a method for treating an HPV-associated disease in an individual, the method comprising administering to the individual an effective amount of a composition comprising modified immune cells, wherein the modified immune cells comprise intracellularly an HPV antigen and intracellularly an adjuvant; wherein the modified immune cells are prepared by a) passing a cell suspension comprising an input cell through a cell-deforming constriction, wherein a diameter of the constriction is a function of a diameter of the input cell in the suspension thereby causing perturbations of the input cell large enough for the antigen and the adjuvant to pass through to form a perturbed input cell; and b) incubating the perturbed input cell with the HPV antigen and the adjuvant for a sufficient time to allow the HPV antigen and the adjuvant to enter the perturbed input cell; thereby generating the modified immune cells. In some embodiments, a deforming force is applied to the input cell as it passes through the constriction.

In some aspects, the disclosure relates to a method for preventing an HPV-associated disease in an individual, the method comprising administering to the individual an effective amount of a composition comprising modified immune cells, wherein the modified immune cells comprise intracellularly an HPV antigen and intracellularly an adjuvant. In some aspects, the disclosure relates to a method for preventing an HPV-associated disease in an individual, the method comprising administering to the individual an effective amount of a composition comprising modified immune cells, wherein the modified immune cells comprise intracellularly an HPV antigen and intracellularly an adjuvant; wherein the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the HPV antigen and the adjuvant to pass through to form a perturbed input cell; and b) incubating the perturbed input cell with the HPV antigen and the adjuvant for a sufficient time to allow the HPV antigen and the adjuvant to enter the perturbed input cell; thereby generating the modified immune cells. In some embodiments, a deforming force is applied to the input cell as it passes through the constriction.

In some aspects, the disclosure relates to a method for modulating an immune response in an individual with an HPV-associated disease, the method comprising administering to the individual an effective amount of a composition comprising modified immune cells, wherein the modified immune cells comprise intracellularly an HPV antigen and intracellularly an adjuvant. In some aspects, the disclosure relates to a method for modulating an immune response in an individual with an HPV-associated disease, the method comprising administering to the individual an effective amount of a composition comprising modified immune cells, wherein the modified immune cells comprise intracellularly an HPV antigen and intracellularly an adjuvant; wherein the modified immune cells are prepared by a) passing a cell suspension comprising an input cell comprising an HPV antigen through a microfluidic channel that includes a cell-deforming constriction, wherein a diameter of the constriction is a function of a diameter of the input cell in the suspension, thereby causing perturbations of the input cell large enough for the HPV antigen and the adjuvant to pass through to form a perturbed input cell; and b) incubating the perturbed input cell with the antigen and the adjuvant for a sufficient time to allow the HPV antigen and the adjuvant to enter the perturbed input cell; thereby generating the modified immune cells. In some embodiments, a deforming force is applied to the input cell as it passes through the constriction. In some embodiments, the immune response is enhanced. In some embodiments, the immune response to the HPV antigen is enhanced.

Some aspects of the invention provide delivery of antigens to an individual with an HPV-associated disease to enhance an immune response to the antigen, by administering an immune cell comprising an intracellular antigen wherein the antigen is delivered to the cell by any of the methods described herein. In some embodiments, the antigen is a single antigen. In some embodiments, the antigen is a mixture of antigens. An antigen is a substance that stimulates a specific immune response, such as a cell or antibody-mediated immune response. Antigens bind to receptors expressed by immune cells, such as T cell receptors (TCRs), which are specific to a particular antigen. Antigen-receptor binding subsequently triggers intracellular signaling pathways that lead to downstream immune effector pathways, such as cell activation, cytokine production, cell migration, cytotoxic factor secretion, and antibody production.

In some embodiments, the modified immune cells are prepared by a) passing a cell suspension comprising an input cell comprising an HPV antigen through a constriction, wherein a diameter of the constriction is a function of a diameter of the input cell in the suspension, thereby causing perturbations of the input cell large enough for the HPV antigen and the adjuvant to pass through to form a perturbed input cell; and b) incubating the perturbed input cell with the antigen and the adjuvant for a sufficient time to allow the HPV antigen and the adjuvant to enter the perturbed input cell; thereby generating the modified immune cells. In further embodiments, the diameter of the constriction is less than the diameter of the cell. In some embodiments, the diameter of the constriction is smaller than the diameter of the immune cells. In some embodiments, the diameter of the constriction is about 20% to about 99% of the diameter of the cell. In some embodiments, the diameter of the constriction is about 20% to less than about 60% of the diameter of the cell. In some embodiments, the diameter of the constriction is any of about 20%, about 30%, about 40%, about 50%, about 60%, about 70%, about 80%, about 90%, about 95%, or about 99% of the diameter of the cell. In some embodiments, the diameter of the constriction is any of between about 20% and about 30%, between about 30% and about 40%, between about 40% and about 50%, between about 50% and about 60%, between about 60% and about 70%, between about 70% and about 80%, between about 80% and about 90%, between about 90% and about 95%, or between about 95% and about 99% of the diameter of the cell. In some embodiments, a deforming force is applied to the input cell as it passes through the constriction. In some embodiments, the constriction is in a channel. In some embodiments, the constriction is contained in a microfluidic channel. In some embodiments, the constriction is contained within a filter. In other embodiments, the constriction is a pore on a filter.

In some embodiments, the modified immune cells comprise intracellular an HPV antigen and an adjuvant. In some embodiments, the HPV antigen and/or the adjuvant are present in the cytosol and/or endosomes. In some embodiments, the antigen and/or adjuvant are present in multiple compartments of the cell. In further embodiments, the antigen and/or adjuvant are present in compartments of the cell including one or more of the endoplasmic recticulum (ER), Golgi apparatus, lysosome, or exosomes. In some embodiments, the antigen and the adjuvant are in the same compartment. In some embodiments, the antigen and adjuvant are in different compartments from each other. For example, in some embodiments, the antigen is present in the cytosol whereas the adjuvant is present in the endosome. In some embodiments, the modified immune cell further comprises an HPV antigen and/or an adjuvant on the outside of the cell.

In some embodiments, the concentration of adjuvant incubated with the perturbed input cell is between about 0.01 μM and about 10 mM. For example, in some embodiments, the concentration of adjuvant incubated with the perturbed input cell is any of less than about 0.01 μM, about 0.1 μM, about 1 μM, about 10 μM, about 100 μM, about 1 mM or about 10 mM. In some embodiments, the concentration of adjuvant incubated with the perturbed input cell is greater than about 10 mM. In some embodiments, the concentration of adjuvant incubated with the perturbed input cell is any of between about 0.01 μM and about 0.1 μM, between about 0.1 µM, and about 1 µM, between about 1µM and about 10 µM, between about 10 µM and about 100 µM, between about 100 µM and about 1 mM, or between 1 mM and about 10 mM. In some embodiments, the concentration of adjuvant incubated with the perturbed input cell is between about 0.1 µM and about 1 mM.

In some embodiments, the concentration of HPV antigen incubated with the perturbed input cell is between about 0.01 µM and about 10 mM. For example, in some embodiments, the concentration of HPV antigen incubated with the perturbed input cell is any of less than about 0.01 µM, about 0.1 µM, about 1 µM, about 10 µM, about 100 µM, about 1 mM or about 10 mM. In some embodiments, the concentration of HPV antigen incubated with the perturbed input cell is greater than about 10 mM. In some embodiments, the concentration of HPV antigen incubated with the perturbed input cell is any of between about 0.01 µM and about 0.1 µM, between about 0.1 µM and about 1 µM, between about 1µM and about 10 µM, between about 10 µM and about 100 between about 100 µM and about 1 mM, or between 1 mM and about 10 mM. In some embodiments, the concentration of HPV antigen incubated with the perturbed input cell is between about 0.1 µM and about 1 mM.

In some embodiments, the molar ratio of HPV antigen to adjuvant incubated with the perturbed input cell is any of between about 10000:1 to about 1:10000. For example, in some embodiments, the molar ratio of HPV antigen to adjuvant incubated with the perturbed input cell is about any of 10000:1, about 1000:1, about 100:1, about 10:1, about 1:1, about 1:10, about 1:100, about 1:1000, or about 1:10000. In some embodiments, the molar ratio of HPV antigen to adjuvant incubated with the perturbed input cell is any of between about 10000:1 and about 1000:1, between about 1000:1 and about 100:1, between about 100:1 and about 10:1, between about 10:1 and about 1:1, between about 1:1 and about 1:10, between about 1:10 and about 1:100, between about 1:100 and about 1:1000, between about 1:1000 and about 1:10000.

In some embodiments, the modified immune cell comprises the adjuvant at a concentration between about 0.01 µM and about 10 mM. For example, in some embodiments, the immune cell comprises the adjuvant at a concentration of any of less than about 0.01 µM, about 0.1 µM, about 1 µM, about 10 µM, about 100 µM, about 1 mM or about 10 mM. In some embodiments, the immune cell comprises the adjuvant at a concentration of greater than about any of 10 mM. in some embodiments, the immune cell comprises the adjuvant at a concentration of any of between about 0.1 µM and about 1 between about 1 µM and about 10 µM, between about 10 µM and about 100 µM, between about 100 µM and about 1 mM, or between 1 mM and about 10 mM. In some embodiments, the modified immune cell comprises the adjuvant at a concentration between about 0.1 µM and about 1 mM.

In some embodiments, the concentration of HPV antigen in the modified immune cell is between about 0.01 µM and about 10 mM. For example, in some embodiments, the concentration of HPV antigen in the modified immune cell is any of less than about 0.01 µM, about 0.1 µM, about 1 µM, about 10 µM, about 100 µM, about 1 mM or about 10 mM. In some embodiments, the concentration of HPV antigen in the modified immune cell is greater than about 10 mM. In some embodiments, the concentration of HPV antigen in the modified immune cell is any of between about 0.1 µM and about 1 between about 1 µM and about 10 between about 10 µM and about 100 µM, between about 100 µM and about 1 mM, or between 1 mM and about 10 mM. In some embodiments, the concentration of HPV antigen in the modified immune cell is between about 0.1 µM and about 1 mM.

In some embodiments, the molar ratio of HPV antigen to adjuvant in the modified immune cell is any of between about 10000:1 to about 1:10000. For example, in some embodiments, the molar ratio of HPV antigen to adjuvant in the modified immune cell is about any of 10000:1, about 1000:1, about 100:1, about 10:1, about 1:1, about 1:10, about 1:100, about 1:1000, or about 1:10000. In some embodiments, the molar ratio of HPV antigen to adjuvant in the modified immune cell is any of between about 10000:1 and about 1000:1, between about 1000:1 and about 100:1, between about 100:1 and about 10:1, between about 10:1 and about 1:1, between about 1:1 and about 1:10, between about 1:10 and about 1:100, between about 1:100 and about 1:1000, between about 1:1000 and about 1:10000.

In some embodiments, the antigen is a polypeptide antigen. In some embodiments, the antigen is modified with a lipid. In some embodiments, the modified antigen is modified with a polysaccharide or a carbohydrate moiety. In some embodiments, the antigen is associated with a virus. In some embodiments, the antigen is a viral antigen. Exemplary viral antigens include HPV antigens. In further embodiments, the antigen is an HPV antigen. In some embodiments, the HPV antigen consists of a selection from the group of: HPV-16, 18, 26, 31, 33, 35, 39, 45, 51, 52, 53, 56, 58, 59, 66, 68, 73, and 82. HPV-16, 18, 31, 33, 35, 39, 45, 51, 52, 56, 58, 59, 68, 73, and 82 are high risk types in causing cancer whereas HPV-26, 53, and 66 are "probably high risk types" in causing cancer. In some embodiments, the HPV antigen is a polypeptide comprising an antigenic HPV epitope and one or more heterologous peptide sequences. In some embodiments, the antigen is an HPV-16 antigen or an HPV-18 antigen. In some embodiments, the HPV antigen is comprised of an HLA-A2 specific epitope. HPV E6 and E7 genes are the oncogenes of the virus and expression of these genes is required for malignant, transformation. The E6 and E7 proteins target a number of negative regulators of the cell cycle, primarily p105Rb and p53, respectively, and thus interfere with cell-cycle regulation. In further embodiments, the HPV antigen is an HPV E6 antigen or an HPV E7 antigen. In some embodiments, the modified immune cells comprise an HPV E6 antigen and an HPV E7 antigen. In some embodiments, the HPV antigen is a polypeptide comprising an immunogenic epitope that is flanked on the N-terminus and/or the C-terminus by one or more heterologous peptide sequences. In some embodiments, the HPV antigen is an HPV E7 epitope flanked by sequences from the HPV E6 polypeptide (E7.6). In some embodiments, the HPV antigen comprises an amino acid sequence with at least 90% similarity to any one of SEQ ID NOs:18-26. In some embodiments, the HPV antigen comprises the amino acid sequence of SEQ ID NO:23. In some embodiments, the HPV antigen comprises the amino acid sequence of any one of SEQ ID NOs:18-26. In some embodiments, the HPV antigen comprises the amino acid sequence of SEQ ID NO:23.

In some embodiments, the antigen is derived from a cell lysate, such as a lysate of disease cells. In some embodiments, the antigen is in a cell lysate. In some embodiments, the antigen is derived from a tumor lysate. In some embodiments, the antigen is derived from a lysate of HPV-associated cancer cells. In some embodiments, the HPV-associated cancer is any one of head and neck cancer, cervical cancer, vulvar cancer, vaginal cancer, penile cancer, anal cancer, perianal cancer, anogenital cancer, oral cancer or salivary cancer.

In some aspects, the disclosure relates to a method for treating a human papilloma virus (HPV)-related cancer in an individual, the method comprising administering to the individual an effective amount of a composition comprising modified immune cells, wherein the modified immune cells comprise an HPV antigen comprising an amino acid sequence with at least 90% similarity to any one of SEQ ID NOs:18-26. In some aspects, the disclosure relates to a method for treating an HPV-associated disease in an individual, the method comprising administering to the individual an effective amount of a composition comprising modified immune cells, wherein the modified immune cells comprise an HPV antigen comprising an amino acid sequence with at least 90% similarity to any one of SEQ ID NOs:18-26; wherein the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the antigen to pass through to form a perturbed input cell; and b) incubating the perturbed input cell with the HPV antigen for a sufficient time to allow the HPV antigen to enter the perturbed input cell; thereby generating the modified immune cells. In some embodiments, a deforming force is applied to the input cell as it passes through the constriction.

In some aspects, the disclosure relates to a method for preventing an HPV-associated disease in an individual, the method comprising administering to the individual an effective amount of a composition comprising modified immune cells, wherein the modified immune cells comprise an HPV antigen comprising an amino acid sequence with at least 90% similarity to any one of SEQ ID NOs:18-26. In some aspects, the disclosure relates to a method for preventing an HPV-associated disease in an individual, the method comprising administering to the individual an effective amount of a composition comprising modified immune cells, wherein the modified immune cells comprise an HPV antigen, wherein the modified immune cells comprise an HPV antigen comprising an amino acid sequence with at least 90% similarity to any one of SEQ ID NOs:18-26; wherein the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the HPV antigen to pass through to form a perturbed input cell; and b) incubating the perturbed input cell with the HPV antigen for a sufficient time to allow the HPV antigen to enter the perturbed input cell; thereby generating the modified immune cells. In some embodiments, a deforming force is applied to the input cell as it passes through the constriction.

In some aspects, the disclosure relates to a method for modulating an immune response in an individual with an HPV-associated disease, the method comprising administering to the individual an effective amount of a composition comprising modified immune cells, wherein the modified immune cells comprise an HPV antigen comprising an amino acid sequence with at least 90% similarity to any one of SEQ ID NOs:18-26. In some aspect, the disclosure relates to a method for modulating an immune response in an individual with an HPV-associated disease, the method comprising administering to the individual an effective amount of a composition comprising modified immune cells, wherein the modified immune cells comprise an HPV antigen comprising an amino acid sequence with at least 90% similarity to any one of SEQ ID NOs:18-26; wherein the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the HPV antigen to pass through to form a perturbed input cell; and b) incubating the perturbed input cell with the HPV antigen for a sufficient time to allow the HPV antigen to enter the perturbed input cell; thereby generating the modified immune cells. In some embodiments, a deforming force is applied to the input cell as it passes through the constriction. In some embodiments, the immune response is enhanced. In some embodiments, the immune response to the HPV antigen is enhanced.

In some embodiments, the HPV antigen is a pool of multiple polypeptides that elicit a response against the same and or different HPV antigens. In some embodiments, the antigens comprised in a pool of multiple antigens do not decrease the immune response directed toward the other antigens. For example, when using a pool of HPV E6 and E7 antigens, the respective immune responses directed towards HPV E6 and E7 antigens would be comparable to using HPV E6 alone or using HPV E7 alone as antigen, respectively.

In some embodiments, the HPV antigen is a polypeptide comprising an immunogenic HPV epitope and one or more heterologous peptide sequences. In some embodiments, the one or more HPV antigen complexes with itself, with other antigens or with the adjuvant.

As used herein, the term "adjuvant" refers to a substance which directly or indirectly modulates and/or engenders an immune response. Generally, the adjuvant is administered in conjunction with an antigen to effect enhancement of an immune response to the antigen as compared to antigen alone. Therefore, adjuvants can be used to boost elicitation of an immune cell response (e.g. T cell response) to an antigen. In some embodiments, the invention provides immune cells modified to comprise intracellularly an HPV antigen and intracellularly an adjuvant. In some embodiments, the immune cells perturbed as described herein are incubated with both the HPV antigen and an adjuvant. Exemplary intracellular adjuvants include, without limitation, CpG ODN, interferon-$\alpha$ (IFN-$\alpha$), stimulator of interferon genes (STING) agonists and retinoic acid-inducible gene I (RIG-I) agonists, and polyinosinic:polycytidylic acid (polyI:C) In some embodiments, the adjuvant is CpG ODN, IFN-$\alpha$, STING agonists, RIG-I agonists or polyI:C. In particular embodiments, the adjuvant is a CpG ODN polynucleotide. In some embodiments, the CpG ODN adjuvant comprise of a selection from the group of CpG ODN 1018, CpG ODN 1585, CpG ODN 2216, CpG ODN 2336, CpG ODN 1668, CpG ODN 1826, CPG ODN 2006, CpG ODN 2007, CpG ODN BW006, CpG ODN D-SL01, CpG ODN 2395, CpG ODN M362, CpG ODN D-SL03. In some embodiments, the CpG ODN adjuvant is CpG ODN 1826 (TCCATGACGTTCCTGACGTT; SEQ ID NO:30) or CpG ODN 2006 (also known as CpG ODN 7909) (TCGTCGTTTTGTCGTTTTGTCGTT; SEQ ID NO:31) oligonucleotide. In some embodiments, the RIG-I agonist comprises polyinosinic:polycytidylic acid (polyI:C). Multiple adjuvants can also be used in conjunction with antigens to enhance the elicitation of immune response. In some embodiments, the modified immune cell comprises more than one adjuvant. Multiple adjuvants can also be used in conjunction with antigens to enhance the elicitation of immune response. In some embodiments, the modified immune cell comprises more than one adjuvant. In some embodiments, the modified immune cell comprises any combination of the adjuvants CpG ODN, IFN-α, STING agonists, RIG-I agonists or polyI:C.

Exemplary adjuvants include, without limitation, CpG ODN, interferon-α (IFN-α), polyinosinic:polycytidylic acid (polyI:C), imiquimod (R837), resiquimod (R848), or lipopolysaccharide (LPS). In some embodiments, the adjuvant is CpG ODN, LPS, IFN-α, STING agonists, RIG-I agonists, poly I:C, R837, R848, a TLR3 agonist, a TLR4 agonist or a TLR 9 agonist. In particular embodiments, the adjuvant is a CpG ODN. In some embodiments, the adjuvant is a CpG ODN. In some embodiments, the CpG ODN is a Class A CpG ODN, a Class B CpG ODN, or a Class C CpG ODN. In some embodiments, the CpG ODN adjuvant comprise of a selection from the group of CpG ODN 1018, CpG ODN 1585, CpG ODN 2216, CpG ODN 2336, CpG ODN 1668, CpG ODN 1826, CPG ODN 2006, CpG ODN 2007, CpG ODN BW006, CpG ODN D-SL01, CpG ODN 2395, CpG ODN M362, CpG ODN D-SL03. In some embodiments, the CpG ODN adjuvant is CpG ODN 1826 (TC-CATGACGTTCCTGACGTT; SEQ ID NO:30) or CpG ODN 2006 (also known as CpG ODN 7909) (TCGTCGTTTTGTCGTTTTGTCGTT; SEQ ID NO:31) oligonucleotide. In some embodiments, the adjuvant is CpG ODN 7909. In some embodiments, the RIG-I agonist comprises polyinosinic:polycytidylic acid (polyI:C). Multiple adjuvants can also be used in conjunction with antigens to enhance the elicitation of immune response. In some embodiments, the modified immune cell comprises more than one adjuvant. Multiple adjuvants can also be used in conjunction with antigens to enhance the elicitation of immune response. In some embodiments, the modified immune cell comprises more than one adjuvant. In some embodiments, the modified immune cell comprises any combination of the adjuvants CpG ODN, LPS, IFN-α, STING agonists, RIG-I agonists, poly I:C, R837, R848, a TLR3 agonist, a TLR4 agonist or a TLR 9 agonist.

In any of the embodiments described herein, unless otherwise indicated, the adjuvant may refer to (a) an adjuvant that is incubated with and passes through a perturbed input immune cell, (b) an adjuvant incubated with PBMCs for the PBMCs to condition, (c) an adjuvant co-administered with modified immune cells to an individual.

In some embodiments, the modified immune cell further comprises an agent that enhances the viability and/or function of the modified immune cell as compared to a corresponding modified immune cell that does not comprise the agent. In some embodiments, the agent is a compound that enhances endocytosis, a stabilizing agent or a co-factor. In some embodiments, the stabilizing agent is complexed to the HPV antigen and/or the adjuvant. In some embodiments, the stabilizing agent increases the solubility and/or solution half-life of the HPV antigen and/or the adjuvant. In some embodiments, the plurality of modified immune cells have greater viability than corresponding modified immune cells that do not comprise the stabilizing agent. In some embodiments, the agent is albumin. In further embodiments, the albumin is mouse, bovine, or human albumin. In further embodiments, the agent is a divalent metal cation, glucose, ATP, potassium, glycerol, trehalose, D-sucrose, PEG1500, L-arginine, L-glutamine, or EDTA. In some embodiments, the divalent metal cation is one more of $Mg^{2+}$, $Zn^{2+}$ or $Ca^{2+}$. In some embodiments, the agent comprises MSA.

In some embodiments according to any one of the methods or compositions described herein, the modified immune cell further comprises an agent that enhances the viability and/or function of the modified immune cell as compared to a corresponding plurality of the modified immune cell that does not comprise the agent. In some embodiments, the modified immune cell further comprises an agent that enhances the viability and/or function of the modified immune cell upon freeze-thaw cycle as compared to a corresponding the modified immune cell that does not comprise the agent. In some embodiments, the agent is a cyropreservation agent and/or a hypothermic preservation agent. In some embodiments, neither the cyropreservation agent nor the hypothermic preservation agent cause more than 10% or 20% of cell death in the modified immune cell comprising the agent compared to a corresponding modified immune cell that does not comprise the agent before any freeze-thaw cycles. In some embodiments, at least about 70%, about 80%, or about 90% of the modified immune cells are viable after up to 1, 2, 3, 4, 5 freeze-thaw cycles. In some embodiments, the agent is a compound that enhances endocytosis, a stabilizing agent or a co-factor. In some embodiments, the agent is albumin. In some embodiments, the albumin is mouse, bovine, or human albumin. In some embodiments, the agent is human albumin. In some embodiments, the agent is one or more of: a divalent metal cation, glucose, ATP, potassium, glycerol, trehalose, D-sucrose, PEG1500, L-arginine, L-glutamine, or EDTA. In some embodiments, the divalent metal cation is one more of $Mg^{2+}$, $Zn^{2+}$ or $Ca^{2+}$. In some embodiments, the agent is one or more of: sodium pyruvate, adenine, trehalose, dextrose, mannose, sucrose, human serum albumin (HSA), DMSO, HEPES, glycerol, glutathione, inosine, dibasic sodium phosphate, monobasic sodium phosphate, sodium metal ions, potassium metal ions, magnesium metal ions, chloride, acetate, gluoconate, sucrose, potassium hydroxide, or sodium hydroxide. In some embodiments, the agent is one or more of: Sodium pyruvate, adenine, Rejuvesol®, trehalose, dextrose, mannose, sucrose, human serum albumin (HSA), PlasmaLyte®, DMSO, Cryostor® CS2, Cryostor® CS5, Cryostor® CS10, Cryostor® CS15, HEPES, glycerol, glutathione, HypoThermosol®.

In some embodiments, the modified immune cells are further modified to increase expression of one or more of co-stimulatory molecules. In further embodiments, the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the cell comprises a nucleic acid that results in increased expression of the one or more co-stimulatory molecules.

In some embodiments, the immune cell is a T cell, a dendritic cell, a monocyte, a macrophage, a myeloid cell, a granulocyte, a neutrophil, a mast cell, a natural killer cell, an innate lymphoid cell, a basophil, or a hematopoetic precursor cell. In some embodiments, the immune cell is not a B cell. In some embodiments, the immune cell is a T cell. In some embodiments, the immune cell other than a B cell. In some embodiments, the modified T cell includes one or more of helper T cells, cytotoxic T cells, memory T cells, CIK cells, or natural killer T cells. In some embodiments, the T cell includes one or more of CD3+ T cells, CD4+ T cells, CD8+ T cells, CD45RA+ T cells, CD45RO+ T cells, and γδ-T cells. MHC expression in allogeneic T cells can result in an innate immune response mounted in an individual in response to their administrations, and will result in a shortened half-life of such T cells. In some embodiments, the T cell comprises a further modification to modulate MHC class I expression. In some embodiments, the T cell comprises a further modification to modulate MHC class II expression. In some embodiments, the T cell comprises a further modification to reduce MHC class I and/or MHC class II expression. In particular embodiments, the further modification comprises reducing MHC class I and/or MHC class II expression using siRNA, shRNA, CRISPR/Cas9, ZFN, TALEN, Cre recombinase or a mega nuclease. In some embodiments, the T cell comprises a further modification to increase MHC class I and/or MHC class II expression. In particular embodiments, the further modification comprises increasing MHC class I and/or MHC class II expression using mRNA, plasmid DNA, or cDNA. In some embodiments, an innate immune response mounted in an individual in response to administration, in an allogeneic context, of the further modified T cells is reduced compared to an innate immune response mounted in an individual in response to administration, in an allogeneic context, of corresponding modified T cells that do not comprise the further modification. In some embodiments, the circulating half-life of the further modified T cells in an individual to which they were administered is increased compared to the circulating half-life of corresponding modified T cells that do not comprise the further modification in an individual to which they were administered. In some embodiments, the modified T cell includes one or more of helper T cells, cytotoxic T cells, memory T cells, CIK cells, or natural killer T cells. In some embodiments, the T cell includes one or more of CD3+ T cells, CD4+ T cells, CD8+ T cells, CD45RA+ T cells, CD45RO+ T cells, or γδ-T cells.

Immune cells and other cells can be used as a source of autologous or allogeneic cells. In some embodiments, the modified immune cell is allogeneic to the individual. In other embodiments, the modified immune cell is autologous to the individual. In some embodiments, the individual to be treated is pre-conditioned to modulate inflammation.

Adjuvants can be employed to further enhance the immune response to HPV antigens. In some embodiments, the method for treating further comprises administering to the individual an adjuvant. Exemplary adjuvant includes, without limitation, IFN-α, CpG ODN, STING agonists, RIG-I agonists and polyI:C. In some embodiments, the adjuvant is IFN-α or CpG ODN. In some embodiments, the adjuvant is IFN-α, CpG ODN, STING agonists, RIG-I agonists or polyI:C. In some embodiments, the adjuvant comprises any combination of IFN-α, CpG ODN, STING agonists, RIG-I agonists or polyI:C.

In some embodiments, the method comprises multiple administrations of the modified immune cells. In some embodiments, the method comprises about 3 to about 9 administrations of the modified immune cells. In some embodiments, the method comprises about any one of 1, 2, 3, 4, 5, 6, 7, 8, 9, 10, 11, 12, 13, 14 or 15 administrations of the modified immune cells. In some embodiments, the method comprises continuous administrations of the modified immune cells as needed. In some embodiments, the time interval between two successive administrations of modified immune cells is between about 1 day and about 30 days. In some embodiments, the time interval between two successive administrations of the modified immune cells is about 21 days. In some embodiments, the time the time interval between two successive administrations of the modified immune cells is about any one of 1, 2, 3, 4, 5, 6, 7, 8, 10, 12, 14, 16, 20, 25, 30, 35, 40, 45, 50, 55, 60, 65, 70, 75, 80, 85, 90, 95, 100, or 150 days. In some embodiments, the modified immune cells are a plurality of modified PBMCs. In some embodiments, the modified immune cells are a conditioned plurality of modified PBMCs. Methods to condition PBMCs is provided by U.S. Provisional Application No.

62/812,225 and European Patent Application No. EP 19161964.2, which are hereby incorporated by reference in their entireties.

In some embodiments, the composition comprising the modified immune cells and the adjuvant are administered simultaneously. In some embodiments, the composition comprising the modified immune cells and the adjuvant are administered sequentially.

In some embodiments, the composition comprising the modified immune cells is administered prior to administering the adjuvant. For example, the composition comprising the modified immune cells is administered from about 1 hour to about 1 week prior to administration of the adjuvant. For example, in some embodiments, the composition comprising the modified immune cells is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the adjuvant. In some embodiments, the composition comprising the modified immune cells is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the adjuvant.

In some embodiments, the composition comprising the modified immune cells is administered following administration of the adjuvant. For example, the composition comprising the modified immune cells is administered from about 1 hour to about 1 week following administration of the adjuvant. For example, in some embodiments, the composition comprising the modified immune cells is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the adjuvant. In some embodiments, the composition comprising the modified immune cells is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the adjuvant.

Immune checkpoints are regulators of the immune system and keep immune responses in check. Immune checkpoint inhibitors can be employed to facilitate the enhancement of immune response. In some embodiments, the composition comprising the modified immune cells is administered in combination with administration of an immune checkpoint inhibitor. In some embodiments, the composition comprising the modified immune cells and the immune checkpoint inhibitor are administered simultaneously. In some embodiments, the composition comprising the modified immune cells and the immune checkpoint inhibitor are administered sequentially.

In some embodiments, the composition comprising the modified immune cells is administered prior to administration of the immune checkpoint inhibitor. In some embodiments, the composition comprising the modified immune cells is administered following administration of the immune checkpoint inhibitor. For example, the composition comprising the modified immune cells is administered from about 1 hour to about 1 week prior to administration of the immune checkpoint inhibitor. For example, in some embodiments, the composition comprising the modified immune cells is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the immune checkpoint inhibitor. In some embodiments, the composition comprising the modified immune cells is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the immune checkpoint inhibitor.

In some embodiments, the composition comprising the modified immune cells is administered following administration of the immune checkpoint inhibitor. For example, the composition comprising the modified immune cells is administered from about 1 hour to about 1 week following administration of the immune checkpoint inhibitor. For example, in some embodiments, the composition comprising the modified immune cells is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the immune checkpoint inhibitor. In some embodiments, the composition comprising the modified immune cells is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the immune checkpoint inhibitor.

In some embodiments, the method comprises multiple administration of the composition comprising the modified immune cells and/or multiple administration of the checkpoint inhibitor. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the modified immune cells and/or the checkpoint inhibitor. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the modified immune cells and/or the checkpoint inhibitor.

Exemplary immune checkpoint inhibitor is targeted to, without limitation, PD-1, PD-L1, CTLA-4, LAG3 or TIM-3. In some embodiments, the immune checkpoint inhibitor is targeted to one or more of PD-1, PD-L1, CTLA-4, LAG3 or TIM-3. In some embodiments, the immune checkpoint inhibitor is one or more of: an antibody that binds to PD-1, an antibody that binds PD-L1, an antibody that binds CTLA-4, an antibody that binds LAG3, or an antibody that binds TIM-3. In further embodiments, the antibody can be a full length antibody or any variants, for example but not limited to, an antibody fragment, a single chain variable fragment (ScFv), or a fragment antigen-binding (Fab). In further embodiments, the antibody can be bispecific, trispecific or multispecific. In some embodiments, the immune checkpoint inhibitor is one or more chemical compounds that binds to and/or inhibits one or more of PD-1, PD-L1, CTLA-4, LAG3 or TIM-3. In some embodiments, the immune checkpoint inhibitor is one or more peptides that binds to and/or inhibits one or more of PD-1, PD-L1, CTLA-4, LAG3 or TIM-3.

Other exemplary immune checkpoint inhibitor is targeted to, without limitation, TIGIT, VISTA, TIM1, B7-H4 (VTCN1) or BTLA. In some embodiments, the immune checkpoint inhibitor is targeted to one or more of TIGIT, VISTA, TIM1, B7-H4 (VTCN1) or BTLA. In some embodiments, the immune checkpoint inhibitor is one or more of: an antibody that binds to TIGIT, an antibody that binds VISTA, an antibody that binds TIM1, an antibody that binds B7-H4 (VTCN1) or an antibody that binds BTLA. In further embodiments, the antibody can be a full length antibody or any variants, for example but not limited to, an antibody fragment, a single chain variable fragment (ScFv), or a fragment antigen-binding (Fab). In further embodiments, the antibody can be bispecific, trispecific or multispecific. In some embodiments, the immune checkpoint inhibitor is one or more chemical compounds that binds to and/or inhibits one or more of PD-1, PD-L1, CTLA-4, LAG3, TIM-3, TIGIT, VISTA, TIM1, B7-H4 (VTCN1) or BTLA. In some embodiments, the immune checkpoint inhibitor is one or more peptides that binds to and/or inhibits one or more of PD-1, PD-L1, CTLA-4, LAG3, TIM-3, TIGIT, VISTA, TIM1, B7-H4 (VTCN1) or BTLA.

Chemotherapy or radiotherapy can be used in combination with any one of the modified immune cells described herein to achieve additive or synergistic effects against cancers, for example, HPV-associated cancers. In some embodiments, the composition comprising the modified immune cells is administered in combination with administration of a chemotherapy. In some embodiments, the composition comprising the modified immune cells and the chemotherapy are administered simultaneously. In some embodiments, the composition comprising the modified immune cells and the chemotherapy are administered sequentially.

In some embodiments, the composition comprising the modified immune cells is administered prior to administration of the chemotherapy. In some embodiments, the composition comprising the modified immune cells is administered following administration of the chemotherapy. For example, the composition comprising the modified immune cells is administered from about 1 hour to about 1 week prior to administration of the chemotherapy. For example, in some embodiments, the composition comprising the modified immune cells is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the chemotherapy. In some embodiments, the composition comprising the modified immune cells is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the chemotherapy.

In some embodiments, the composition comprising the modified immune cells is administered following administration of the chemotherapy. For example, the composition comprising the modified immune cells is administered from about 1 hour to about 1 week following administration of the chemotherapy. For example, in some embodiments, the composition comprising the modified immune cells is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the chemotherapy. In some embodiments, the composition comprising the modified immune cells is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the chemotherapy.

In some embodiments, the method comprises multiple administration of the composition comprising the modified immune cells and/or multiple administration of the chemotherapy. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the modified immune cells and/or the chemotherapy. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the modified immune cells and/or the chemotherapy.

Exemplary chemotherapy can be cell cycle dependent or cell cycle independent. In some embodiments, the chemotherapy comprises one or more chemotherapeutic agents. In some embodiments, a chemotherapeutic agent can target one or more of cell division, DNA, or metabolism in cancer. In some embodiments, the chemotherapeutic agent is a platinum-based agent, such as but not limited to cisplatin, oxaliplatin or carboplatin. In some embodiments, the chemotherapeutic agent is a taxane (such as docetaxel or paclitaxel). In some embodiments, the chemotherapeutic agent is 5-fluorouracil, doxorubicin, or irinotecan. In some embodiments, the chemotherapeutic agent is one or more of: an alkylating agent, an antimetabolite, an antitumor antibiotic, a topoisomerase inhibitor or a mitotic inhibitor. In some embodiments, the chemotherapy comprises cisplatin. In some embodiments, one or more of chemotherapies or immune checkpoint inhibitors can be combined with any one of the modified immune cells described herein for treating or preventing a HPV-associated disease.

Radiotherapy can be used in combination with any one of the modified T cells described herein to achieve additive or synergistic effects against cancers, for example, HPV-associated cancers. In some embodiments, the composition comprising the modified T cells is administered in combination with administration of a radiotherapy. In some embodiments, the composition comprising the modified T cells and the radiotherapy are administered simultaneously. In some embodiments, the composition comprising the modified T cells and the radiotherapy are administered sequentially. In some embodiments, the composition comprising the modified T cells is administered in combination with administration of a radiotherapy, in combination with a chemotherapy, and/or in combination with an immune checkpoint inhibitor.

In some embodiments, the composition comprising the modified T cells is administered prior to administration of the radiotherapy. In some embodiments, the composition comprising the modified T cells is administered following administration of the radiotherapy. For example, the composition comprising the modified T cells is administered from about 1 hour to about 1 week prior to administration of the radiotherapy. For example, in some embodiments, the composition comprising the modified T cells is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the radiotherapy. In some embodiments, the composition comprising the modified T cells is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the radiotherapy.

In some embodiments, the composition comprising the modified T cells is administered following administration of the radiotherapy. For example, the composition comprising the modified T cells is administered from about 1 hour to about 1 week following administration of the radiotherapy. For example, in some embodiments, the composition comprising the modified T cells is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the radiotherapy. In some embodiments, the composition comprising the modified T cells is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the radiotherapy.

In some embodiments, the method comprises multiple administration of the composition comprising the modified T cells and/or multiple administration of the radiotherapy. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the modified T cells and/or the radiotherapy. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the modified T cells and/or the radiotherapy.

When HPV antigens are processed and presented on MHC to immune cells, an immune response against the presented HPV epitope can be triggered or enhanced. In some embodiments, the HPV antigen is capable of being processed into an MHC class I-restricted peptide. In some embodiments, the HPV antigen is capable of being processed into an MHC class II-restricted peptide. In some embodiments, the immune response is enhanced. In further embodiments, the immune response to the HPV antigen is enhanced. In some embodiments, administration of the composition comprising the modified immune cells to the individual results in activation and/or expansion of cytotoxic T lymphocytes (CTLs) specific for the HPV antigen. In some embodiments, administration of the composition comprising the modified immune cells to the individual results in activation and/or expansion of helper T ($T_h$) cells specific for the antigen.

In some embodiments, the effective amount of the composition comprises between about $1\times10^6$ and about $1\times10^{12}$ modified immune cells. In some embodiments, the effective amount of the composition comprises any of about $1\times10^6$, about $1\times10^7$, about $1\times10^8$, about $1\times10^9$, about $1\times10^{10}$, about $1\times10^{11}$, or about $1\times10^{12}$ modified immune cells. In some embodiments, the effective amount of the composition comprises any of between about $1\times10^6$ to about $1\times10^7$, between about $1\times10^7$ to about $1\times10^8$, between about $1\times10^8$ to about $1\times10^9$, between about $1\times10^9$ to about $1\times10^{10}$, between about $1\times10^{10}$ to about $1\times10^{11}$, or between about $1\times10^{11}$ to about $1\times10^{12}$ modified immune cells.

In some embodiments, the method comprises multiple administrations of the composition comprising the modified immune cells. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the modified immune cells. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the modified immune cells. For example, in some embodiments, the method comprises a first administration of the composition comprising the modified immune cells followed by a second administration of the composition comprising the modified immune cells. The timing of the administration can also be modified to achieve desired results. In some embodiments, the first administration of the composition to the individual occurs before second administration of the composition. In some embodiments, the first administration is introduced to the individual more than any of about 1 week, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, about 12 months, about 18 months, or about 24 months before introduction of the second administration.

In some embodiments, the method comprises multiple administrations of the modified T cell. In some embodiments, the method comprises any of about 2, 3, 4, 5, 6, 7, 8, 9, 10, or more than about 10 administrations. In some embodiments, the time interval between two successive administrations of the modified T cell is between about 1 day and about 1 month. In some embodiments, the administration is daily, every 2 days, every 3 days, every 4 days, every 5 days, every 6 days, weekly, biweekly, or monthly. In some embodiments, successive administrations are given for up to one year or more.

In certain aspects, the composition comprising modified cells can be used to treat, prevent an HPV-associated disease, and/or modulate an immune response in an individual with an HPV-associated disease. In some embodiments, the HPV-associated disease is an HPV-associated cancer. In some embodiments, the HPV-associated cancer is cervical disease, anal disease, oropharyngeal disease, vaginal disease, vulvar disease, penile disease, skin disease, or head and heck disease. In some embodiments, the HPV-associated disease is an HPV-associated infectious disease. Other HPV-associated diseases can include common warts, plantar warts, flat warts, anogenital warts, anal lesions, epidermodysplasia, focal epithelial hyperplasia, mouth papillomas, verrucous cyst and laryngeal papillomatosis.

In some aspects, the disclosure relates to the use of modified immune cells for treating an HPV-associated disease, wherein the modified immune cells comprise intracellularly an HPV antigen and intracellularly an adjuvant. In some aspects, the disclosure relates to the use of modified immune cells for treating an HPV-associated disease, the method comprising administering to the individual an effective amount of a composition comprising modified immune cells, wherein the modified immune cells comprise intracellularly an HPV antigen and intracellularly an adjuvant; wherein the modified immune cells are prepared by a) passing a cell suspension comprising an input cell through a cell-deforming constriction, wherein a diameter of the constriction is a function of a diameter of the input cell in the suspension, such that a deforming force is applied to the input cell as it passes through the constriction, thereby causing perturbations of the input cell large enough for the HPV antigen and the adjuvant to pass through to form a perturbed input cell; and b) incubating the perturbed input cell with the HPV antigen and the adjuvant for a sufficient time to allow the HPV antigen and the adjuvant to enter the perturbed input cell; thereby generating the modified immune cells.

In some aspects, the disclosure relates to a composition comprising modified immune cells for the manufacture of a medicament used for treating an HPV-associated disease, wherein the modified immune cells comprise intracellularly an HPV antigen and intracellularly an adjuvant. In some aspects, the disclosure relates to a composition comprising modified immune cells for the manufacture of a medicament used for treating an HPV-associated disease, the method comprising administering to the individual an effective amount of a composition comprising modified immune cells, wherein the modified immune cells comprise intracellularly an HPV antigen and intracellularly an adjuvant; wherein the modified immune cells are prepared by a) passing a cell suspension comprising an input cell through a cell-deforming constriction, wherein a diameter of the constriction is a function of a diameter of the input cell in the suspension, such that a deforming force is applied to the input cell as it passes through the constriction, thereby causing perturbations of the input cell large enough for the HPV antigen and the adjuvant to pass through to form a perturbed input cell; and b) incubating the perturbed input cell with the HPV antigen and the adjuvant for a sufficient time to allow the HPV antigen and the adjuvant to enter the perturbed input cell; thereby generating the modified immune cells.

In some aspects, the disclosure relates to a composition comprising modified immune cells for use in a method of medical treatment, wherein the modified immune cells comprise intracellularly an HPV antigen and intracellularly an adjuvant. In some aspects, the disclosure relates to a composition comprising modified immune cells for use in a method of medical treatment, the method comprising administering to the individual an effective amount of a composition comprising modified immune cells, wherein the modified immune cells comprise intracellularly an HPV antigen and intracellularly an adjuvant; wherein the modified immune cells are prepared by a) passing a cell suspension comprising an input cell through a cell-deforming constriction, wherein a diameter of the constriction is a function of a diameter of the input cell in the suspension, such that a deforming force is applied to the input cell as it passes through the constriction, thereby causing perturbations of the input cell large enough for the HPV antigen and the adjuvant to pass through to form a perturbed input cell; and b) incubating the perturbed input cell with the HPV antigen and the adjuvant for a sufficient time to allow the HPV antigen and the adjuvant to enter the perturbed input cell; thereby generating the modified immune cells.

In some aspects, the disclosure relates to a composition comprising modified immune cells for use in a method of treating cancer, an infectious disease or a viral-associated disease, wherein the modified immune cells comprise intracellularly an HPV antigen and intracellularly an adjuvant. In some aspects, the disclosure relates to a composition comprising modified immune cells for use in treating an HPV-associated disease, the method comprising administering to the individual an effective amount of a composition comprising modified immune cells, wherein the modified immune cells comprise intracellularly an HPV antigen and intracellularly an adjuvant; wherein the modified immune cells are prepared by a) passing a cell suspension comprising an input cell through a cell-deforming constriction, wherein a diameter of the constriction is a function of a diameter of the input cell in the suspension, such that a deforming force is applied to the input cell as it passes through the constriction, thereby causing perturbations of the input cell large enough for the HPV antigen and the adjuvant to pass through to form a perturbed input cell; and b) incubating the perturbed input cell with the HPV antigen and the adjuvant for a sufficient time to allow the HPV antigen and the adjuvant to enter the perturbed input cell; thereby generating the modified immune cells.

In some aspects, this disclosure relates to a method for treating or preventing an HPV-associated disease in an individual comprising administering to the individual a modified immune cell associated with an HPV antigen, wherein the modified immune cell is prepared by a process comprising the steps of: a) incubating an input cell with the HPV antigen and/or an adjuvant for a sufficient time to allow the HPV antigen to associate with the cell surface of the input cell; thereby generating the modified immune cell associated with the antigen.

In some embodiments, the modified immune cells of the invention do not induce tolerance in an individual. In some embodiments, the modified immune cells do not suppress an immune response in an individual. In some embodiments, the modified immune cells do not comprise a tolerogenic factor. In some embodiments, the modified immune cells are not administered in combination with a tolerogenic factor. In some embodiments, the modified immune cells are not administered before, simultaneous with, or after administration of a tolerogenic factor.

Compositions

In certain aspects, the invention provides a composition comprising modified immune cells, wherein the modified immune cells comprise intracellular HPV antigen and an intracellular CpG ODN. In other aspects, the disclosure relates to a composition comprising modified immune cells, wherein the modified immune cells comprise intracellularly an HPV antigen, wherein the HPV antigen comprises an amino acid sequence with at least 90% similarity to any one of SEQ ID NOs:18-26. In some embodiments, the HPV antigen comprises t an amino acid sequence with at least 90% similarity to SEQ ID NO:23. In some embodiments, the HPV antigen comprises the amino acid sequence of SEQ ID NO:23. In some embodiments, the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the HPV antigen to pass through to form a perturbed input cell; and b) incubating the perturbed input cell with the HPV antigen for a sufficient time to allow the HPV antigen to enter the perturbed input cell; thereby generating the modified immune cells. In further embodiments, a deforming force is applied to the input cell as it passes through the constriction. In some embodiments, the composition further comprises intracellularly an adjuvant.

In some embodiments, the HPV antigen and/or the adjuvant are present in the cytosol or endosomes. In some embodiments, the antigen and/or adjuvant are present in multiple compartments of the cell. In further embodiments, the antigen and/or adjuvant are present in compartments of the cell comprising the endoplasmic recticulum (ER), Golgi apparatus, lysosome, exosomes, cell surface or cell membrane. In some embodiments, the antigen and the adjuvant are in the same compartment. In some embodiments, the antigen and adjuvant are in different compartments from each other. For example, in some embodiments, the antigen is present in the cytosol whereas the adjuvant is present in the endosome. In some embodiments, the modified immune cell further comprises an HPV antigen and/or an adjuvant on the outside of the cell.

In some embodiments, the antigen is a polypeptide antigen. In some embodiments, the antigen is a modified antigen. For example, antigens may be fused with therapeutic agents or targeting peptides. In some embodiments, the modified antigen is fused with a polypeptide. In some embodiments, the antigen is modified with a lipid. In some embodiments, the antigen is modified with a polysaccharide or a carbohydrate moiety. In some embodiments, the antigen is associated with a virus. In some embodiments, the antigen is a viral antigen. Exemplary viral antigens include HPV antigens. In further embodiments, the antigen is an HPV antigen. In some embodiments, the HPV antigen consists of a selection from the group of: HPV-16, 18, 26, 31, 33, 35, 39, 45, 51, 52, 53, 56, 58, 59, 66, 68, 73, and 82. HPV-16, 18, 31, 33, 35, 39, 45, 51, 52, 56, 58, 59, 68, 73, and 82 are high risk types in causing cancer whereas HPV-26, 53, and 66 are "probably high risk types" in causing cancer. In some embodiments, the antigen is an HPV-16 antigen or an HPV-18 antigen. In some embodiments, the HPV antigen is comprised of an HLA-A2 specific epitope. HPV E6 and E7 genes are the oncogenes of the virus and expression of these genes is required for malignant transformation. The E6 and E7 proteins target a number of negative regulators of the cell cycle, primarily p105Rb and p53, respectively, and thus interfere with cell-cycle regulation. In further embodiments, the HPV antigen is an HPV E6 antigen or an HPV E7 antigen. In some embodiments, the modified immune cells comprise an HPV E6 antigen and an HPV E7 antigen. In some embodiments, the HPV antigen is a polypeptide comprising an immunogenic epitope that is flanked on the N-terminus and/or the C-terminus by one or more heterologous peptide sequences. In some embodiments, the HPV antigen is an HPV E7 epitope flanked by sequences from the HPV E6 polypeptide. In some embodiments, the HPV antigen comprises an amino acid with at least 90% similarity to any one of SEQ ID NOs:18-26. In some embodiments, the HPV antigen comprises the amino acid sequence of SEQ ID NO:23.

An adjuvant, when added to an immunogenic agent, nonspecifically enhances or potentiates an immune response to the agent in the recipient host upon exposure to the mixture. Therefore, adjuvants can be used to boost elicitation of an immune cell response (e.g. T cell response) to an antigen. In some embodiments, the perturbed cells are incubated with both the HPV antigen and an adjuvant. Exemplary intracellular adjuvants include, without limitation, CpG ODN, Interferon-α (IFN-α), stimulator of interferon genes (STING) agonists, retinoic acid-inducible gene I (RIG-I) agonists and polyinosinic:polycytidylic acid (polyI:C.). In some embodiments, the adjuvant is CpG ODN, IFN-α, STING agonists, RIG-I agonists or polyI:C. In particular embodiments, the adjuvant is a CpG ODN polynucleotide. In some embodiments, the CpG ODN adjuvant comprise of a selection from the group of CpG ODN 1585, CpG ODN2216, CpG ODN 2336, CpG ODN 1668, CpG ODN 1826, CPG ODN 2006, CpG ODN 2007, CpG ODN BW006, CpG ODN D-SL01, CpG ODN 2395, CpG ODN M362, CpG ODN D-SL03 (InvivoGen). In some embodiments, the CpG ODN adjuvant is CpG ODN 1826 (TC-CATGACGTTCCTGACGTT; SEQ ID NO:30) or CpG ODN 2006 (also known as CpG ODN 7909) (TCGTCGTTTTGTCGTTTTGTCGTT; SEQ ID NO:31) oligonucleotide. Multiple adjuvants can also be used in conjunction with antigens to enhance the elicitation of immune response. In some embodiments, the modified immune cell comprises more than one adjuvant. In some embodiments, the modified immune cell comprises any combination of the adjuvants CpG ODN, IFN-α, STING agonists, RIG-I agonists and polyI:C.

In some embodiments, the modified immune cell comprises the adjuvant at a concentration between about 0.01 μM and about 10 mM. For example, in some embodiments, the modified immune cell comprises the adjuvant at a concentration of any of less than about 0.01 μM, about 0.1 μM, about 1 μM, about 10 μM, about 100 μM, about 1 mM or about 10 mM. In some embodiments, the modified immune cell comprises the adjuvant at a concentration of more than about 10 mM. In some embodiments, the modified immune cell comprises the adjuvant at a concentration of less than any of about 0.01 μM, about 0.1 μM, about 1 μM, about about 100 μM, about 1 mM or about 10 mM. In some embodiments, the modified immune cell comprises the adjuvant at a concentration of more than any of about 10 mM. In some embodiments, the modified immune cell comprises the adjuvant at a concentration any of between about 0.1 μM and about 1 μM, between about 1 μM and about 10 μM, between about 10 μM and about 100 μM, between about 100 μM and about 1 mM, or between 1 mM and about 10 mM.

In some embodiments, the modified immune cell comprises the HPV antigen at a concentration between about 0.01 μM and about 10 mM. For example, in some embodiments, the modified immune cell comprises the adjuvant at a concentration of any of less than about 0.01 μM, about 0.1 μM, about 1 μM, about 10 μM, about 100 μM, about 1 mM or about 10 mM. In some embodiments, the modified immune cell comprises the adjuvant at a concentration of more than about 10 mM. In some embodiments, the modified immune cell comprises the HPV antigen at a concentration of less than any of about 0.01 μM, about 0.1 μM, about 1 μM, about about 100 μM, about 1 mM or about 10 mM. In some embodiments, the modified immune cell comprises the adjuvant at a concentration of more than any of about 10 mM. In some embodiments, the modified immune cell comprises the HPV antigen at a concentration any of between about 0.1 μM and about 1 between about 1 μM and about 10 μM, between about 10 μM and about 100 μM, between about 100 μM and about 1 mM, or between 1 mM and about 10 mM.

In some embodiments, the ratio of the HPV antigen to the adjuvant is between about 10000:1 to about 1:10000. For example, in some embodiments, the ratio of HPV antigen to the adjuvant is any of about 10000:1, about 1000:1, about 200:1, about 100:1, about 10:1, about 1:1, about 1:10, about 1:100, about 1:1000, or about 1:10000. In some embodiments, the ratio of HPV antigen to the adjuvant between about 10000:1 and about 1000:1, between about 1000:1 and about 100:1, between about 100:1 and about 10:1, between about 10:1 and about 1:1, between about 1:1 and about 1:10, between about 1:10 and about 1:100, between about 1:100 and about 1:1000, between about 1:1000 and about 1:10000.

In some embodiments, the modified immune cell further comprises an agent that enhances the viability and/or function of the modified immune cell as compared to a corresponding modified immune cell that does not comprise the agent. In some embodiments, the agent is a compound that enhances endocytosis, a stabilizing agent or a co-factor. In some embodiments, the stabilizing agent is complexed to the HPV antigen and/or the adjuvant. In some embodiments, the stabilizing agent increases the solubility and/or solution half-life of the HPV antigen and/or the adjuvant. In some embodiments, the plurality of modified immune cells have greater viability than corresponding modified immune cells that do not comprise the stabilizing agent. In some embodiments, the agent is albumin. In further embodiments, the albumin is mouse, bovine, or human albumin. In further embodiments, the agent is a divalent metal cation, glucose, ATP, potassium, glycerol, trehalose, D-sucrose, PEG1500, L-arginine, L-glutamine, or EDTA. In some embodiments, the divalent metal cation is one more of $Mg^{2+}$, $Zn^{2+}$ or $Ca^{2+}$. In some embodiments, the agent comprises MSA.

In some embodiments according to any one of the methods or compositions described herein, the modified immune cell further comprises an agent that enhances the viability and/or function of the modified immune cell as compared to a corresponding plurality of the modified immune cell that does not comprise the agent. In some embodiments, the modified immune cell further comprises an agent that enhances the viability and/or function of the modified immune cell upon freeze-thaw cycle as compared to a corresponding the modified immune cell that does not comprise the agent. In some embodiments, the agent is a cyropreservation agent and/or a hypothermic preservation agent. In some embodiments, the cyropreservation agent nor the hypothermic preservation agent cause not more than 10% or 20% of cell death in a the modified immune cell comprising the agent compared to a corresponding the modified immune cell that does not comprise the agent before any freeze-thaw cycles. In some embodiments, at least about 70%, about 80%, or about 90% of the modified immune cells are viable after up to 1, 2, 3, 4, 5 freeze-thaw cycles. In some embodiments, the agent is a compound that enhances endocytosis, a stabilizing agent or a co-factor. In some embodiments, the agent is albumin. In some embodiments, the albumin is mouse, bovine, or human albumin. In some embodiments, the agent is human albumin. In some embodiments, the agent is one or more of: a divalent metal cation, glucose, ATP, potassium, glycerol, trehalose, D-sucrose, PEG1500, L-arginine, L-glutamine, or EDTA. In some embodiments, the divalent metal cation is one more of $Mg^{2+}$, $Zn^{2+}$ or $Ca^{2+}$. In some embodiments, the agent is one or more of: sodium pyruvate, adenine, trehalose, dextrose, mannose, sucrose, human serum albumin (HSA), DMSO, HEPES, glycerol, glutathione, inosine, dibasic sodium phosphate, monobasic sodium phosphate, sodium metal ions, potassium metal ions, magnesium metal ions, chloride, acetate, gluoconate, sucrose, potassium hydroxide, or sodium hydroxide. In some embodiments, the agent is one or more of: Sodium pyruvate, adenine, Rejuvesol®, trehalose, dextrose, mannose, sucrose, human serum albumin (HSA), PlasmaLyte®, DMSO, Cryostor® CS2, Cryostor® CS5, Cryostor® CS10, Cryostor® CS15, HEPES, glycerol, glutathione, HypoThermosol®.

In some embodiments, the modified immune cells are further modified to increase expression of one or more of co-stimulatory molecules. In further embodiments, the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the cell comprises a nucleic acid that results in increased expression of the one or more co-stimulatory molecules.

In some embodiments, the immune cell is a T cell, a dendritic cell, a monocyte, a macrophage, a myeloid cell, a granulocyte, a neutrophil, a mast cell, a natural killer cell, an innate lymphoid cell, a basophil, or a hematopoetic precursor cell. In some embodiments, the immune cell is not a B cell. In some embodiments, the immune cell is a T cell. In some embodiments, the immune cell other than a B cell. In some embodiments, the modified T cell includes one or more of helper T cells, cytotoxic T cells, memory T cells, CIK cells, or natural killer T cells. In some embodiments, the T cell includes one or more of CD3+ T cells, CD4+ T cells, CD8+ T cells, CD45RA+ T cells, CD45RO+ T cells, and γδ-T cells. MHC expression in allogeneic T cells can result in an innate immune response mounted in an individual in response to their administrations, and will result in a shortened half-life of such T cells. In some embodiments, the T cell comprises a further modification to modulate MHC class I expression. In some embodiments, the T cell comprises a further modification to modulate MHC class II expression. In some embodiments, the T cell comprises a further modification to reduce MHC class I and/or MHC class II expression. In particular embodiments, the further modification comprises reducing MHC class I and/or MHC class II expression using siRNA, shRNA, CRISPR/Cas9, ZFN, TALEN, Cre recombinase or a mega nuclease. In some embodiments, the T cell comprises a further modification to increase MHC class I and/or MHC class II expression. In particular embodiments, the further modification comprises increasing MHC class I and/or MHC class II expression using mRNA, plasmid DNA, or cDNA. In some embodiments, an innate immune response mounted in an individual in response to administration, in an allogeneic context, of the further modified T cells is reduced compared to an innate immune response mounted in an individual in response to administration, in an allogeneic context, of corresponding modified T cells that do not comprise the further modification. In some embodiments, the circulating half-life of the further modified T cells in an individual to which they were administered is increased compared to the circulating half-life of corresponding modified T cells that do not comprise the further modification in an individual to which they were administered. In some embodiments, the modified T cell includes one or more of helper T cells, cytotoxic T cells, memory T cells, CIK cells, or natural killer T cells. In some embodiments, the T cell includes one or more of CD3+ T cells, CD4+ T cells, CD8+ T cells, CD45RA+ T cells, CD45RO+ T cells, or γδ-T cells.

Immune cells and other cells can be used as a source of autologous or allogeneic cells. In some embodiments, the modified immune cell is allogeneic to the individual. In other embodiments, the modified immune cell is autologous to the individual. In some embodiments, the individual to be treated is pre-conditioned to have decreased inflammation or a modulated immune response.

PBMC Composition

As used herein, PBMCs may be isolated by leukapheresis from whole blood obtained from an individual. Also provided are PBMC compositions are reconstituted by mixing different pools of PBMCs from the same individual or different individuals. In other examples, PBMCs may also be reconstituted by mixing different populations of cells into a mixed cell composition with a generated profile. In some embodiments, the populations of cells used for reconstituting PBMCs are mixed populations of cells (such as a mixture of one or more of T cells, B cells, NK cells or monocytes). In some embodiments, the populations of cells used for reconstituting PBMCs are purified populations of cells (such as purified T cells, B cells, NK cells or monocytes). In additional examples, the different populations of cells used in reconstituting a PBMC composition can be isolated from the same individual (e.g. autologous) or isolated from different individuals (e.g. allogenic and/or heterologous).

Therefore in some embodiments according to any one of the methods or compositions described herein, wherein the immune cell is a plurality of PBMCs, the plurality of input PBMCs comprises one or more of T cells, B cells, NK cells, monocytes, dendritic cells or NK-T cells. In some embodiments, the plurality of input PBMCs comprises T cells, B cells, NK cells, monocytes, dendritic cells or NK-T cells. In some embodiments, the plurality of input PBMCs comprises one or more of CD3+ T cells, CD20+ B cells, CD14+ monocytes, CD56+ NK cells. In some embodiments, the plurality of input PBMCs comprises T cells, B cells, NK cells and monocytes, and the ratio of T cells, B cells, NK cells and monocytes to the total number of PBMCs in the plurality of input PBMCs is essentially the same as the ratio of T cells, B cells, NK cells and monocytes to the total number of PBMCs in whole blood. In some embodiments, the plurality of input PBMCs comprises T cells, B cells, NK cells and monocytes, and the ratio of T cells, B cells, NK cells and monocytes to the total number of PBMCs in the plurality of input PBMCs is essentially the same as the ratio of T cells, B cells, NK cells and monocytes to the total number of PBMCs in a leukapheresis product from whole blood. In some embodiments, the plurality of input PBMCs comprises T cells, B cells, NK cells and monocytes, and the ratio of T cells, B cells, NK cells and monocytes to the total number of PBMCs in the plurality of input PBMCs differs by not more than any one of 1%, 2%, 5%, 10% 15%, 20%, 25%, 30%, 40%, or 50% from the ratio of T cells, B cells, NK cells and monocytes to the total number of PBMCs in whole blood. In some embodiments, the plurality of input PBMCs comprises T cells, B cells, NK cells and monocytes, and the ratio of T cells, B cells, NK cells and monocytes to the total number of PBMCs in the plurality of input PBMCs differs by not more than any one of 10% from the ratio of T cells, B cells, NK cells and monocytes to the total number of PBMCs in whole blood. In some embodiments, the plurality of input PBMCs comprises T cells, B cells, NK cells and monocytes, and the ratio of T cells, B cells, NK cells and monocytes to the total number of PBMCs in the plurality of input PBMCs differs by not more than any one of 1%, 2%, 5%, 10% 15%, 20%, 25%, 30%, 40%, or 50% from the ratio of T cells, B cells, NK cells and monocytes to the total number of PBMCs in a leukapheresis product from whole blood. In some embodiments, the plurality of input PBMCs comprises T cells, B cells, NK cells and monocytes, and the ratio of T cells, B cells, NK cells and monocytes to the total number of PBMCs in the plurality of input PBMCs differs by not more than any one of 10% from the ratio of T cells, B cells, NK cells and monocytes to the total number of PBMCs in a leukapheresis product from whole blood.

In some embodiments according to any one of the methods or compositions described herein, wherein the immune cell is a plurality of PBMCs, about 25% to about 70% of the modified PBMCs are T cells. In some embodiments, about 2.5% to about 14% of the modified PBMCs are B cells. In some embodiments, about 3.5% to about 35% of the modified PBMCs are NK cells. In some embodiments, about 4% to about 25% of the modified PBMCs are NK cells. In some embodiments according to any one of the methods or compositions described herein, wherein the immune cell is a plurality of PBMCs, at least about 90% to about 99% of the input PBMCs consist of T cells, B cells, NK cells and monocytes. In some embodiments, at least any one of about 80% to about 85%, about 85% to about 90%, about 90% to about 95% or about 95% to about 99% of the input PBMCs consist of T cells, B cells, NK cells and monocytes. In some embodiments, at least about any one of 80%, 81%, 82%, 83%, 84%, 85%, 86%, 87%, 88%, 89%, 90%, 91%, 92%, 93%, 94%, 95%, 96%, 97%, 98%, or 99% of the input PBMCs consist of T cells, B cells, NK cells and monocytes. In some embodiments, at least about 90% of the input PBMCs consist of T cells, B cells, NK cells and monocytes. In some embodiments, the input PBMCs consist of T cells, B cells, NK cells and monocytes.

In some embodiments according to any one of the methods or compositions described herein, wherein the immune cell is a plurality of PBMCs, at least about 90% to about 99% of the modified PBMCs consist of T cells, B cells, NK cells and monocytes. In some embodiments, at least any one of about 80% to about 85%, about 85% to about 90%, about 90% to about 95% or about 95% to about 99% of the modified PBMCs consist of T cells, B cells, NK cells and monocytes. In some embodiments, at least about any one of 80%, 81%, 82%, 83%, 84%, 85%, 86%, 87%, 88%, 89%, 90%, 91%, 92%, 93%, 94%, 95%, 96%, 97%, 98%, or 99% of the modified PBMCs consist of T cells, B cells, NK cells and monocytes. In some embodiments, at least about 90% of the modified PBMCs consist of T cells, B cells, NK cells and monocytes. In some embodiments, the modified PBMCs consist of T cells, B cells, NK cells and monocytes.

In some embodiments according to any one of the methods or compositions described herein, wherein the immune cell is a plurality of PBMCs, at least about any one of 15%, 20%, 25%, 30%, 35%, 40%, 45%, 50%, 55%, 60%, 65%, 70%, or 75% of the input PBMCs are T cells. In some embodiments, at least about 25% of the input PBMCs are T cells. In some embodiments, at least about any one of 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25%, or 30% of the input PBMCs are B cells. In some embodiments, at least about 2.5% of the input PBMCs are B cells. In some embodiments, at least about any one of 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25%, or 30% of the input PBMCs are NK cells. In some embodiments, at least about 3.5% of the input PBMCs are NK cells. In some embodiments, at least about any one of 1%, 2%, 3%, 4%, 5%, 6%, 7%, 8%, 9%, 10%, 12%, 14%, 16%, 18%, 20%, 25%, 30%, 35% or 40% of the input PBMCs are monocytes. In some embodiments, at least about 4% of the input PBMCs are monocytes. In some embodiments, at least about 25% of the input PBMCs are T cells; at least about 2.5% of the input PBMCs are B cells; at least about 3.5% of the input PBMCs are NK cells; and at least about 4% of the input PBMCs are monocytes.

In some embodiments according to any one of the methods or compositions described herein, wherein the immune cell is a plurality of PBMCs, at least about any one of 10%, 15%, 20%, 25%, 30%, 35%, 40%, 45%, 50%, 55%, 60%, 65%, or 70% of the modified PBMCs are T cells. In some embodiments, at least about 20% of the modified PBMCs are T cells. In some embodiments, at least about any one of 0.25%, 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25% or 30% of the modified PBMCs are B cells. In some embodiments, at least about 2% of the modified PBMCs are B cells. In some embodiments, at least about any one of 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25%, or 30% of the modified PBMCs are NK cells. In some embodiments, at least about 3% of the modified PBMCs are NK cells. In some embodiments, at least about any one of 1%, 2%, 3%, 4%, 5%, 6%, 7%, 8%, 9%, 10%, 12%, 14%, 16%, 18%, 20%, 25%, 30%, 35% or 40% of the modified PBMCs are monocytes. In some embodiments, at least about 3% of the modified PBMCs are monocytes. In some embodiments, at least about 20% of the modified PBMCs are T cells; at least about 2% of the modified PBMCs are B cells; at least about 3% of the modified PBMCs are NK cells; and at least about 3% of the modified PBMCs are monocytes.

In some embodiments according to any one of the methods or compositions described herein, wherein the immune cell is a plurality of PBMCs, not more than about any one of 40%, 45%, 50%, 55%, 60%, 65%, 70%, 75%, 80%, 85%, or 90% of the input PBMCs are T cells. In some embodiments, not more than about 70% of the input PBMCs are T cells. In some embodiments, not more than about any one of 5%, 10%, 12%, 14%, 16%, 18%, 20%, 22%, 25%, 30%, 35%, 40%, or 50% of the input PBMCs are B cells. In some embodiments, not more than about 14% of the input PBMCs are B cells. In some embodiments, not more than about any one of 10%, 15%, 20%, 25%, 30%, 35%, 40%, 45%, 50% or 60% of the input PBMCs are NK cells. In some embodiments, not more than about 35% of the input PBMCs are NK cells. In some embodiments, not more than about any one of 5%, 10%, 12%, 14%, 16%, 18%, 20%, 22%, 25%, 30%, 35%, 40%, or 50% of the input PBMCs are monocytes. In some embodiments, not more than about 4% of the input PBMCs are monocytes. In some embodiments, not more than about 25% of the input PBMCs are T cells; not more than about 2.5% of the input PBMCs are B cells; not more than about 3.5% of the input PBMCs are NK cells; and not more than about 4% of the input PBMCs are monocytes.

In some embodiments according to any one of the methods or compositions described herein, wherein the immune cell is a plurality of PBMCs, not more than about any one of 10%, 15%, 20%, 25%, 30%, 35%, 40%, 45%, 50%, 55%, 60%, 65%, or 70% of the modified PBMCs are T cells. In some embodiments, not more than about 20% of the modified PBMCs are T cells. In some embodiments, not more than about any one of 0.25%, 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25% or 30% of the modified PBMCs are B cells. In some embodiments, not more than about 2% of the modified PBMCs are B cells. In some embodiments, not more than about any one of 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25%, or 30% of the modified PBMCs are NK cells. In some embodiments, not more than about 3% of the modified PBMCs are NK cells. In some embodiments, not more than about any one of 1%, 2%, 3%, 4%, 5%, 6%, 7%, 8%, 9%, 10%, 12%, 14%, 16%, 18%, 20%, 25%, 30%, 35% or 40% of the modified PBMCs are monocytes. In some embodiments, not more than about 3% of the modified PBMCs are monocytes. In some embodiments, not more than about 20% of the modified PBMCs are T cells; not more than about 2% of the modified PBMCs are B cells; not more than about 3% of the modified PBMCs are NK cells; and not more than about 3% of the modified PBMCs are monocytes.

In some embodiments according to any one of the methods or compositions described herein, wherein the immune cell is a plurality of PBMCs, about any one of 20% to 25%, 25% to 30%, 30% to 35%, 35% to 40%, 40% to 45%, 45% to 50%, 50% to 55%, 55% to 60%, 60% to 65%, 65% to 70%, or 70% to 75% of the modified PBMCs are T cells. In some embodiments, about 25% to about 70% of the modified PBMCs are T cells. In some embodiments, about any one of 1% to 2.5%, 2.5% to 4%, 4% to 6%, 6% to 8%, 8% to 10%, 10% to 12%, 12% to 14%, 14% to 16%, 16% to 20% or 20% to 25% of the modified PBMCs are B cells. In some embodiments, about 2.5% to about 14% of the modified PBMCs are B cells. In some embodiments, about any one of 1% to 2%, 2% to 3.5%, 3.5% to 5%, 5% to 8%, 8% to 10%, 10% to 12%, 12% to 14%, 14% to 16%, 16% to 20% or 20% to 25% of the modified PBMCs are B cells. In some embodiments, about 3.5% to about 35% of the modified PBMCs are NK cells. In some embodiments, about any one of 2% to 4%, 4% to 6%, 6% to 8%, 8% to 10%, 10% to 12%, 12% to 14%, 14% to 16%, 16% to 20%, 20% to 25%, 25% to 30%, 30% to 35%, or 35% to 40% of the modified PBMCs are monocytes. In some embodiments, about 4% to about 25% of the modified PBMCs are monocytes.

As used herein, PBMCs can also be generated after manipulating the composition of a mixed cell population of mononuclear blood cells (such as lymphocytes and monocytes). In some instances, the input PBMCs are generated after reducing (such as depleting) certain subpopulations (such as B cells) within a mixed cell population of mononuclear blood cells. The composition in a mixed cell population of mononuclear blood cells in an individual can be manipulated to make the cell population more closely resemble a leukapheresis product from whole blood in the same individual. In other examples, the composition in a mixed cell population of mononuclear blood cells (for example, mouse splenocytes) can also be manipulated to make the cell population more closely resemble human PBMCs isolated from a leukapheresis product from human whole blood.

In some embodiments, the construction-mediated delivery does not differentially modulate the viability of different subpopulations (such as B cells, T cells, NK cells or monocytes) within PBMCs in a significant manner. In some embodiments, the conditioning process does not differentially modulate the viability of different subpopulations within PBMCs in a significant manner. In some embodiments, the further addition of agents (including but not limited to any one of: biopreservation agents or agents that enhance the function and/or viability of PBMCs) does not differentially modulate the viability of various subpopulations within PBMCs in a significant manner. Therefore in some embodiments according to any one of the methods or compositions described herein, wherein the immune cell is a plurality of PBMCs, the percentage of T cells within the plurality of modified PBMCs and the percentage of T cells within the plurality of input PBMCs differ by no more than about 10% by number. In some embodiments, the percentage of T cells within the plurality of modified PBMCs and the percentage of T cells within the plurality of input PBMCs differ by no more than about any one of 5%, 8%, 10%, 12%, 14%, 16%, 18% or 20% by number. In some embodiments, the percentage of B cells within the plurality of modified PBMCs and the percentage of B cells within the plurality of input PBMCs differ by no more than about 10% by number. In some embodiments, the percentage of B cells within the plurality of modified PBMCs and the percentage of B cells within the plurality of input PBMCs differ by no more than about any one of 5%, 8%, 10%, 12%, 14%, 16%, 18% or 20% by number. In some embodiments, the percentage of NK cells within the plurality of modified PBMCs and the percentage of NK cells within the plurality of input PBMCs differ by no more than about 10% by number. In some embodiments, the percentage of NK cells within the plurality of modified PBMCs and the percentage of NK cells within the plurality of input PBMCs differ by no more than about any one of 5%, 8%, 10%, 12%, 14%, 16%, 18% or 20% by number. In some embodiments, the percentage of monocytes within the plurality of modified PBMCs and the percentage of monocytes within the plurality of input PBMCs differ by no more than about 10% by number. In some embodiments, the percentage of monocytes within the plurality of modified PBMCs and the percentage of monocytes within the plurality of input PBMCs differ by no more than about any one of 5%, 8%, 10%, 12%, 14%, 16%, 18% or 20% by number.

Conditioning of PBMCs

In some embodiments according to any one of methods or compositions described herein, wherein the immune cell is a plurality of PBMCs, the plurality of modified PBMCs is conditioned. In further embodiments, the plurality of modified PBMCs is matured. In some embodiments, the plurality of PBMCs is conditioned subsequent to constriction mediated delivery. Therefore in some embodiments, the process of preparing the plurality of modified PBMCs further comprises incubating the plurality of modified PBMCs comprising the antigen and/or adjuvant with a second adjuvant for a sufficient time for the modified PBMCs comprising the antigen to condition, thereby generating the conditioned plurality of modified PBMCs comprising the antigen and/or the adjuvant. In some embodiments, the process further comprises isolating the plurality of modified PBMCs comprising the antigen and/or the adjuvant from the cell suspension before incubation with the adjuvant to condition the modified PBMCs.

In some embodiments, the concentration of antigen incubated with the modified PBMCs is between about 0.01 μM and about 10 mM. For example, in some embodiments, the concentration of antigen incubated with the modified PBMCs is any of less than about 0.01 μM, about 0.1 μM, about 1 μM, about 10 μM, about 100 μM, about 1 mM or about 10 mM. In some embodiments, the concentration of antigen incubated with the modified PBMCs is greater than about 10 mM. In some embodiments, the concentration of antigen incubated with the modified PBMCs is any of between about 0.01 μM and about 0.1 μM, between about 0.1 μM and about 1 μM, between about 1 μM and about 10 μM, between about 10 μM and about 100 μM, between about 100 μM and about 1 mM, or between 1 mM and about 10 mM. In some embodiments, the concentration of antigen incubated with the modified PBMCs is between about 0.1 μM and about 1 mM. In some embodiments, the concentration of antigen incubated with the modified PBMCs is between about 0.1 μM and about 10 μM. In some embodiments, the concentration of antigen incubated with the modified PBMCs is 1 μM.

In some embodiments according to any one of methods or compositions described herein, wherein the immune cell is a plurality of PBMCs, the plurality of modified PBMCs is incubated with the adjuvant for about 1 to about 24 hours for the modified PBMCs to condition. In some embodiments, the plurality of modified PBMCs is incubated with the adjuvant for about 2 to about 10 hours for the modified PBMCs to condition. In some embodiments, the plurality of modified PBMCs is incubated with the adjuvant for about 3 to about 6 hours for the modified PBMCs to condition. In some embodiments, the plurality of modified PBMCs is incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the modified PBMCs to condition. In some embodiments, the plurality of modified PBMCs is incubated with the adjuvant for about 4 hours for the modified PBMCs to condition.

In some embodiments according to any one of methods or compositions described herein, wherein the immune cell is a plurality of PBMCs, the plurality of PBMCs is conditioned prior to constriction mediated delivery. Therefore in some embodiments, the process of preparing the plurality of modified PBMC further comprises incubating a plurality of input PBMCs with an adjuvant for a sufficient time for the input PBMCs to condition, thereby generating a conditioned plurality of input PBMCs. In some embodiments, there is provided a conditioned plurality of modified PBMCs comprising an antigen, prepared by a process comprising the steps of: a) incubating a plurality of input PBMCs with an adjuvant for a sufficient time for the input PBMCs to condition, thereby generating a conditioned plurality of input PBMCs; b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for the antigen to pass through to form a conditioned plurality of perturbed input PBMCs; and c) incubating the conditioned plurality of perturbed input PBMCs with the antigen for a sufficient time to allow the antigen to enter the perturbed input PBMCs, thereby generating the conditioned plurality of modified PBMCs comprising the antigen. In some embodiments, the process further comprises isolating the conditioned plurality of input PBMCs from the conditioning adjuvant before passing the conditioned plurality of input PBMCs through a cell-deforming constriction.

In some embodiments, the concentration of antigen incubated with the input PBMCs is between about 0.01 μM and about 10 mM. For example, in some embodiments, the concentration of antigen incubated with the input PBMCs is any of less than about 0.01 μM, about 0.1 μM, about 1 μM, about 10 μM, about 100 μM, about 1 mM or about 10 mM. In some embodiments, the concentration of antigen incubated with the input PBMCs is greater than about 10 mM. In some embodiments, the concentration of antigen incubated with the input PBMCs is any of between about 0.01 μM and about 0.1 between about 0.1 μM and about 1 μM, between about 1 μM and about 10 μM, between about 10 μM and about 100 μM, between about 100 μM and about 1 mM, or between 1 mM and about 10 mM. In some embodiments, the concentration of antigen incubated with the input PBMCs is between about 0.1 μM and about 1 mM. In some embodiments, the concentration of antigen incubated with the input PBMCs is between about 0.1 μM and about 10 μM. In some embodiments, the concentration of antigen incubated with the input PBMCs is 1 μM.

In some embodiments according to any one of methods or compositions described herein, wherein the immune cell is a plurality of PBMCs, the plurality of input PBMCs is incubated with the adjuvant for about 1 to about 24 hours for the input PBMCs to condition. In some embodiments, the plurality of input PBMCs is incubated with the adjuvant for about 2 to about 10 hours for the input PBMCs to condition. In some embodiments, the plurality of input PBMCs is incubated with the adjuvant for about 3 to about 6 hours for the input PBMCs to condition. In some embodiments, the plurality of input PBMCs is incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the input PBMCs to condition. In some embodiments, the plurality of input PBMCs is incubated with the adjuvant for about 4 hours for the input PBMCs to condition.

In some embodiments, there is provided a conditioned plurality of PBMCs comprising an antigen, prepared by incubating the plurality of PBMCs comprising the antigen with an adjuvant for a sufficient time for the PBMCs to condition, thereby generating the conditioned plurality of PBMCs comprising the antigen. In some embodiments, there is provided a conditioned plurality of PBMCs comprising an antigen, prepared by incubating the plurality of PBMCs with an adjuvant for a sufficient time for the PBMCs to condition prior to introducing the antigen to the PBMCs, thereby generating the conditioned plurality of PBMCs comprising the antigen.

In some embodiments according to any one of methods or compositions described herein, wherein the immune cell is a plurality of PBMCs, the concentration of antigen incubated with the PBMCs is between about 0.01 μM and about 10 mM. For example, in some embodiments, the concentration of antigen incubated with the PBMCs is any of less than about 0.01 μM, about 0.1 μM, about 1 μM, about 10 μM, about 100 μM, about 1 mM or about 10 mM. In some embodiments, the concentration of antigen incubated with the PBMCs is greater than about 10 mM. In some embodiments, the concentration of antigen incubated with the PBMCs is any of between about 0.01 μM and about 0.1 between about 0.1 μM and about 1 μM, between about 1 μM and about 10 μM, between about 10 μM and about 100 μM, between about 100 μM and about 1 mM, or between 1 mM and about 10 mM. In some embodiments, the concentration of antigen incubated with the PBMCs is between about 0.1 μM and about 1 mM. In some embodiments, the concentration of antigen incubated with the PBMCs is between about 0.1 μM and about 10 μM. In some embodiments, the concentration of antigen incubated with the PBMCs is 1 μM.

In some embodiments according to any one of methods or compositions described herein, wherein the immune cell is a plurality of PBMCs, the plurality of PBMCs is incubated with the adjuvant for about 1 to about 24 hours for the PBMCs to condition. In some embodiments, the plurality of PBMCs is incubated with the adjuvant for about 2 to about 10 hours for the PBMCs to condition. In some embodiments, the plurality of PBMCs is incubated with the adjuvant for about 3 to about 6 hours for the PBMCs to condition. In some embodiments, the plurality of PBMCs is incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the PBMCs to condition. In some embodiments, the plurality of PBMCs is incubated with the adjuvant for about 4 hours for the PBMCs to condition.

In some embodiments, one or more co-stimulatory molecules are upregulated in the conditioned plurality of modified PBMCs compared to an unconditioned plurality of modified PBMCs. In some embodiments, one or more co-stimulatory molecules are upregulated in a subpopulation of cells in the conditioned plurality of modified PBMCs compared to the subpopulation of cells in an unconditioned plurality of modified PBMCs. In some embodiments, one or more co-stimulatory molecules are upregulated in the B cells of the conditioned plurality of modified PBMCs compared to the B cells in an unconditioned plurality of modified PBMCs. In some embodiments, the co-stimulatory molecule is CD80 and/or CD86. In some embodiments, the co-stimulatory molecule is CD86. In some embodiments, the CD80 and/or CD86 is upregulated in the B cells of the conditioned plurality of modified PBMCs by about 1.2-fold, 1.5-fold, 1.8-fold, 2-fold, 3-fold, 4-fold, 5-fold, 8-fold, or more than 10-fold compared to the B cells in an unconditioned plurality of modified PBMCs. In some embodiments, the CD80 and/or CD86 is upregulated in the B cells of the conditioned plurality of modified PBMCs by any of about 1.2-fold to about 1.5-fold, about 1.5-fold to about 1.8-fold, about 1.8-fold to about 2-fold, about 2-fold to about 3-fold, about 3-fold to about 4-fold, about 4-fold to about 5-fold, about 5-fold to about 8-fold, about 8-fold to about 10-fold, about 10-fold to about 20-fold, about 20-fold to about 50-fold, about 50-fold to about 100-fold, about 100-fold to about 200-fold, about 200-fold to about 500-fold, or more than about 500-fold compared to the B cells in an unconditioned plurality of modified PBMCs. In some embodiments, the expression of one or more of IFN-γ, IL-6, MCP-1, MIP-1β, IP-10, or TNF-α is increased in the conditioned plurality of modified PBMCs compared to an unconditioned plurality of modified PBMCs. In some embodiments, the expression of one or more of IFN-γ, IL-6, MCP-1, MIP-1β, IP-10, or TNF-α is increased a subpopulation of cells in the conditioned plurality compared to the subpopulation of cells in an unconditioned plurality of modified PBMCs. In some embodiments, the expression of one or more of IFN-γ, IL-6, MCP-1, MIP-1β, IP-10, or TNF-α is increased by about 1.2-fold, 1.5-fold, 1.8-fold, 2-fold, 3-fold, 4-fold, 5-fold, 8-fold, or more than 10-fold in the conditioned plurality of modified PBMCs compared to an unconditioned plurality of modified PBMCs. In some embodiments, the expression of one or more of IFN-γ, IL-6, MCP-1, MIP-1β, IP-10, or TNF-α is increased by any of about 1.2-fold to about 1.5-fold, about 1.5-fold to about 1.8-fold, about 1.8-fold to about 2-fold, about 2-fold to about 3-fold, about 3-fold to about 4-fold, about 4-fold to about 5-fold, about 5-fold to about 8-fold, about 8-fold to about 10-fold, about 10-fold to about 20-fold, about 20-fold to about 50-fold, about 50-fold to about 100-fold, about 100-fold to about 200-fold, about 200-fold to about 500-fold, or more than about 500-fold in the conditioned plurality of modified PBMCs compared to an unconditioned plurality of modified PBMCs.

Applications

In some aspects, the present invention provides methods for treating and preventing an HPV-associated disease, and/or modulating the immune response in an individual with an HPV-associated disease comprising administering to the individual a composition comprising modified immune cells, wherein the modified immune cells comprise intracellularly an HPV antigen and intracellularly an adjuvant. In some embodiments, the cell is isolated from a patient, modified according to the methods disclosed, and introduced back into the patient. For example, a population of immune cells is isolated from a patient, passed through the constriction to achieve delivery of HPV antigen and adjuvant, and then re-infused into the patient to augment a therapeutic immune response to the HPV antigen. In some embodiments, the cell is isolated from an individual with HPV-associated disease, modified according to the disclosed methods, and introduced back into the individual. For example, a population of immune cells is isolated from an individual with HPV-associated disease, passed through the constriction to achieve delivery of HPV antigen and adjuvant, and then re-infused into the patient to induce or enhance immune response to the HPV antigen in the individual.

In some embodiments, the HPV antigen and/or adjuvant to deliver are purified. In some embodiments, the compound is at least about 60% by weight (dry weight) the compound of interest. In some embodiments, the purified compound is at least about 75%, 90%, or 99% the compound of interest. In some embodiments, the purified compound is at least about 90%, 91%, 92%, 93%, 94%, 95%, 98%, 99%, or 100% (w/w) the compound of interest. Purity is determined by any known methods, including, without limitation, column chromatography, thin layer chromatography, HPLC analysis, NMR, mass spectrometry, or SDS-PAGE. Purified DNA or RNA is defined as DNA or RNA that is free of exogenous nucleic acids, carbohydrates, and lipids.

In some embodiments, the invention provides methods of treating an individual with an HPV-associated disease by introducing the cell, modified by passing through a constriction such that an HPV antigen and an adjuvant enters the cell, to the individual. In some embodiments, the cell is an autologous cell. For example, the immune cell is isolated from an individual (e.g, a patient), modified according to the methods disclosed, and introduced back into the individual. In some embodiments, the immune cell is isolated from an individual, modified according to the disclosed methods, and introduced back into the same individual. In some embodiments, the cell is an allogeneic cell. For example, the cell is isolated from a different individual, modified according to the methods disclosed, and introduced into the first individual (e.g., the patient). In some embodiments, the cell is isolated from an individual, modified according to the disclosed methods, and introduced into a different individual.

Any of the methods described above are carried out in vitro, ex vivo, or in vivo. For in vivo applications, the device may be implanted in a vascular lumen, e.g., an in-line stent in an artery or vein. In some embodiments, the methods are used as part of a bedside system for ex vivo treatment of patient cells and immediate reintroduction of the cells into the patient. In some embodiments, the method can be implemented in a typical hospital laboratory with a minimally trained technician. In some embodiments, a patient operated treatment system can be used.

Systems and Kits

In some aspects, the invention provides a system comprising one or more of the constriction, an immune cell suspension, HPV antigens or adjuvants for use in the methods disclosed herein. The system can include any embodiment described for the methods disclosed above, including microfluidic channels or a surface having pores to provide cell-deforming constrictions, cell suspensions, cell perturbations, delivery parameters, compounds, and/or applications etc. In some embodiment, the cell-deforming constrictions are sized for delivery to immune cells. In some embodiments, the delivery parameters, such as operating flow speeds, cell and compound concentration, velocity of the cell in the constriction, and the composition of the cell suspension (e.g., osmolarity, salt concentration, serum content, cell concentration, pH, etc.) are optimized for maximum response of a compound for suppressing an immune response or inducing tolerance.

Also provided are kits or articles of manufacture for use in treating individuals with an HPV-associated disease. In some embodiments, the kit comprises a modified immune cell comprising intracellularly an HPV antigen and intracellularly an adjuvant. In some embodiments, the kit comprises one or more of the constriction, an immune cell suspension, HPV antigens or adjuvants for use in generating modified immune cells for use in treating an individual with an HPV-associated disease. In some embodiments, the kits comprise the compositions described herein (e.g. a microfluidic channel or surface containing pores, cell suspensions, and/or compounds) in suitable packaging. Suitable packaging materials are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The invention also provides kits comprising components of the methods described herein and may further comprise instructions for performing said methods treat an individual with an HPV-associated disease and/or instructions for introducing an HPV antigen and an adjuvant into an immune cell. The kits described herein may further include other materials, including other buffers, diluents, filters, needles, syringes, and package inserts with instructions for performing any methods described herein; e.g., instructions for treating an individual with an HPV-associated disease or instructions for modifying an immune cell to contain intracellularly an HPV antigen and intracellularly an adjuvant.

EXEMPLARY EMBODIMENTS

Embodiment 1. A method for treating a human papilloma virus (HPV)-associated disease in an individual, the method comprising administering to the individual an effective amount of a composition comprising modified immune cells, wherein the modified immune cells comprise an HPV antigen and an adjuvant, wherein the adjuvant is presented intracellularly.

Embodiment 2. A method for preventing an HPV-associated disease in an individual, the method comprising administering to the individual an effective amount of a composition comprising modified immune cells, wherein the modified immune cells comprise an HPV antigen and an adjuvant, wherein the adjuvant is presented intracellularly.

Embodiment 3. A method for modulating an immune response in an individual with an HPV-associated disease, the method comprising administering to the individual an effective amount of a composition comprising modified immune cells, wherein the modified immune cells comprise an HPV antigen and an adjuvant, wherein the adjuvant is presented intracellularly.

Embodiment 4. A method for treating an HPV-associated disease in an individual, the method comprising administering to the individual an effective amount of a composition comprising modified immune cells, wherein the modified immune cells comprise an HPV antigen and an adjuvant, wherein the adjuvant is presented intracellularly;
wherein the modified immune cells are prepared by
a) passing a cell suspension comprising an input cell through a cell-deforming constriction, wherein a diameter of the constriction is a function of a diameter of the input cell in the suspension, thereby causing perturbations of the input cell large enough for the antigen and the adjuvant to pass through to form a perturbed input cell; and
b) incubating the perturbed input cell with the HPV antigen and the adjuvant for a sufficient time to allow the HPV antigen and the adjuvant to enter the perturbed input cell;
thereby generating the modified immune cells.

Embodiment 5. A method for preventing an HPV-associated disease in an individual, the method comprising administering to the individual an effective amount of a composition comprising modified immune cells, wherein the modified immune cells comprise an HPV antigen and an adjuvant, wherein the adjuvant is presented intracellularly;
wherein the modified immune cells are prepared by
a) passing a cell suspension comprising an input cell through a cell-deforming constriction, wherein a diameter of the constriction is a function of a diameter of the input cell in the suspension, thereby causing perturbations of the input cell large enough for the HPV antigen and the adjuvant to pass through to form a perturbed input cell; and
b) incubating the perturbed input cell with the HPV antigen and the adjuvant for a sufficient time to allow the HPV antigen and the adjuvant to enter the perturbed input cell;
thereby generating the modified immune cells.

Embodiment 6. A method for modulating an immune response in an individual with an HPV-associated disease, the method comprising administering to the individual an effective amount of a composition comprising modified immune cells, wherein the modified immune cells comprise an HPV antigen and an adjuvant, wherein the adjuvant is presented intracellularly;
wherein the modified immune cells are prepared by
a) passing a cell suspension comprising an input cell comprising an HPV antigen through a cell-deforming constriction, wherein a diameter of the constriction is a function of a diameter of the input cell in the suspension, thereby causing perturbations of the input cell large enough for the HPV antigen and the adjuvant to pass through to form a perturbed input cell; and
b) incubating the perturbed input cell with the antigen and the adjuvant for a sufficient time to allow the HPV antigen and the adjuvant to enter the perturbed input cell;
thereby generating the modified immune cells.

Embodiment 7. The method of any one of embodiments 4 to 6, wherein the diameter of the constriction is less than the diameter of the cell.

Embodiment 8. The method of any one of embodiments 4-7, wherein the diameter of the constriction is about 20% to 99% of the diameter of the cell.

Embodiment 9. The method of any one of embodiments 4-8, wherein the diameter of the constriction is about 20% to less than about 60% of the diameter of the cell.

Embodiment 10. The method of any one of embodiments 4-9, wherein the constriction is in a channel.

Embodiment 11. The method of any one of embodiments 4-10, wherein a deforming force is applied to the input cell as it passes through the constriction.

Embodiment 12. The method of any of embodiments 1-11, wherein the HPV antigen and/or the adjuvant are present in the cytosol and/or endosomes.

Embodiment 13. The method of any one of embodiments 1-12, wherein the antigen and/or adjuvant are present in multiple compartments of the cell.

Embodiment 14. The method of any one of embodiments 1-13, wherein the modified immune cell further comprises an HPV antigen and/or an adjuvant on the outside of the cell.

Embodiment 15. The method of any one of embodiments 1-14, wherein the concentration of adjuvant incubated with the perturbed input cell is between about 0.1 μM and about 1 mM.

Embodiment 16. The method of any one of embodiments 1-15, wherein the concentration of HPV antigen incubated with the perturbed input cell is between about 0.1 μM and about 1 mM.

Embodiment 17. The method of any one of embodiments 4-16, wherein the ratio of HPV antigen to adjuvant incubated with the perturbed input cell is between about 10000:1 and about 1:10000.

Embodiment 18. The method of embodiment 3 or 6, wherein the immune response is enhanced.

Embodiment 19. The method of embodiment 18, wherein the immune response to the HPV antigen is enhanced.

Embodiment 20. The method of any one of embodiments 1-19, wherein the adjuvant is CpG ODN, IFN-α, STING agonists, RIG-I agonists or poly I:C.

Embodiment 21. The method of embodiment 20, wherein the adjuvant is CpG ODN.

Embodiment 22. The method of embodiment 21, wherein the CpG ODN is CpG ODN 1018, CpG ODN 1826 or CpG ODN 2006.

Embodiment 23. The method of any one of embodiments 1-22, wherein the modified immune cell comprises more than one adjuvant.

Embodiment 24. The method of any one embodiments 1-23, wherein the HPV antigen is a pool of multiple polypeptides that elicit a response against the same and or different HPV antigens.

Embodiment 25. The method of embodiment 24, wherein an antigen in the pool of multiple antigens does not decrease the immune response directed toward other antigens in the pool of multiple antigens.

Embodiment 26. The method of any one of embodiments 1-25, wherein the HPV antigen is a polypeptide comprising an antigenic HPV epitope and one or more heterologous peptide sequences.

Embodiment 27. The method of any one of embodiments 1-26, wherein the HPV antigen complexes with itself, with other antigens, or with the adjuvant.

Embodiment 28. The method of any one of embodiments 1-27, wherein the HPV is antigen is derived from a cell lysate.

Embodiment 29. The method of any one of embodiments 1-28, wherein the HPV antigen is an HPV-16 or an HPV-18 antigen.

Embodiment 30. The method of embodiment 29, wherein the HPV antigen is comprised of an HLA-A2-specific epitope.

Embodiment 31. The method of any one of embodiments 1-30, wherein the HPV antigen is an HPV E6 antigen or an HPV E7 antigen.

Embodiment 32. The method of any one of embodiments 1-31, wherein the modified immune cell comprises an HPV E6 antigen and an HPV E7 antigen.

Embodiment 33. The method of any one of embodiments 1-32, wherein the HPV antigen is a polypeptide comprising an antigenic epitope that is flanked on the N-terminus and/or the C-terminus by one or more heterologous peptide sequences.

Embodiment 34. The method of embodiment 33, wherein the HPV antigen comprises an amino acid sequence with at least 90% similarity to any one of SEQ ID NOs:18-26.

Embodiment 35. The method of embodiment 34, wherein the HPV antigen comprises an amino acid sequence with at least 90% similarity to SEQ ID NO:23.

Embodiment 36. The method of any one of embodiments 1-35, wherein the HPV antigen is capable of being processed into an MHC class I-restricted peptide.

Embodiment 37. The method of any one of embodiments 1-36, wherein the HPV antigen is capable of being processed into an MHC class II-restricted peptide.

Embodiment 38. The method of any one of embodiments 1-37, wherein the modified immune cell comprises the adjuvant at a concentration between about 0.1 μM and about 1 mM.

Embodiment 39. The method of any one of embodiments 1-38, wherein the modified immune cell comprises the HPV antigen at a concentration between about 0.1 μM and about 1 mM.

Embodiment 40. The method of any one of embodiments 1-39, wherein the ratio of the HPV antigen to the adjuvant is between about 10000:1 to about 1:10000.

Embodiment 41. The method of any one of embodiments 1-40, wherein the modified immune cell further comprises an agent that enhances the viability and/or function of the modified immune cell as compared to a corresponding modified immune cell that does not comprise the agent.

Embodiment 42. The method of embodiment 41, wherein the agent is a compound that enhances endocytosis, a stabilizing agent or a co-factor.

Embodiment 43. The method of embodiment 41, wherein the agent is albumin.

Embodiment 44. The method of embodiment 43, wherein the albumin is mouse, bovine, or human albumin.

Embodiment 45. The method of embodiment 41, wherein the agent is a divalent metal cation, glucose, ATP, potassium, glycerol, trehalose, D-sucrose, PEG1500, L-arginine, L-glutamine, or EDTA.

Embodiment 46. The method of embodiments 41, wherein the agent comprises mouse serum albumin (MSA).

Embodiment 47. The method of any one of embodiments 1-46, wherein the modified immune cells are further modified to increase expression of one or more of co-stimulatory molecules.

Embodiment 48. The method of embodiment 47, wherein the co-stimulatory molecule is B7-H2, B7-1, B7-2, CD70, LIGHT, HVEM, CD40, 4-1BBL, OX40L, TL1A, GITRL, CD30L, TIM4, SLAM, CD48, CD58, CD155, or CD112.

Embodiment 49. The method of embodiments 47 or 48, wherein the cell comprises a nucleic acid that results in increased expression of the one or more co-stimulatory molecules.

Embodiment 50. The method of any one of embodiments 1-49, wherein the immune cell is a T cell, a dendritic cell, a monocyte, a macrophage, a myeloid cell, a granulocyte, a neutrophil, a mast cell, a natural killer cell, an innate lymphoid cell, a basophil, or a hematopoetic precursor cell.

Embodiment 51. The method of any one of embodiments 1-50, wherein the immune cell is not a B cell.

Embodiment 52. The method of any one of embodiments 1-50, wherein the immune cell is a B cell.

Embodiment 53. The method of any one of embodiments 1-51, wherein the immune cell is a T cell.

Embodiment 54. The method of any one of embodiments 1-49, wherein the immune cells are a mixed cell population.

Embodiment 55. The method of embodiment 54, wherein the immune cells are a plurality of PBMCs.

Embodiment 56. The method of embodiment 53, wherein the T cell comprises a further modification to modulate MHC class I expression.

Embodiment 57. The method of embodiment 53, wherein the T cell comprises a further modification to modulate MHC class II expression.

Embodiment 58. The method of embodiment 56 or 57, wherein the T cell comprises a further modification to reduce MHC class I and/or MHC class II expression.

Embodiment 59. The method of embodiment 56 or 57, wherein the further modification comprises reducing MHC class I and/or MHC class II expression using siRNA, shRNA, CRISPR/Cas9, ZFN, TALEN, Cre recombinase or a mega nuclease.

Embodiment 60. The method of embodiment 56 or 57, wherein the T cell comprises a further modification to increase MHC class I and/or MHC class II expression.

Embodiment 61. The method of embodiment 56 or 57, wherein the further modification comprises increasing MHC class I and/or MHC class II expression using RNA or plasmid DNA.

Embodiment 62. The method of any one of embodiments 53 and 56-59, wherein an innate immune response mounted in an individual in response to administration, in an allogeneic context, of the further modified T cells is reduced compared to an innate immune response mounted in an individual in response to administration, in an allogeneic context, of corresponding modified T cells that do not comprise the further modification.

Embodiment 63. The method of any one of embodiments 53 and 56-59, wherein the circulating half-life of the further modified T cells in an individual to which they were administered is modulated compared to the circulating half-life of corresponding modified T cells that do not comprise the further modification in an individual to which they were administered.

Embodiment 64. The method of any one of embodiments 53 and 56-63, wherein the T cell includes one or more of helper T cells, cytotoxic T cells, memory T cells, CIK cells and natural killer T cells.

Embodiment 65. The method of any one of embodiments 53 and 56-63, wherein the T cell includes one or more of CD3+ T cells, CD4+ T cells, CD8+ T cells, CD45RA+ T cells, CD45RO+ T cells, and γδ-T cells.

Embodiment 66. The method of any one of embodiments 1-65, wherein the modified cell is allogeneic to the individual.

Embodiment 67. The method of any one of embodiments 1-65, wherein the modified cell is autologous to the individual.

Embodiment 68. The method of any one of embodiments 1-67, wherein the individual is pre-conditioned to have modulated inflammation and/or a modulated immune response.

Embodiment 69. The method of any one of embodiments 1-68, further comprising administering to the individual an adjuvant.

Embodiment 70. The method of embodiment 69, wherein the adjuvant is IFNα or CpG ODN.

Embodiment 71. The method of embodiment 69 or 70, wherein the composition comprising the modified immune cells and the adjuvant are administered simultaneously.

Embodiment 72. The method of embodiment 69 or 70, wherein the composition comprising the modified immune cells and the adjuvant are administered sequentially.

Embodiment 73. The method of embodiment 72, wherein the composition comprising the modified immune cells is administered prior to administering the adjuvant.

Embodiment 74. The method of embodiment 72, wherein the composition comprising the modified immune cells is administered following administration of the adjuvant.

Embodiment 75. The method of any one of embodiments 1-74, wherein the composition comprising the modified immune cells is administered in combination with administration of an immune checkpoint inhibitor.

Embodiment 76. The method of embodiment 75, wherein the composition comprising the modified immune cells and the immune checkpoint inhibitor are administered simultaneously.

Embodiment 77. The method of embodiment 75, wherein the composition comprising the modified immune cells and the immune checkpoint inhibitor are administered sequentially.

Embodiment 78. The method of embodiment 77, wherein the composition comprising the modified immune cells is administered prior to administering the immune checkpoint inhibitor.

Embodiment 79. The method of embodiment 77, wherein the composition comprising the modified immune cells is administered following administration of the immune checkpoint inhibitor.

Embodiment 80. The method of any one of embodiments 75-79, wherein the immune checkpoint inhibitor is targeted to one or more of PD-1, PD-L1, CTLA-4, LAG3, TIM-3, TIGIT, VISTA, TIM1, B7-H4 (VTCN1) or BTLA.

Embodiment 81. The method of any one of embodiments 1-80, wherein the composition comprising the modified immune cells is administered in combination with administration of a chemotherapy.

Embodiment 82. The method of embodiment 81, wherein the composition comprising the modified immune cells and the chemotherapy are administered simultaneously.

Embodiment 83. The method of embodiment 81, wherein the composition comprising the modified immune cells and the chemotherapy are administered sequentially.

Embodiment 84. The method of embodiment 83, wherein the composition comprising the modified immune cells is administered prior to administering the chemotherapy.

Embodiment 85. The method of embodiment 83, wherein the composition comprising the modified immune cells is administered following administration of the chemotherapy.

Embodiment 86. The method of any one of embodiments 81 to 85, wherein the chemotherapy comprises a platinum based agent.

Embodiment 87. The method of any one of embodiments 81 to 86, wherein the chemotherapy comprises cisplatin.

Embodiment 88. The method of any one of embodiments 1-87, wherein administration of the composition comprising the modified immune cells to the individual results in activation and/or expansion of cytotoxic T lymphocytes (CTLs) specific for the HPV antigen.

Embodiment 89. The method of any one of embodiments 1-87, wherein administration of the composition comprising the modified immune cells to the individual results in activation and/or expansion of helper T (Th) cells specific for the antigen.

Embodiment 90. The method of any one of embodiments 1-89, wherein the effective amount of the composition comprises between about 1×106 and about 1×1012 modified immune cells.

Embodiment 91. The method of any one of embodiments 1-90, wherein the method comprises multiple administrations of the composition comprising the modified immune cells.

Embodiment 92. The method of embodiment 91, wherein the method comprises a first administration of the composition comprising the modified immune cells followed by a second administration of the composition comprising the modified immune cells.

Embodiment 93. The method of embodiment 92, wherein the second administration is about one month following the first administration.

Embodiment 94. The method of any one of embodiments 1-93, wherein the HPV-associated disease is an HPV-associated cancer.

Embodiment 95. The method of embodiment 94, wherein the HPV-associated cancer is cervical cancer, anal cancer, oropharyngeal cancer, vaginal cancer, vulvar cancer, penile cancer, skin cancer or head and neck cancer.

Embodiment 96. The method of any one of embodiments 1-95, wherein the HPV-associated disease is an HPV-associated infectious disease.

Embodiment 97. A method for treating a human papilloma virus (HPV)-related disease in an individual, the method comprising administering to the individual an effective amount of a composition comprising modified immune cells, wherein the modified immune cells comprise an HPV antigen comprising an amino acid with at least 90% similarity to any one of SEQ ID NOs:18-25.

Embodiment 98. A method for preventing an HPV-associated disease in an individual, the method comprising administering to the individual an effective amount of a composition comprising modified immune cells, wherein the modified immune cells comprise an HPV antigen comprising an amino acid sequence with at least 90% similarity to any one of SEQ ID NOs:18-25.

Embodiment 99. A method for modulating an immune response in an individual with an HPV-associated disease, the method comprising administering to the individual an effective amount of a composition comprising modified immune cells, wherein the modified immune cells comprise an HPV antigen comprising an amino acid sequence with at least 90% similarity to any one of SEQ ID NOs:18-25.

Embodiment 100. A method for treating an HPV-associated disease in an individual, the method comprising administering to the individual an effective amount of a composition comprising modified immune cells, wherein the modified immune cells comprise an HPV antigen comprising an amino acid sequence with at least 90% similarity to any one of SEQ ID NOs:18-25; wherein the modified immune cells are prepared by
  a) passing a cell suspension comprising an input cell through a cell-deforming constriction, wherein a diameter of the constriction is a function of a diameter of the input cell in the suspension, thereby causing perturbations of the input cell large enough for the antigen to pass through to form a perturbed input cell; and
  b) incubating the perturbed input cell with the HPV antigen for a sufficient time to allow the HPV antigen to enter the perturbed input cell;
  thereby generating the modified immune cells.

Embodiment 101. A method for preventing an HPV-associated disease in an individual, the method comprising administering to the individual an effective amount of a composition comprising modified immune cells, wherein the modified immune cells comprise an HPV antigen, wherein the modified immune cells comprise an HPV antigen comprising an amino acid sequence with at least 90% similarity to any one of SEQ ID NOs:18-25;
  wherein the modified immune cells are prepared by
  a) passing a cell suspension comprising an input cell through a cell-deforming constriction, wherein a diameter of the constriction is a function of a diameter of the input cell in the suspension, thereby causing perturbations of the input cell large enough for the HPV antigen to pass through to form a perturbed input cell; and
  b) incubating the perturbed input cell with the HPV antigen for a sufficient time to allow the HPV antigen to enter the perturbed input cell;
  thereby generating the modified immune cells.

Embodiment 102. A method for modulating an immune response in an individual with an HPV-associated disease, the method comprising administering to the individual an effective amount of a composition comprising modified immune cells, wherein the modified immune cells comprise an HPV antigen comprising an amino acid sequence with at least 90% similarity to any one of SEQ ID NOs:18-25;
  wherein the modified immune cells are prepared by
  a) passing a cell suspension comprising an input cell through a cell-deforming constriction, wherein a diameter of the constriction is a function of a diameter of the input cell in the suspension, thereby causing perturbations of the input cell large enough for the HPV antigen to pass through to form a perturbed input cell; and
  b) incubating the perturbed input cell with the HPV antigen for a sufficient time to allow the HPV antigen to enter the perturbed input cell;
  thereby generating the modified immune cells.

Embodiment 103. The method of any one of embodiments 100-102, wherein the diameter of the constriction is less than the diameter of the cell.

Embodiment 104. The method of any one of embodiments 100-103, wherein the diameter of the constriction is about 20% to 99% of the diameter of the cell.

Embodiment 105. The method of any one of embodiments 100-104, wherein the diameter of the constriction is about 20% to less than about 60% of the diameter of the cell.

Embodiment 106. The method of any one of embodiments 100-105, wherein the constriction is in a channel.

Embodiment 107. The method of any one of embodiments 100-106, wherein a deforming force is applied to the input cell as it passes through the constriction, Embodiment 108. The method of any one of embodiments 86-107, further comprising administering to the individual an adjuvant.

Embodiment 109. The method of embodiment 108, wherein the adjuvant is IFNα or CpG ODN.

Embodiment 110. The method of embodiment 108 or 109, wherein the composition comprising the modified immune cells and the adjuvant are administered simultaneously.

Embodiment 111. The method of embodiment 108 or 109, wherein the composition comprising the modified immune cells and the adjuvant are administered sequentially.

Embodiment 112. The method of embodiment 111, wherein the composition comprising the modified immune cells is administered prior to administering the adjuvant.

Embodiment 113. The method of embodiment 111, wherein the composition comprising the modified immune cells is administered following administration of the adjuvant.

Embodiment 114. The method of any one of embodiments 97-113, wherein the modified immune cell further comprises an adjuvant.

Embodiment 115. The method of any one of embodiments 100-113, wherein the perturbed immune cell of step b is incubated with the HPV antigen and an adjuvant.

Embodiment 116. The method of embodiment 114 or 115, wherein the HPV antigen and/or the adjuvant are present in the cytosol and/or endosomes.

Embodiment 117. The method of any one of embodiments 114-116, wherein the antigen and/or adjuvant are present in multiple compartments of the cell.

Embodiment 118. The method of any one of embodiments 114-117, wherein the modified immune cell further comprises an HPV antigen and/or an adjuvant on the outside of the cell.

Embodiment 119. The method of any one of embodiments 115-118, wherein the concentration of adjuvant incubated with the perturbed input cell is between about 0.1 μM and about 1 mM.

Embodiment 120. The method of any one of embodiments 115-119, wherein the concentration of HPV antigen incubated with the perturbed input cell is between about 0.1 μM and about 1 mM.

Embodiment 121. The method of any one of embodiments 115-120, wherein the ratio of HPV antigen to adjuvant incubated with the perturbed input cell is between about 10000:1 to about 1:10000.

Embodiment 122. The method of embodiment 99 or 102, wherein the immune response is enhanced.

Embodiment 123. The method of embodiment 122, wherein the immune response to the HPV antigen is enhanced.

Embodiment 124. The method of any one of embodiments 114-123, wherein the adjuvant is CpG ODN, IFN-α, STING agonists, RIG-I agonists or poly I:C.

Embodiment 125. The method of embodiment 124, wherein the adjuvant is CpG ODN.

Embodiment 126. The method of embodiment 125, wherein the CpG ODN is CpG ODN 1018, CpG ODN 1826 or CpG ODN 2006.

Embodiment 127. The method of any one of embodiments 114-126, wherein the modified immune cell comprises more than one adjuvant.

Embodiment 128. The method of any one embodiments 97-127, wherein the HPV antigen is a pool of multiple polypeptides that elicit a response against the same and or different HPV antigens.

Embodiment 129. The method of embodiment 128, wherein an antigen in the pool of multiple antigens does not decrease the immune response directed toward other antigens in the pool of multiple antigens.

Embodiment 130. The method of any one of embodiments 97-129, wherein the HPV antigen is a polypeptide comprising an antigenic HPV epitope and one or more heterologous peptide sequences.

Embodiment 131. The method of any one of embodiments 97-130, wherein the HPV antigen complexes with itself, with other antigens, or with the adjuvant.

Embodiment 132. The method of any one of embodiments 97-131, wherein the HPV antigen is comprised of an HLA-A2-specific epitope.

Embodiment 133. The method of any one of embodiments 97-132, wherein the HPV antigen is capable of being processed into an MHC class I-restricted peptide.

Embodiment 134. The method of any one of embodiments 97-133, wherein the HPV antigen is capable of being processed into an MHC class II-restricted peptide.

Embodiment 135. The method of any one of embodiments 114-134, wherein the modified immune cell comprises the adjuvant at a concentration between about 0.1 μM and about 1 mM.

Embodiment 136. The method of any one of embodiments 97-135, wherein the modified immune cell comprises the HPV antigen at a concentration between about 0.1 μM and about 1 mM.

Embodiment 137. The method of any one of embodiments 114-136, wherein the ratio of the HPV antigen to the adjuvant is between about 10000:1 and about 1:10000.

Embodiment 138. The method of any one of embodiments 97-137, wherein the modified immune cell further comprises an agent that enhances the viability and/or function of the modified immune cell as compared to a corresponding modified immune cell that does not comprise the agent.

Embodiment 139. The method of embodiment 138, wherein the agent is a compound that enhances endocytosis, a stabilizing agent or a co-factor.

Embodiment 140. The method of embodiment 138, wherein the agent is albumin.

Embodiment 141. The method of embodiment 140, wherein the albumin is mouse, bovine, or human albumin.

Embodiment 142. The method of embodiment 138, wherein the agent is a divalent metal cation, glucose, ATP, potassium, glycerol, trehalose, D-sucrose, PEG1500, L-arginine, L-glutamine, or EDTA.

Embodiment 143. The method of embodiment 138, wherein the agent comprises MSA.

Embodiment 144. The modified T cell of any one of embodiments 97-143, wherein the cells are further modified to increase expression of one or more of co-stimulatory molecules.

Embodiment 145. The modified T cell of embodiment 144, wherein the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112.

Embodiment 146. The modified T cell of embodiments 144 or 145, wherein the cell comprises a nucleic acid that results in increased expression of the one or more co-stimulatory molecules.

Embodiment. The method of any one of embodiments 97-146, wherein the immune cell is a T cell, a dendritic cell, a monocyte, a macrophage, a myeloid cell, a granulocyte, a neutrophil, a mast cell, a natural killer cell, an innate lymphoid cell, a basophil, or a hematopoetic precursor cell.

Embodiment 148. The method of any one of embodiments 97-147, wherein the immune cell is not a B cell.

Embodiment 149. The method of any one of embodiments 97-148, wherein the immune cell is a B cell.

Embodiment 150. The method of any one of embodiments 97-148, wherein the immune cell is a T cell.

Embodiment 151. The method of any one of embodiments 97-148, wherein the immune cell is a mixed cell population.

Embodiment 152. The method of embodiment 151, wherein the immune cell is a plurality of PBMCs.

Embodiment 153 The method of embodiment 150, wherein the T cell comprises a further modification to modulate MHC class I expression.

Embodiment 154. The method of embodiment 150, wherein the T cell comprises a further modification to modulate MHC class II expression.

Embodiment 155. The method of embodiment 153 or 154, wherein the T cell comprises a further modification to reduce MHC class I and/or MHC class II expresion.

Embodiment 156. The method of embodiment 153 or 154, wherein the further modification comprises reducing MHC class I and/or MHC class II expression using siRNA, shRNA, CRISPR/Cas9, ZFN, TALEN, Cre recombinase or a mega nuclease.

Embodiment 157. The method of embodiment 153 or 154, wherein the T cell comprises a further modification to increase MHC class I and/or MHC class II expression.

Embodiment 158. The method of embodiment 153 or 154, wherein the further modification comprises increasing MHC class I and/or MHC class II expression using RNA or plasmid DNA.

Embodiment 159. The method of any one of embodiments 150 and 153-156, wherein an innate immune response mounted in an individual in response to administration, in an allogeneic context, of the further modified T cells is reduced compared to an innate immune response mounted in an individual in response to administration, in an allogeneic context, of corresponding modified T cells that do not comprise the further modification.

Embodiment 160. The method of any one of embodiments 150 and 153-156, wherein the circulating half-life of the further modified T cells in an individual to which they were administered is modulated compared to the circulating half-life of corresponding modified T cells that do not comprise the further modification in an individual to which they were administered.

Embodiment 161. The method of any one of embodiments 150 and 153-160, wherein the T cell includes one or more of helper T cells, cytotoxic T cells, memory T cells, CIK cells and natural killer T cells.

Embodiment 162. The method of any one of embodiments 150 and 153-160, wherein the T cell includes one or more of CD3+ T cells, CD4+ T cells, CD8+ T cells, CD45RA+ T cells, CD45RO+ T cells, and γδ-T cells.

Embodiment 163. The method of any one of embodiments 97-162, wherein the modified cell is allogeneic to the individual.

Embodiment 164. The method of any one of embodiments 97-162, wherein the modified cell is autologous to the individual.

Embodiment 165. The method of any one of embodiments 97-164, wherein the individual is pre-conditioned to have modulated inflammation and/or a modulated immune response.

Embodiment 166. The method of any one of embodiments 97-165, wherein the composition comprising the modified immune cells is administered in combination with administration of an immune checkpoint inhibitor.

Embodiment 167. The method of embodiment 166, wherein the composition comprising the modified immune cells and the immune checkpoint inhibitor are administered simultaneously.

Embodiment 168. The method of embodiment 166, wherein the composition comprising the modified immune cells and the immune checkpoint inhibitor are administered sequentially.

Embodiment 169. The method of embodiment 168, wherein the composition comprising the modified immune cells is administered prior to administering the immune checkpoint inhibitor.

Embodiment 170. The method of embodiment 168, wherein the composition comprising the modified immune cells is administered following administration of the immune checkpoint inhibitor.

Embodiment 171. The method of any one of embodiments 152-156, wherein the immune checkpoint inhibitor is targeted to one or more of PD-1, PD-L1, CTLA-4, LAG3, TIM-3, TIGIT, VISTA, TIM1, B7-H4 (VTCN1) or BTLA.

Embodiment 172. The method of any one of embodiments 97-171, wherein the composition comprising the modified immune cells is administered in combination with administration of a chemotherapy.

Embodiment 173. The method of embodiment 172, wherein the composition comprising the modified immune cells and the chemotherapy are administered simultaneously.

Embodiment 174. The method of embodiment 172, wherein the composition comprising the modified immune cells and the chemotherapy are administered sequentially.

Embodiment 175. The method of embodiment 174, wherein the composition comprising the modified immune cells is administered prior to administering the chemotherapy.

Embodiment 176. The method of embodiment 174, wherein the composition comprising the modified immune cells is administered following administration of the chemotherapy.

Embodiment 177. The method of any one of embodiments 172 to 176, wherein the chemotherapy comprises cisplatin.

Embodiment 178. The method of any one of embodiments 97-177, wherein administration of the composition comprising the modified immune cells to the individual results in activation and/or expansion of cytotoxic T lymphocytes (CTLs) specific for the HPV antigen.

Embodiment 179. The method of any one of embodiments 97-177 wherein administration of the composition comprising the modified immune cells to the individual results in activation and/or expansion of helper T (Th) cells specific for the HPV antigen.

Embodiment 180. The method of any one of embodiments 97-179, wherein the effective amount of the composition comprises between about 1×106 and about 1×1012 modified immune cells.

Embodiment 181. The method of any one of embodiments 97-180, wherein the method comprises multiple administrations of the composition comprising the modified immune cells.

Embodiment 182. The method of embodiment 181, wherein the method comprises a first administration of the composition comprising the modified immune cells followed by a second administration of the composition comprising the modified immune cells.

Embodiment 183. The method of embodiment 182, wherein the second administration is about one month following the first administration.

Embodiment 184. The method of any one of embodiments 97-183, wherein the HPV-associated disease is an HPV-associated cancer.

Embodiment 185. The method of embodiment 184, wherein the HPV-associated cancer is cervical cancer, anal cancer, oropharyngeal cancer, vaginal cancer, vulvar cancer, penile cancer, skin cancer or head and neck cancer.

Embodiment 186. A composition comprising modified immune cells, wherein the modified immune cells comprise intracellularly a CpG ODN and an HPV antigen with at least 90% similarity to any one of SEQ ID NOs:18-25.

Embodiment 187. The composition in embodiment 166, wherein the HPV antigen comprises the amino acid sequence with at least 90% similarity to SEQ ID NO:23.

Embodiment 188. The composition in embodiment 186 or 187, wherein the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the HPV antigen and the CpG ODN to pass through to form a perturbed input cell; and b) incubating the perturbed input cell with the HPV antigen and the CpG ODN for a sufficient time to allow the HPV antigen and the CpG ODN to enter the perturbed input cell; thereby generating the modified immune cells.

Embodiment 189. The composition in embodiment 188, wherein the diameter of the constriction is less than the diameter of the cell.

Embodiment 190. The composition of embodiment 188 or 189, wherein the diameter of the constriction is about 20% to about 99% of the diameter of the cell.

Embodiment 191. The composition of any one of embodiments 188-190, wherein the diameter of the constriction is about 20% to less than about 60% of the diameter of the cell.

Embodiment 192. The composition of any one of embodiments 188-191, wherein the constriction is in a channel.

Embodiment 193. The composition of any one of embodiments 188-192, wherein a deforming force is applied to the input cell as it passes through the constriction, Embodiment 194. The composition any one of embodiments 186-193, wherein the composition further comprises an adjuvant.

Embodiment 195. The composition of any of embodiments 186-194, wherein the HPV antigen and/or the CpG ODN are present in the cytosol and/or endosomes.

Embodiment 196. The composition of any one of embodiments 186-195, wherein the antigen and/or the CpG ODN are present in multiple compartments of the cell.

Embodiment 197. The composition of any one of embodiments 186-196, wherein the modified immune cell further comprises an HPV antigen and/or a CpG ODN on the surface of the cell.

Embodiment 198. The composition of any one of embodiments 188-197, wherein the concentration of CpG ODN incubated with the perturbed input cell is between about 0.1 µM and about 1 mM.

Embodiment 199. The composition of any one of embodiments 188-198, wherein the concentration of HPV antigen incubated with the perturbed input cell is between about 0.1 µM and about 1 mM.

Embodiment 200. The composition of any one of embodiments 188-199, wherein the ratio of HPV antigen to CpG ODN incubated with the perturbed input cell is between about 10000:1 to about 1:10000.

Embodiment 201. The composition of any one of embodiments 186-200, wherein the CpG ODN is CpG ODN 1018, CpG ODN 1826 or CpG ODN 2006.

Embodiment 202. The composition of any one of embodiments 186-201, wherein the modified immune cell comprises more than one adjuvant.

Embodiment. The composition of embodiment 202, wherein the adjuvant comprises CpG ODN, IFN-α, STING agonists, RIG-I agonists, or poly I:C.

Embodiment 204. The composition of any one embodiments 186-203, wherein the HPV antigen is a pool of multiple polypeptides that elicit a response against the same and or different HPV antigens.

Embodiment 205. The composition of embodiment 204, wherein an antigen in the pool of multiple antigens does not decrease the immune response directed toward other antigens in the pool of multiple antigens.

Embodiment 206. The composition of any one of embodiments 186-205, wherein the HPV antigen is a polypeptide comprising an antigenic HPV epitope and one or more heterologous peptide sequences.

Embodiment 207. The composition of any one of embodiments 186-206, wherein the HPV antigen complexes with itself, with other antigens, with an adjuvant or with the CpG ODN.

Embodiment 208. The composition of embodiment 186-207, wherein the HPV antigen is comprised of an HLA-A2-specific epitope.

Embodiment 209. The composition of any one of embodiments 186-208, wherein the HPV antigen is a polypeptide comprising an antigenic epitope that is flanked on the N-terminus and/or the C-terminus by one or more heterologous peptide sequences.

Embodiment 210. The composition of any one of embodiments 186-209, wherein the modified immune cell comprises the CpG ODN at a concentration between about 0.1 µM and about 1 mM.

Embodiment 212. The composition of any one of embodiments 186-211, wherein the ratio of the HPV antigen to the CpG ODN is between about 10000:1 to about 1:10000.

Embodiment 213. A composition comprising modified immune cells, wherein the modified immune cells comprise an HPV antigen, wherein the HPV antigen comprises an amino acid sequence with at least 90% similarity to any one of SEQ ID NOs:18-25.

Embodiment 214. The composition in embodiment 213, wherein the HPV antigen comprises the amino acid sequence with at least 90% similarity to SEQ ID NO:23.

Embodiment 215. The composition in embodiment 213 or 214, wherein the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the HPV antigen to pass through to form a perturbed input cell; and b) incubating the perturbed input cell with the HPV antigen for a sufficient time to allow the HPV antigen to enter the perturbed input cell;

thereby generating the modified immune cells.

Embodiment 216. The composition in embodiment 215, wherein the diameter of the constriction is less than the diameter of the cell.

Embodiment 217. The composition of any one of embodiments 215-216, wherein the diameter of the constriction is about 20% to about 99% of the diameter of the cell.

Embodiment 218 The composition of any one of embodiments 215-217, wherein the diameter of the constriction is about 20% to less than about 60% of the diameter of the cell.

Embodiment 219. The composition of any one of embodiments 215-218, wherein the constriction is in a channel.

Embodiment 220. The composition of any one of embodiments 215-219, wherein a deforming force is applied to the input cell as it passes through the constriction.

Embodiment 221. The composition any one of embodiments 213-220, wherein the composition further comprises an adjuvant.

Embodiment 222. The composition of any of embodiments 213-221, wherein the HPV antigen and/or the adjuvant are present in the cytosol and/or endosomes.

Embodiment 223. The composition of any one of embodiments 213-222, wherein the antigen and/or adjuvant are present in multiple compartments of the cell.

Embodiment 224. The composition of any one of embodiments 213-223, wherein the modified immune cell further comprises an HPV antigen and/or an adjuvant on the surface of the cell.

Embodiment 225. The composition of any of embodiments 215-224, wherein the concentration of adjuvant incubated with the perturbed input cell is between about 0.1 μM and about 1 mM.

Embodiment 226. The composition of any one of embodiments 215-225, wherein the concentration of HPV antigen incubated with the perturbed input cell is between about 0.1 μM and about 1 mM.

Embodiment 227. The composition of any one of embodiments 215-226, wherein the ratio of HPV antigen to adjuvant incubated with the perturbed input cell is between about 10000:1 to about 1:10000.

Embodiment 228. The composition of any one of embodiments 213-227, wherein the adjuvant is CpG ODN, IFN-α, STING agonists, RIG-I agonists, or poly I:C.

Embodiment 229. The composition of embodiment 228, wherein the adjuvant is CpG ODN.

Embodiment 230. The composition of embodiment 229, wherein the CpG ODN is CpG ODN 1018, CpG ODN 1826 or CpG ODN 2006.

Embodiment 231. The composition of any one of embodiments 213-230, wherein the modified immune cell comprises more than one adjuvant.

Embodiment 232. The composition of any one embodiments 213-231, wherein the HPV antigen is a pool of multiple polypeptides that elicit a response against the same and or different HPV antigens.

Embodiment 233. The composition of embodiment 232, wherein an antigen in the pool of multiple antigens does not decrease the immune response directed toward other antigens in the pool of multiple antigens.

Embodiment 234. The composition of any one of embodiments 213-233, wherein the HPV antigen is a polypeptide comprising an antigenic HPV epitope and one or more heterologous peptide sequences.

Embodiment 235. The composition of any one of embodiments 213-234, wherein the HPV antigen complexes with itself, with other antigens, or with the adjuvant.

Embodiment 236. The composition of embodiment 213-235, wherein the HPV antigen is comprised of an HLA-A2-specific epitope.

Embodiment 237. The composition of any one of embodiments 213-236, wherein the modified immune cell comprises the adjuvant at a concentration between about 0.1 μM and about 1 mM.

Embodiment 238. The composition of any one of embodiments 213-237, wherein the modified immune cell comprises the HPV antigen at a concentration between about 0.1 μM and about 1 mM.

Embodiment 239. The composition of any one of embodiments 213-238, wherein the ratio of the HPV antigen to the adjuvant is between about 10000:1 to about 1:10000.

Embodiment 240. The composition of any one of embodiments 186-239, wherein the HPV antigen is capable of being processed into an MHC class I-restricted peptide.

Embodiment 241. The composition of any one of embodiments 186-240, wherein the HPV antigen is capable of being processed into an MHC class II-restricted peptide.

Embodiment 242. The composition of any one of embodiments 186-241, wherein the modified immune cell further comprises an agent that enhances the viability and/or function of the modified immune cell as compared to a corresponding modified immune cell that does not comprise the agent.

Embodiment 243. The composition of embodiment 242, wherein the agent is a compound that enhances endocytosis, a stabilizing agent or a co-factor.

Embodiment 244. The composition of embodiment 242, wherein the agent is albumin.

Embodiment 245. The composition of embodiment 244, wherein the albumin is mouse, bovine, or human albumin.

Embodiment 246. The composition of embodiment 242, wherein the agent is a divalent metal cation, glucose, ATP, potassium, glycerol, trehalose, D-sucrose, PEG1500, L-arginine, L-glutamine, or EDTA.

Embodiment 247. The composition of embodiment 242, wherein the agent comprises MSA.

Embodiment 248. The composition of any one of embodiments 186-247, wherein the cells are further modified to increase expression of one or more of co-stimulatory molecules.

Embodiment 249. The composition of embodiment 248, wherein the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112.

Embodiment 250. The composition of embodiments 248 or 249, wherein the cell comprises a nucleic acid that results in increased expression of the one or more co-stimulatory molecules.

Embodiment 251. The composition of any one of embodiments 186-250, wherein the immune cell is a T cell, a dendritic cell, a monocyte, a macrophage, a myeloid cell, a granulocyte, a neutrophil, a mast cell, a natural killer cell, an innate lymphoid cell, a basophil, or a hematopoetic precursor cell.

Embodiment 252. The composition of any one of embodiments 186-251, wherein the immune cell is not a B cell.

Embodiment 253. The composition of any one of embodiments 186-252, wherein the immune cell is a T cell.

Embodiment 254. The composition of embodiment 253, wherein the T cell comprises a further modification to modulate MHC class I expression.

Embodiment 255. The composition of embodiment 253, wherein the T cell comprises a further modification to modulate MHC class II expression.

Embodiment 256. The composition of embodiment 254 or 255, wherein the T cell comprises a further modification to reduce MHC class I and/or MHC class II expression.

Embodiment 257. The composition of embodiment 254 or 255, wherein the further modification comprises reducing MHC class I and/or MHC class II expression using siRNA, shRNA, CRISPR/Cas9, ZFN, TALEN, Cre recombinase or a mega nuclease.

Embodiment 258. The composition of embodiment 254 or 255, wherein the T cell comprises a further modification to increase MHC class I and/or MHC class II expression.

Embodiment 259. The composition of embodiment 254 or 255, wherein the further modification comprises increasing MHC class I and/or MHC class II expression using RNA or plasmid DNA.

Embodiment 260. The composition of any one of embodiments 253-257, wherein an innate immune response mounted in an individual in response to administration, in an allogeneic context, of the further modified T cells is reduced compared to an innate immune response mounted in an individual in response to administration, in an allogeneic context, of corresponding modified T cells that do not comprise the further modification.

Embodiment 261. The composition of any one of embodiments 253-257, wherein the circulating half-life of the further modified T cells in an individual to which they were administered is modulated compared to the circulating half-life of corresponding modified T cells that do not comprise the further modification in an individual to which they were administered.

Embodiment 262. The composition of any one of embodiments 253-261, wherein the T cell includes one or more of helper T cells, cytotoxic T cells, memory T cells, CIK cells and natural killer T cells.

Embodiment 263. The composition of any one of embodiments 253-261, wherein the T cell includes one or more of CD3+ T cells, CD4+ T cells, CD8+ T cells, CD45RA+ T cells, CD45RO+ T cells, and γδ-T cells.

Embodiment 264. The composition of any one of embodiments 186-263, wherein the modified cell is allogeneic to an individual.

Embodiment 265. The composition of any one of embodiments 186-263, wherein the modified cell is autologous to an individual.

Embodiment 266. The composition of any one of embodiments 186-265, wherein an individual is pre-conditioned to have modulated inflammation and/or a modulated immune response.

Embodiment 267. The composition of any one of embodiments 186-266, wherein the composition further comprises an immune checkpoint inhibitor.

Embodiment 268. The composition of embodiment 267, wherein the immune checkpoint inhibitor is targeted to one or more of PD-1, PD-L1, CTLA-4, LAG3, TIM-3, TIGIT, VISTA, TIM1, B7-H4 (VTCN1) or BTLA.

Embodiment 269. The composition of any one of embodiments 186-268, wherein administration of the composition comprising the modified immune cells to an individual results in activation and/or expansion of cytotoxic T lymphocytes (CTLs) specific for the HPV antigen.

Embodiment 270. The composition of any one of embodiments 186-268, wherein administration of the composition comprising the modified immune cells to an individual results in activation and/or expansion of helper T (Th) cells specific for the antigen.

Embodiment 271. The composition of any one of embodiments 186-270, wherein the effective amount of the composition comprises between about 1×106 and about 1×1012 modified immune cells.

Embodiment 272. A composition comprising an antigen, wherein the antigen comprises an amino acid sequence with at least 90% similarity to SEQ ID NO:23.

Embodiment 273. The composition of embodiment 272, wherein the antigen comprises the amino acid sequence of SEQ ID NO: 23.

Embodiment 274. A method for treating or preventing an HPV-associated disease in an individual, the method comprising administering to the individual an effective amount of a composition comprising modified immune cells, wherein the modified immune cells comprise an HPV antigen and an adjuvant, wherein the adjuvant is presented intracellularly;

wherein the modified immune cells are prepared by
a) passing a cell suspension comprising an input cell comprising an HPV antigen through a cell-deforming constriction, wherein a diameter of the constriction is a function of a diameter of the input cell in the suspension, thereby causing perturbations of the input cell large enough for the antigen and the adjuvant to pass through to form a perturbed input cell; and
b) incubating the perturbed input cell with the adjuvant for a sufficient time to allow the adjuvant to enter the perturbed input cell;
thereby generating the modified immune cells.

Embodiment 275. A method for treating or preventing an HPV-associated disease in an individual, the method comprising administering to the individual an effective amount of a composition comprising modified immune cells, wherein the modified immune cells comprise an HPV antigen and an adjuvant, wherein the adjuvant is presented intracellularly;

wherein the modified immune cells are prepared by
a) passing a cell suspension comprising an input cell comprising the adjuvant through a cell-deforming constriction, wherein a diameter of the constriction is a function of a diameter of the input cell in the suspension, thereby causing perturbations of the input cell large enough for the HPV antigen to pass through to form a perturbed input cell; and
b) incubating the perturbed input cell with the HPV antigen for a sufficient time to allow the HPV antigen to enter the perturbed input cell;
thereby generating the modified immune cells.

Embodiment 276. The method of embodiment 274 or 275, wherein the diameter of the constriction is less than the diameter of the cell.

Embodiment 277. The method of any one of embodiments 274-276, wherein the diameter of the constriction is about 20% to 99% of the diameter of the cell.

Embodiment 278. The method of any one of embodiments 274-277, wherein the diameter of the constriction is about 20% to less than about 60% of the diameter of the cell.

Embodiment 279. The method of any one of embodiments 274-278, wherein the constriction is in a channel.

Embodiment 280. The method of any one of embodiments 274-279, wherein a deforming force is applied to the input cell as it passes through the constriction.

Embodiment 281. The method of any of embodiments 274-280, wherein the HPV antigen and/or the adjuvant are present in the cytosol and/or endosomes.

Embodiment 282. The method of any one of embodiments 274-281, wherein the antigen and/or adjuvant are present in multiple compartments of the cell.

Embodiment 283. The method of embodiment 274, wherein the concentration of adjuvant incubated with the perturbed input cell is between about 0.1 μM and about 1 mM Embodiment 284. The method of embodiment 275, wherein the concentration of HPV antigen incubated with the perturbed input cell is between about 0.1 μM and about 1 mM.

Embodiment 285. The method of any one of embodiments 274-285, wherein the adjuvant is CpG ODN, IFN-α, STING agonists, RIG-I agonists or poly I:C.

Embodiment 286. The method of embodiment 285, wherein the adjuvant is CpG ODN.

Embodiment 287. The method of embodiment 286, wherein the CpG ODN is CpG ODN 1018, CpG ODN 1826 or CpG ODN 2006.

Embodiment 288. The method of any one of embodiments 274-287, wherein the HPV antigen is derived from a cell lysate.

Embodiment 289. The method of any one of embodiments 274-288, wherein the HPV antigen is an HPV-16 or an HPV-18 antigen.

Embodiment 290. The method of any one of embodiments 274-289, wherein the HPV antigen is an HPV E6 antigen or an HPV E7 antigen.

Embodiment 291. The method of embodiment 290, wherein the HPV antigen comprises an amino acid sequence with at least 90% similarity to any one of SEQ ID NOs:18-25.

Embodiment 292. The method of embodiment 289, wherein the HPV antigen comprises an amino acid sequence of any one of SEQ ID NOs:18-25.

Embodiment 293. The method of embodiment 290, wherein the HPV antigen comprises an amino acid sequence with at least 90% similarity to SEQ ID NO:23.

Embodiment 294. The method of embodiment 290, wherein the HPV antigen comprises an amino acid sequence of SEQ ID NO:23.

Embodiment 295. A method for treating or preventing an HPV-associated disease in an individual comprising administering to the individual a modified immune cell associated with an HPV antigen, wherein the modified immune cell is prepared by a process comprising the steps of:

a) incubating an input cell with the HPV antigen and/or an adjuvant for a sufficient time to allow the HPV antigen to associate with the input cell;

thereby generating the modified immune cell associated with the antigen.

Embodiment 296. The method in embodiment 295, wherein the HPV antigen comprises an amino acid sequence with at least 90% similarity to any one of SEQ ID NOs:18-25.

Embodiment 297. The method in embodiment 296, wherein the HPV antigen comprises the amino acid sequence of SEQ ID NO:23.

Embodiment 298. The method in any one of embodiments 295-297, wherein the adjuvant is CpG ODN.

Embodiment 299. The method of embodiment 298, wherein the CpG ODN is CpG ODN 1018, CpG ODN 1826 or CpG ODN 2006.

Embodiment 300. A composition comprising the modified immune cells of any one of embodiments 186-273 for use as a medicament.

Embodiment 301. A composition comprising the modified immune cells of any one of embodiments 186-273 for use in a method of treatment of the human or animal body by surgery, therapy or diagnosis.

Embodiment 302. A composition comprising the modified immune cells of any one of embodiments 186-273 for use in the treatment of a cancer, an infectious disease or a viral-associated disease.

Embodiment 303. A composition comprising the modified immune cells of any one of embodiments 186-273, wherein the cancer is head and neck cancer, cervical cancer, vulvar cancer, vaginal cancer, penile cancer, anal cancer, perianal cancer, anogenital cancer, oral cancer or salivary cancer.

Embodiment 304. A composition comprising the modified immune cells of any one of embodiments 300-303, wherein the modified PBMCs is administered prior to, concurrently with, or following administration of an immune checkpoint inhibitor.

Embodiment 305. The composition of embodiment 304, wherein the immune checkpoint inhibitor is targeted to any one of PD-1, PD-L1, CTLA-4, LAG3, VISTA, and TIM-3.

Embodiment 306. The composition of embodiment 305, wherein the immune checkpoint inhibitor is targeted to PD-1.

Embodiment 307. The composition of embodiment 305, wherein the immune checkpoint inhibitor is targeted to PD-L1.

Embodiment 308. The composition of any one of embodiments 300-307, wherein the modified PBMCs is administered prior to, concurrently with, or following administration of a therapeutic agent.

Embodiment 309. The composition of embodiment 308, wherein the therapeutic agent is a chemotherapeutic agent.

Embodiment 310. The composition of embodiment 309, wherein the infectious disease is associated with HIV, HPV, EBV, MCV, HBV or HCV.

EXAMPLES

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Example 1

In order to determine the minimum effective cell dose of $T_{APC}$s needed to lead to tumor growth inhibition in a therapeutic setting, four different doses of prime/boost $T_{APC}$s were tested in a TC1 tumor model, with the area of the tumors plotted against time.

C57BL/6J female mice were injected in the right rear flank with TC1 tumor cells (50 k cells/mouse) at Day 0. On Days 4 (prime) and 7 (boost), T cells from C57BL/6J female donor mice were isolated and loaded using SQZ with 200 μg/mL CpG ODN 1826 and pre-complexed 40 μM E7 SLP (GQAEPDRAHYNIVTFSSKSDSTLRLSVQSTHVDIR; SEQ ID NO:25)+40 μM mouse serum albumin (MSA). Animals (10 mice/group) were injected intravenously with the relevant dose of E7+MSA+CpG loaded T cells (50M cells/mL) and TC-1 tumor growth was measured beginning 1 week post-tumor implantation two times per week and compared to tumor growth in untreated mice. A representative schematic of the treatment groups and schedule is outlined in FIG. 1A.

Tumor growth, as measured by the formula ((length×width$^2$)/2), was compared between mice from the untreated group (no adoptive transfer of T cells) and the treatment groups B-E outlined in FIG. 1A is shown in FIG. 1B. All treatment conditions led to complete tumor reduction, indicative that the lowest cell dose tested (2.5M cells prime, 1M cells boost) was still capable of achieving the same tumor reduction as higher cell doses, each reaching statistical significance relative to untreated at Day 18 (#P<0.0001).

Example 2

To determine the E7 SLP design, two different E7 SLPs, the native E7 SLP and one in which the native sequence has all cysteines replaced with serine, were SQZ'd into T APCs along with CpG co-administration, and each condition was assessed for IFN-γ production by ICS.

Figure 2B:
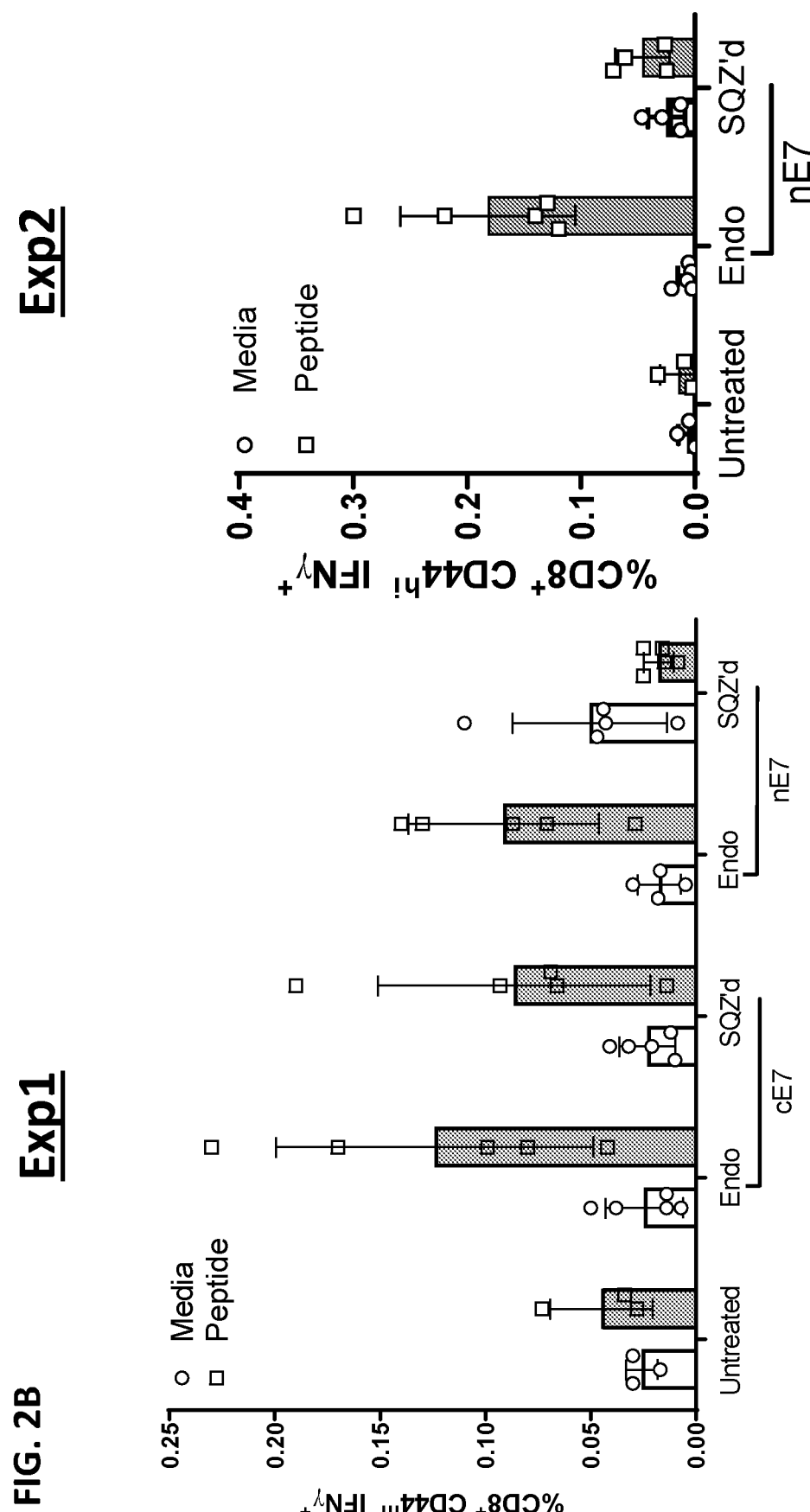
FIG. 2B shows that the impact of SLP sequence on IFN-γ-producing CD8+ T cells generated in response to $T_{APC}$ vaccination.

T cells from C57BL/6J female donor mice were isolated and loaded using SQZ with varying doses (Left—200 μg/mL, Right—25 μg/mL) CpG ODN 1826 and pre-complexed 40 μM E7 native or classic SLP+40 μM mouse serum albumin (MSA) or T cells were incubated with the same conditions in the absence of SQZ as a negative control (Endo—Groups B and D). Animals (5 mice/group) were injected intravenously with 5M loaded or incubated T cells in 100 μL volume (50M cells/mL). On Day 8, spleens were harvested and the % of IFN-γ-producing CD8+ T cells was quantified by ICS. A representative schematic of the treatment groups and schedule is outlined in FIG. 2A.

The % of IFN-γ-producing CD8+ T cells was highest in the Endo control group using cE7, which was not significantly different from SQZ with cE7 or Endo with nE7. Unexpectedly, there was no benefit to SQZ vs. Endo, but there was a notable decrease in % of IFN-γ-producing CD8+ T cells in the SQZ nE7 condition relative to all others. This data shows that the SLP sequence has an impact on % of IFN-γ-producing CD8+ T cells generated in response to T APC vaccination, particularly when the antigen is loaded into the T cell using SQZ.

Example 3

To determine the ability of E6 SLPs to induce an antigens-specific immune response in E6 responder T cells in an in vitro human model, primary human T cells were loaded with an E6 SLP and responder cell IFN-γ secretion was measured by ELISA.

Human T cells were isolated from the PBMCs of HLA-A02+ donors (10M cells/mL) and 50 μM E6 SLP containing the HLA-A02-restricted minimal $E6_{29-38}$ epitope (LPQL-STELQTTIHDIILECVYSKQQLLRREVYDFAF; SEQ ID NO:18) was delivered intracellularly by SQZ and the level of IFN-γ, as measured by ELISA, was compared between the SQZ conditions and a control wherein the E6 SLP is incubated with the $T_{APC}$s in the absence of SQZing (Endo). $T_{APC}$s were then co-cultured with E6-specific CD8+ responder cells in a ratio of 1:1 stimulator:effector and cultured in the presence of IL-2 (100 U/mL). After 18 h, supernatant is harvested from each condition and the level of IFN-γ production was assessed by IFN-γ ELISA (Biolegend).

Figure 3:
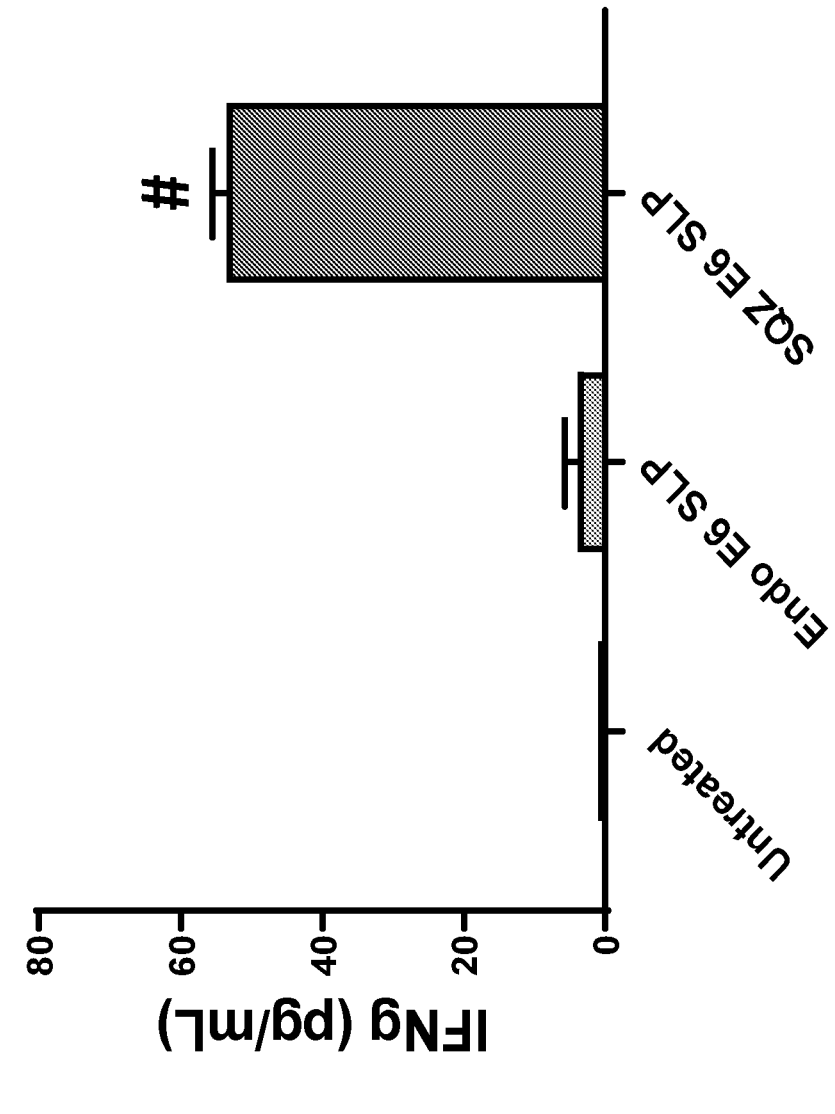
FIG. 3 is a graph showing the ability of E6 SLPs to induce an antigens-specific immune response in E6 responder T cells in an in vitro human model.

The E6 SLP tested, when delivered intracellularly using SQZ, led to a >10-fold increase in IFN-γ production when co-cultured with E6 responder CD8+ T cells ($\#P<0.0001$) as shown in FIG. 3. These findings show the ability of T APCs to elicit an antigen-specific immune response to multiple HPV antigens (E6 and E7).

Example 4

To determine the ability of E7 SLPs to induce an antigen-specific immune response in $E7_{11-20}$ responder T cells, as well as the impact of SLP sequence on SQZ T cell APC ($T_{app}$) activation in an in vitro human model, primary human T cells from multiple donors were loaded with different E7 SLPs and responder cell IFN-γ secretion was measured by ELISA.

Human T cells were isolated from the PBMCs of HLA-A02+ donors (10M cells/mL) and 50 μM OL-$E7_{1-35}$ (MHGDTPTLHEYMLDLQPETTDLYCYEQLNDSSEEE; SEQ ID NO:22) or E7.6 (QLCTELQTYMLDLQPET- TYCKQQLL; SEQ ID NO:23) SLPs were delivered intracellularly by SQZ and the level of IFN-γ, as measured by ELISA, were compared between the SQZ conditions and a control wherein the E7 SLP were incubated with the $T_{apc}$s in the absence of SQZing (Endo). $T_{APC}$s were then co-cultured with $E7_{11-20}$-specific CD8+ responder cells in a ratio of 4:1 stimulator:effector and cultured in the presence of IL-2 (100 U/mL). After 24 h, supernatant is harvested from each condition and the level of IFN-γ production was assessed by IFN-γ ELISA (Biolegend).

Figure 4:
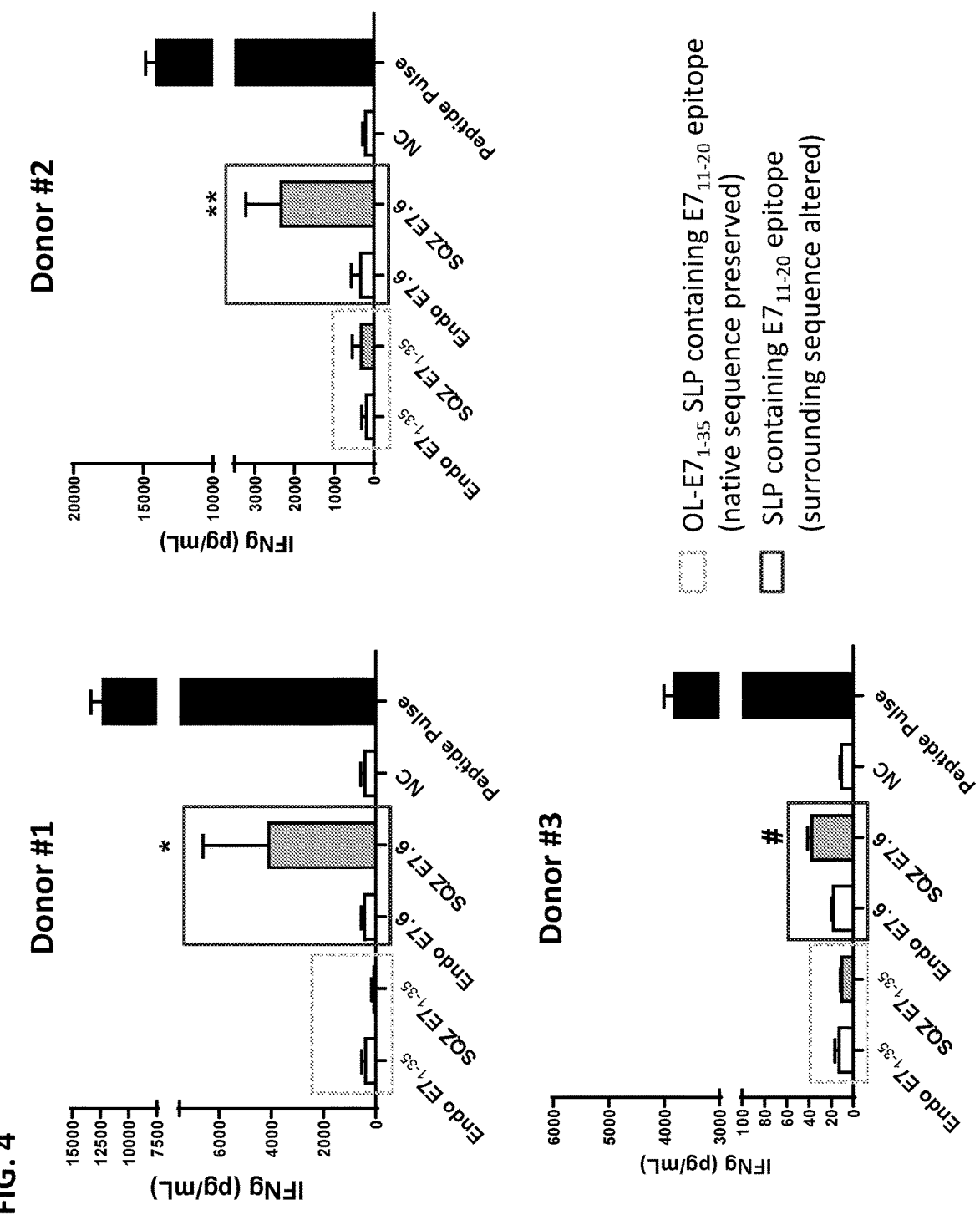
FIG. 4 shows the ability of E7 SLPs to induce an antigen-specific immune response in $E7_{11-20}$ responder T cells, as well as the impact of SLP sequence on SQZ T cell APC ($T_{apc}$) activation in an in vitro human model.

The native OL-$E7_{1-35}$ SLP elicited a minimal IFN-γ response when delivered using SQZ compared to Endo (FIG. 4). However, the E7.6, which comprises the E7 minimal epitope (YMLDLQPETT; SEQ ID NO:3) inserted in between the flanking regions of another reactive SLP ($E6_{21-45}$—QLCTELQTXXXXXXXXXXYCKQQLL), induced a greater IFN-γ response relative to the matched Endo control in all three donors tested when compared to the Endo controls ($*P<0.05$, $**P<0.01$; $\#P<0.0001$). This finding highlights the importance of the flanking region sequence in the immunogenicity of the SLP and provides support that flanking regions of other SLPs, which are known to be reactive, can be used in conjunction with orthogonal minimal epitopes to achieve increased immune responses.

Example 5

To evaluate the dose of antigen for SQZ T cell APCs in an in vitro human model, primary human T cells were loaded with an E7 SLP at varying doses and assessed for IFN-γ by ELISA.

Human T cells were isolated from the PBMCs of HLA-A02+ donors (10M cells/mL) and varying doses (50 and 100 μM) E7 SLP (QLCTELQTYMLDLQPETTYCKQQLL; SEQ ID NO:23) were delivered intracellularly by SQZ and the level of IFN-γ, as measured by ELISA, were compared between the SQZ conditions and a control wherein the E7 SLP is incubated with the T APCs in the absence of SQZing (Endo). T APCs were then co-cultured with $E7_{11-20}$-specific CD8+ responder cells in a ratio of 4:1 stimulator:effector and cultured in the presence of IL-2 (100 U/mL). After 24 h, supernatant is harvested from each condition and the level of IFN-γ production was assessed by IFN-γ ELISA (Biolegend). Additionally, a peptide pulse positive control was employed wherein B-LCL cells were incubated in the presence of the minimal E7 epitope (YMLDLQPETT; SEQ ID NO:3) for 1 h prior to ELISA.

Figure 5:
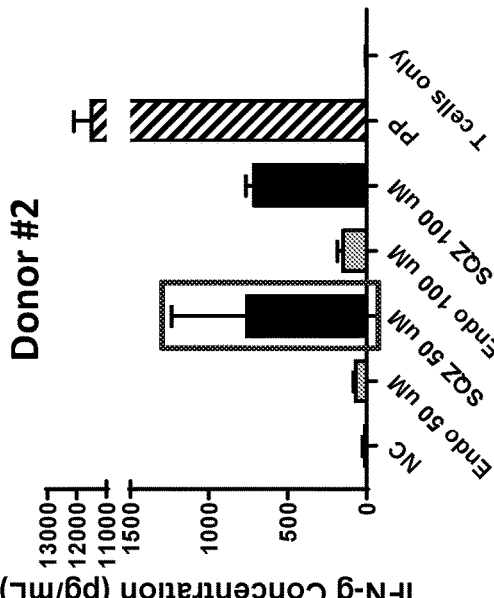
FIG. 5 shows results of a study to evaluate the dose of antigen for SQZ T cell APCs in an in vitro human model.
Figure 5:
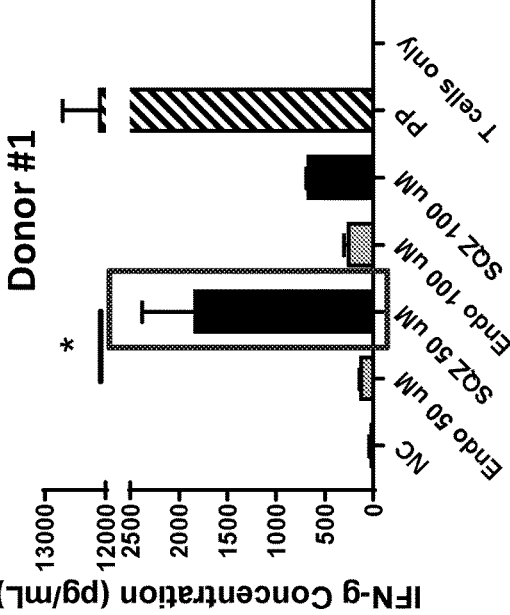
Figure 5:
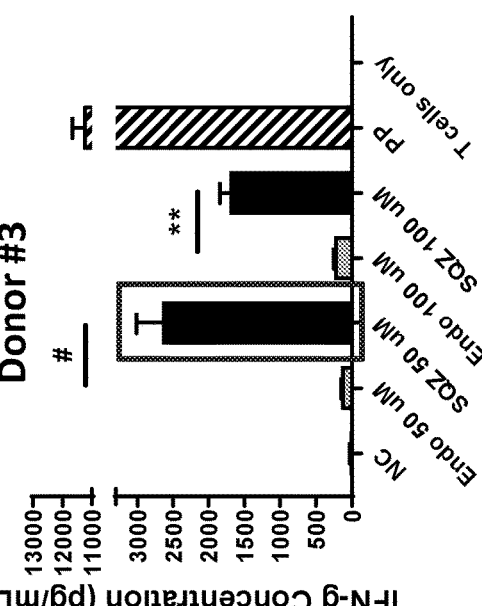

Across the three donors tested, consistent increases in IFN-γ occurs with all SQZ conditions relative to comparable control (Endo) where the SLP is incubated with the T cell in the absence of SQZ (FIG. 5). Donors 1 and 3 exhibited statistically significant increases with 50 μM E7 SLP (8668—$*P<0.05$; 8299—$\#P<0.0001$), and a trend towards significance at the higher 100 μM E7 SLP. While there was no statistically significant difference between 50 and 100 μM for any donor, there was consistently equal or higher IFN-γ response with 50 μM E7 SLP.

Example 6

To determine the donor variability for SQZ T cell APCs in an in vitro human model, along with identify optimum combinations and doses of E6 and E7 SLPs that induce a significant immune response against E7 in primary human T cells from multiple HLA-A02+ donors were loaded with a E6 and E7 SLPs and assessed for IFN-γ by ELISA.

Human T cells were isolated from the PBMCs of HLA-A02+ donors (10M cells/mL) and 25 or 50 µM E6 SLP (QLCTELQTTIHDIILECVYCKQQLL) and E7.6 SLP (QLCTELQTYMLDLQPETTYCKQQLL; SEQ ID NO:23) was delivered intracellularly by SQZ and the levels of IFN-γ, as measured by ELISA, were compared between the SQZ conditions and a control wherein the SLPs are incubated with the $T_{APC}$s in the absence of SQZing (Endo). A peptide pulse positive control was employed wherein B-LCL cells were incubated in the presence of the minimal E7 epitope (YMLDLQPETT; SEQ ID NO:3) at the same time as $T_{APC}$ generation. $T_{APC}$s and the positive control were then co-cultured with $E7_{11-20}$-specific CD8+ responder cells in a ratio of 4:1 stimulator:effector and cultured in the presence of IL-2 (100 U/mL). After 24 h, supernatant is harvested from each condition and the level of IFN-γ production was assessed by IFN-γ ELISA (Biolegend).

Figure 6:
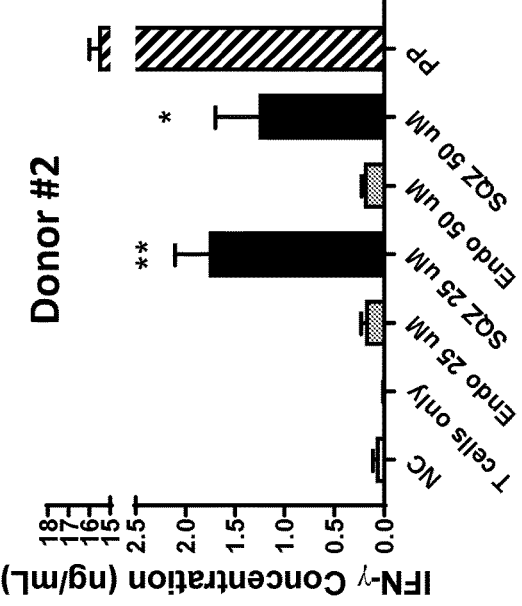
FIG. 6 shows the results of a study to determine the donor variability for SQZ T cell APCs in an in vitro human model.
Figure 6:
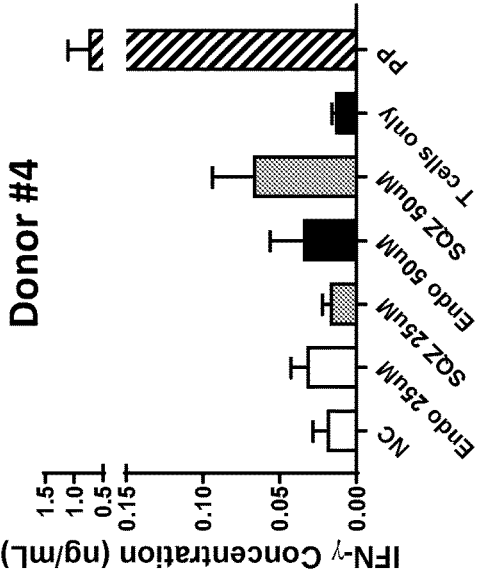
Figure 6:
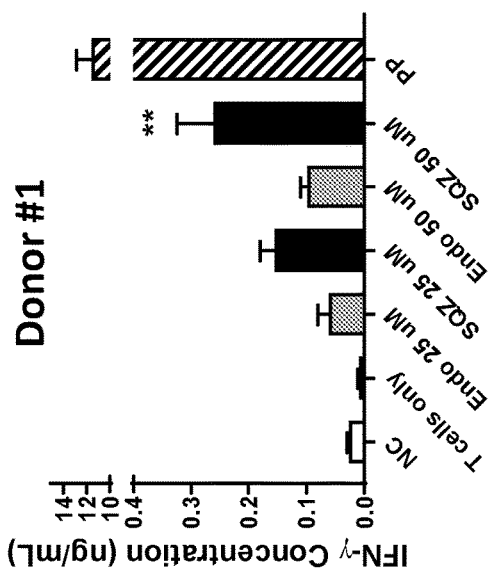
Figure 6:
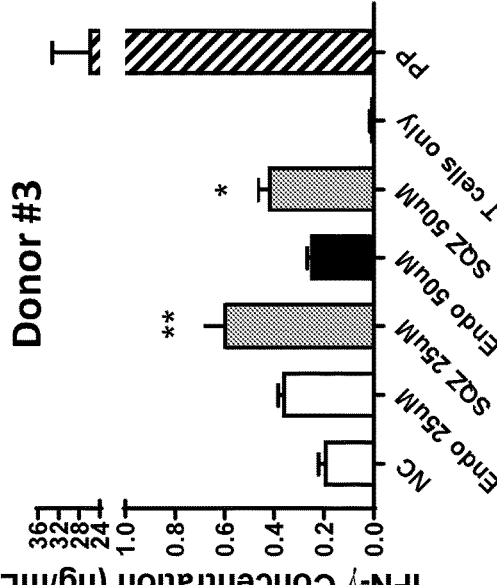
Figure 6:
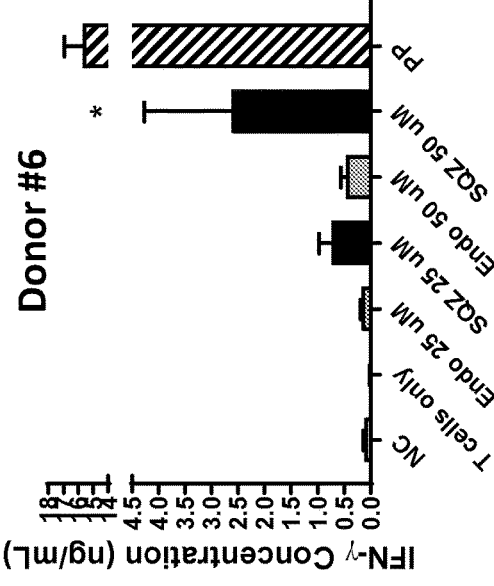
Figure 6:
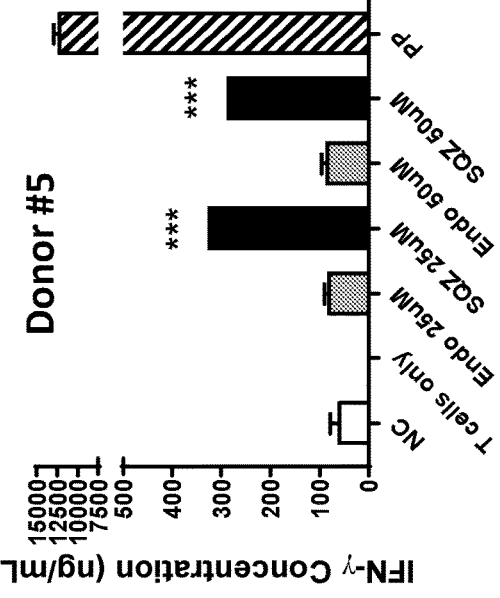
Figure 6:
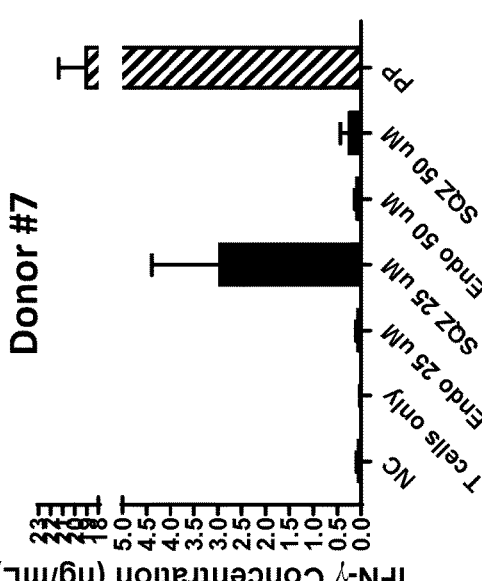

Five out of seven donors shown exhibited consistent increases in IFN-γ when treated with SQZ E6+E7 SLPs relative to comparable control (Endo) where the SLP is incubated with the T cell in the absence of SQZ (Donors 1-3, 5-6: *P<0.05, P<0.01, *P<0.005) as shown in FIG. 6. Of the two donors that did not have statistically significant increases when treated with SQZ'd T APCs relative to Endo controls, both donors (Donors 4 & 7) had conditions where there was detectable increases with one dose of SQZ'd T APCs tested (Donor 4—50 µM, Donor 7—25 µM), trending towards significance. Taken together, these data show that while different donor T APCs have differential immunostimulatory activity, we can see a consistent increase in IFN-γ production across multiple donors and that the E7-specific immune response is still significant when combined with multiple antigens/SLPs, in this case the HPV-specific E6 antigen.

Example 7

To help determine the adjuvant that leads to the most robust immune response, we tested the effect of two adjuvants that act on different pathways on the ability of the T APCs to induce an in vivo antigen-specific response. This effect was quantified by tetramer and ICS staining by flow cytometry.

Figure 7A:
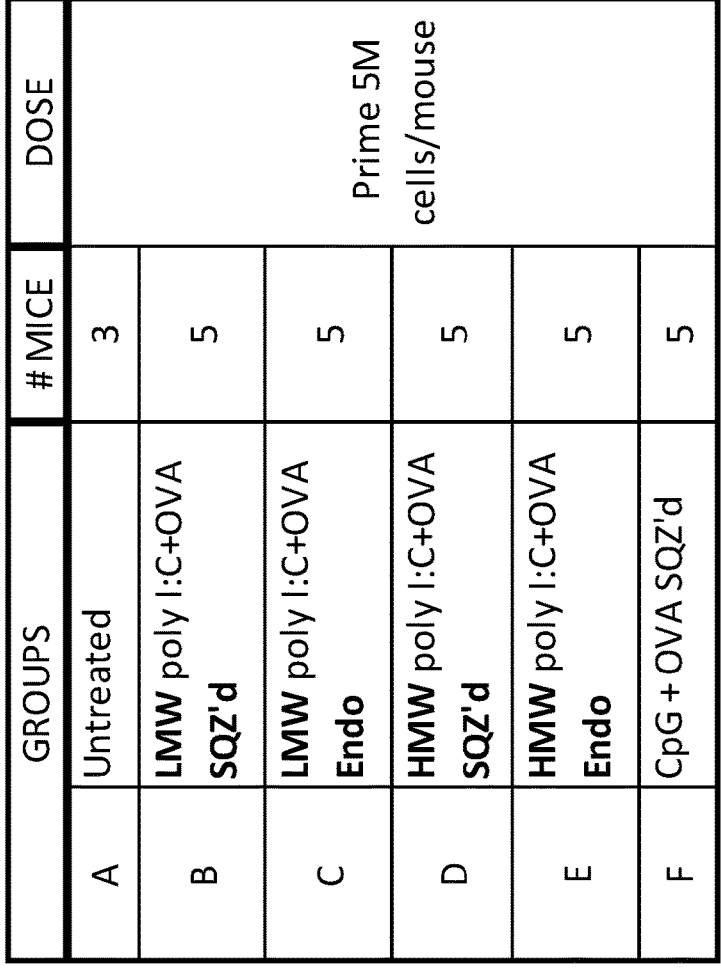
FIG. 7A is a schematic of an experiment to compare the robustness of immune responses using different adjuvants.
Figure 7A:
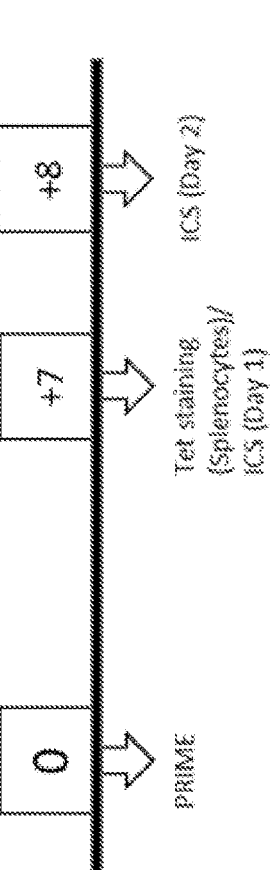

T cells from C57BL/6J female donor mice were isolated and loaded using SQZ with 400 µg/mL Ova+various concentrations of high- and low-molecular weight poly I:C (10, 30, 100, 300, 1000 µg/mL) and compared to T cells incubated with the same conditions in the absence of SQZ as a negative control (Endo—Groups C & E). T cells SQZ'd with Ova+200 µg/mL CpG were used as a positive control (Group F). On Day 0, mice (5/group, 3 untreated) were injected with 5M loaded or incubated T cells in 100 µL volume (50M cells/mL). On Day 7, spleens were harvested and Ova-specific T cells were quantified by tetramer staining using flow cytometry, while some splenocytes were permeabilized and fixed overnight. The next day (Day 8), the levels of IFN-γ was determined by ICS, with PMA/ionomycin acting as a positive control. A representative schematic of the treatment groups and schedule is outlined in FIG. 7A.

Figure 7B:
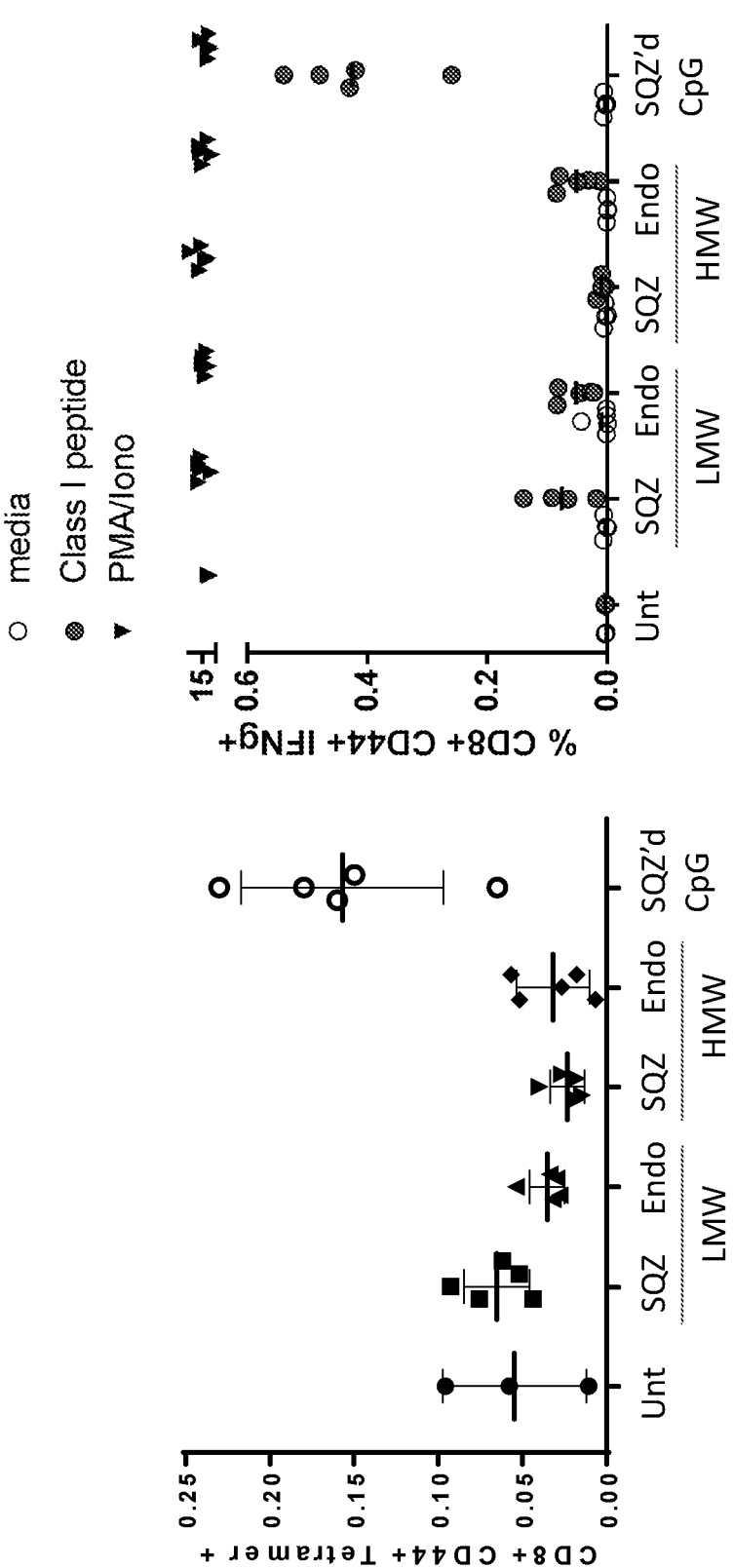
FIG. 7B shows the results of the experiment to compare robustness of immune responses using poly I:C and a CpG ODN.

The % of tetramer or IFN-γ-producing CD8+ T cells was highest in the group adjuvanted with CpG, while all conditions adjuvanted with LMW or HMW poly I:C did not increase the percentage of Ova-specific or IFN γ-producing CD8+ T cells over untreated (FIG. 7B). As poly I:C is a TLR3 agonist, and CpG is a TLR9 agonist, this data supports the superiority of CpG over poly I:C as an adjuvant with T APC vaccination, while suggesting that TLR3 activation may not be beneficial in this setting.

Example 8

To help determine the concentration of CpG adjuvant that leads to the most robust immune response, we tested the effect of multiple doses of CpG on the ability of the T APCs to induce an in vivo antigen-specific response. This effect was quantified by tetramer and ICS staining by flow cytometry.

Figure 8A:
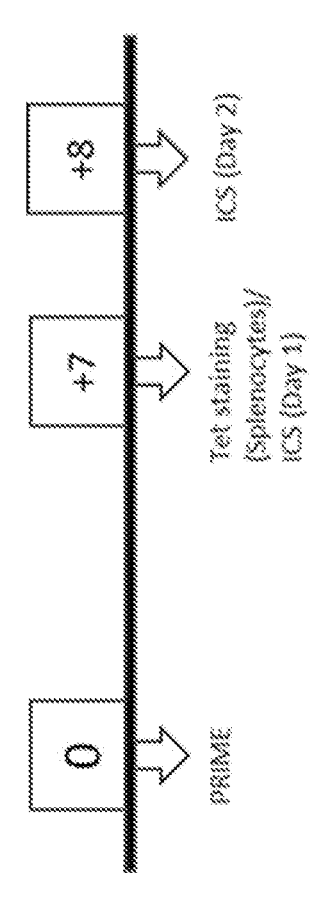
FIG. 8A is a schematic of an experiment evaluating the effect of concentration of CpG ODN on immune responses.

T cells from C57BL/6J female donor mice were isolated and loaded using SQZ with 400 µg/mL Ova+various concentrations of CpG 1826 (50, 100, 200 µg/mL) and compared to T cells incubated with the same conditions in the absence of SQZ as a negative control (Endo—Groups B, D & F). On Day 0, mice (5/group, 3 untreated) were injected with 5M loaded or incubated T cells in 100 µL volume (50M cells/mL). On Day 7, spleens were harvested and Ova-specific T cells were quantified by tetramer staining using flow cytometry, while some splenocytes were permeabilized and fixed overnight. The next day (Day 8), the levels of IFN-γ was determined by ICS, with PMA/ionomycin acting as a positive control. A representative schematic of the treatment groups and schedule is outlined in FIG. 8A.

Figure 8B:
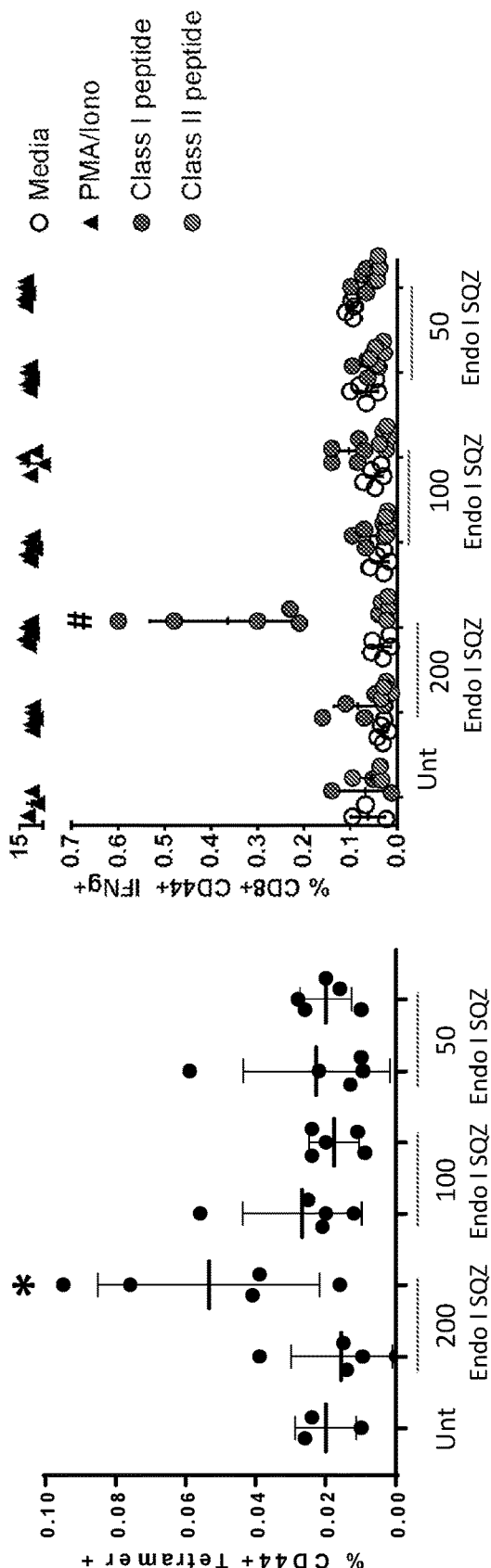
FIG. 8B shows the results of the experiment evaluating the effect of concentration of CpG ODN on immune responses.

The % of tetramer or IFN-γ-producing CD8+ T cells was highest in the group with 200 µg/mL CpG and was significantly different from the related Endo control (*P<0.05 for tetramer, #P<0.0001 for IFN-γ) for Class I peptide/MHC-I, while all other conditions did not elicit a significant response over untreated or their respective Endo controls (FIG. 8B). The activation of Ova-specific T cells was only observed with the Class I peptide, supporting the direct presentation of Ova antigens to effect a CD8+ T cell response.

Example 9

To help evaluate schedule for CpG adjuvant administration that leads to a robust immune response, we tested the effect of multiple dosing schedules of CpG on the ability of the T APCs to induce an in vivo antigen-specific response. This effect was quantified by tetramer and ICS staining by flow cytometry.

T cells from C57BL/6J female donor mice were isolated and loaded using SQZ with 400 µg/mL Ova and mice (5/group, 3 untreated) were injected with 5M loaded or incubated T cells in 100 µL volume (50M cells/mL). CpG 1826 (25 µg/mL) systemic co-administration of donor mice occurred either at the same time as the T APC prime (Day 0), or 1 or 2 days following prime (Day 1 or 2, respectively) and compared to T cells incubated with the same conditions in the absence of SQZ as a negative control (Groups B, D & F). T cells SQZ'd with (Ova+200 µg/mL CpG) were used as a positive control (Group H). On Day 7, spleens were harvested and Ova-specific T cells were quantified by tetramer staining using flow cytometry, while some splenocytes were permeabilized and fixed overnight. The next day (Day 8), the levels of IFN-γ was determined by ICS, with PMA/ionomycin acting as a positive control. A representative schematic of the treatment groups and schedule is outlined in FIG. 9A.

Figure 9B:
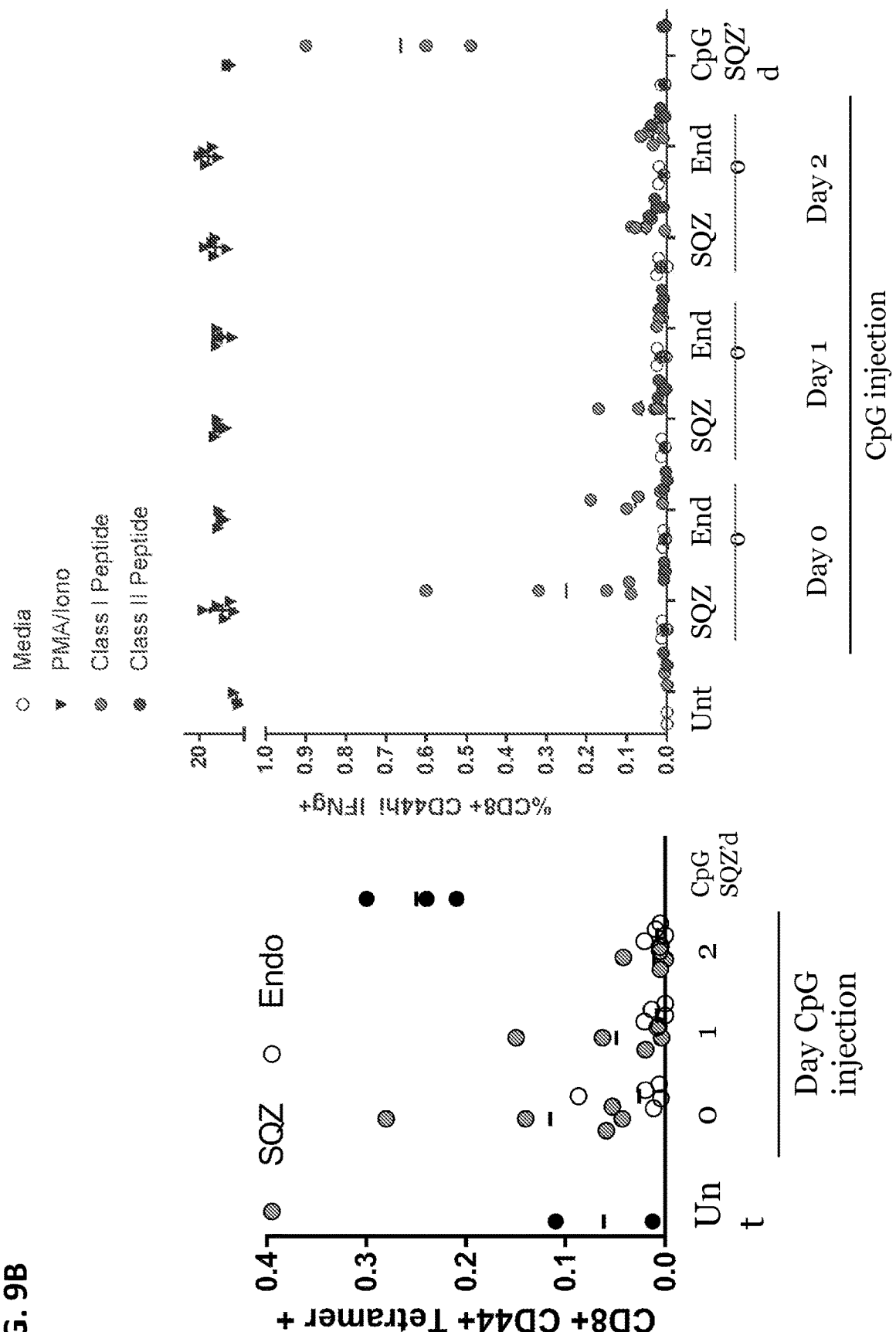
FIG. 9B shows the results of the experiment evaluating the dosing schedule of CpG ODN on immune responses.

The % of tetramer or IFN-γ-producing CD8+ T cells was highest in the group where Ova and CpG were co-delivered to T APCs, while co-administration the same day as prime (Group B) was the only co-administered CpG group to show some level of Ova-specific activation, trending towards significance (FIG. 9B). However, this data supports the observation that antigen+CpG co-delivery can lead to the greatest activation of Ova-specific CD8+ T cells, while delaying systemic administration of CpG leads to lower responses compared to simultaneous prime and co-administration of adjuvant.

Example 10

In order to determine a combination of intracellular and system adjuvant administration for T APC antitumor function, multiple routes of administration of CpG vs. IFN-α were compared in conjunction with our E7-specific T APC in a prophylactic TC-1 murine tumor model. Antigen-specific T cell responses were measured by tetramer staining and flow cytometry, while antitumor effect was measured by tumor growth prevention.

Figure 10A:
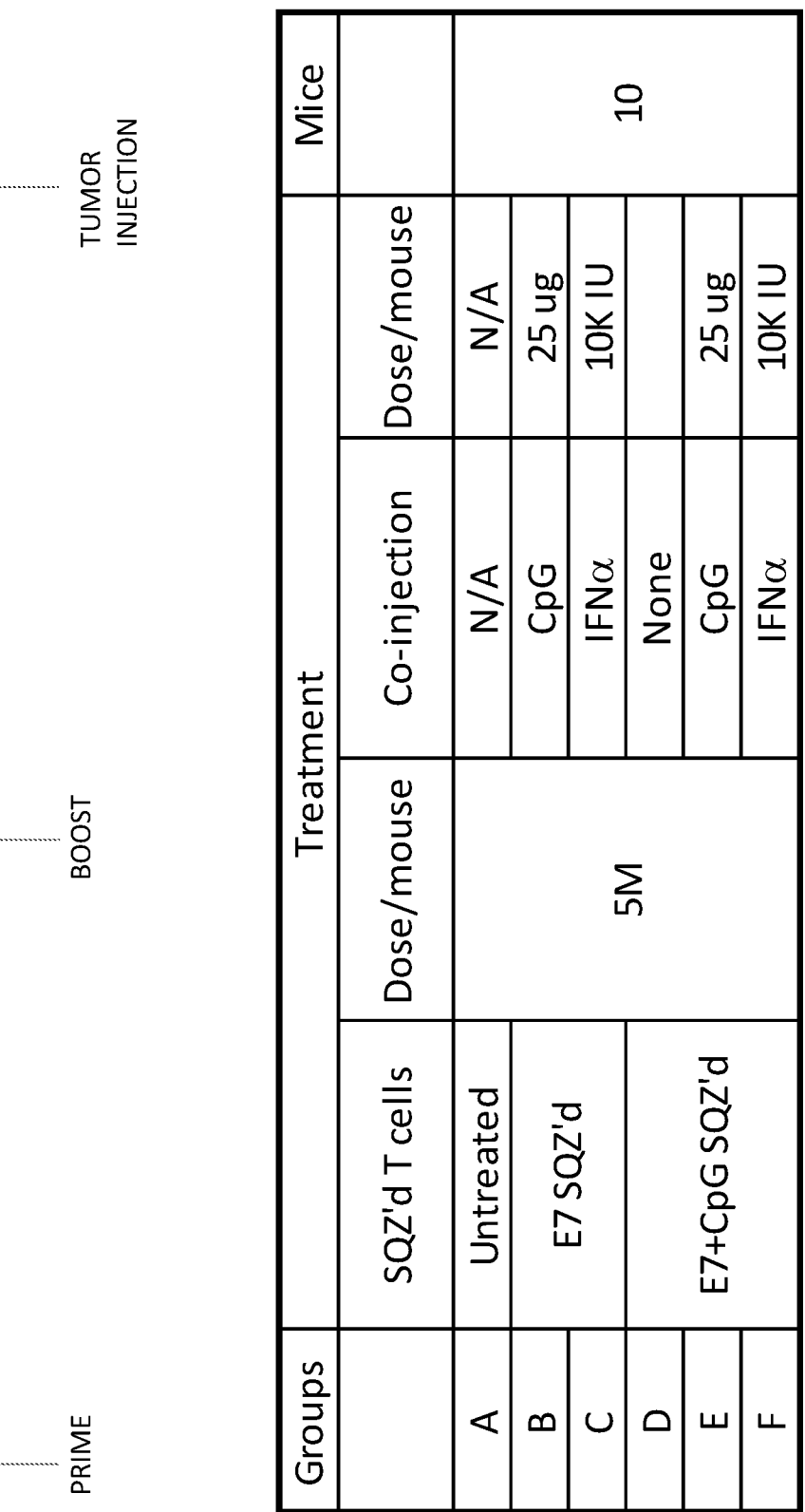
FIG. 10A is a schematic of an experiment to evaluate the combination of intracellular and systemic adjuvant administration for $T_{APC}$ antitumor function.

On Days –14 (prime) and –7 (boost), T cells from C57BL/6J female donor mice were isolated and loaded using SQZ with pre-complexed 40 μM E7 SLP (GQAE-PDRAHYNIVTFSSKSDSTLRLSVQSTHVDIR; SEQ ID NO:25)+40 μM mouse serum albumin (MSA) (Groups B and C) or E7 SLP+MSA+200 μg/mL CpG ODN 1826 (Groups D, E and F). C57BL/6J female recipient mice (10 mice/group) were injected intravenously with 100 μL of loaded T cells (5M cells/animal), while groups B and E animals also received intravenous CpG (25 μg) and groups C and F received IV IFN-α(10 k IU). On Days –8 and –3, 100 μL of murine blood was collected and the % of E7-specific CD8+ T cells was quantified by tetramer staining and flow cytometry. On Day 0, recipient mice were injected in the right rear flank with TC1 tumor cells (100 k cells/mouse) and TC-1 tumor growth was measured two times per week beginning on Day 11 and compared to tumor growth in untreated mice. A representative schematic of the treatment groups and schedule is outlined in FIG. 10A.

Figure 10B:
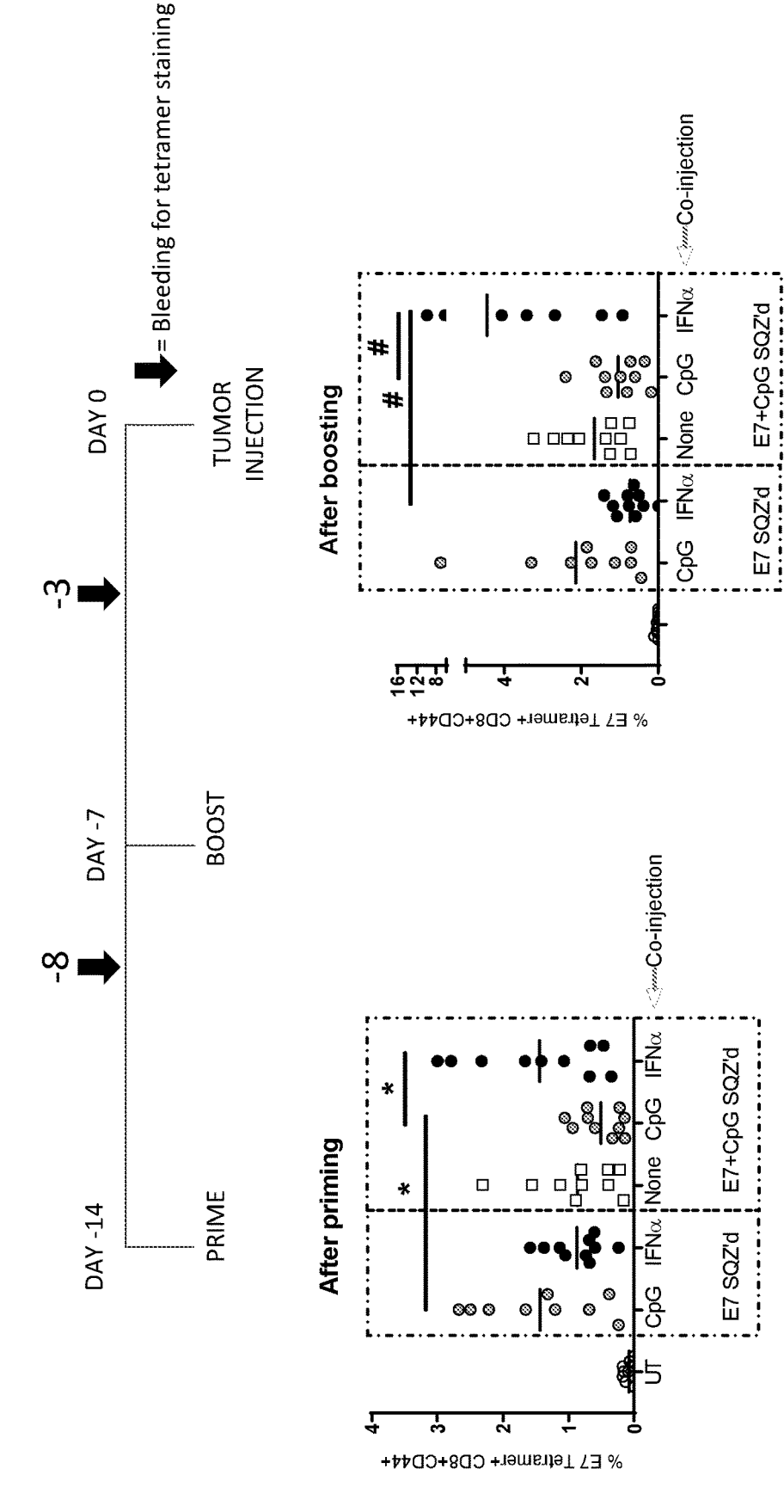
FIG. 10B shows T cell responses for each experimental group and FIG. 10C shows growth of tumors for each experimental group.
Figure 10C:
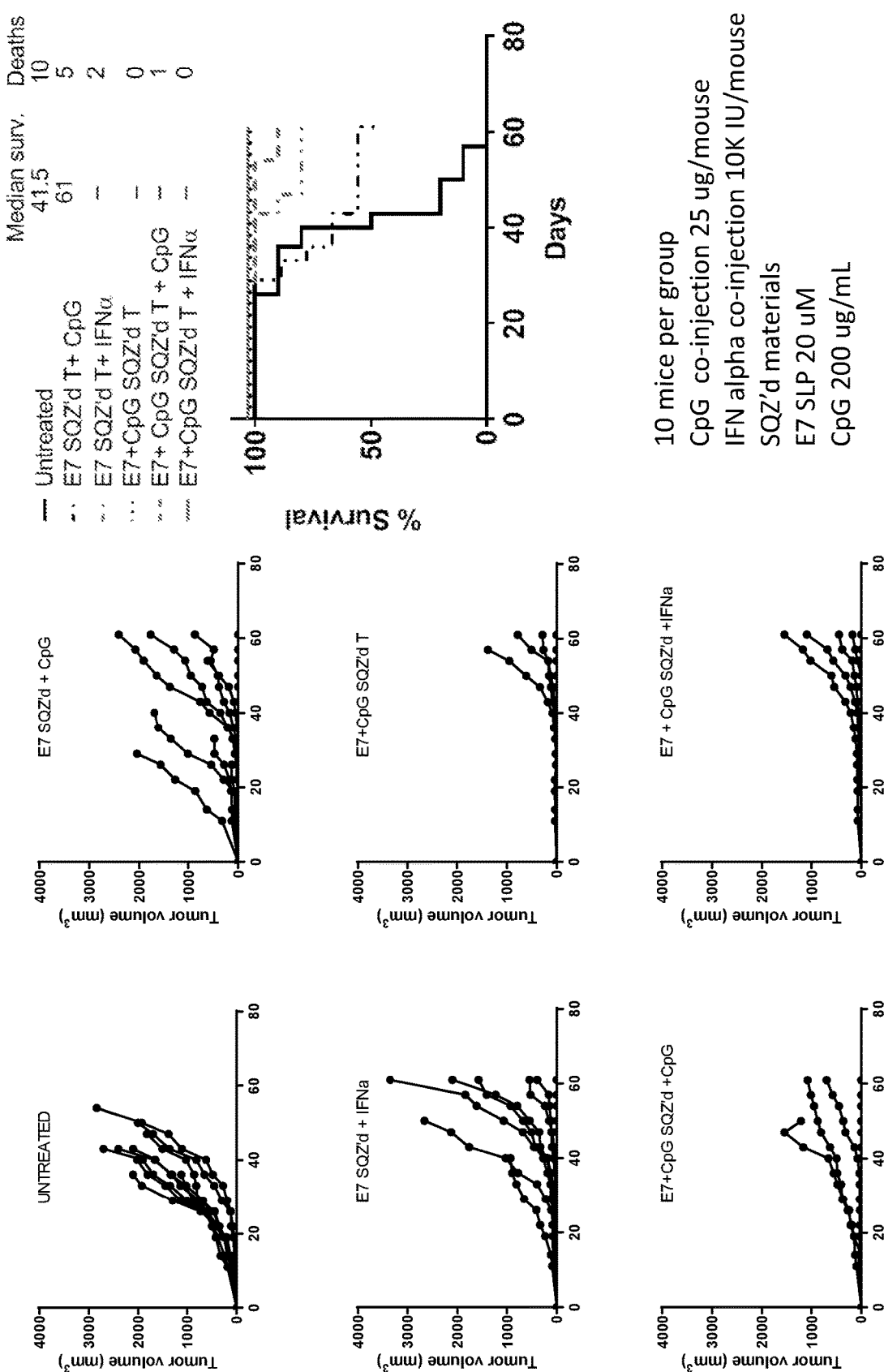
Figure 10D:
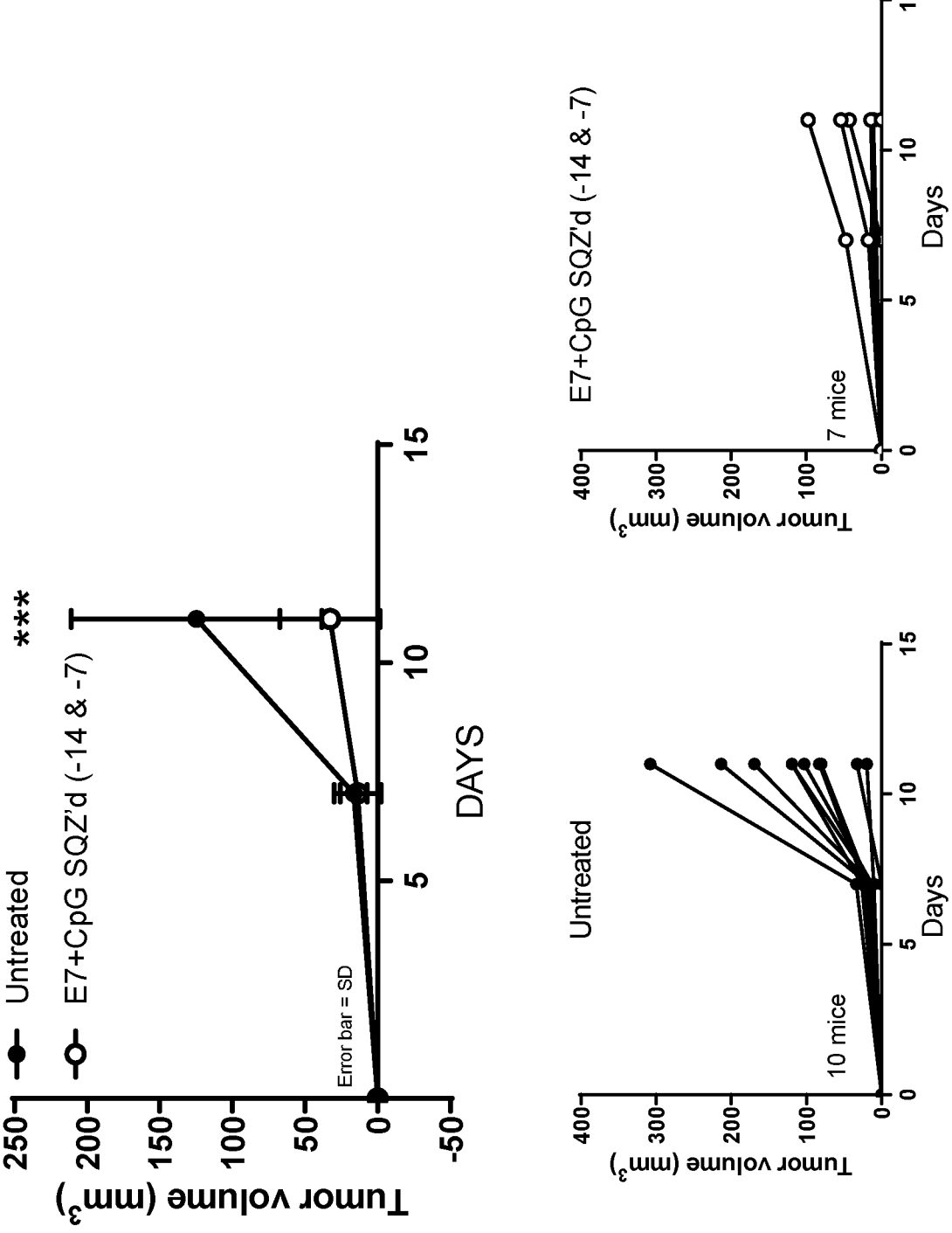
FIG. 10D shows tumor growth following rechallenge in animals treated with SQZ (E7+CpG) relative to untreated animals.

The percentage of E7-specific T cell were measured in mice by E7 tetramer staining after prime (Day –8) and boost (Day –3) with E7+MSA or E7+MSA+CpG SQZ'd T cells+/–co-administration of CpG or IFN-α(FIG. 10B). The highest relative proportion of E7-specific T cells were observed in the SQZ E7+ CpG co-administration and SQZ (E7+CpG)+IFN-α co-administration groups. The relative number of E7-specific post-prime CD8+ T cells was surprisingly lower in the SQZ (E7+CpG)+ co-administration of CpG relative to the SQZ E7+ co-administration of CpG (*P<0.05), whereas the co-administration of IFN-α with SQZ (E7+CpG) T cells led to a significantly higher number of E7-specific T cells than co-administration of CpG with SQZ (E7+CpG) T cells (*P<0.05). After boost (Day –3), a similar trend was observed where SQZ E7+ CpG co-administration and SQZ (E7+CpG)+ IFN-α co-administration groups led to the highest % E7-specific T cells. However, the highest response came from the SQZ (E7+CpG)+ IFN-α co-administration group, which was significantly higher than SQZ E7+IFN-α co-administration and SQZ (E7+CpG)+ co-administration of CpG, showing that IFN-α co-administration leads to a higher percentage of antigen-specific T cells when used in combination with SQZ (E7+CpG) T cells. Tumor growth, as measured by the formula ((length×width$^2$)/2), was compared between mice from the untreated group (no adoptive transfer of T cells) and the treatment groups B-F outlined in FIG. 10C. The high tumor growth reduction and survival advantage of the SQZ (E7+CpG)+IFN-α co-administration group corresponds well with the tetramer staining, showing that the highest induction of E7-specific T cells led to the best antitumor activity. Interestingly, despite the low % of E7-specific T cells in the SQZ (E7+CpG) group, this treatment also afforded a very high level of antitumor activity, with this being the only other group (in addition to SQZ (E7+CpG)+IFN-α co-administration) that extended survival of all of the mice past 60 days. While slightly lower than the previously mentioned Groups D and F, there was a discernable survival extension and tumor growth inhibition in Groups C and E. On Day 78, the 7 tumor free mice from Group D were rechallenged with 50 k cells to the opposite (left) flank and compared to age-matched untreated animals (10 mice) (FIG. 10D). Mice from Group D had a significant reduction in tumor growth after re-challenge, compared to untreated mice that have received their first challenge (***P<0.005), providing support that this antitumor effect is durable past 2 months.

Example 11

In order to determine the effect of combining multiple HPV antigens for T APC antitumor function, E6 and E7 synthetic long peptides (SLPs) alone and in combination in with our E7-specific T APCs in a prophylactic TC-1 murine tumor model. E7-specific T cell responses were measured by tetramer staining and flow cytometry, while antitumor effect was measured by tumor growth prevention.

Figure 11A:
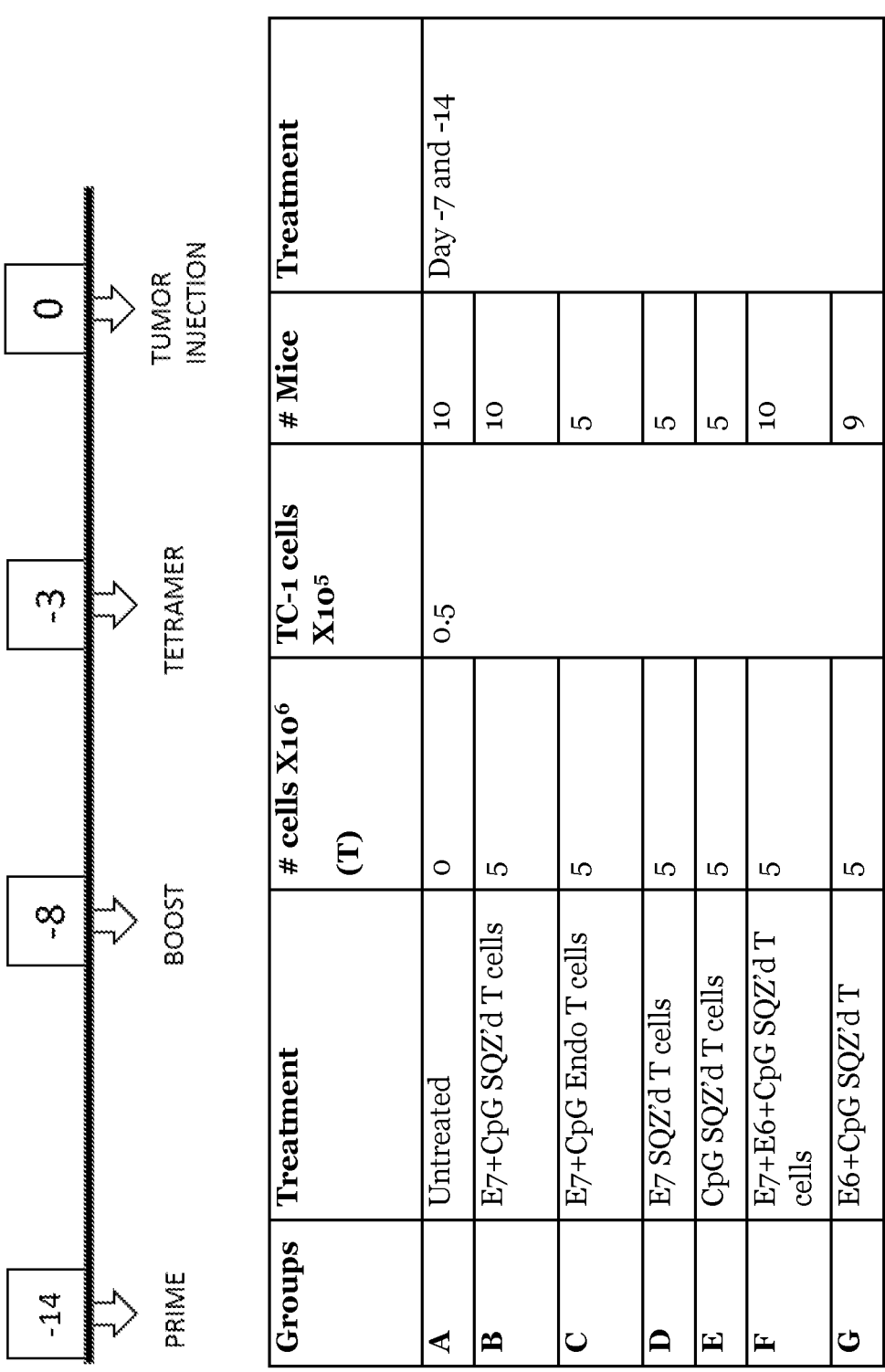
FIG. 11A is a schematic of an experiment to evaluate the effect of combining multiple HPV antigens for $T_{APC}$ antitumor function.

On Days –14 (prime) and –8 (boost), T cells from C57BL/6J female donor mice were isolated and loaded using SQZ with pre-complexed 20 μM mouse serum albumin (MSA)+20 μM E6 (VYSKQQLLRREVYDFAFRDL-SIVYRDGNPYAVSDK; SEQ ID NO:21) and/or E7 SLP (GQAEPDRAHYNIVTFSSKSDSTLRLSVQSTHVDIR; SEQ ID NO:25) or the combination of both+/–200 μg/mL CpG ODN 1826 according to Table XX. T cells incubated with the same conditions as Group B in the absence of SQZ were used as a negative control (Group C). C57BL/6J female recipient mice (5-10 mice/group) were injected intravenously with 100 μL of loaded T cells (5M cells/animal). On Day –3, 100 μL of murine blood was collected and the % of E7-specific CD8+ T cells was quantified by tetramer staining and flow cytometry. On Day 0, recipient mice were injected in the right rear flank with TC1 tumor cells (100 k cells/mouse) and TC-1 tumor growth was measured two times per week beginning on Day 11 and compared to tumor growth in untreated mice. A representative schematic of the treatment groups and schedule is outlined in FIG. 11A.

Figure 11B:
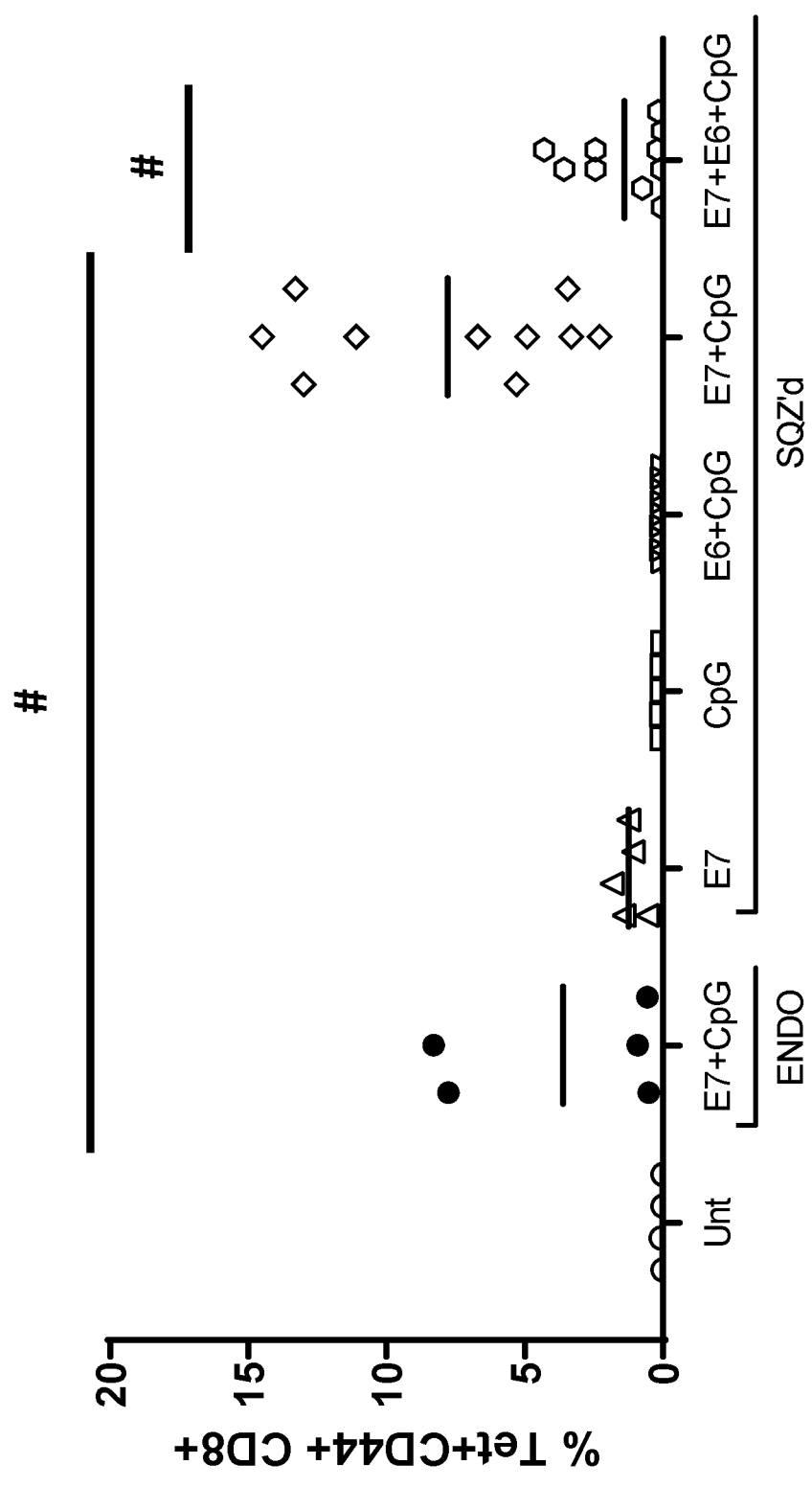
FIG. 11B shows T cell responses for each experimental group and FIG. 11C shows growth of tumors for each experimental group.
Figure 11C:
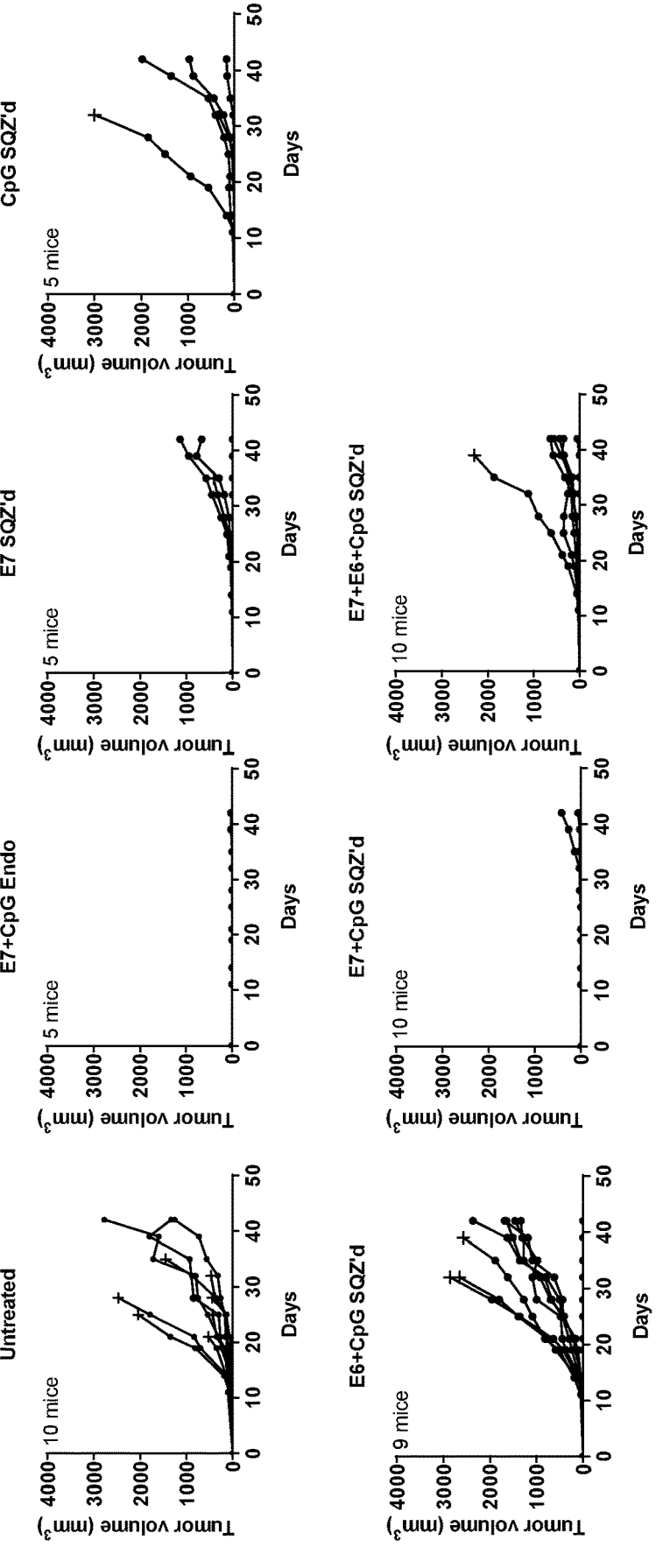

The percentage of E7-specific T cell were measured in mice by E7 tetramer staining after boost (Day –3) with the greatest effect observed with the CpG+E7 SQZ T APCs (Group B) as shown in FIG. 11B. Interestingly, Group B responses were significantly higher than untreated and the combination of E7 and E6 (Group F-#P<0.0001), providing evidence that the addition of the E6 SLP blunts the E7-specific response. Group B was significantly different from the other treatment groups, with the notable exception of the Endo control (Group C), wherein Group B was notably higher and trending towards statistical significance. As shown in FIG. 11C, tumor growth, as measured by the formula ((length×width$^2$)/2), was compared between mice from the untreated group (no adoptive transfer of T cells) and the treatment groups B-G outlined in FIG. 11A. High tumor growth prevention occurred in groups with T cells SQZ'd with E7+CpG, as well as T cells that were incubated in the presence of E7+CpG in the absence of SQZ. Groups D-F showed some level of tumor growth inhibition relative to untreated (Group A) and E6+CpG SQZ'd T cells (Group G), but were all less effective than Groups B and C.

Example 12

In order to determine the importance of the route of administration of CpG adjuvant for the E7-specific T APC antitumor effect, an E7 SLP was delivered to T cells in combination with CpG, either delivered to the T cell or systemically co-administered to the recipient animal and the antitumor effect was measured by tumor growth inhibition.

Figure 12A:
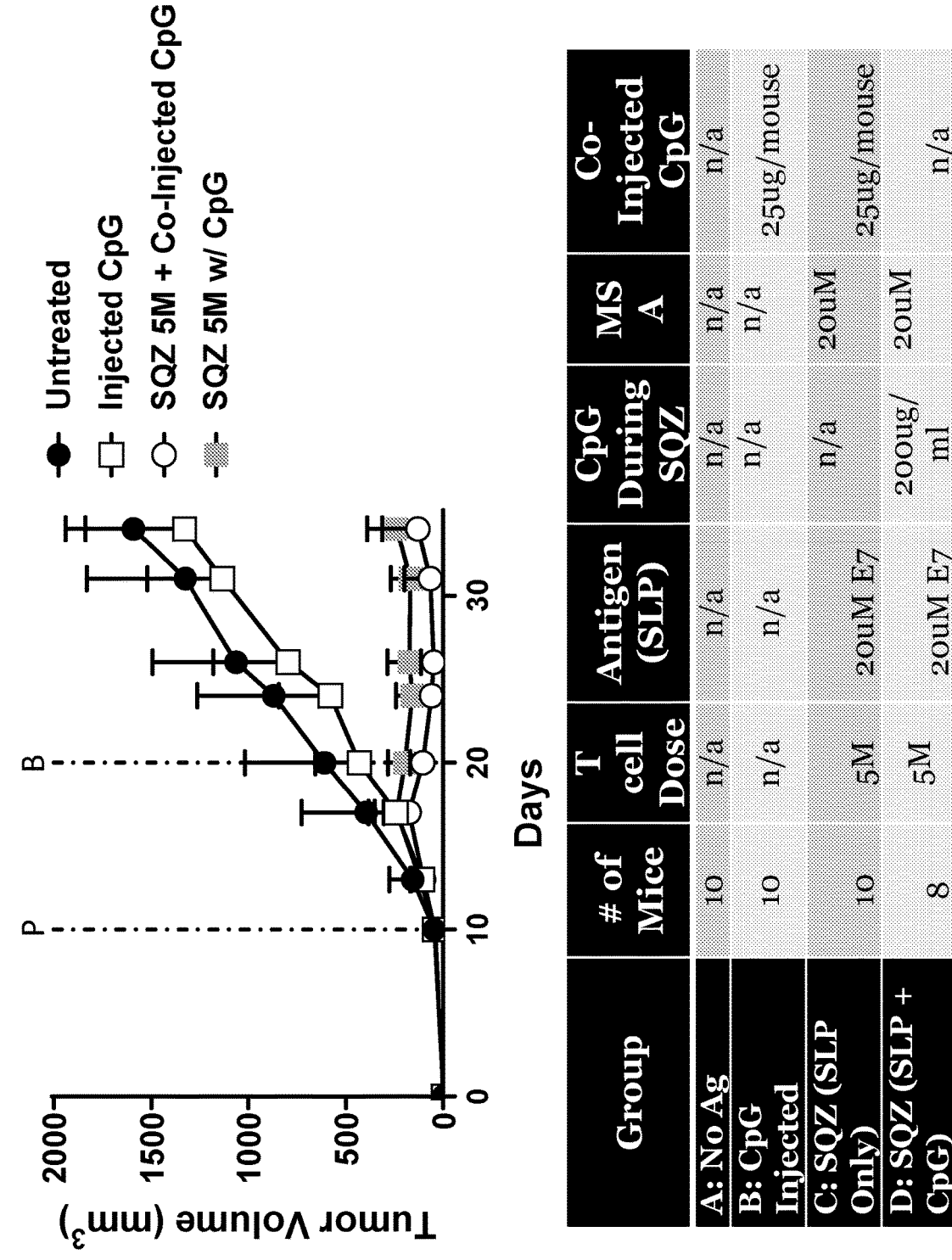
FIG. 12A shows the results of an experiment evaluating the importance of the route of administration of CpG adjuvant for the E7-specific $T_{APC}$ antitumor effect. The dosing schedule is provided.

On Day 0, recipient mice were injected in the right rear flank with TC1 tumor cells (50 k cells/mouse). On Days 10 (prime) and 20 (boost), T cells from C57BL/6J female donor mice were isolated and loaded using SQZ with pre-complexed 20 μM mouse serum albumin (MSA)+20 μM E7 (GQAEPDRAHYNIVTFSSKSDSTLRLSVQSTHVDIR; SEQ ID NO:25) and ODN 1826 was either co-delivered (Group D) by SQZ at 200 μg/mL or co-administered to the animals systemically at 25 μg/mouse (Group C) and compared to untreated (Group A) and systemic administration of CpG alone (Group B). Recipient mice (8-10 mice/group) were treated with 100 μL of loaded T cells (5M cells/animal). TC-1 tumor growth was measured two times per week beginning on Day 10. A representative schematic of the treatment groups and schedule is outlined in FIG. 12A.

Figure 12B:
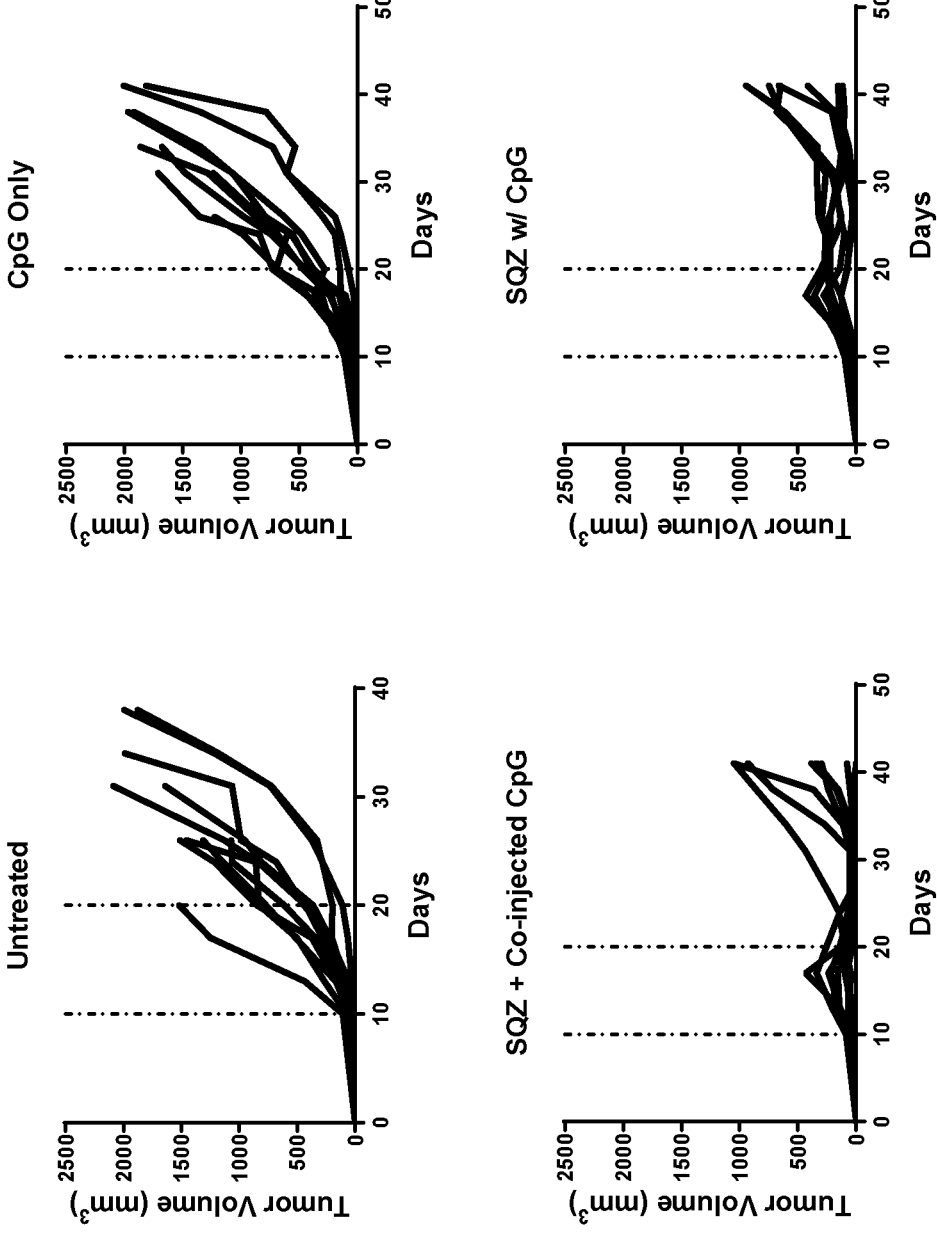
FIG. 12B shows tumor volume over time for individual mice within each treatment group.

In a therapeutic model of HPV-associated cancer (TC-1), T APCs that were SQZ'd with E7 SLP led to a significant reduction in tumor burden relative to untreated and CpG injection alone (Day 17: Group C—P<0.05; Day 20: Groups C & D—P<0.0001) (FIG. 12B). These data show that in a therapeutic setting both systemic co-administration and intracellular delivery of CpG adjuvant leads to a significant reduction in tumor burden relative to untreated or adjuvant alone.

Example 13

In order to assess the ability of co-administered adjuvants to lead to E7-specific T cell tumor infiltration, CpG vs. IFN-α were compared in combination with our E7-specific T APC in a therapeutic TC-1 murine tumor model. Antigen-specific T cell responses were measured in tumor infiltration lymphocytes by tetramer staining and flow cytometry.

On Day 0, recipient mice were injected in the right rear flank with TC1 tumor cells (50 k cells/mouse). On Day 10, T cells from C57BL/6J female donor mice were isolated and loaded using SQZ with pre-complexed 20 μM E7 SLP (GQAEPDRAHYNIVTFSSKSDSTLRLSVQSTHVDIR; SEQ ID NO:25)+20 μM mouse serum albumin (MSA). SQZ-loaded T cells (5M cells/animal) were administered alone (Group C), with CpG ODN 1826 (25 μg/mouse—Group D), or IFN-α (10 k IU/mouse—Group E) and were injected intravenously in 100 μL total volume. Mice were also injected with systemic CpG (25 μg—Group A) or IFN-α alone (10 k IU—Group B). On Day 17, tumors were harvested and CD8+ tumor infiltrating T cells were isolated and E7-specific reactivity was assessed by tetramer staining. A representative schematic of the treatment groups and schedule is outlined in FIG. 13.

Figure 13:
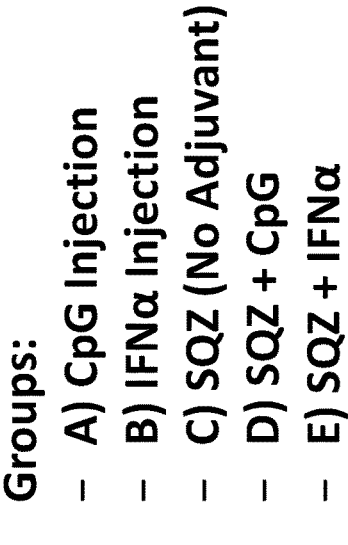
FIG. 13 shows a schematic of an experiment to assess the ability of co-administered adjuvants to lead to E7-specific T cell tumor infiltration. T cell responses are shown in the lower panel.

The percentage of E7-specific CD8+ T cell were measured in mice by E7 tetramer staining 7 days after prime (Day 17) and a representative example of the percentage of E7-specific T cells out of the CD8+ cells is shown in the bottom panel of FIG. 13. While injection of adjuvants alone did not generate an appreciable amount of E7-specific T cells, SQZ delivery of an E7 SLP afforded a 40% increase in E7-specific T cells and E7 delivered T cells in combination with CpG and IFN-α led to even higher percentages of antigen-specific T cells (70 and 80%, respectively). This data shows that a more robust E7-specific T cell response is generated when E7 SLP-loaded T cells are administered in combination with systemic adjuvants such as CpG or IFN-α.

Example 14

In order to determine a vaccination schedule for both prime and boost of T APCs loaded with an E7 synthetic long peptide (SLP)+CpG, we used a therapeutic TC-1 murine tumor model treated with our T APC vaccine at different time points and with differential number of boosts. The antitumor effect was measured by tumor growth inhibition.

Figure 14B:
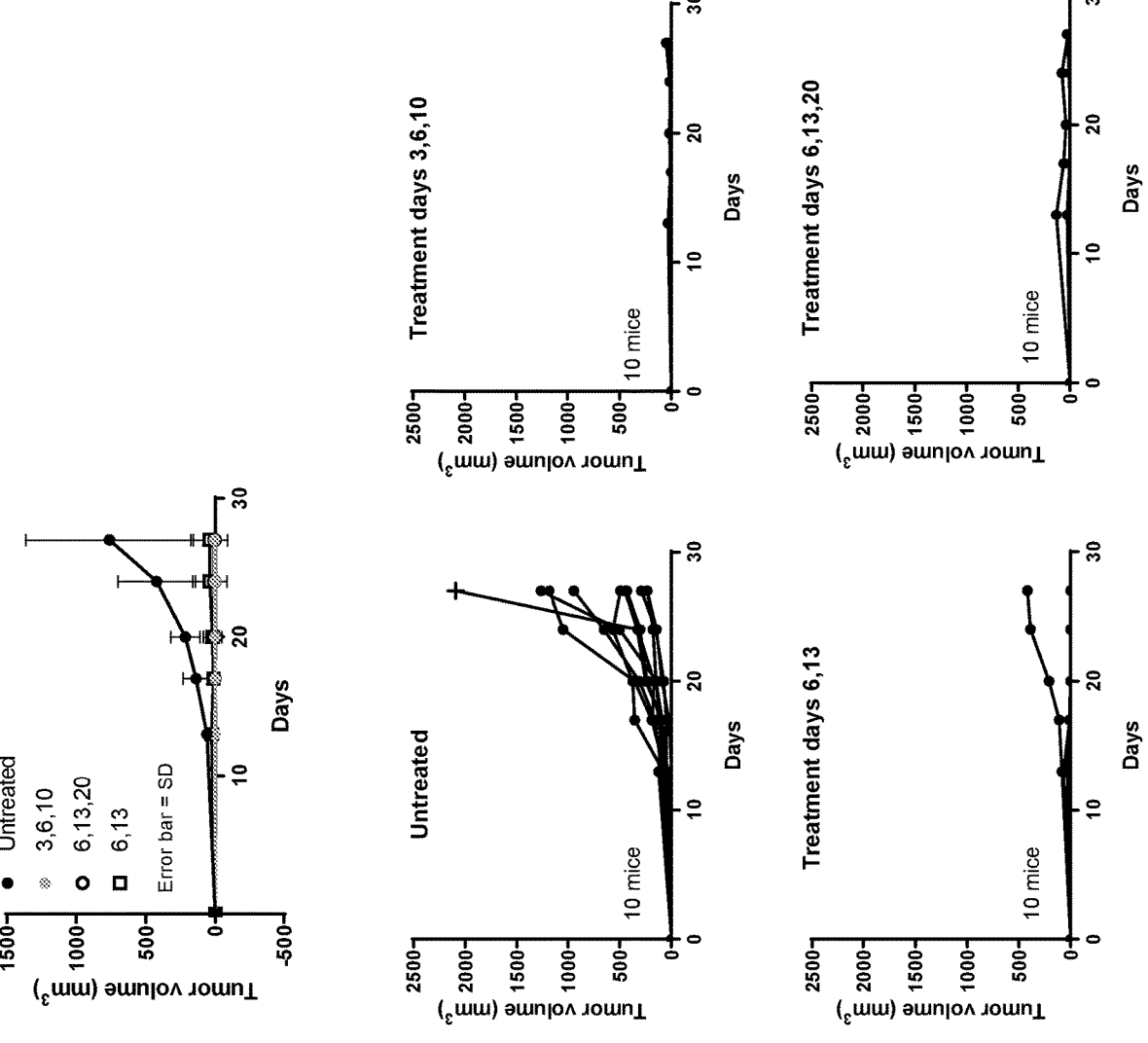
FIG. 14B shows growth of tumors for each experimental group.

On Day 0, recipient mice were injected in the right rear flank with TC1 tumor cells (50 k cells/mouse) and TC-1 tumor growth was measured two times per week beginning on Day 11 and compared to tumor growth in untreated mice. On Days 3 or 6, T cells from C57BL/6J female donor mice were isolated and loaded using SQZ with pre-complexed 20 μM mouse serum albumin (MSA)+20 μM E7 SLP (GQAE-PDRAHYNIVTFSSKSDSTLRLSVQSTHVDIR; SEQ ID NO:25)+200 μg/mL CpG ODN 1826 according to Table XX, followed by intravenous injection of recipient mice with 100 μL of loaded T cells (5M cells/animal). A representative schematic of the treatment groups and schedule is outlined in FIG. 14A.

Tumor growth inhibition occurred in all groups with T cells SQZ'd with E7+CpG, with statistical significance over untreated occurring at Day 20 (Day 20—All groups P<0.05; Day 24—All groups P<0.0001). This data shows that the dosing schedule with the T APC vaccine can work equally well when priming at Day 6 vs. Day 3 and there was no discernable benefit to adding a second boost at Day 21.

Example 15

In order to better understand the mechanism of antigen presentation by T cells that have had intracellular antigen delivery by SQZ, Ova was delivered to or incubated in the absence of SQZ with wild-type T cells injected into a wild-type mouse or into MHC-I knockout mice. Spleens were harvested and the amount of Ova-specific T cell (OT-I) proliferation was quantified by CFSE staining.

On Day 0, T cells from OT-I female donor mice were isolated and labeled with 2 μM CFSE and 2.5M cells were injected retro-orbitally (RO) in 100 μL PBS into either wild-type or MHC-I knockout mice. Also on Day 0, 400 μg/mL Ova was loaded into or incubated with T cells isolated from CD45.1 donor mice (4 mice/group), and 5M T cells were injected RO. On Day 3, spleens were harvested and the level of Ova-specific T cell proliferation was assessed by CFSE staining.

Figure 15:
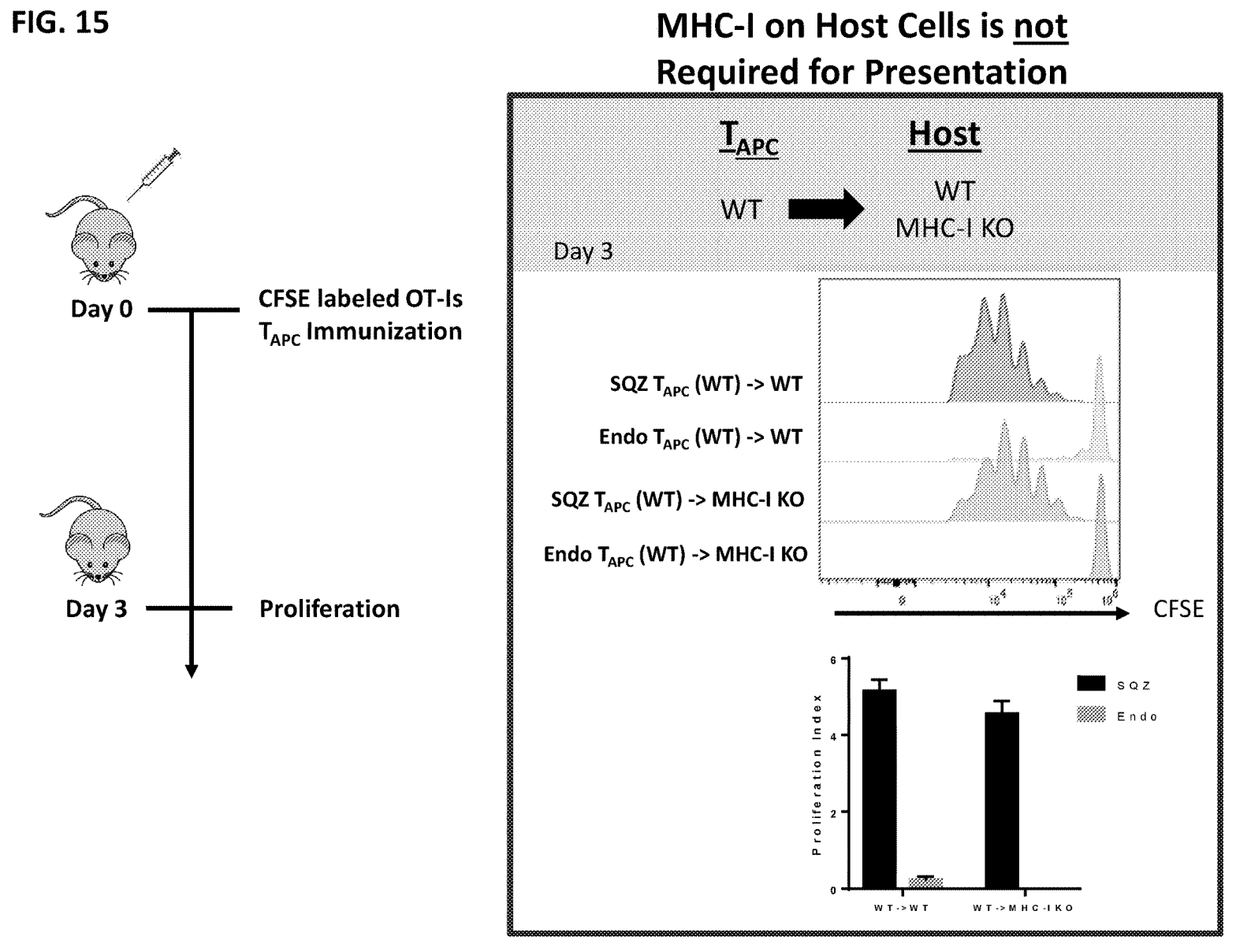

The amount of Ova-specific T cell proliferation was assessed by CFSE labeling of Ova-responsive OT-I CD8+ T cells. To determine the mechanism of presentation of antigen-loaded $T_{APC}$s, mice deficient in MHC-I were used as recipient mice. This would preclude presentation of Ova antigens by endogenous murine APCs due to indirect uptake of antigen by dying SQZ'd T cells and cross-presentation on MHC-I to adoptively transferred OT-I cells. It was found that when recipient mice lack MHC-I, Ova-specific OT-I cell proliferation still occurred, providing evidence that SQZ'd T APCs are presenting antigen directly (FIG. 15). These data support the direct presentation of SQZ-mediated intracellularly delivered antigen.

Example 16

In order to assess the propensity of SQZ to alter cytokine production, T cells were SQZ delivered with CpG and assessed for the ability to alter T cell cytokine levels in an in vitro murine model. Cytokine levels in the supernatant were profiled using a multiplex cytokine kit.

C57BL/6J female recipient mice were primed with T cells from C57BL/6J female donor mice were isolated and SQZ'd with 200 μg/mL CpG and supernatants were collected after 24 h (N=2). Supernatant was assessed for cytokine levels by Millipore Milliplex multiplex cytokine kit and expressed as a fold-change difference relative to untreated T cells.

Figure 16:
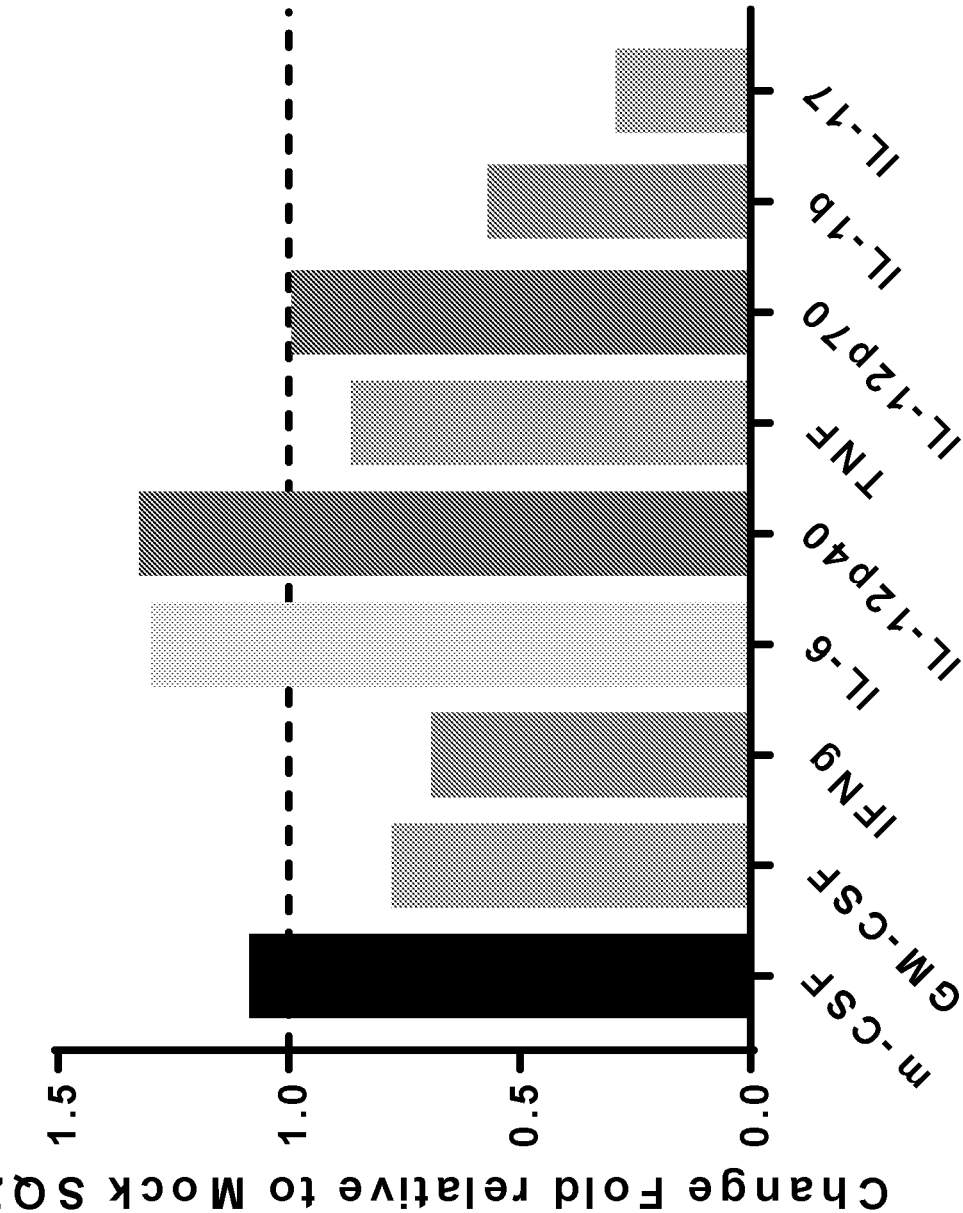
FIG. 16 shows that SQZ delivery of an adjuvant does not significantly alter T cell cytokine levels in vitro.

There were no significant changes between cytokine levels in the supernatant of T cells loaded with CpG via SQZ relative to untreated cells (FIG. 16). This data shows that SQZ delivery of an adjuvant does not significantly alter T cell cytokine levels in vitro.

Example 17

In order to assess the propensity of SQZ to alter cytokine production, T cells SQZ delivered with either Ova or Ova+ CpG were assessed for the ability to alter serum cytokine levels in an in vivo murine model. Serum cytokines were profiled using a multiplex cytokine kit.

C57BL/6J female recipient mice were primed with T cells from C57BL/6J female donor mice were isolated and SQZ'd with either 400 μg/mL Ova or Ova+200 μg/mL CpG and blood was drawn from the tail vein at 6 h and via cardiac puncture at 24 h post-priming. Serum was assessed for cytokine levels by Millipore Milliplex multiplex cytokine kit and expressed as a fold change vs. untreated T cells.

Figure 17:
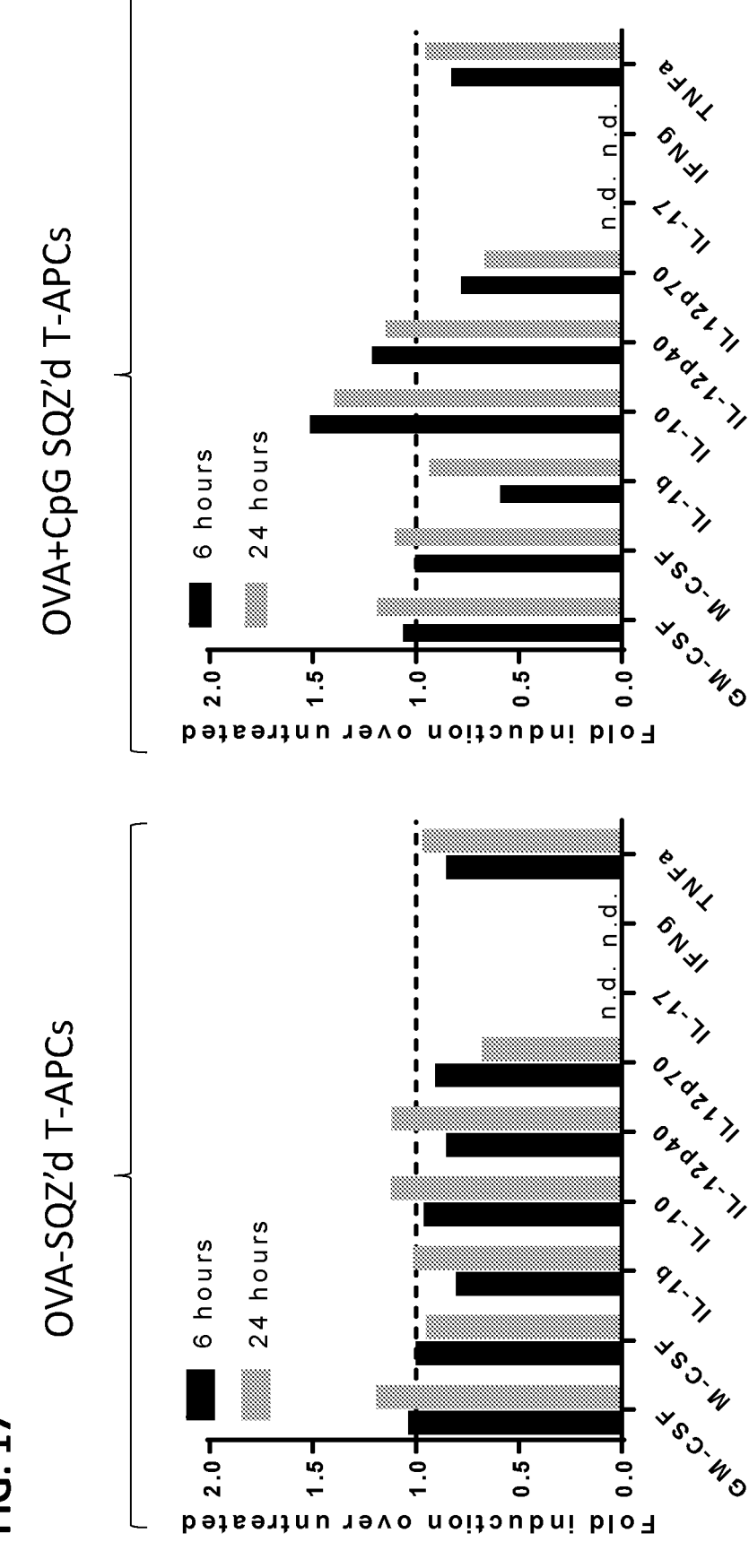
FIG. 17 shows that SQZ delivery of antigen+/−adjuvant does not significantly alter serum cytokine levels in vivo.
Figure 18:
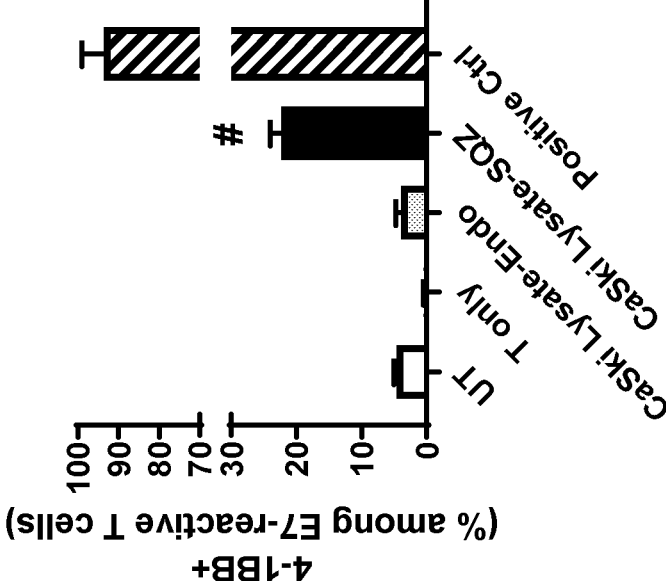
FIG. 18 shows that SQZ delivery of HPV-E7 containing cell lysates in dendritic cells (as APCs), followed by co-culturing the SQZ'd dendritic cells with CD8 T cell responders leads to a more robust T cell response compared to delivery of same lysates into dendritic cells by endocytosis.

There were no significant changes between cytokine levels in the serum of mice primed with T cells loaded with Ova or Ova+CpG via SQZ (FIG. 17). Additionally, no significant differences were observed between 6 h and 24 h post-priming. These data show that SQZ delivery of antigen+/−adjuvant does not significantly alter serum cytokine levels in vivo.

Example 18

In order to determine the ability of primary human monocyte-derived dendritic cells (MoDCs) to elicit an HPV E7-specific immune response in E7 responder T cells using tumor cell lysate (TCL) as an antigen source in an in vitro human model, primary human MoDCs were loaded with lysate from CaSki tumor cells and percent 4-1BB expression was measured by flow cytometry.

Human monocytes were isolated from the PBMCs of HLA-A02+ donors and immature MoDCs were generated by addition of rhIL-4 (1000 U/mL) and rhGM-CSF (800 U/mL) over 4-6 days, replenishing the cytokine-containing media after 3 days. The CaSki cervical cancer cell line was used as an antigen source and TCL from CaSki cells (23 mg/mL) was delivered intracellularly to MoDCs ($1\times10^6$ cells/mL) by SQZ or CaSki TCL is incubated with the MoDCs in the absence of SQZing (Endo). Additionally a peptide pulsed control, wherein MoDCs were incubated in the presence of known reactive E7 epitope (YMLDLQ-PETT; SEQ ID NO:3—0.1 μM—Positive Ctrl) was employed. All conditions were cultured for 1 h with LPS (60 EU/mL) and rhIFN-γ (20000 IU/mL) to activate the MoDCs, followed by 16-24 h incubation in 60 EU/mL LPS containing media (no IFN-γ). MoDCs were then co-cultured for 16-24 h with E7-reactive T cells (Astarte) at a 3:1 stimulator: responder ratio. After co-culture, the % of 4-1BB expression on E7-reactive CD8+ T cells was measured by flow cytometry.

CaSki lysate, derived from an HPV-positive cervical cancer cell line known to highly express the HPV antigen E7, when delivered intracellularly using SQZ, led to a 20% increase in the percent of E7-reactive CD8+ T cells expressing 4-1BB, a marker of antigen-specific activation, when compared to both the untreated and corresponding Endo control (#P<0.0001). These findings show the ability of intracellular TCL by SQZ to induce an antigen-specific immune response to the HPV antigen E7 in primary human MoDCs, providing support for the use of TCL as a complex antigen source for additional indication wherein the oncogenic antigens may be unknown.

Example 19

In order to determine the endogenous response to antigen-presenting cells (APCs) that have been loaded with antigen by SQZ, B cells were SQZ-loaded and the levels of inflammatory cytokines were measured by intracellular cytokine staining (ICS).

Murine B cells ($B_{APC}$) from C56BL/6J mice were isolated and SQZ-loaded with 400 μg/mL Ova protein or with 20 μM HPV 16 E7 peptide, then injected into donor mice along with 1 μM CpG1826 (5 mice/group). On Day 7, splenocytes were harvested from untreated mice as well as mice treated with SQZ-loaded $B_{APCs}$, re-challenged with Ins B9-23 peptide, and subsequently intracellular cytokine staining (ICS) was conducted for IFN-γ and measured by flow cytometry (FIG. 19A).

For both the model antigen Ova (FIG. 19B) and disease-relevant HPV E7 (FIG. 19C), the results showed that splenocytes from mice treated with SQZ-loaded $B_{APC}$ exhibited statistically significant increases in IFN-γ production when re-stimulated with Ova or HPV E7 respectively (P<0.005, both), compared to the splenocytes harvested from untreated mice. Taken together, these data show that B cells can be engineered to elicit antigen-specific responses to multiple antigens in vivo.

Example 20

In order to determine the ability of SQZ-loaded B cells to act as antigen-presenting cells ($B_{APCs}$) for the prophylactic treatment of tumors, mice were treated with $B_{APC}$ SQZ-loaded with antigens, followed by injection with TC-1 tumor cells. Tumor growth inhibition was measured to assess in vivo prophylactic vaccine efficacy.

To test the ability of a prophylactic HPV antigen-based B cell vaccine, i.e. $B_{APC}$ SQZ-loaded with HPV antigens, to control TC-1 tumor growth, an E7 SLP was SQZ-delivered into B cells and injected into mice prior to tumor implantation. Specifically, on Day −7, murine B cells ($B_{APC}$) from C56BL/6J mice were isolated and SQZ-loaded with HPV 16 E7 peptide, then injected into donor mice along with 1 μM CpG1826 (10 mice/group). On Day 0, TC-1 tumor cells were implanted (1E6 cells/mL in 100 μL) subcutaneously in the rear flank of each mouse. TC-1 is a tumor cell line known to express HPV antigens E6 & E7. Tumor volumes were measured over time and mice were sacrificed at Day 48 or when their tumors reach >1500 mm$^3$, whichever came first.

Figures 20A, 20B:
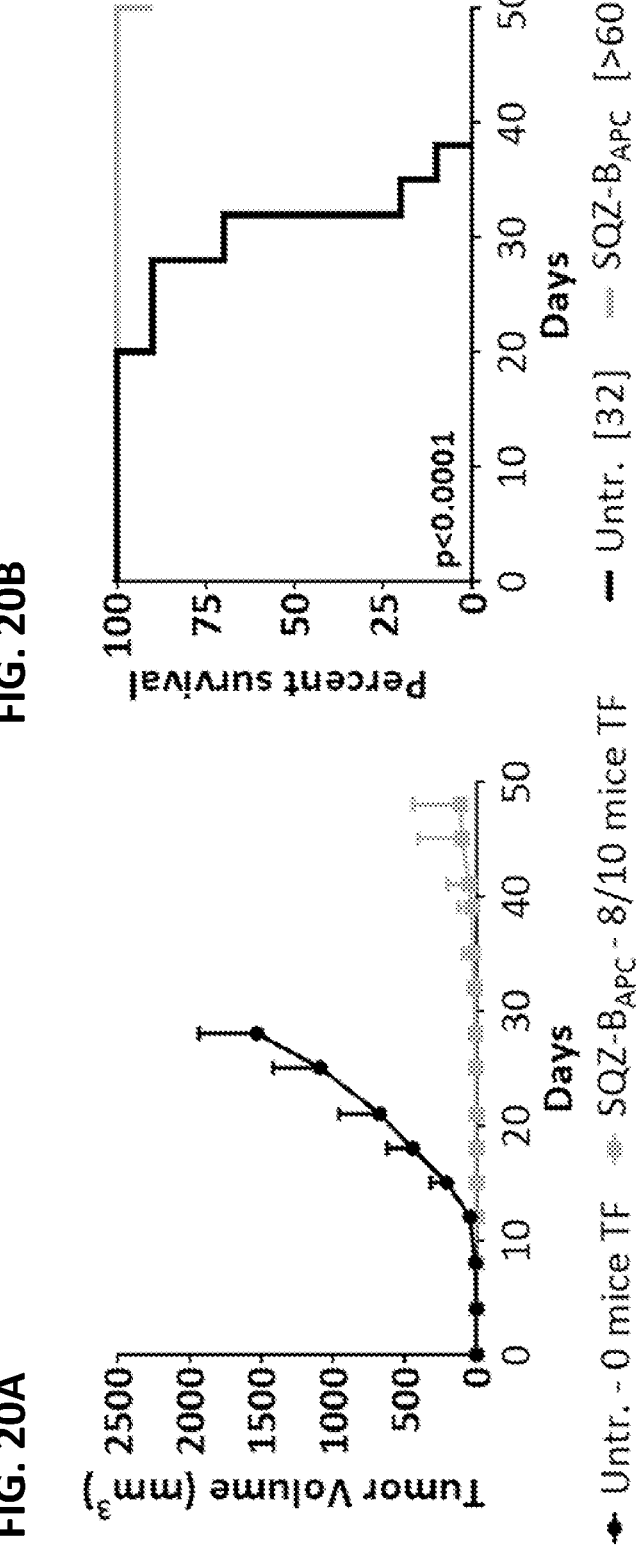
FIG. 20A shows the tumor volume over time in an experiment to determine the ability of SQZ-loaded B cells to act as APCs for prophylactic treatment for HPV-associated tumors.
FIG. 20B shows the corresponding survival data over time from B cell APC prophylactic treatment for HPV-associated tumors.

Tumor growth was drastically inhibited in the mice that received E7-loaded $B_{APC}$, with 8 out of 10 mice in the treatment group remaining tumor-free (TF) throughout the study duration, compared to 0 out of 10 mice in the control group (FIG. 20A). The $B_{APC}$ vaccine also led to statistically significant improvements (P<0.0001) in the survival of $B_{APC}$-immunized mice relative to control, with the median survival for the treatment group being >60 days, compared to 32 days for the control group (FIG. 20B) Taken together, this data shows that B cells loaded with antigen via SQZ can act as a potent APC-based vaccine for an antigen-specific prophylactic treatment of tumors.

Example 21

In order to determine the ability of SQZ-loaded B cells to act as antigen-presenting cells ($B_{APCs}$) for the therapeutic treatment of tumors, mice were implanted with TC-1 tumor cells, followed by therapeutic immunization with $B_{APCs}$ loaded with antigens. Tumor growth inhibition was measured to assess in vivo therapeutic vaccine efficacy.

To test the ability of a therapeutuic HPV antigen-based B cell vaccine, i.e. $B_{APC}$ SQZ-loaded with HPV antigens, to control TC-1 tumor growth, an E7 SLP was SQZ-delivered into B cells and injected into mice after tumor implantation. Specifically, on Day 0, TC-1 tumor cells (50 k cells/mouse) were injected subcutaneously into the right flank of C56BL/6J mice (10 mice/group). TC-1 is a tumor cell line known to express HPV antigens E6 & E7. On Day 9, mice were either left untreated or primed with 1M cells/mouse of murine B cells ($B_{APCs}$) SQZ-loaded with E7 SLP. Tumor volumes were measured over time and mice were sacrificed at Day 48 or when their tumors reach >1500 mm³, whichever came first.

Figures 21A, 21B:
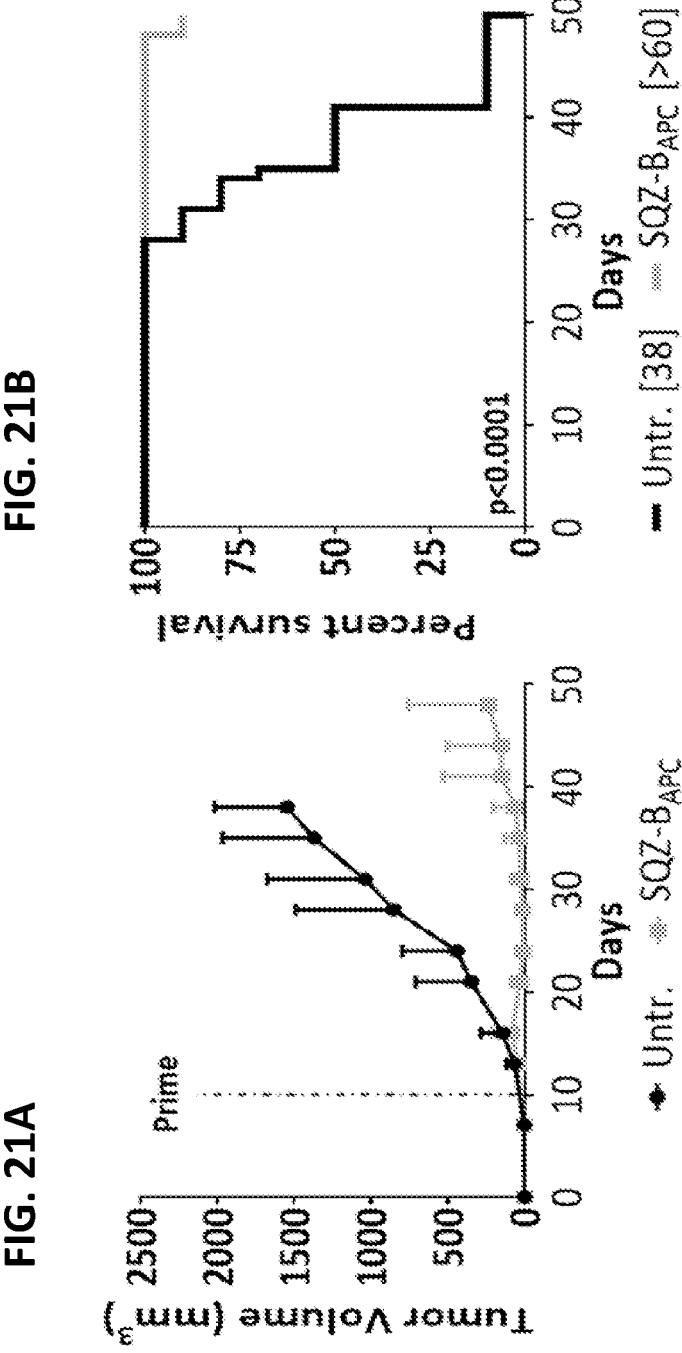
FIG. 21A shows the tumor volume over time in an experiment to determine the ability of SQZ-loaded B cells to act as APCs for therapeutic treatment for HPV-associated tumors.
FIG. 21B shows the corresponding survival data over time from B cell APC therapeutic treatment for HPV-associated tumors.

Tumor growth was drastically inhibited in the mice that received E7-loaded $By_{APC}$, with the average tumor volume remaining <500 mm³ for the duration of the study (FIG. 21A). The survival of mice treated with E7-loaded $B_{APC}$ was also significantly increased (P<0.0001), with the median survival for the treatment group being >60 days, compared to 38 days for the control group. Taken together, this data shows that B cells loaded with antigen via SQZ can act as a potent APC-based vaccine for an antigen-specific therapeutic treatment of tumors.

Example 22

In order to determine the ability of SQZ-loaded B cells to promote tumor-infiltrating lymphocyte (TIL) recruitment to tumors, tumor bearing mice were treated with loaded B cell APCs (prime and boost), and tumor growth inhibition was measured in addition to analysis of tumors for numbers and relative percentages of antigen-specific T cells by flow cytometry.

On Day 0, TC-1 tumor cells (50 k cells/mouse) were injected subcutaneously into the right flank of C56BL/6J mice (20 mice/group). On Day 14, mice were primed with either (i) 150 µg/mouse of E7 SLP+50 µg of CpG1826 injected subcutaneously (S.C. SLP), (ii) murine B cells pulsed with 1 µg/mL E7 minimal epitope+1 µM CpG (Min. Epi.) injected retro-orbitally, or (iii) B cells loaded (SQZ) with E7 SLP (20 µM)+1 µM CpG (5M cells/mouse) injected retro-orbitally. Tumor volumes were measured over time until reaching >1500 mm³ or by Day 34, whichever came first. On Day 27, a subset of animals (5 mice/group) were sacrificed, where the tumors were resected and the T cells were isolated and analyzed by flow cytometry.

Figures 22A, 22B:
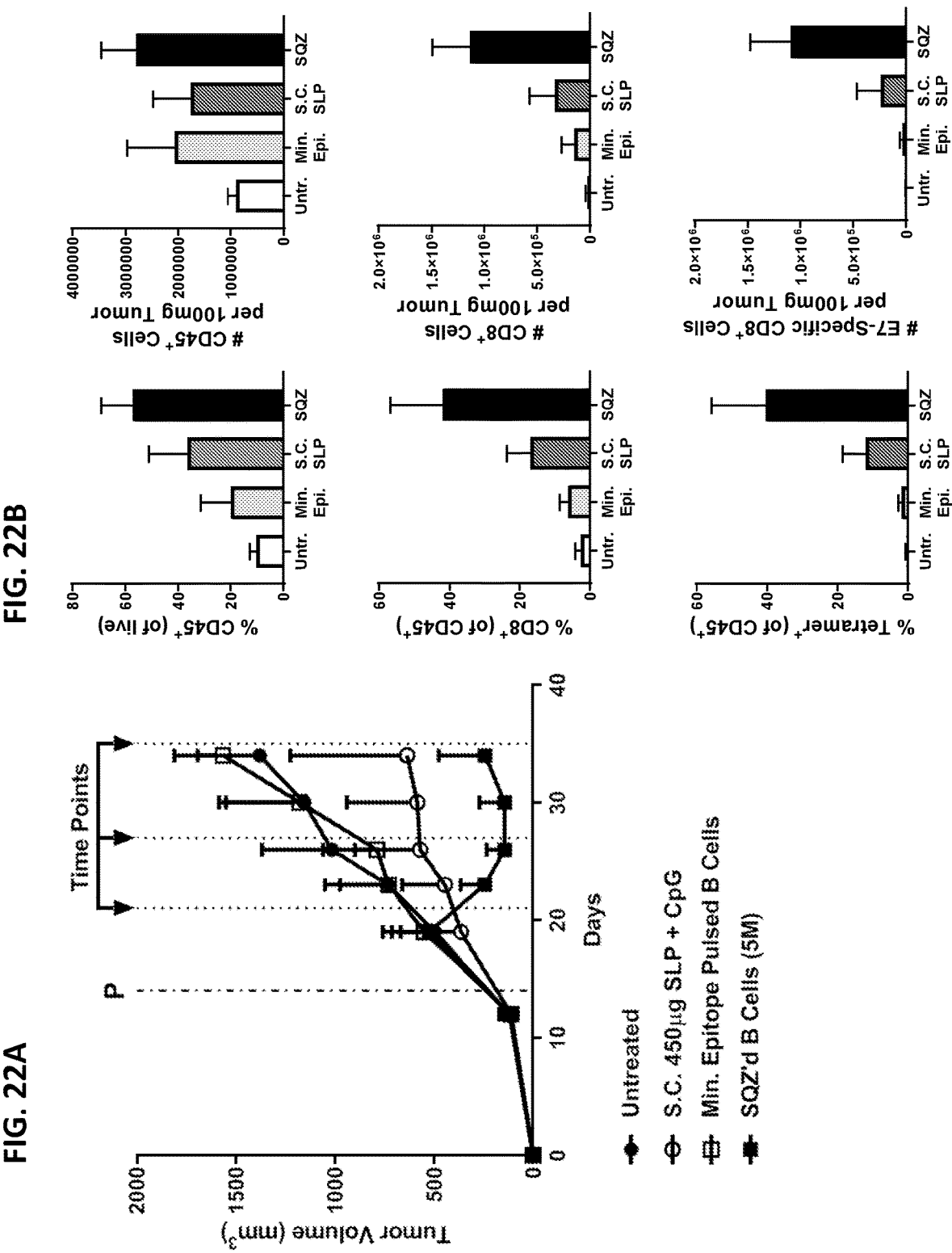
FIG. 22A shows the tumor volume over time in an experiment to determine the ability of SQZ-loaded B cells to act as APCs for therapeutic treatment for HPV-associated tumors.
FIG. 22B shows the profiles and percentages of various phenotypes of tumor infiltrating cells that were recruited to the tumors.
Figure 23:
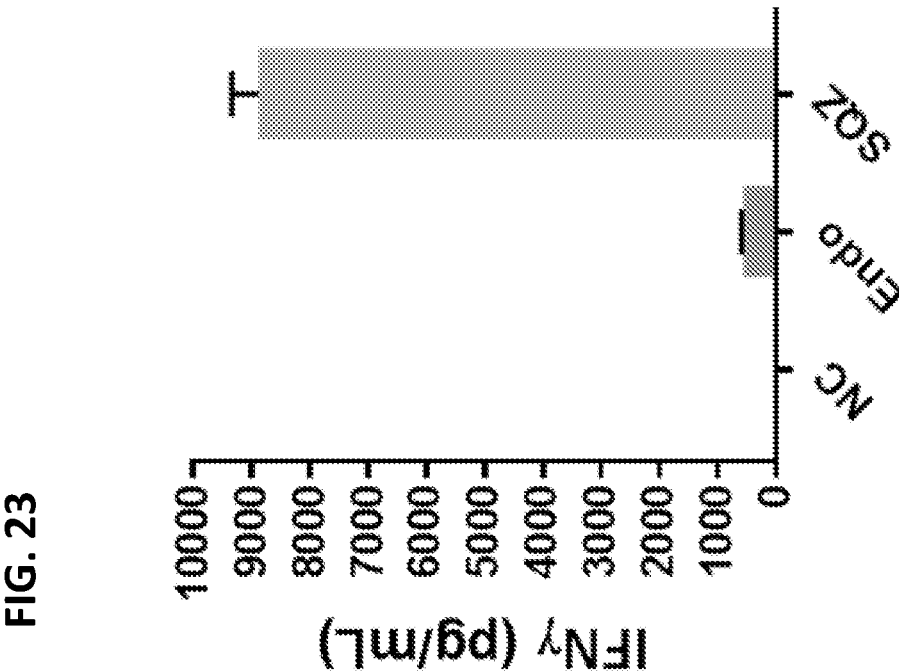
FIG. 23 shows the IFN-γ secretion by E7 responders, as an in vitro antigen-specific response to $B_{APC}$ SQZ-loaded with HPV16 E7 SLP.
Figure 24:
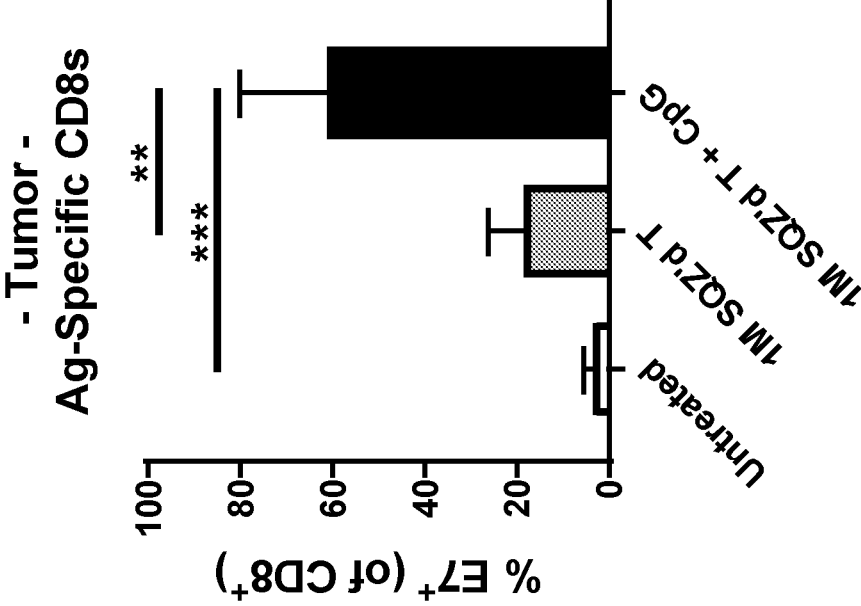
FIG. 24 shows the relative amounts of tumor infiltrating lymphocyte (TIL) recruitment to tumors administered with $T_{APC}$ SQZ-loaded with HPV16 E7 SLP, with or without co-administration of adjuvant.
Figure 25:
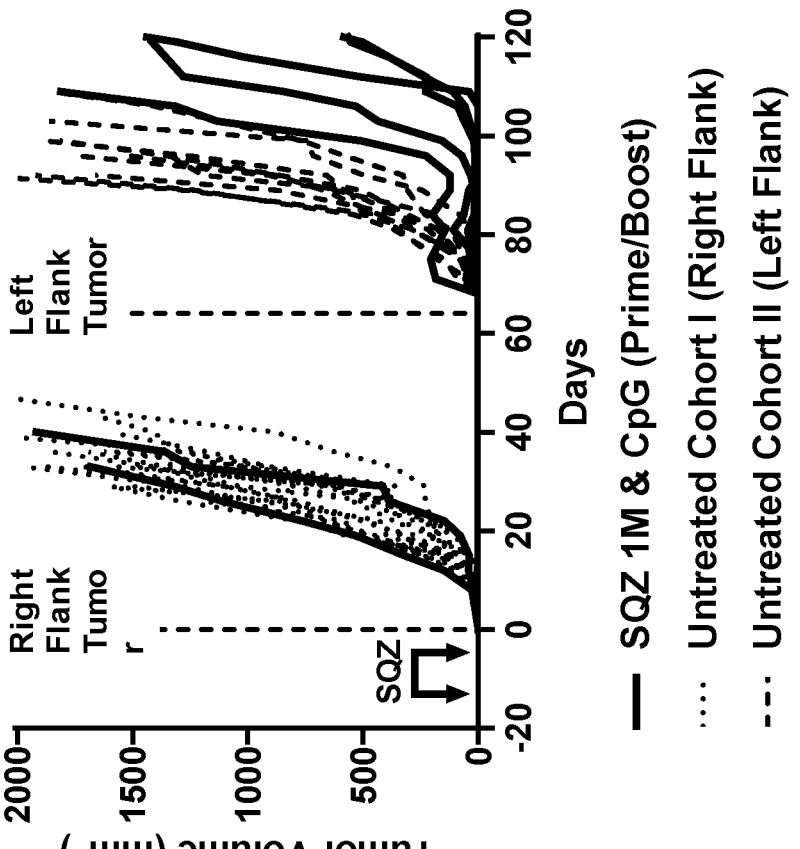
FIG. 25 shows the tumor volume over time in an experiment to determine the ability of SQZ-loaded T cells to act as APCs for prophylactic treatment for HPV-associated tumors, for both shorter term (right flank tumor, injected on Day 0) as well as longer term protection (left flank tumor, injected on Day 60)
Figure 26:
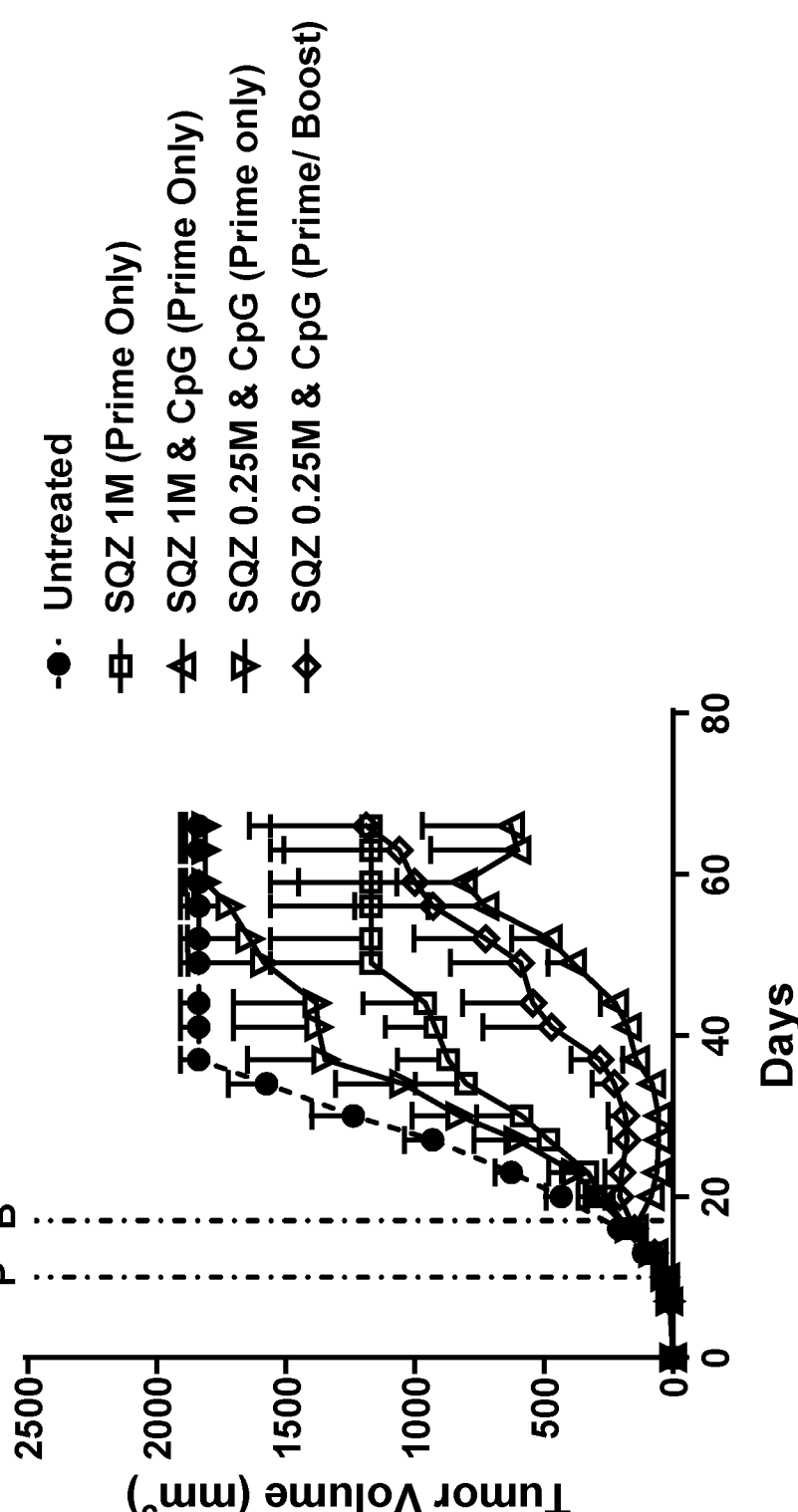
FIG. 26 shows the tumor volume over time in an experiment to determine the effect of T cell dose, co-administration of adjuvant as well as number of administrations (prime vs. prime/boost) on the ability of SQZ-loaded T cells to act as APCs for therapeutic treatment for HPV-associated tumors. "P" indicates prime, and "B" indicates boost in FIG. 26.

In the therapeutic treatment setting as described, only S.C. SLP and SQZ treatments led to appreciable tumor growth inhibition, with only the SQZ treatment leading to tumor regression relative to the maximum volume observed on Day 19 (FIG. 22A). Analysis of the TIL recruitment to tumor, as well as the relative phenotype of these T cells showed that the SQZ-loaded B cell vaccine (SQZ) resulted in significant increase in the percentage of infiltrating T cells in the tumor, as well as a higher number of cells normalized to 100 mg tumor weight. In addition to total number of infiltrating T cells, it was observed that both the CD8+ T cells, as well as the E7-specific CD8+ T cells in SQZ treatment were increased more significantly as a percentage of CD45$^+$ cells, compared to S.C. SLP and Min. EP., and this trend was also observed when normalized to tumor weight as well (FIG. 22B). All comparisons between SQZ and every other treatment group were statistically significant (P<0.001). Taken together, these data support the finding that the SQZ-loaded $B_{APC}$ vaccine leads to tumor regression due to the promotion of T cell infiltration into the tumor, specifically antigen-specific CD8+ cytotoxic T cells.

Example 23

In order to determine the in vitro antigen-specific response to human antigen-presenting cells (APCs) that have been loaded with antigen by SQZ, B cells were SQZ-loaded and the levels of induced inflammatory cytokine secretion were measured by ELISA.

Specifically, Human B cells were isolated from HLA-A2+ donors and an HPV 16 E7 SLP (50 µM) was either incubated with B cells (Endo), or delivered to B cells by SQZ (SQZ). The Endo or SQZ B cells (60 k cells/well) were then incubated with E7 responder T cells (30 k cells/well) in a 2:1 ratio, and co-cultured in the presence of IL-2 (100 U/mL) and CpG 2006 (1 µM) for 24 hr. Supernatants were then harvested and analyzed for IFN-γ secretion by ELISA.

The results show that SQZ-loaded B cells can act as antigen presenting cells ($B_{APC}$) to stimulate an HPV E7 antigen-specific response in vitro. The B cell APCs that were loaded with antigen stimulated the E7-specific responder cells to secrete IFN-γ at significantly higher levels than those cell that were incubated with antigen (P<0.005).

Example 24

In order to evaluate the importance of adjuvant on the ability of a SQZ-loaded vaccine to induce antigen-specific tumor infiltrating lymphocytes (TILs), cells were loaded with a model antigen, matured with adjuvant and injected into tumor bearing mice. The relative percentage of antigen-specific T cells recruited to the tumor was measured by flow cytometry.

C57BL/6J female mice were injected in the right rear flank with TC1 tumor cells (50 k cells/mouse) at Day 0. On Day 15 (prime), murine T cells were obtained from spleens of female C57BL/6J donor mice and were loaded with pre-complexed 5 µM E7 SLP (GQAE-PDRAHYNIVTFSSKSDSTLRLSVQSTHVDIR; SEQ ID NO:25)+5 µM mouse serum albumin (MSA) via SQZ (40 psi, 3.5 µm constriction, room temperature) and incubated for 1 h at 37° C. Female C57BL/6J recipient mice (10/group) were injected retro-orbitally on Day 15 with 100 µL of either vehicle (PBS—Untreated) or E7-loaded T cells (1M cells/mouse)+/−CpG 1826 (25 µg/mouse). On Day 25, tumors were harvested and the amount of E7-specific TILs was measured by flow cytometry.

SQZ-loaded T APCs alone led to a small (~15%) but statistically insignificant increase in the number of E7-specific TILs, but when co-injected with CpG, there was higher and significant increase in the number of TILs (~55%, P<0.01 compared to T APC alone; *P<0.0005 compared to untreated). This data shows that co-injecting CpG along with the E7-loaded T APC leads to much higher recruitment of TILs compared to T APC alone.

Example 25

In order to evaluate the durability of the T APC+adjuvant vaccine in a prophylactic setting, T APC-treated mice were compared to untreated mice for the tumor growth of an HPV E7-expressing TC1 tumor model both for the initial response, as well as a re-challenge 60 days later, with the area of the tumors plotted against time.

At Day −14, splenocyte were harvested from C57BL/6J female donor mice and T cells were isolated by immuno-magnetic separation. Next, murine T cells were loaded with pre-complexed 20 μM E7 SLP (GQAE-PDRAHYNIVTFSSKSDSTLRLSVQSTHVDIR; SEQ ID NO:25)+20 μM mouse serum albumin (MSA) via SQZ (45 psi; 3.5 μm constriction) and incubated for 1 hour at 37° C. Female C57BL/6J recipient mice (10 mice/group, except untreated cohort I, which was 20 mice/group) were injected retro-orbitally with 100 μL of either vehicle (PBS—Un-treated) or E7-loaded T cells (1M cells/mouse)+CpG 1826 (25 μg/mouse) [Prime]. On Day −7, spleens were harvested from C57BL/6J female donor mice and T cells were isolated and SQZ'd and injected into recipient mice exactly as on Day −14 [Boost]. On Day 0, C57BL/6J female mice were injected in the right rear flank (except the 10 untreated cohort 2 that were not implanted with tumor cells until Day 64 with TC1 tumor cells (50 k cells/mouse). TC-1 tumor growth was measured beginning 1 week post-tumor implantation two times per week and compared to tumor growth in untreated mice for up to 120 days.

Tumor growth, as measured by the formula ((length× $width^2$)/2), was compared between mice from the untreated group and the T APC-treated group challenged with tumor cells at Day 0, and while all mice reached the humane endpoint in the untreated group by Day 47, there was significant tumor growth delay for the T APC group in all but 2 of the T APC mice, with the remainder of the mice (8) remaining tumor-free until re-challenged with tumors. Interestingly, when untreated mice that were implanted with tumors on Day 64 and compared to T APC-treated mice that had tumors re-implanted in their opposite flank, there was still a tumor growth delay, with 3 of the mice never growing measurable tumors, even after the secondary tumor challenge. These data suggest that treatment with E7-loaded T APCs+adjuvant can not only lead to antigen-specific tumor growth inhibition, but also tumor prevention that can even be durable over >100 days despite a secondary tumor challenge.

Example 26

In order to evaluate the impact of differing T APC concentration as well as prime-boosting schedules in a therapeutic vaccine setting, T APC-treated mice (multiple concentrations and prime-boost schedules) were compared to untreated mice for the tumor growth of an HPV E7-ex-pressing TC1 tumor model, with the area of the tumors plotted against time.

At Day 0, C57BL/6J female mice were injected in the right rear flank with TC1 tumor cells (50 k cells/mouse). On Day 10 (prime), murine T cells were obtained from spleens of female C57BL/6J donor mice by immunomagnetic sepa-ration and were loaded with pre-complexed 20 μM E7 SLP (GQAEPDRAHYNIVTFSSKSDSTLRLSVQSTHVDIR; SEQ ID NO:25)+20 μM mouse serum albumin (MSA) via SQZ (45 psi; 3.5 μm constriction) and incubated for 1 hour at 37° C. Then, female C57BL/6J recipient mice (10/group) were injected retro-orbitally with 100 μL of either vehicle (PBS) or T APCs (0.25 or 1M cells/mouse)+CpG 1826 (25 μg/mouse). On Day 17, the Prime/Boost group received a second injection with T APCs in an identical manner to Day 10. TC-1 tumor growth was measured beginning 1 week post-tumor implantation two times per week and compared to tumor growth in untreated mice for up to 66 days.

Tumor growth, as measured by the formula ((length× $width^2$)/2) and the low dose T APC group (0.25M cells/mouse)+CpG (prime only) only led to a slight delay in tumor growth rate compared to untreated. The inclusion of a boost at Day 17 with the low dose of T APC+CpG (0.25M prime/boost) saw an enhancement of the tumor growth inhibition relative to the same concentration prime only condition and much larger inhibition relative to untreated. Increasing the dose of antigen-loaded T APCs to 1M/mouse (prime only) led to a slight tumor growth inhibition relative to the lower dose T APC+CpG (prime only). Interestingly, the use of the high dose T APC+CpG (prime only) led to the best protection from tumor growth, with tumor regression occurring between Days 20-40 and the highest level of growth inhibition of any of the observed groups. Taken together, these data highlight that increased cell dose, inclu-sion of adjuvant, or prime+boost dosing schedules can enhance the efficacy of a T APC vaccine.

Example 27

In order to compare the efficacy of a high-dose peptide vaccine versus B cells incubated or SQZ-loaded with pep-tide, mice were treated with either E7 peptide, E7-incubated B cells (Pulsed B cells) or E7-loaded B APCs after challenge with the HPV E7-expressing TC1 tumor model in a thera-peutic setting, with the area of the tumors and survival plotted over time.

At Day 0, C57BL/6J female mice were injected in the right rear flank with TC1 tumor cells (50 k cells/mouse). On Day 13 (prime), B cells were obtained from spleens of female C57BL/6J donor mice by immunomagnetic separa-tion, and either incubated (10 μg/mL) or loaded with pre-complexed 20 μM E7 SLP (GQAE-PDRAHYNIVTFSSKSDSTLRLSVQSTHVDIR; SEQ ID NO:25)+20 μM mouse serum albumin (MSA) via SQZ (60 psi; 4 μm constriction, room temperature) and incubated with CpG 1826 (1 μM) for 16 hours. On Day 14, female C57BL/6J recipient mice (10/group) were injected retro-orbitally with 100 μL of either vehicle (PBS), E7-incubated B APCs (5M cells/mouse), E7-loaded B APCs (5M cells/mouse) or injected subcutaneously in the left rear flank with E7 SLP (450 μg/mouse)+CpG (50 μg/mouse). On Day 28, the peptide only mice were boosted with subcutaneous peptide in an identical manner to Day 14 (boost). TC-1 tumor growth and survival was measured beginning 1 week post-tumor implantation two times per week and compared to tumor growth in untreated mice for up to 80 days.

Figure 27A:
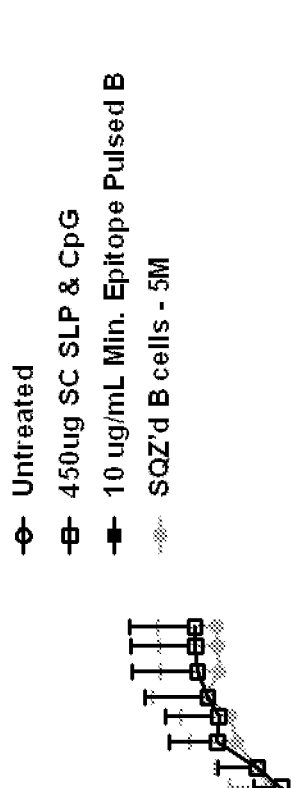
FIG. 27A shows the tumor volume over time in an experiment to determine the ability of SQZ-loaded B cells to act as APCs for therapeutic treatment for HPV-associated tumors, as compared to electroporated B cells, and a high dosage peptide vaccine at high dose (SC SLP).
Figure 27A:
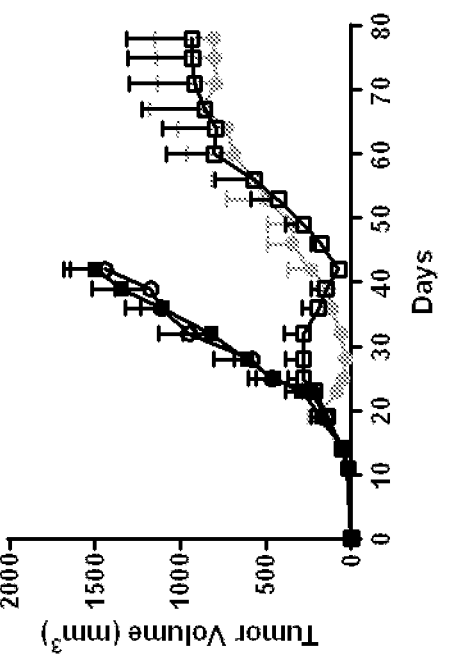
Figure 27B:
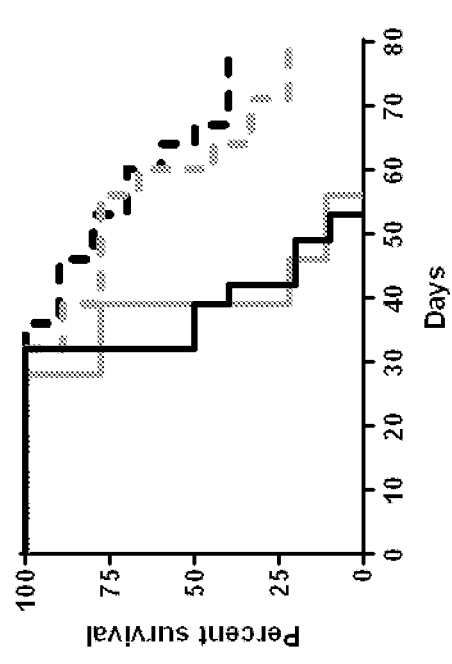
FIG. 27B shows the corresponding survival data over time from B cell APC therapeutic treatment for HPV-associated tumors, as compared to lectroporated B cells, and a high dosage peptide vaccine.

Tumor growth, as measured by the formula ((length× $width^2$)/2), was not affected by treatment with peptide-pulsed B APCs as compared to untreated mice (FIG. 27A). Interestingly, the SQZ-loaded B APC-treated mice exhibited stark tumor growth inhibition compared to untreated and peptide-pulsed B cells. This effect was similar to the effect of the peptide vaccine (SC SLP), despite the fact that the amount of peptide delivered to the mice is much higher than the loaded B APCs, and that the peptide vaccine group received and prime and a boost of the peptide vaccine, while SQZ B APC group only received a single prime dose. The trends observed with tumor growth correlated with overall survival, with both the untreated and peptide-pulsed B cell groups having equivalent median survival (~36 days—right). Both the high-dose peptide vaccine and the E7-loaded B APCs had almost double the median survival relative to the two other groups (60 [peptide] vs. 65.5 days [SQZ B APCs]) (FIG. 27B). These data show that B APCs loaded by SQZ can induce tumor regression in a therapeutic model of HPV-associated cancer and that it is as or more effective than a much higher-dose of a classic peptide vaccine.

Example 28

In order to determine the endogenous response to antigen-presenting cells (APCs) that have been loaded with antigen by SQZ, crafted splenocytes were SQZ-loaded and the levels of inflammatory cytokines were measured by intracellular cytokine staining (ICS).

Murine splenocytes (Spleno APC) from C56BL/6J mice were isolated and SQZ'd with 400 μg/mL Ova protein (FIG. 28B) or HPV 16 E7 peptide (20 μM—FIG. 28C), then injected into donor mice along with 1 μM CpG1826 (5 mice/group). On Day 7, splenocytes were harvested, re-challenged with Ins B9-23 and intracellular cytokine staining (ICS) was conducted for IFN-γ and IL-2 by flow cytometry and compared to untreated mice.

For both the model antigen Ova (FIG. 28B) and disease-relevant HPV E7 (FIG. 28C), it was found that Spleno APC-treated mice exhibited statistically significant increases in both IFN-γ and IL-2 when re-stimulated with either Ova or E7 (P<0.005 for all APC conditions compared to their respective untreated conditions). Taken together, these data show that mixed splenocytes can be engineered to elicit antigen-specific responses to multiple antigens in vivo.

Example 29

In order to determine the ability of SQZ-loaded B cells or mixed splenocytes to act as antigen-presenting cells (APCs) for the therapeutic treatment of tumors, mice were treated with loaded splenocyte APCs, followed by injection with TC-1 tumor cells. Tumor growth inhibition was measured to assess in vivo vaccine efficacy.

On Day 0, TC-1 tumor cells (50 k cells/mouse) were injected subcutaneously into the right flank of C56BL/6J mice (10 mice/group). On Day 9, mice were primed with either 1M cells/mouse of splenocytes (FIG. 28, Spleno$_{APC}$), tumor volumes were measured over time and mice were sacrificed at Day 48 or when their tumors reach >1500 mm³, whichever came first.

Figures 29A, 29B:
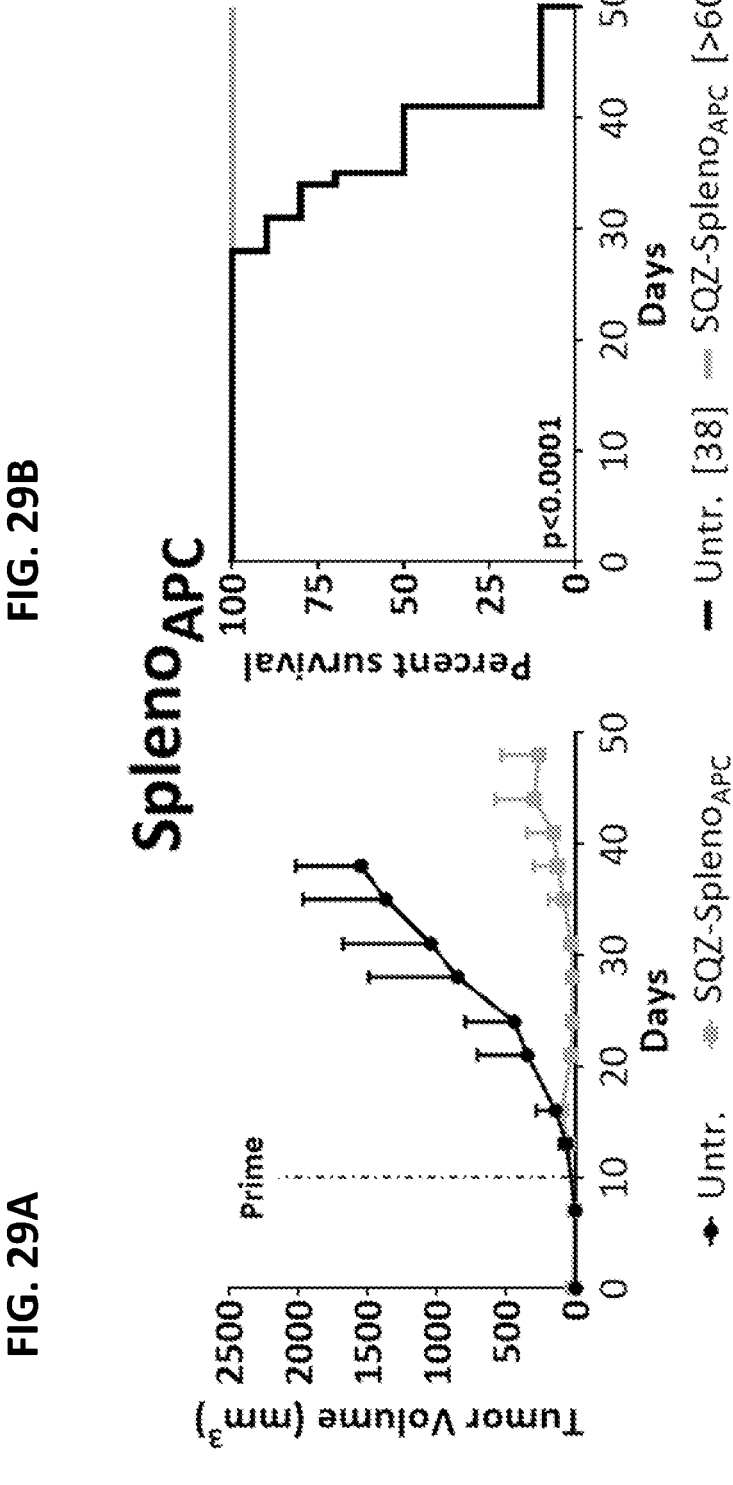
FIG. 29A shows the tumor volume over time in an experiment to determine the ability of SQZ-loaded splenocytes to act as APCs for therapeutic treatment for HPV-associated tumors.
FIG. 29B shows the corresponding survival data over time from splenocyte APC therapeutic treatment for HPV-associated tumors.
Figure 30:
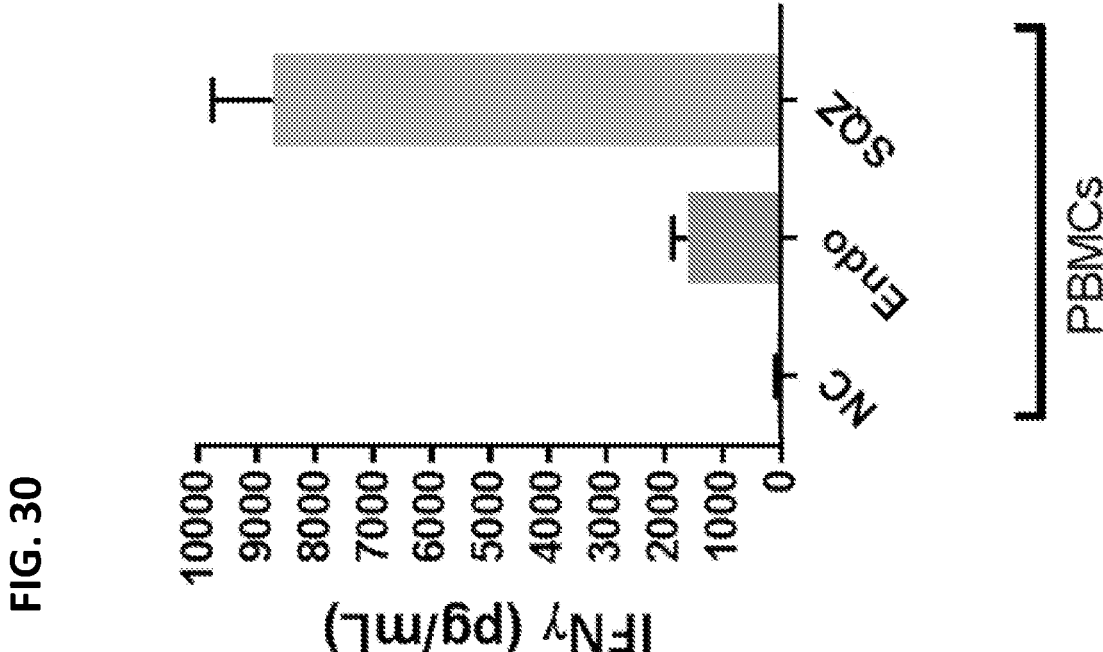
FIG. 30 shows the IFN-γ secretion by E7 responders, as an in vitro antigen-specific response to PBMC$_{APC}$ SQZ-loaded with HPV16 E7 SLP.

The ability of a therapeutic HPV antigen-based spleno-cyte vaccine to control TC-1 tumor growth, a line known to express HPV antigens E6 & E7, was tested by loading an E7 SLP into B cells or splenocytes 9 days after tumor implantation. Tumor growth was drastically inhibited in both the Spleno$_{APC}$ treated mice, with the average tumor volume remaining <500 mm3 for the duration of the study (FIG. 29A). The survival of mice treated with either APC was also significantly increased (P<0.0001), with none of the Spleno$_{APC}$-treated mice reaching the humane endpoint before the end of the study (FIG. 29B). Taken together, this data shows that splenocytes loaded with antigen via SQZ can act as a potent APC-based vaccine for the antigen-specific treatment of tumors.

Example 30

In order to determine the in vitro antigen-specific response to human antigen-presenting cells (APCs) that have been loaded with antigen by SQZ, B cells or PBMCs were SQZ-loaded and the levels of inflammatory cytokines were measured by intracellular cytokine staining (ICS).

Human PBMCs were isolated from HLA-A2+ donors and an HPV 16 E7 SLP (50 μM) was either incubated with PBMCs (Endo), or delivered by SQZ (SQZ). The loaded PBMCs (60 k cells/well) were then co-cultured with Astarte E7 responder T cells (30 k cells/well) in a 2:1 ratio, and cultured in the presence of IL-2 (100 U/mL) and CpG 2006 (1 μM) for 24 h. Supernatants were then harvested and analyzed for IFN-γ by ELISA.

PBMCs were tested as APCs to stimulate an HPV E7 antigen-specific response in vitro. PBMC APCs that were loaded with antigen stimulated the E7-specific responder cells to secrete IFN-γ at much higher levels than those cell that were incubated with antigen (P<0.005).

Taken together, these data show that human PBMCs can act as efficient APCs to stimulate disease-relevant antigen-specific responses in vitro.

Sequence Listing

| SEQ ID NO | Sequence | Description |
|---|---|---|
| 1 | TIHDIILECV | HPV16-E6(29-38), human epitope |
| 2 | EVYDFAFRDL | HPV16-E6(48-57), murine epitope |
| 3 | YMLDLQPETT | HPV16-E7(11-20), human epitope |
| 4 | RAHYNIVTF | HPV16-E7(49-57), murine epitope |
| 5 | LPQLSTELQT | HPV16-E6(19-28) N-terminal polypeptide, human |
| 6 | QLCTELQT | HPV16-E6(21-28) N-terminal polypeptide, human |
| 7 | KQQLLRR | HPV16-E6(41-47) N-terminal polypeptide, native murine |
| 8 | VYSKQQLLRR | HPV16-E6(38-47) N-terminal polypeptide, classic murine |
| 9 | MHGDTPTLHE | HPV16-E7(1-10) N-terminal polypeptide, human |
| 10 | GQAEPD | HPV16-E7(43-48) N-terminal polypeptide, murine |
| 11 | YSKQQLLRREVYDFAF | HPV16-E6(39-54) C-terminal polypeptide, human |

-continued

| Sequence Listing | | |
| --- | --- | --- |
| SEQ ID NO | Sequence | Description |
| 12 | YCKQQLL | HPV16-E6(39-45) C-terminal polypeptide, human |
| 13 | CIVYRDGN | HPV16-E6(58-65) C-terminal polypeptide, native murine |
| 14 | SIVYRDGNPYAVSDK | HPV16-E6(58-72) C-terminal polypeptide, classic murine |
| 15 | DLYCYEQLNDSSEEE | HPV16-E7(21-35) C-terminal polypeptide, human |
| 16 | CCKCDSTLRLCVQSTHVDIR | HPV16-E7(58-77) C-terminal polypeptide, native murine |
| 17 | SSKSDSTLRLSVQSTHVDIR | HPV16-E7(58-77) C-terminal polypeptide, classic murine |
| 18 | LPQLSTELQTTIHDIILECVYSKQQ LLRREVYDFAF | HPV16-E6(19-54) SLP, human |
| 19 | QLCTELQTTIHDIILECVYCKQQLL | HPV16-E6(21-45) SLP, human |
| 20 | KQQLLRREVYDFAFRDLCIVYRDGN | HPV16-E6(41-65) SLP, native murine |
| 21 | VYSKQQLLRREVYDFAFRDLSIVYR DGNPYAVSDK | HPV16-E6(38-72) SLP, classic murine |
| 22 | MHGDTPTLHEYMLDLQPETTDLYCY EQLNDSSEEE | HPV16-E7(1-35) SLP, human |
| 23 | QLCTELQTYMLDLQPETTYCKQQLL | HPV16-E7.6 SLP, human |
| 24 | GQAEPDRAHYNIVTFCCKCDSTLRL CVQSTHVDIR | HPV16-E7(43-77) SLP, native murine |
| 25 | GQAEPDRAHYNIVTFSSKSDSTLRL SVQSTHVDIR | HPV16-E7(43-77) SLP, classic murine |
| 26 | ggGGTCAACGTTGAgggggg Bases shown in capital letters are phosphosdi-ester, and those in lower case are phosphorothioate | ODN 1585 (Class A, mouse-specific) |
| 27 | ggGGGACGA:TCGTCgggggg Bases shown in capital letters are phosphodi-ester, and those in lower case are phosphorothioate | ODN 2216 (Class A, human-selective) |

-continued

| Sequence Listing | | |
| --- | --- | --- |
| SEQ ID NO | Sequence | Description |
| 28 | gggGACGAC:GTCGTGgggggg Bases shown in capital letters are phosphodi-ester, and those in lower case are phosphorothioate | ODN 2336 (Class A, human preferred) |
| 29 | tccatgacgttcctgatgct Bases shown in capital letters are phosphodi-ester, and those in lower case are phosphorothioate | ODN 1668 (Class B, mouse specific) |
| 30 | tccatgacgttcctgacgtt Bases are phosphorothioate | ODN 1826 (Class B, mouse specific) |
| 31 | tcgtcgttttgtcgttttgtcgtt Bases are phosphorothioate | ODN 2006 (Class B, human selective) |
| 32 | tcg tcg ttg tcg ttt tgt cgt t Bases are phosphorothioate | ODN 2007 (Class B, bovine/porcine) |
| 33 | tcg acg ttc gtc gtt cgt cgt tc Bases are phosphorothioate | ODN BW006 (Class B, human & mouse) |
| 34 | tcg cga cgt tcg ccc gac gtt cgg ta Bases are phosphorothioate | ODN D-SL01 (Class B, multi-species) |
| 35 | tcgtcgttttcggcgc:gcgccg Bases are phosphorothioate | ODN 2395 (Class C, human/mouse) |
| 36 | tcgtcgtcgttc:gaacgacgttgat Bases are phosphorothioate | ODN M362 (Class C, human/mouse) |
| 37 | tcg cga acg ttc gcc gcg ttc gaa cgc gg Bases are phosphorothioate | ODN D-SL03 (Class C, multi-species) |
| 38 | MHGDTPTLHEYMLDLQPETTDLYCY EQLNDSSEEE | E7 |
| 39 | LYCYEQLNDSSEEEDEIDGPAGQAE PDRAHYNIVT | E7 |
| 40 | GQAEPDRAHYNIVTFCCKCDSTLRL CVQSTHVDIR | E7 |
| 41 | TLRLCVQSTHVDIRTLEDLLMGTLG IVCPICSQKP | E7 |
| 42 | MHQKRTAMFQDPQERPRKLPQLCTE LQTTIHD | E6 |
| 43 | LPQLCTELQTTIHDIILECVYCKQQ LLRREVY | E6 |

-continued

| SEQ ID NO | Sequence | Description |
|---|---|---|
| | Sequence Listing | |
| 44 | KQQLLRREVYDFAFRDLCIVYRDGN | E6 |
| 45 | RDLCIVYRDGNPYAVCDKCLKFYSK I | E6 |
| 46 | DKCLKFYSKISEYRHYCYSLYGTTL | E6 |
| 47 | HYCYSLYGTTLEQQYNKPLCDLLIR | E6 |

-continued

| SEQ ID NO | Sequence | Description |
|---|---|---|
| | Sequence Listing | |
| 48 | YGTTLEQQYNKPLCDLLIRCINCQK PLCPEEK | E6 |
| 49 | RCINCQKPLCPEEKQRHLDKKQRFH NIRGRWT | E6 |
| 50 | DKKQRFHNIRGRWTGRCMSCCRSSR TRRETQL | E6 |

What is claimed is:

1. A composition comprising modified immune cells, wherein the immune cells are modified to comprise intracellularly a CpG ODN and an HPV antigen with at least 90% similarity to any one of SEQ ID NOs:18-25.

2. The composition in claim 1, wherein the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the HPV antigen and the CpG ODN to pass through to form a perturbed input cell; and b) incubating the perturbed input cell with the HPV antigen and the CpG ODN for a sufficient time to allow the HPV antigen and the CpG ODN to enter the perturbed input cell; thereby generating the modified immune cells.

3. A composition comprising modified immune cells, wherein the immune cells are modified to comprise an HPV antigen, wherein the HPV antigen comprises an amino acid sequence with at least 90% similarity to any one of SEQ ID NOs:18-25.

4. The composition in claim 3, wherein the modified immune cells are prepared by a) passing a cell suspension comprising an input cell through a cell-deforming constriction, wherein a diameter of the constriction is a function of a diameter of the input cell in the suspension, thereby causing perturbations of the input cell large enough for the IPV antigen to pass through to form a perturbed input cell; and b) incubating the perturbed input cell with the HPV antigen for a sufficient time to allow the HPV antigen to enter the perturbed input cell;

thereby generating the modified immune cells.

5. A composition comprising an antigen, wherein the antigen comprises an amino acid sequence with at least 90% similarity to SEQ ID NO:23.

6. A plurality of modified peripheral blood mononuclear cells (PBMCs), wherein the PBMCs are modified to comprise an antigen and an increased expression of one or more of IFN-γ, IL-6, MCP-1, MIP-1β, IP-10, or TNF-α compared to a plurality of unmodified PBMCs, wherein the expression of one or more of IFN-γ, IL-6, MCP-1, MIP-1β, IP-10 or TNF-α is increased upon incubation of the plurality of modified PBMCs with an adjuvant, and wherein the antigen is exogenous to the modified PBMCs.

7. A plurality of modified PBMCs, wherein the PBMCs are modified to comprise an antigen and an adjuvant and an increased expression of one or more of IFN-γ, IL-6, MCP-1, MIP-1β, IP-10, or TNF-α compared to a plurality of unmodified PBMCs, wherein the expression of one or more of IFN-γ, IL-6, MCP-1, MIP-1β, IP-10, or TNF-α is increased upon incubation of the plurality of modified PBMCs with a second adjuvant, and wherein the antigen is exogenous to the modified PBMCs.

8. A plurality of modified PBMCs, wherein the PBMCs are modified to comprise an antigen and an increased expression of one or more of IFN-γ, IL-6, MCP-1, MIP-1β, IP-10, or TNF-α compared to a plurality of unmodified PBMCs, prepared by a process comprising the steps of:

a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs;

b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time to generate the modified PBMCs comprising the antigen with increased expression of one or more of IFN-γ, IL-6, MCP-1, MIP-1β, IP-10, or TNF-α.

9. A plurality of modified PBMCs, wherein the PBMCs are modified to comprise an antigen and an increased expression of one or more of IFN-γ, IL-6, MCP-1, MIP-1β, IP-10, or TNF-α compared to a plurality of unmodified PBMCs, prepared by a process comprising the steps of;

a) incubating a plurality of input PBMCs with an adjuvant for a sufficient time to generate PBMCs with increased expression of one or more of IFN-γ, IL-6, MCP-1, MIP-1β, IP-10, or TNF-α;

b) passing a cell suspension comprising the plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; and c) incubating the plurality of perturbed input PBMCs with the antigen for a sufficient time to allow the antigen to enter the perturbed input PBMCs, thereby generating the plurality of modified PBMCs comprising the antigen.

\* \* \* \* \*